(12) United States Patent
Urano et al.

(10) Patent No.: US 7,135,493 B2
(45) Date of Patent: Nov. 14, 2006

(54) HDAC INHIBITOR

(75) Inventors: Yasuharu Urano, Osaka (JP); Shigeki Satoh, Osaka (JP); Naoki Ishibashi, Osaka (JP); Kazunori Kamijo, Osaka (JP)

(73) Assignee: Astellas Pharma Inc., Tokyo (JP)

( * ) Notice: Subject to any disclaimer, the term of this patent is extended or adjusted under 35 U.S.C. 154(b) by 262 days.

(21) Appl. No.: 10/754,541

(22) Filed: Jan. 12, 2004

(65) Prior Publication Data

US 2004/0229889 A1 Nov. 18, 2004

(30) Foreign Application Priority Data

Jan. 13, 2003 (AU) .............................. 2003900116
Oct. 6, 2003 (AU) .............................. 2003905406

(51) Int. Cl.
*A61K 31/4188* (2006.01)
*A61K 31/484* (2006.01)
*A61K 31/4164* (2006.01)
*C07D 233/61* (2006.01)
*C07D 491/113* (2006.01)
*C07D 487/04* (2006.01)
*C07D 235/08* (2006.01)

(52) U.S. Cl. .................. 514/394; 514/300; 514/262.1; 514/397; 514/396; 548/335.1; 548/302.7; 546/28; 544/262

(58) Field of Classification Search ................ 544/262; 546/28; 514/262.1, 300, 396, 397, 394; 548/302.7, 548/335.1, 302.1
See application file for complete search history.

(56) References Cited

FOREIGN PATENT DOCUMENTS

| WO | WO 93/12075 | 6/1993 |
|---|---|---|
| WO | WO 95/13264 | 5/1995 |
| WO | WO 97/24117 | 7/1997 |
| WO | WO 01/38322 | 5/2001 |
| WO | WO 02/18326 | 3/2002 |
| WO | WO 02/22577 | 3/2002 |
| WO | WO 200222577 A2 * | 3/2002 |
| WO | WO 200224653 A1 * | 3/2002 |
| WO | WO 02/30872 | 4/2002 |
| WO | WO 02/074298 | 9/2002 |
| WO | WO 03/082288 | 10/2003 |
| WO | WO 03/087066 | 10/2003 |

* cited by examiner

*Primary Examiner*—Kamal A. Saeed
*Assistant Examiner*—Michael Barker
(74) *Attorney, Agent, or Firm*—Oblon, Spivak, McClelland, Maier & Neustadt, P.C.

(57) ABSTRACT

A compound having the following formula (I):

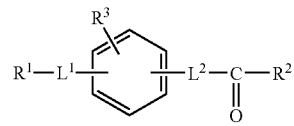

wherein
$R^1$ is N-containing heterocyclic ring optionally substituted with one or more suitable substituent(s),
$R^2$ is hydroxyamino,
$R^3$ is hydrogen or a suitable substituent,
$L^1$ is —$(CH_2)_n$— (wherein n is an integer of 0 to 6) optionally substituted with one or more suitable substituent(s), wherein one or more methylene(s) may be replaced with suitable heteroatom(s), and
$L^2$ is lower alkenylene,
or a salt thereof. The compound is useful as a histone deacetylase inhibitor.

36 Claims, No Drawings

HDAC INHIBITOR

TECHNICAL FIELD

The present invention relates to a compound useful as a medicament, and to a pharmaceutical composition comprising the same.

BACKGROUND ART

Histone deacetylase (hereinafter also referred as HDAC) is known to play an essential role in the transcriptional machinery for regulating gene expression, induce histone hyperacetylation and to affect the gene expression. Therefore, it is useful as a therapeutic or prophylactic agent for diseases caused by abnormal gene expression such as inflammatory disorders, diabetes, diabetic complications, homozygous thalassemia, fibrosis, cirrhosis, acute promyelocytic leukaemia (APL), organ transplant rejections, autoimmune diseases, protozoal infections, tumors, etc.

WO 01/38322 discloses an inhibitor of histone deacetylase represented by the following formula:

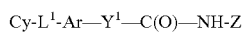

Cy-L$^1$-Ar—Y$^1$—C(O)—NH-Z wherein
Cy is cycloalkyl, aryl, heteroaryl or heterocyclyl, each of which is optionally substituted;
L$^1$ is —(CH$_2$)$_m$—W— wherein m is an integer of 0 to 4, and W is selected from the group consisting of —C(O)NH—, —S(O)$_2$NH—, etc.;
Ar is optionally substituted arylene, which is optionally fused to an aryl, heteroaryl ring, etc.;
Y$^1$ is a chemical bond or a straight- or branched-chain saturated alkylene, wherein said alkylene is optionally substituted; and
Z is selected from the group consisting of anilinyl, pyridyl, thiadiazolyl and —O-M wherein M is H or a pharmaceutically acceptable cation.

WO 02/22577 discloses the following hydroxamate compound as a deacetylase inhibitor:

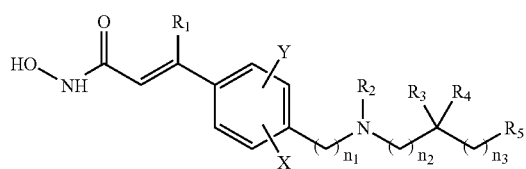

wherein
R$_1$ is H, halo or a straight chain C$_1$–C$_6$ alkyl;
R$_2$ is selected from H, C$_1$–C$_{10}$ alkyl, C$_4$–C$_9$ cycloalkyl, C$_4$–C$_9$ heterocycloalkyl, C$_4$–C$_9$ heterocycloalkylalkyl, cycloalkylalkyl, aryl, heteroaryl, etc.;
R$_3$ and R$_4$ are the same or different and independently H, C$_1$–C$_6$ alkyl, acyl or acylamino, or
R$_3$ and R$_4$ together with the carbon to which they are bound to represent C═O, C═S, etc., or
R$_2$ together with the nitrogen to which it is bound and R$_3$ together with the carbon to which it is bound to form a C$_4$–C$_9$ heterocycloalkyl, a heteroaryl, a polyheteroaryl, a non-aromatic polyheterocycle, or a mixed aryl and non-aryl polyheterocycle ring;
R$_5$ is selected from H, C$_1$–C$_6$ alkyl, etc.;
n, n$_1$, n$_2$ and n$_3$ are the same or different and independently selected from 0–6, when n$_1$ is 1–6, each carbon atom can be optionally and independently substituted with R$_3$ and/or R$_4$;
X and Y are the same or different and independently selected from H, halo, C$_1$–C$_4$ alkyl, etc.;
or a pharmaceutically acceptable salt thereof.

SUMMARY OF THE INVENTION

The present invention relates to a novel compound useful as a medicament, and to a pharmaceutical composition comprising the same.

More particularly, the present invention relates to a compound having a potent inhibitory effect on the activity of histone deacetylase.

The inventors of the present invention have also found that histone deacetylase inhibitors, such as a compound of the formula (I) (hereinafter compound [I]), have a potent immunosuppressive effect and potent antitumor effect. Therefore, a histone deacetylase inhibitors such as compound [I] is useful as an active ingredient for an immunosuppressant and an antitumor agent, and useful as an active ingredient for a therapeutic or prophylactic agent for diseases such as inflammatory disorders, diabetes, diabetic complications, homozygous thalassemia, fibrosis, cirrhosis, acute promyelocytic leukaemia (APL), organ transplant rejections, autoimmune diseases, protozoal infections, tumors, etc.

Accordingly, one object of the present invention is to provide a compound having biological activities for treating or preventing the diseases as stated above.

A further object of the present invention is to provide a pharmaceutical composition containing the compound [I] as an active ingredient.

A yet further object of the present invention is to provide use of the histone deacetylase inhibitors, such as compound [I], for treating and preventing the diseases as stated above.

A yet further object of the present invention is to provide a commercial package comprising the pharmaceutical composition containing the compound [I] and a written matter associated therewith, the written matter stating that the pharmaceutical composition may or should be used for treating or preventing the diseases as stated above.

Thus, the present invention provides

[1] A compound having the following formula (I):

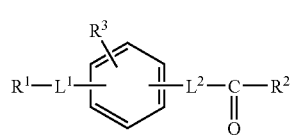

(I)

wherein
R$^1$ is N-containing heterocyclic ring optionally substituted with one or more suitable substituent(s),
R$^2$ is hydroxyamino,
R$^3$ is hydrogen or a suitable substituent,
L$^1$ is —(CH$_2$)$_n$— (wherein n is an integer of 0 to 6) optionally substituted with one or more suitable substituent(s), wherein one or more methylene(s) may be replaced with suitable heteroatom(s), and L² is lower alkenylene,
or a salt thereof.

[2] The compound of the above-mentioned [1], wherein
R¹ is N-containing heterocyclic ring represented by the following formula:

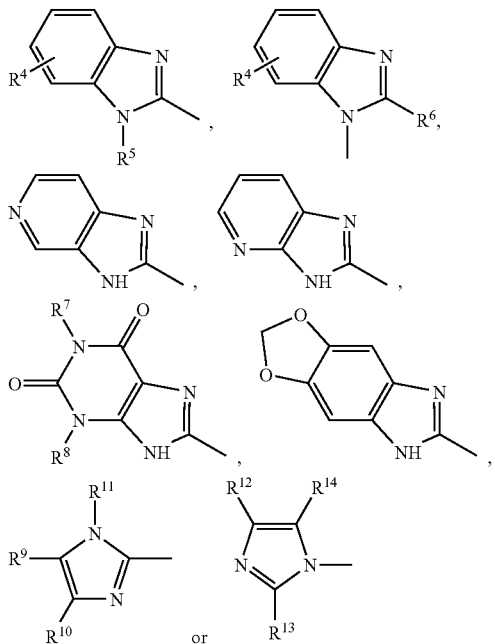

wherein
R⁴ is hydrogen or a group selected from the group consisting of
  (1) lower alkyl optionally substituted with di(lower)alkylamino or hydroxy,
  (2) lower alkoxy,
  (3) aryl optionally substituted with the substituent selected from the group consisting of halogen, lower alkanoyl, lower alkylsulfonyl, lower alkoxy and di(lower)alkylamino,
  (4) lower alkanoyl,
  (5) lower alkoxy-carbonyl,
  (6) arylcarbonyl,
  (7) aryl(lower)alkoxy,
  (8) amino optionally mono- or di-substituted with substituent(s) selected from the group consisting of lower alkyl, lower alkanoyl and cycloalkyl,
  (9) halo(lower)alkyl,
  (10) aryloxy,
  (11) aryl(lower)alkyl optionally substituted with hydroxy,
  (12) carboxyl,
  (13) nitro,
  (14) cyano,
  (15) halogen,
  (16) heteroaryl,
  (17) non-aromatic heterocycle optionally substituted with lower alkyl,
  (18) hydroxy,
  (19) (lower)alkylsulfonylcarbamoyl and
  (20) non-aromatic heterocycle carbonyl,
R⁵ is hydrogen or a group selected from the group consisting of lower alkyl and aryl(lower)alkyl, and R⁶, R⁷ and R⁸ are each hydrogen or lower alkyl,
R⁹ is hydrogen or a group selected from the group consisting of
  (1) lower alkyl optionally substituted with di(lower)alkylamino,
  (2) aryl optionally substituted with lower alkoxy,
  (3) (lower)alkoxy-carbonyl,
  (4) cyano,
  (5) carbamoyl optionally mono- or di-substituted with (lower)alkyl,
  (6) halogen,
  (7) (lower)alkyl-carbonyl,
  (8) arylcarbonyl and
  (9) cyclo(lower)alkyl,
R¹⁰ is hydrogen or a group selected from the group consisting of
  (1) (lower)alkylcarbamoyl,
  (2) di(lower)alkylcarbamoyl,
  (3) aryl optionally substituted with halogen,
  (4) (lower)alkoxy-carbonyl,
  (5) carboxy,
  (6) non-aromatic heterocycle carbonyl,
  (7) halogen,
  (8) (lower)alkyl optionally substituted with hydroxy, (lower)alkoxy, non-aromatic heterocycle, aryl, di(lower)alkylamino or halogen and
  (9) adamantyl,
R¹¹ is hydrogen or aryl(lower)alkyl in which the aryl portion is substituted with lower alkoxy,
R¹² is hydrogen or a group selected from the group consisting of lower alkyl and aryl optionally substituted with halogen,
R¹³ is hydrogen or a group selected from the group consisting of lower alkyl and aryl, and
R¹⁴ is hydrogen or lower alkyl,
R² is hydroxyamino,
R³ is hydrogen or lower alkoxy,
L¹ is —(CH₂)ₙ— (wherein n is 1 to 5) optionally substituted with one or more substituent(s) selected from lower alkyl(s) and aryl(lower)alkyl, and wherein one methylene may be replaced with an oxygen atom, and
L² is vinylene,
or a salt thereof.

[3] The compound of the above-mentioned [2], wherein
R¹ is N-containing condensed heterocyclic ring represented by the following formula:

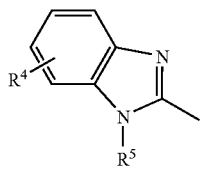

wherein R⁴ and R⁵ are each as defined in the above-mentioned [2].

[4] The compound of the above-mentioned [3], wherein
R⁴ and R⁵ are each hydrogen,
R² is hydroxyamino,
R³ is hydrogen,
L¹ is —CH₂—, and
L² is vinylene,
or a salt thereof.

[5] The compound of the above-mentioned [2], wherein
R¹ is N-containing heterocyclic ring represented by the following formula:

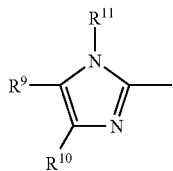

wherein R⁹, R¹⁰ and R¹¹ are each as defined in the above-mentioned [2].

[6] The compound of the above-mentioned [5], wherein
R⁹ is hydrogen or aryl optionally substituted with lower alkoxy,
R¹⁰ is hydrogen or aryl optionally substituted with halogen, and
R¹¹ is hydrogen,
R² is hydroxyamino,
R³ is hydrogen,
L¹ is —CH₂—, and
L² is vinylene,
or a salt thereof.

[7] A compound of the following formula

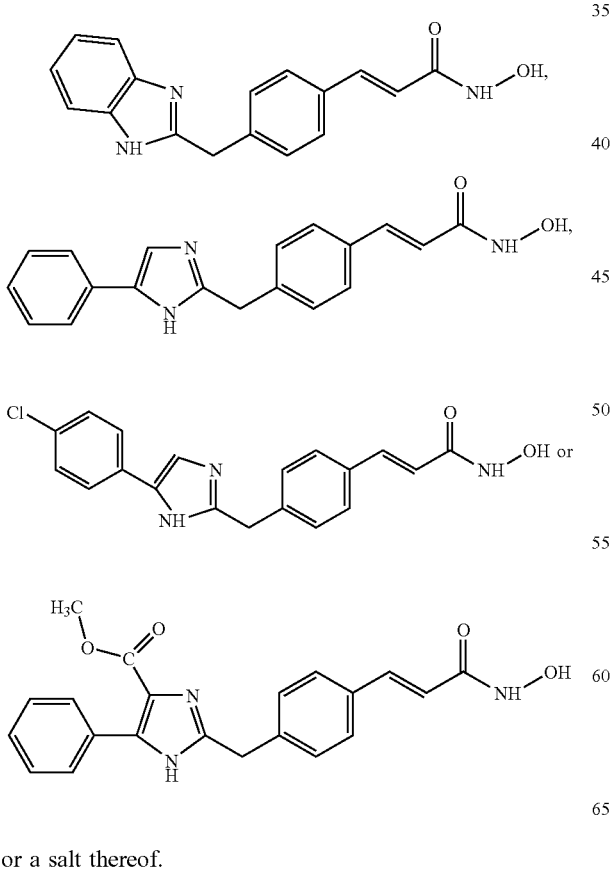

or a salt thereof.

[8] A compound having the following formula (I'):

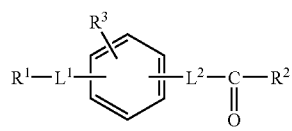

wherein
R¹ is N-containing condensed heterocyclic ring optionally substituted with one or more suitable substituent(s),
R² is hydroxyamino,
R³ is hydrogen or a suitable substituent,
L¹ is —(CH₂)$_n$— (wherein n is an integer of 0 to 6) optionally substituted with one or more suitable substituent(s), wherein one or more methylene(s) may be replaced with suitable heteroatom(s), and
L² is lower alkenylene,
or a salt thereof.

[9] The compound of the above-mentioned [8], wherein
R¹ is N-containing condensed heterocyclic ring represented by the following formula:

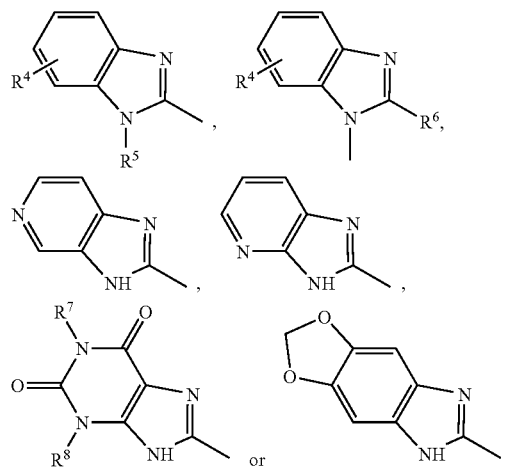

wherein
R⁴ is hydrogen or a group selected from the group consisting of
(1) lower alkyl,
(2) lower alkoxy,
(3) aryl optionally substituted with the substituent selected from the group consisting of halogen, lower alkanoyl, lower alkylsulfonyl, lower alkoxy and di(lower)alkylamino,
(4) lower alkanoyl,
(5) lower alkoxy-carbonyl,
(6) arylcarbonyl,
(7) aryl(lower)alkoxy,
(8) amino optionally mono- or di-substitited with substituent(s) selected from the group consisting of lower alkyl, lower alkanoyl and cycloalkyl,
(9) halo(lower)alkyl,
(10) aryloxy,
(11) aryl(lower)alkyl optionally substituted with hydroxy,
(12) carboxyl,

(13) nitro,
(14) cyano,
(15) halogen,
(16) heteroaryl and
(17) non-aromatic heterocycle optionally substituted with lower alkyl, $R^5$ is hydrogen or a group selected from the group consisting of lower alkyl and aryl(lower)alkyl, and $R^6$, $R^7$ and $R^8$ are each hydrogen or lower alkyl, $R^2$ is hydroxyamino, $R^3$ is hydrogen or lower alkoxy, $L^1$ is —(CH$_2$)$_n$— (wherein n is 1 or 2) optionally substituted with one or more substituent(s) selected from lower alkyl(s) and aryl(lower)alkyl, and wherein one methylene may be replaced with an oxygen atom, and $L^2$ is vinylene, or a salt thereof.

[10] A compound having the following formula (I"):

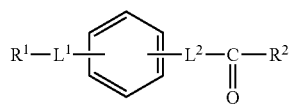
(I")

wherein $R^1$ is N-containing condensed heterocyclic ring optionally substituted with one or more suitable substituent(s), $R^2$ is hydroxyamino, $L^1$ is —(CH$_2$)$_n$— (wherein n is an integer of 0 to 6) optionally substituted with one or more suitable substituent(s), and $L^2$ is lower alkenylene, or a salt thereof.

[11] The compound of the above-mentioned [10], wherein $R^1$ is N-containing condensed heterocyclic ring represented by the following formula:

wherein $R^4$ is hydrogen or a group selected from the group consisting of lower alkyl and aryl, and $R^5$ is hydrogen or a group selected from the group consisting of lower alkyl and aryl(lower)alkyl, $R^2$ is hydroxyamino, $L^1$ is —(CH$_2$)$_n$— (wherein n is 1 or 2) optionally substituted with aryl(lower)alkyl, and $L^2$ is vinylene, or a salt thereof.

Of the above-mentioned compounds, the compounds represented by the general formulas (I') and (I") are also encompassed in the scope of the compound represented by the general formula (I). Hereinafter "compound [I]" also encompasses "compound [I']" and "compound [I"]".

The above-mentioned compounds and salts thereof can be prepared by the processes as illustrated in the following reaction schemes or by the methods disclosed in the Preparations and Examples.

In the above and subsequent descriptions of the present specification, suitable examples and illustration of the various definitions which the present invention intends to include within the scope thereof are explained in detail as follows.

In the following Processes, the compound [I-1] and [I-2] are encompassed in the scope of the compound [I], and the compound [II-A], [II-B], [II-C], [II-C'], [II-D], [II-E], [II-F], [II-G], [II-H], [II-I], [II-J], [II-K], [II-L], [II-M] and [II-N] are also encompassed in the scope of the compound [II].

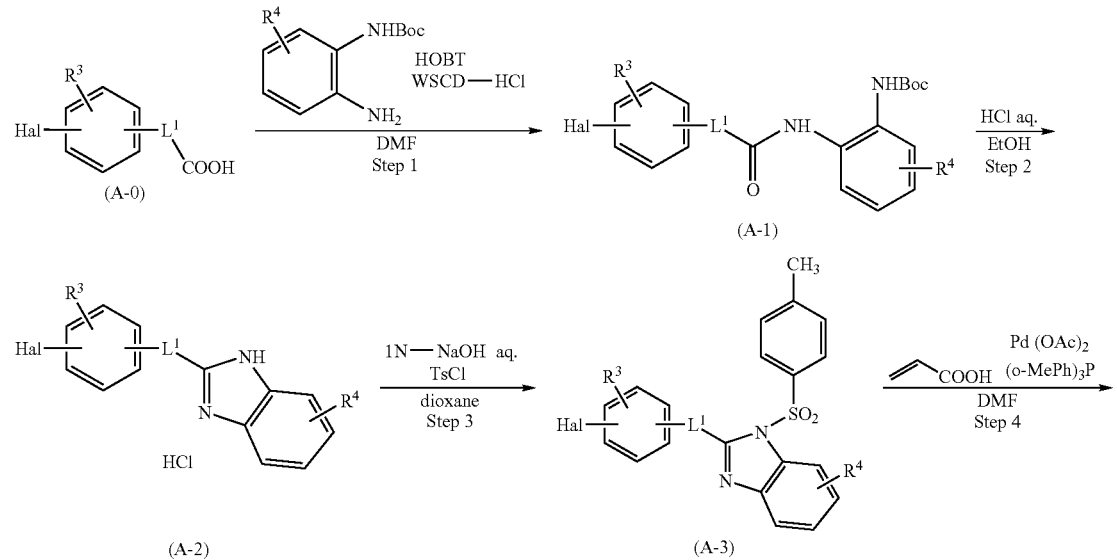

-continued
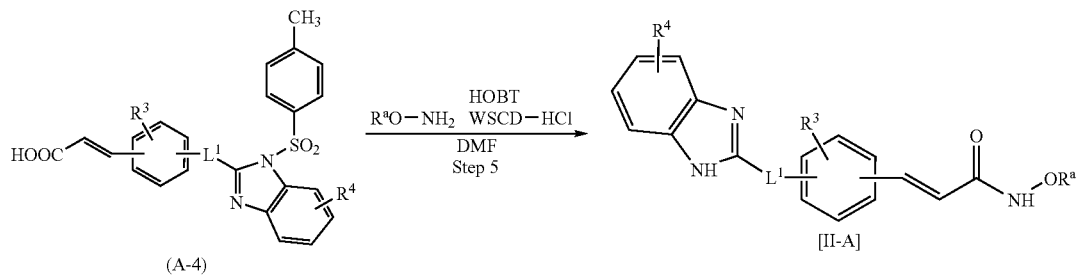
(A-4)
[II-A]
Process B
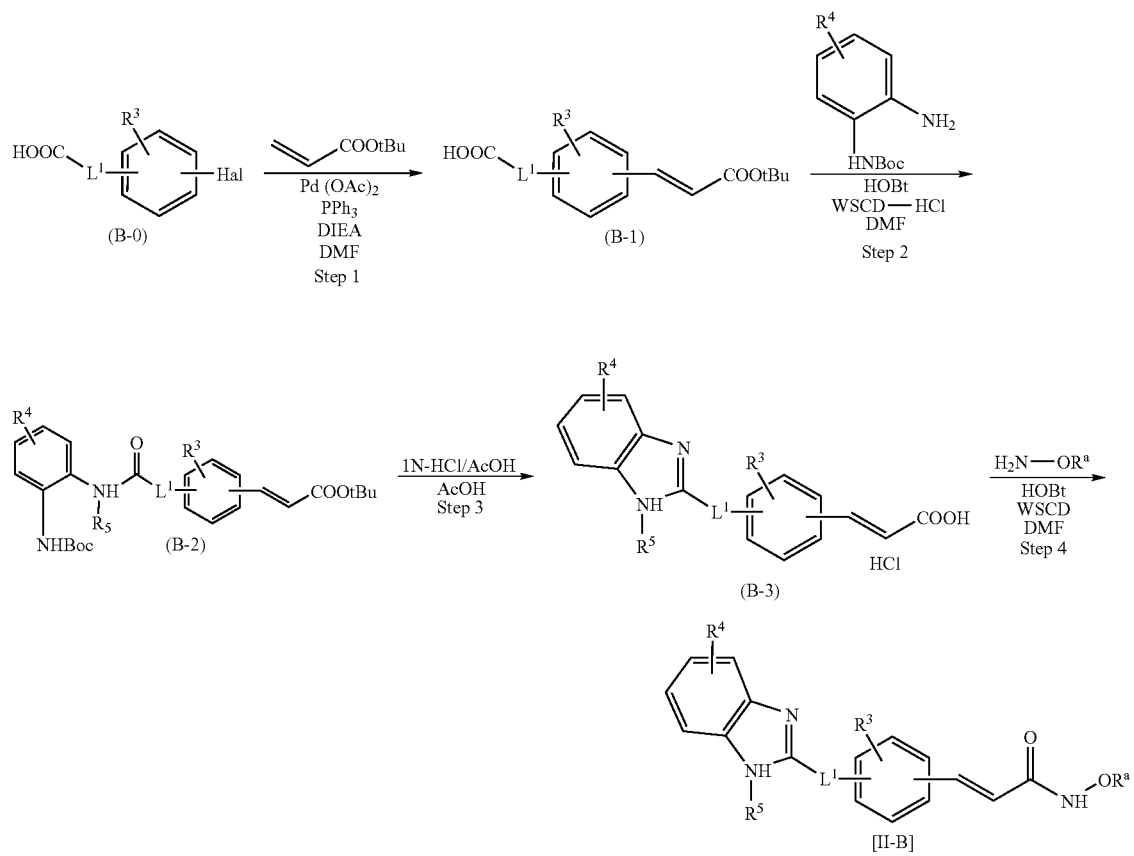
Process C
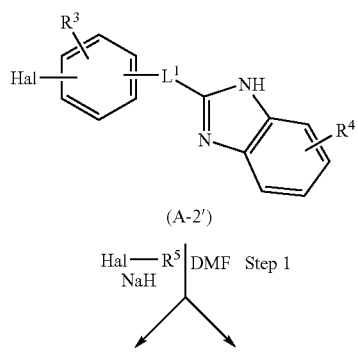

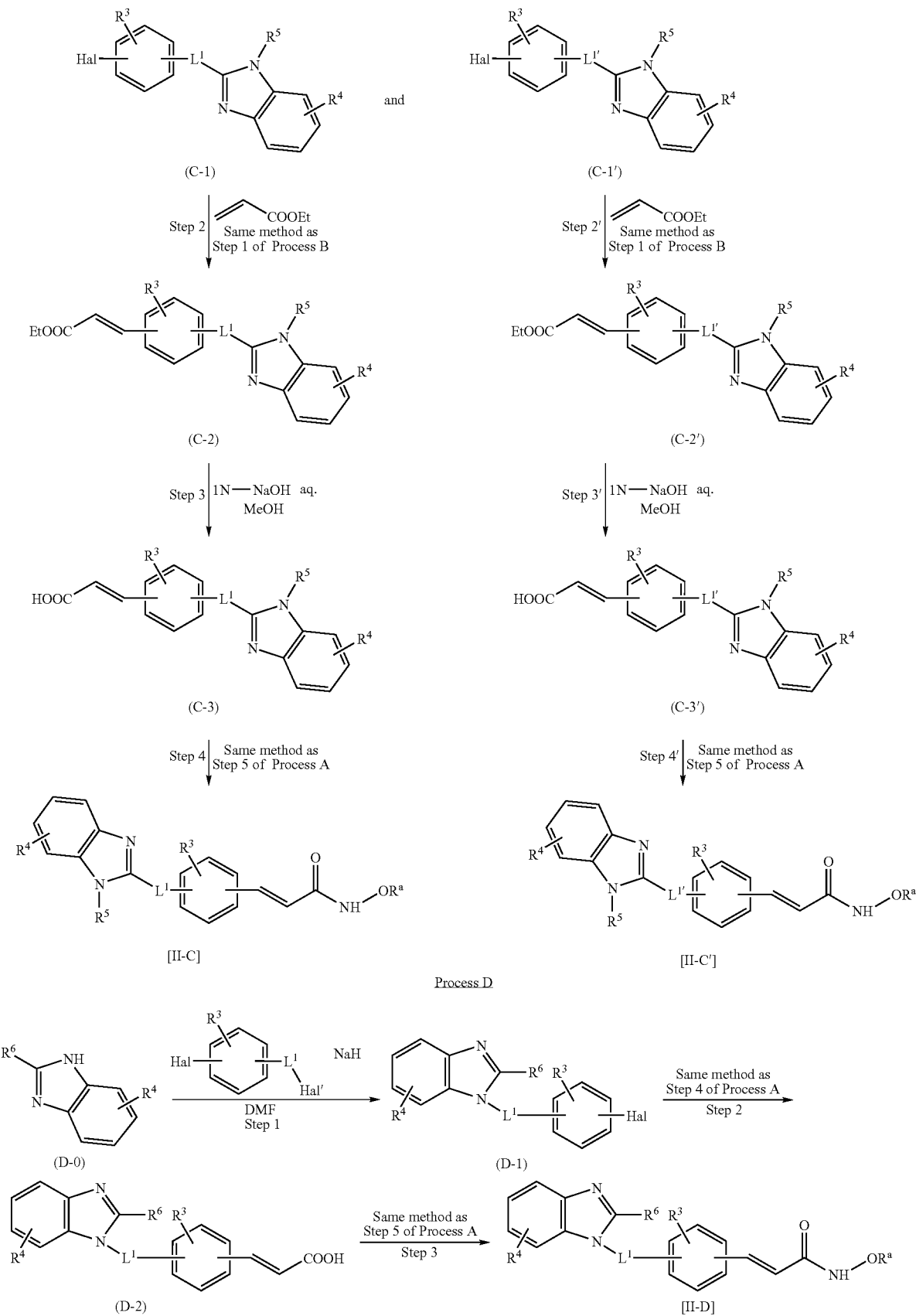

-continued
Process E
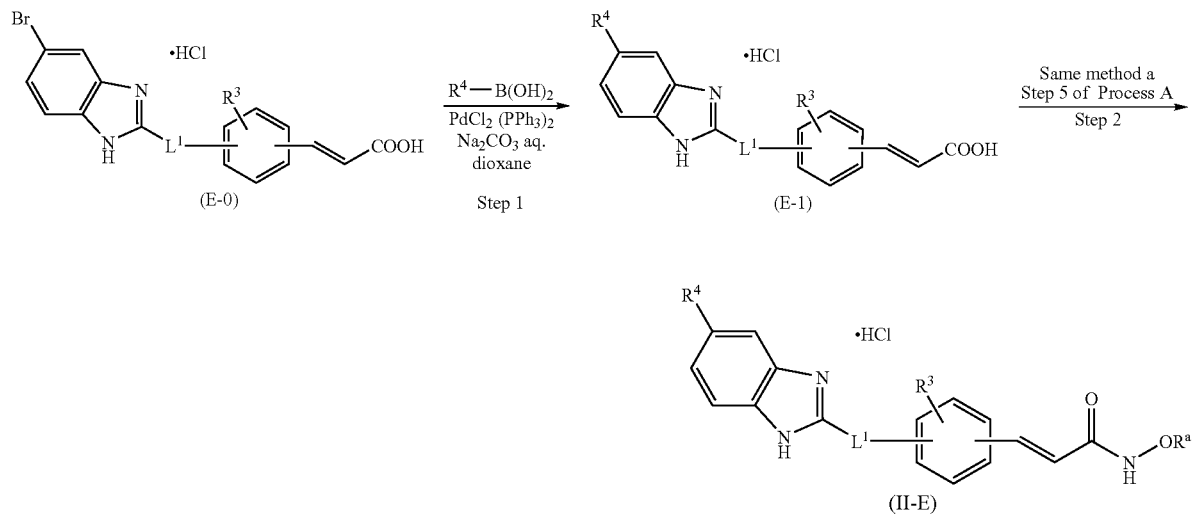
Process F
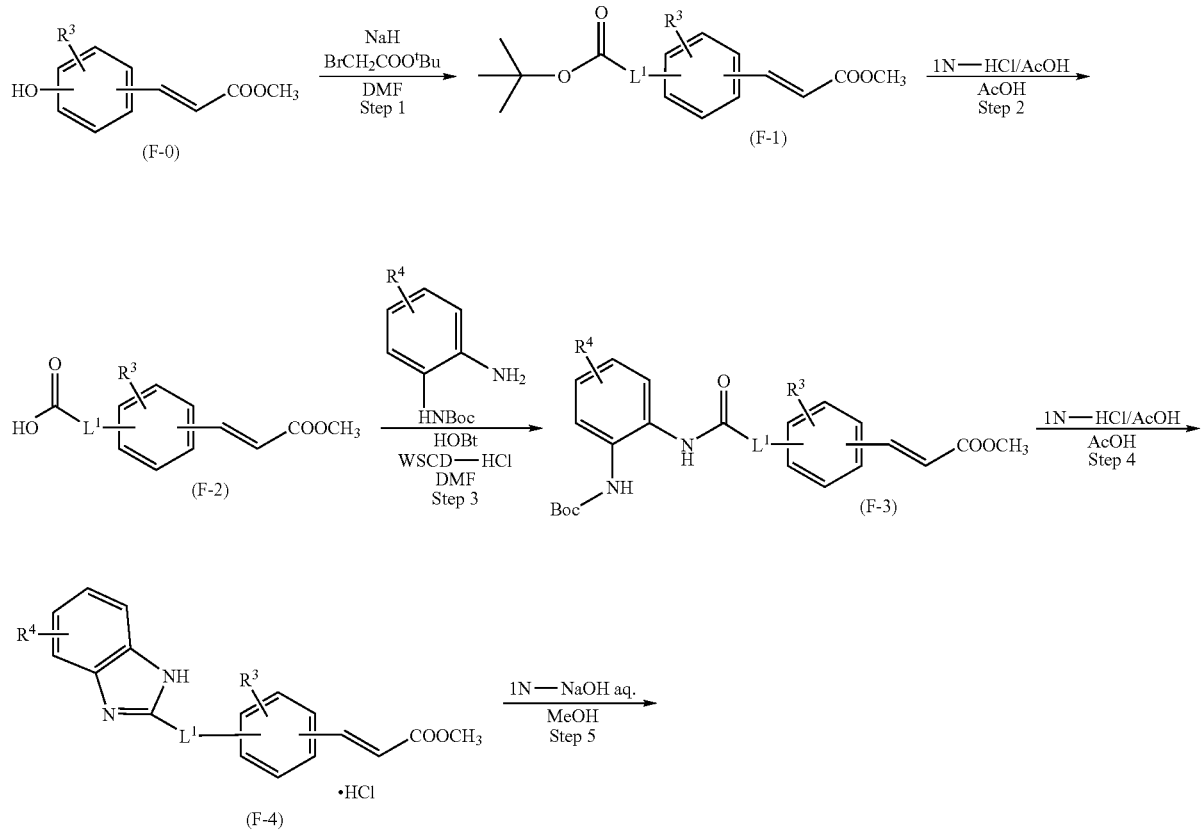

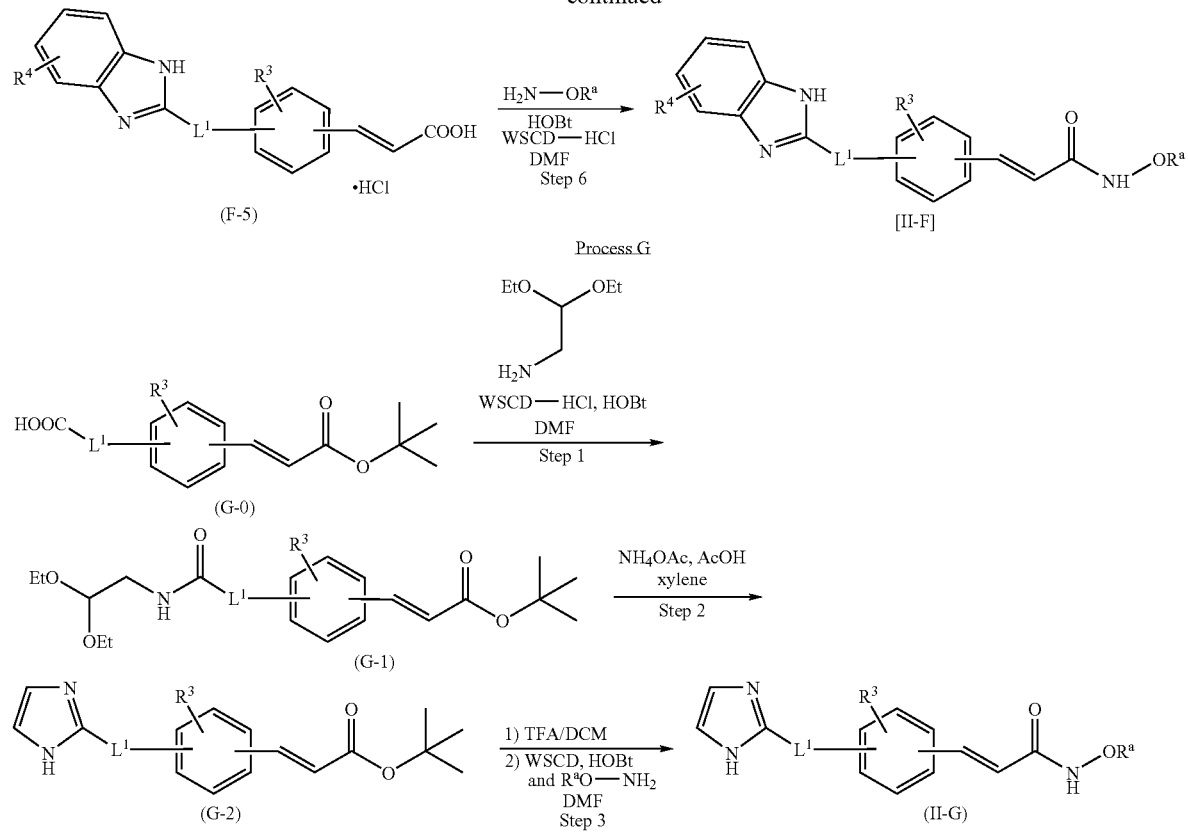
Process G
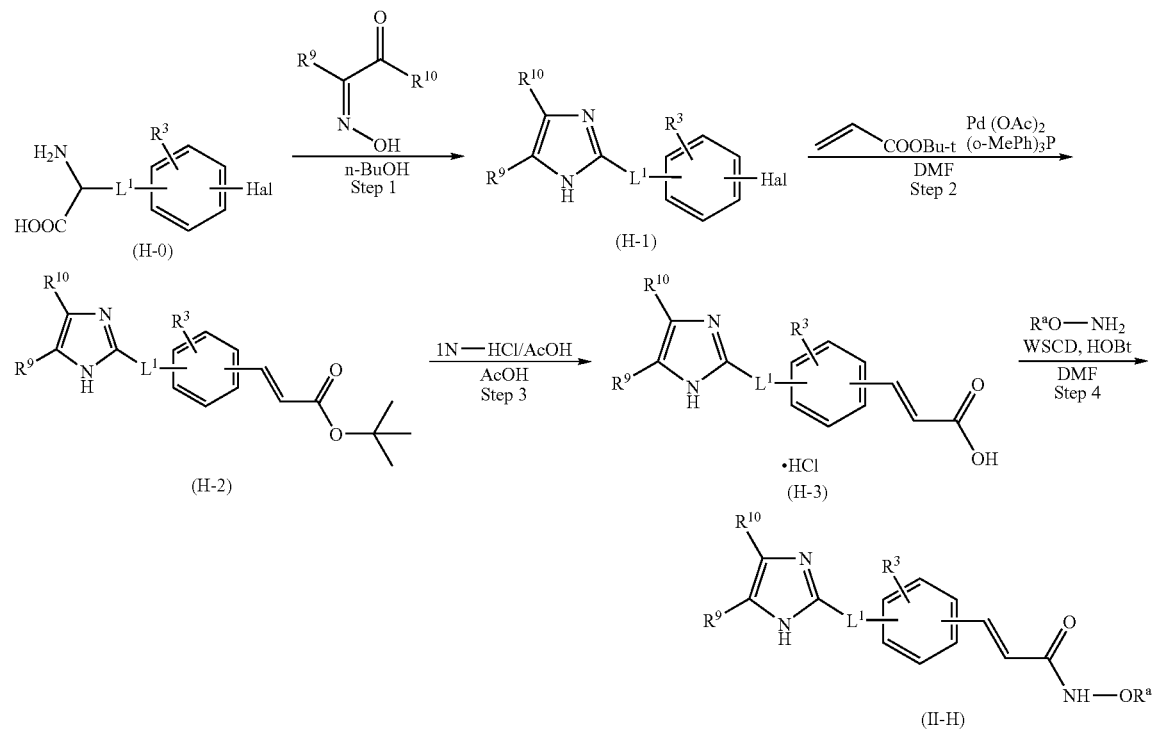
Process H

-continued
Process I
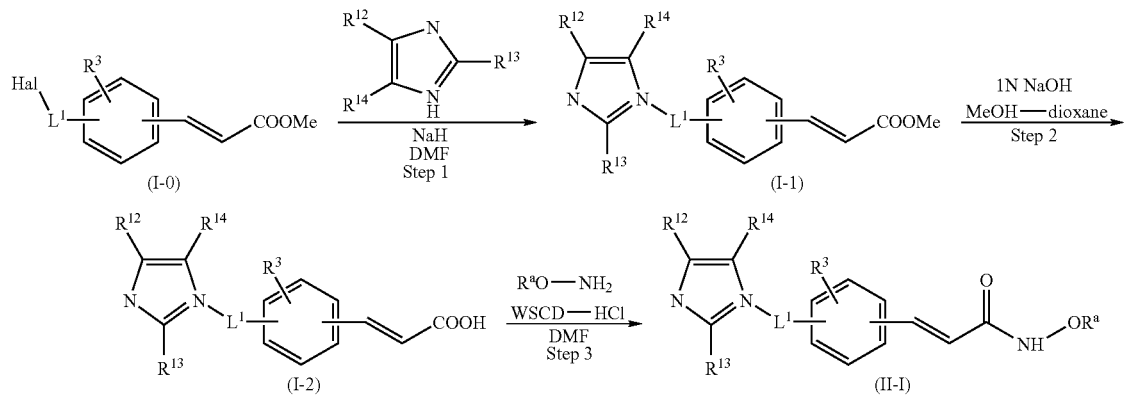
Process J
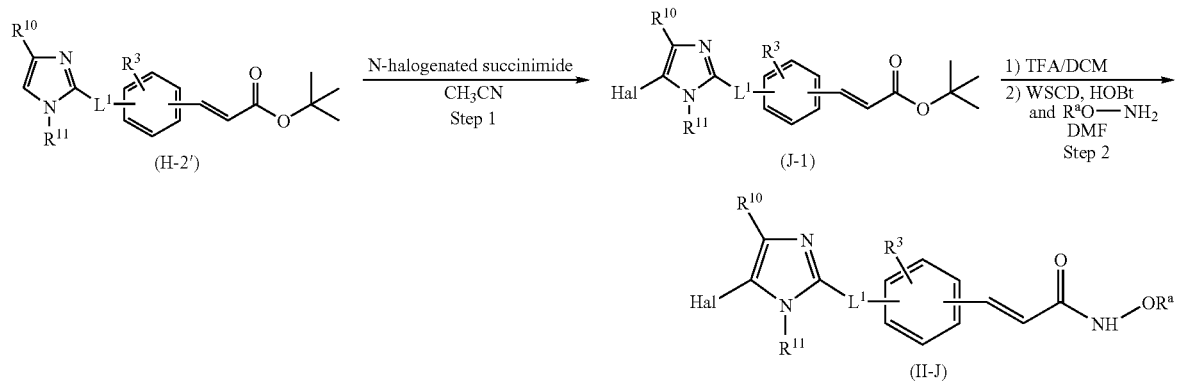
Process K
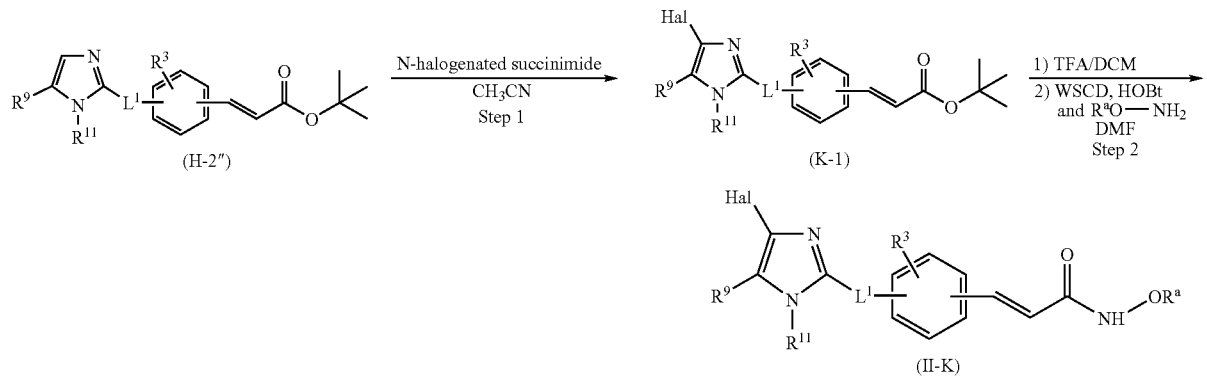
Process L
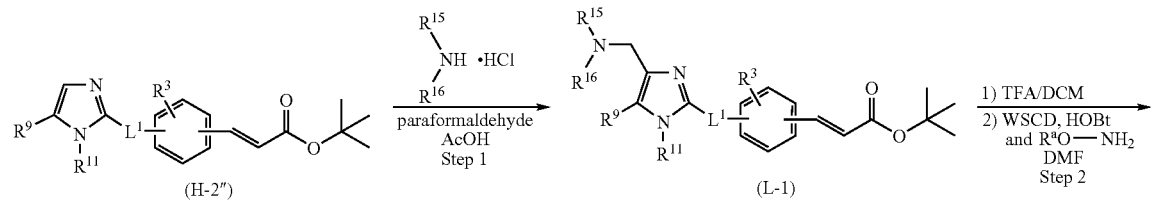

-continued

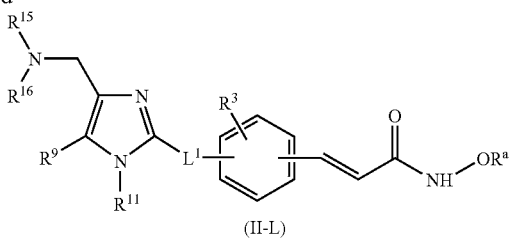

(II-L)

Process M

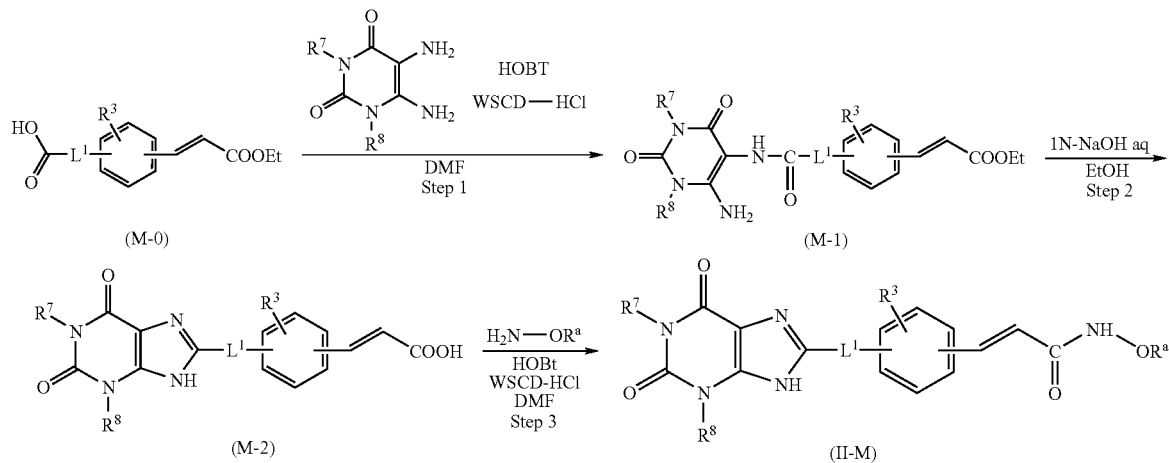

Process N

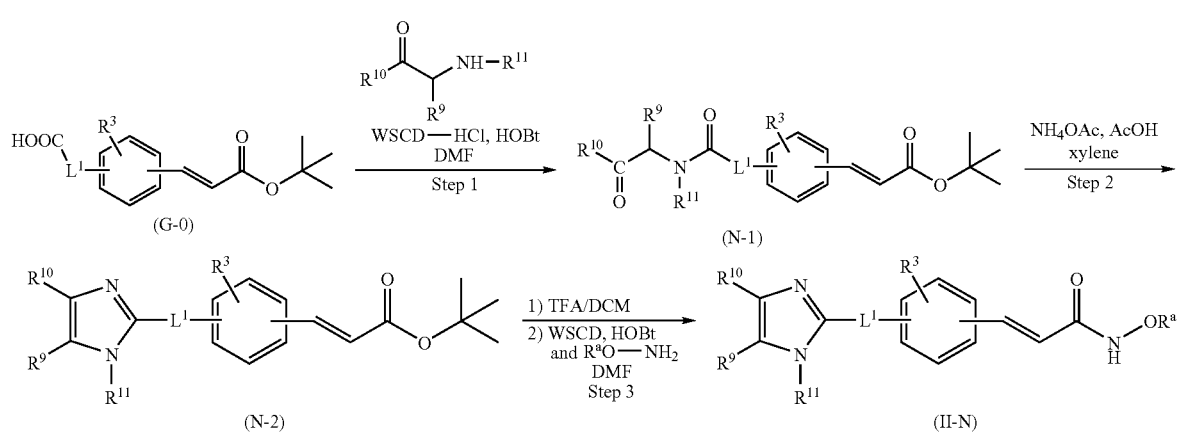

Wherein
R¹, R², R³, R⁴, R⁵, R⁶, R⁷, R⁸, R⁹, R¹⁰, R¹¹, R¹², R¹³, R¹⁴ and L¹ are as defined above.

Hal and Hal' are each halogen,

L¹' is L¹ in which one of the carbon atoms is substituted with R⁵ (wherein R⁵ is as defined above), R¹⁵ and R¹⁶ are each lower alkyl (e.g., alkyl having 1 to 6 carbon atom(s) such as methyl, ethyl, propyl, butyl, tert-butyl, pentyl, hexyl, etc.), or R¹⁵, R¹⁶ and the nitrogen atom to which they are attached may be together to form non-aromatic heterocycle in which one or more carbon(s) of said heterocycle is(are) optionally replaced with one or more heteroatom(s) selected from oxygen, nitrogen and sulfur (e.g., piperidino, morpholino, etc.), and R$^a$ is a hydroxy protecting group.

In the above-mentioned Processes A, B, C, D, E, F, G, H, I, J, K, L, M and N, each of the starting compounds can be prepared, for example, according to the procedures as illustrated in Preparations in the present specification or in a manner similar thereto.

For example, compounds (A-1), (A-2), (A-3) and (A-4) can be obtained by the procedures as illustrated in Preparations 1, 2, 3 and 4 respectively; compounds (B-1), (B-2) and (B-3) can be obtained by the procedures as illustrated in Preparations 6, 7 and 8 respectively; compound (C-1) and (C-1') can be obtained by the procedure as illustrated in Preparation 10; compound (C-2) and (C-3) can be obtained by the procedure as illustrated in Preparations 11 and 12 respectively; compound (C-2') and (C-3') can be obtained by the procedure as illustrated in Preparations 23 and 24 respectively; compound (D-1) and (D-2) can be obtained by the procedure as illustrated in Preparations 20 and 21 respectively; compound (E-1) can be obtained by the procedure as illustrated in Preparation 35; compounds (F-1), (F-2), (F-3), (F-4) and (F-5) can be obtained by the procedures as illustrated in Preparations 127, 128, 129, 130 and 131, respectively; compounds (G-1) and (G-2) can be obtained by the procedures as illustrated in Preparations 195 and 196, respectively; compounds (H-1), (H-2) and (H-3) can be obtained by the procedures as illustrated in Preparations 204, 206 and 201, respectively; compounds (I1) and (I-2) can be obtained by the procedures as illustrated in Preparations 212 and 219, respectively; compound (J-1) can be obtained by the procedure as illustrated in Preparation 226; Compound (K-1) can be obtained by the procedure as illustrated in Preparation 293; Compound (L-1) can be obtained by the procedure as illustrated in Preparation 294; Compounds (M-1) and (M-2) can be obtained by the procedures illustrated in Preparations 101 and 102; and Compounds (N-1) and (N-2) can be obtained by the procedures illustrated in Preparations 233 and 249. The compounds [II-A], [II-B], [II-C], [II-C'], [II-D], [II-E], [II-F], [II-G], [II-H], [II-I], [II-J'], [II-K], [II-L], [II-M] and [II-N] can be obtained, for example, by the procedures as illustrated in Preparations 5, 9, 13, 25, 22, 39, 132, 197, 208, 222, 191, 282, 284, 103 and 189, respectively.

The compound [I] of the present invention is obtained from compound [II], for example, according to the following processes or methods disclosed in the Examples.

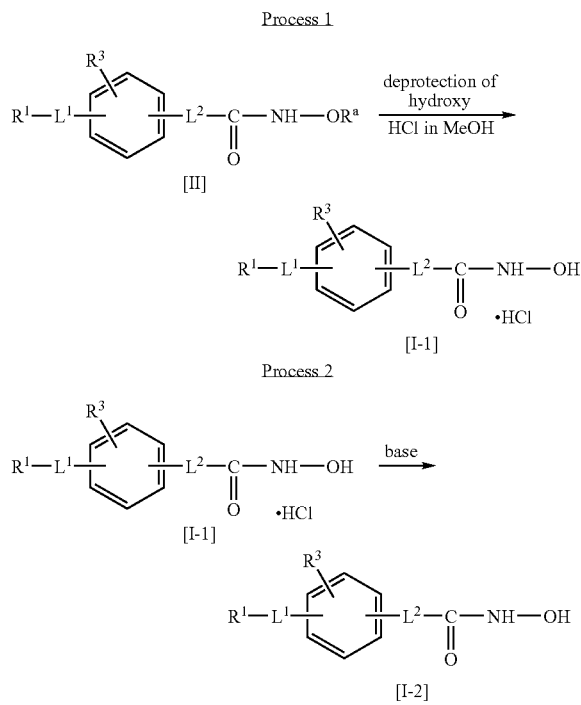

Wherein $R^1$, $R^3$, $L^1$, $L^2$ and $R^a$ are as defined above.

Process 1

The compound [I-1] is obtained as an acid addition salt by deprotecting the hydroxy group of the compound [II] in the presence of an acid.

The acid includes such as hydrogen chloride solution (e.g. hydrogen chloride in solvent such as methanol, dioxane, ethyl acetate, diethyl ether, etc.), acetic acid, p-toluenesulfonic acid, boric acid, etc.

Optionally, one or more suitable solvent(s) for the deprotection is(are) used. Such solvent includes such as methanol, ethanol, ethyl acetate, dioxane, diethyl ether, acetic acid, etc.

The temperature of the reaction is not critical, and the reaction is usually carried out from under cooling to heating.

This Process is exemplified by Examples 1, 58, etc.

Process 2

The compound [I-2] is obtained as a free form by reacting the above-mentioned compound [I-1], which is an acid salt addition salt, with a base.

Suitable base includes such as sodium hydroxide, potassium hydroxide, lithium hydroxide, aqueous sodium hydrogen carbonate solution, aqueous potassium hydrogen carbonate solution, aqueous sodium hydroxide solution, etc.

Optionally, one or more suitable solvent(s) for the deprotection is(are) used for this reaction. Such solvent includes such as methanol, ethanol, ethyl acetate, dioxane, diethyl ether, acetic acid, etc.

The temperature of the reaction is not critical, and the reaction is usually carried out from under cooling to heating.

This Process is exemplified by Examples 116, etc.

Furthermore, the compound [I-2] can be converted to a suitable salt, which is also encompassed in the scope of the present invention, by a conventional method or the methods explained in the present specification (e.g., Examples 113, 118, 119, 120, 123, etc.).

The compound [I] may be a salt, which is also encompassed in the scope of the present invention. For example, when a basic group such as an amino group is present in a molecule, the salt is exemplified by an acid addition salt (e.g. salt with an inorganic acid such as hydrochloric acid, hydrobromic acid, sulfuric acid, etc., salt with an organic acid such as methanesulfonic acid, benzenesulfonic acid, 4-toluenesulfonic acid, camphorsulfonic acid (e.g., [(1S, 4R)-7,7-dimethyl-2-oxobicyclo[2.2.1]hept-1-yl]methanesulfonic acid or an enantiomer thereof, etc.), fumaric acid, maleic acid, mandelic acid, citric acid, salicylic acid, malonic acid, glutaric acid, succinic acid, etc.), etc., and when an acidic group such as carboxyl group is present, the salt is exemplified by a basic salt (e.g. salt with a metal such as lithium, sodium, potassium, calcium, magnesium, aluminium, etc., a salt with amino acid such as lysine, etc.), etc.

In addition, solvates of the compound [I] such as hydrate, ethanolate, etc., are also encompassed in the scope of the present invention.

When the compound [I] has stereoisomers, such isomers are also encompassed in the scope of the present invention.

In the above and subsequent descriptions of the present specification, suitable examples and illustration of the various definitions which the present invention intends to include within the scope thereof are explained in detail as follows.

Each of the terms "halogen", "halo" and "Hal" includes fluorine, chlorine, bromine and iodine.

The term "heteroatom" includes nitrogen atom, oxygen atom and sulfur atom.

The term "lower" used in the description is intended to mean 1 to 6 carbon atom(s) unless otherwise indicated.

Suitable "one or more" includes the number of 1 to 6, preferably 1 to 3.

Suitable "lower alkyl" includes straight or branched alkyl having 1 to 6 carbon atom(s) such as methyl, ethyl, propyl, isopropyl, butyl, isobutyl, sec-butyl, tert-butyl, pentyl, tert-pentyl, neopentyl, hexyl, isohexyl, etc.

Suitable "cyclo(lower)alkyl" includes cycloalkyl having 3 to 6 carbon atoms such as cyclopropyl, cyclobutyl, cyclopentyl, cyclohexyl, etc.

Suitable "lower alkoxy" includes straight or branched alkoxy having 1 to 6 carbon atom(s) such as methoxy, ethoxy, propoxy, isopropoxy, butoxy, isobutoxy, sec-butoxy, tert-butoxy, pentyloxy, tert-pentyloxy, neopentyloxy, hexyloxy, isohexyloxy, etc.

Suitable "lower alkanoyl" includes formyl and alkanoyl in which the alkyl portion is straight or branched alkyl having 1 to 6 carbon atom(s) such as acetyl, ethylcarbonyl, propylcarbonyl, isopropylcarbonyl, butylcarbonyl, isobutylcarbonyl, sec-butylcarbonyl, tert-butylcarbonyl, pentylcarbonyl, tert-pentylcarbonyl, neopentylcarbonyl, hexylcarbonyl, isohexylcarbonyl, etc.

Suitable "lower alkoxy-carbonyl" includes alkoxycarbonyl in which the alkyl portion is straight or branched alkyl having 1 to 6 carbon atom(s) such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, tert-pentyloxycarbonyl, neopentyloxycarbonyl, hexyloxycarbonyl, isohexyloxycarbonyl, etc.

Suitable "halo(lower)alkyl" includes lower alkyl substituted with 1 to 3 halogen atom(s) such as monochloromethyl, dichloromethyl, trichloromethyl, monofluoromethyl, difluoromethyl, trifluoromethyl, monobromomethyl, dibromomethyl, tribromomethyl, monochloroethyl, dichloroethyl, trichloroethyl, monofluoroethyl, difluoroethyl, trifluoroethyl, etc.

Suitable "lower alkenylene" includes straight or branched alkylene having 1 to 6 carbon atom(s) such as vinylene, 1-methylvinylene, 2-methylvinylene, 1-propenylene, 2-propenylene, 2-methyl-1-propenylene, 2-methyl-2-propenylene, 1-butenylene, 2-butenylene, 3-butenylene, 1-pentenylene, 2-pentenylene, 3-pentenylene, 4-pentenylene, 1-hexenylene, 2-hexenylene, 3-hexenylene, 4-hexenylene, 5-hexenylene, etc. Suitable lower alkenylene for $L^2$ is, for example, vinylene, 1-methylvinylene, 2-methylvinylene, etc.

Suitable "aryl" includes $C_6$–$C_{16}$ aryl such as phenyl, naphthyl, anthryl, pyrenyl, phenanthryl, azulenyl, etc.

Suitable "aryloxy" includes $C_6$–$C_{16}$ aryloxy such as phenoxy, naphthyloxy, anthryloxy, pyrenyloxy, phenanthryloxy, azulenyloxy, etc.

Suitable "aryl(lower)alkyl" includes phenyl($C_1$–$C_6$)alkyl such as benzyl, phenethyl, phenylpropyl, phenylbutyl, phenylhexyl, etc., naphthyl($C_1$–$C_6$)alkyl such as naphthylmethyl, naphthylethyl, naphthylpropyl, naphthylbutyl, naphthylpentyl, naphtylhexyl, etc.

Suitable "arylcarbonyl" includes arylcarbonyl in which the aryl portion is $C_6$–$C_{16}$ aryl such as phenylcarbonyl (benzoyl), naphthylcarbonyl, anthrylcarbonyl, pyrenylcarbonyl, phenanthrylcarbonyl, azulenylcarbonyl, etc.

Suitable "aryl(lower)alkoxy" includes phenyl($C_1$–$C_6$) alkoxy such as benzyloxy, phenethyloxy, phenylpropyloxy, phenylbutyloxy, phenylhexyloxy, etc., naphthyl($C_1$–$C_6$) alkyloxy such as naphthylmethyloxy, naphthylethyloxy, naphthylpropyloxy, naphthylbutyloxy, naphthylpentyloxy, naphtylhexyloxy, etc.

Suitable "amino" includes unsubstituted amino, and amino mono- or di-substituted with substituent(s) selected from lower alkyl, lower alkanoyl and cycloalkyl such as N-($C_1$–$C_6$ alkyl)amino (e.g., N-methylamino, N-ethylamino, N-propylamino, N-(n-butyl)amino, N-isobutylamino, N-(t-butyl)amino, etc.), N-($C_1$–$C_6$ alkanoyl)amino (e.g., N-acetylamino, N-ethylcarbonylamino, N-propylcarbonylamino, N-(n-butylcarbonyl)amino, N-isobutylcarbonylamino, N-(t-butylcarbonyl) amino, etc.), N-($C_3$–$C_6$ cycloalkyl)amino. (e.g., N-cyclopropylamino, N-cyclobutylamino, N-cyclopentylamino, N-cyclohexylamino, etc.), N,N-di ($C_1$–$C_6$ alkyl)amino (e.g., N,N-dimethylamino, N,N-diethylamino, N-ethyl-N-methylamino, etc.), etc.

Suitable "carbamoyl optionally mono- or di-substituted with lower alkyl(s)" includes carbamoyl; N-(lower)alkylcarbamoyl in which the alkyl portion is alkyl having 1 to 6 carbon atom(s) such as N-methylcarbamoyl, N-ethylcarbamoyl, N-propylcarbamoyl, N-butylcarbamoyl, N-isobutylcarbamoyl, N-tert-butylcarbamoyl, N-pentylcarbamoyl, N-neopentylcarbamoyl, N-isopentylcarbamoyl, N-hexylcarbamoyl, etc.; N,N-di(lower)alkylcarbamoyl in which the alkyl portions are each alkyl having 1 to 6 carbon atom(s) such as N,N-dimethylcarbamoyl, N,N-diethylcarbamoyl, N,N-dipropylcarbamoyl, N,N-dibutylcarbamoyl, N,N-diisobutylcarbamoyl, N,N-di-tert-butylcarbamoyl, N,N-dipentylcazbamoyl, N,N-dineopentylcarbamoyl, N,N-diisopentylcarbamoyl, N,N-dihexylcarbamoyl, N-ethyl-N-methylcarbamoyl, N-methyl-N-propylcarbamoyl, N-butyl-N-methylcarbamoyl, N-methyl-N-isobutylcarbamoyl, etc.

The "heteroaryl" includes groups having 5 to 14 ring atoms and π electrons shared in a cyclic array and containing 1 to 4 heteroatoms selected from the group consisting of nitrogen, oxygen and sulfur besides carbon atoms. Suitable "heteroaryl" includes such as thienyl, benzothienyl, furyl, benzofuryl, dibenzofuryl, pyrrolyl, imidazolyl, pyrazolyl, pyridyl, pyrazinyl, pyrimidinyl, indolyl, quinolyl, isoquinolyl, quinoxalinyl, tetrazolyl, oxazolyl, thiazolyl, isoxazolyl, etc.

The "heteroaryl" and "(lower)alkyl" of the "heteroaryl (lower)alkyl" are similar to those exemplified for the "heteroaryl" and "(lower)alkyl" respectively. Suitable "heteroaryl(lower)alkyl" includes pyridylmethyl, pyridylethyl, quinolylmethyl, etc.

Each of the two "(lower)alkyl" of the "(lower)alkyl-carbonyl(lower)alkyl" is similar to that exemplified for the "(lower)alkyl". Suitable "(lower)alkyl-carbonyl (lower) alkyl" includes acetylmethyl, ethylcarbonylmethyl, etc.

The "non-aromatic heterocycle" includes group having 5 to 14 ring atoms and containing 1 to 3 heteroatoms selected from the group consisting of nitrogen, oxygen and sulfur besides carbon atoms. Suitable "non-aromatic heterocycle" includes such as pyrrolidinyl, pyrazolidinyl, imidazolidinyl, isoxazolidinyl, isothiazolidinyl, piperidyl (e.g., piperidino etc.), piperazinyl, morpholinyl (e.g., morpholino etc.), thiomorpholinyl (e.g., thiomorpholino etc.), etc.

Suitable "N-containing heterocyclic ring" for the "N-containing heterocyclic ring optionally substituted with one or more substituent(s)" includes N-containing condensed heterocyclic ring such as indolyl, isoindolyl, indolidinyl, benzimidazolyl, quinolyl, isoquinolyl, indazolyl, benzotriazolyl, quinoxalinyl, imidazopyridyl (e.g., imidazo[4,5-c] pyridyl, etc.), tetrahydroimidazopyridyl (e.g., 4,5,6,7-tetrahydro[4,5-c]pyridyl, etc.), 7-azabicyclo[2.2.1]heptyl, 3-azabicyclo[3.2.2]nonanyl, pyridoimidazolyl (e.g. pyrido[3,2-d]imidazolyl, pyrido[4,3-d]imidazolyl, etc.), azabenzimidazolyl, etc., and N-containing heteroaryl ring such as imidazolyl, thiazolyl, pyrazolyl, oxazolyl, etc.

Specifically, the preferred N-containing heterocyclic ring optionally substituted with one or more substituent(s) represented by $R^1$ includes, for example, the groups represented by the following formula

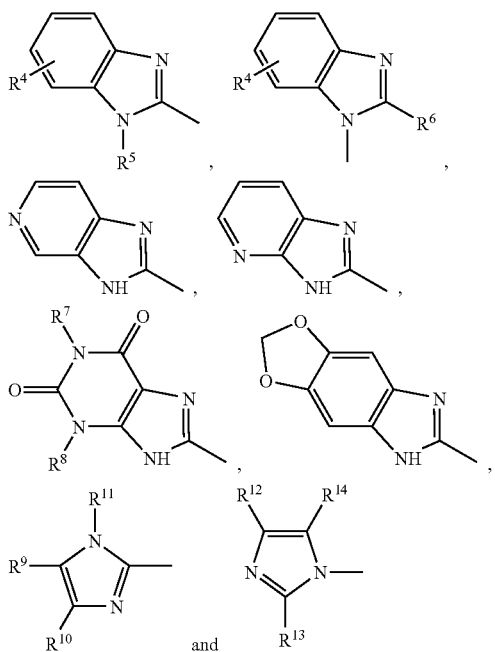

wherein $R^4$, $R^5$, $R^6$, $R^7$, $R^8$, $R^9$, $R^{10}$, $R^{11}$, $R^{12}$, $R^{13}$ and $R^{14}$ are as defined above.

In the above formulas, $R^4$ is hydrogen or a group such as (1) lower alkyl (e.g. methyl, ethyl, propyl, isopropyl, butyl, pentyl, hexyl, etc.); (2) lower alkoxy (e.g. methoxy, ethoxy, propoxy, butoxy, pentyloxy, hexyloxy, etc.); (3) aryl optionally substituted with the substituent selected from the group consisting of halogen, lower alkanoyl, lower alkylsulfonyl, lower alkoxy and di(lower)alkylamino (e.g., phenyl, 4-methoxyphenyl, 4-ethoxyphenyl, 4-acetylphenyl, 4-(N,N-dimethylamino)phenyl, 4-fluorophenyl, 4-methylsulfonylphenyl, etc.); (4) lower alkanoyl (e.g., acetyl, etc.); (5) lower alkoxy-carbonyl (e.g., methoxycarbonyl, etc.); (6) arylcarbonyl (e.g., benzylcarbonyl, etc.); (7) aryl(lower)alkoxy (e.g., benzyloxy, etc.); (8) amino optionally mono- or di-substitited with substituent(s) selected from the group consisting of lower alkyl, lower alkanoyl and cycloalkyl (e.g., amino, N,N-dimethylamino, N,N-diethylamino, N-propylcarbonylamino, N-cyclopentylamino, etc.); (9) halo(lower)alkyl (e.g., trifluoromethyl, etc.); (10) aryloxy (e.g., phenoxy, etc.); (11) aryl(lower)alkyl optionally substituted with hydroxy (e.g., hydroxyphenylmethyl, etc.); (12) carboxyl; (13) nitro; (14) cyano; (15) halogen (e.g., fluorine, chlorine, bromine, etc.); (16) heteroaryl (e.g., thienyl, tetrazolyl, pyridyl, etc.); (17) non-aromatic heterocycle optionally substituted with lower alkyl (e.g., 4-methylpiperadinyl, morpholino, piperidino, etc.); (18) hydroxy, (19) (lower)alkylsulfonylcarbamoyl (e.g., methylsulfonylcarbamoyl, etc.), (20) non-aromatic heterocycle carbonyl (e.g., pyrrolidin-1-ylcarbonyl, etc.). Furthermore, heteroaryl(lower)alkyl (e.g. pyridyl(lower)alkyl such as pyridylmethyl, etc.), lower alkyl-carbonyl(lower)alkyl (e.g. acetylmethyl, etc.), etc. can be also used for $R^4$.

In the above formulas, $R^5$ is hydrogen or a group selected from the group consisting of lower alkyl (e.g. methyl, ethyl, propyl, butyl, etc.), aryl(lower)alkyl(e.g. benzyl, phenetyl, etc.), heteroaryl(lower)alkyl (e.g. pyridyl(lower)alkyl such as pyridylmethyl, etc.) and lower alkyl-carbonyl(lower)alkyl (e.g. acetylmethyl, etc.). Preferably, $R^5$ is hydrogen or a group selected from the group consisting of lower alkyl and aryl(lower)alkyl.

In the above formulas, $R^6$, $R^7$ and $R^8$ are each hydrogen or lower alkyl (e.g. methyl, ethyl, propyl, butyl, etc.) In the above formulas, $R^9$ is hydrogen or a group such as (1) lower alkyl optionally substituted with di(lower)alkylamino (e.g., dimethylaminoethyl, etc.); (2) aryl optionally substituted with lower alkoxy (e.g., phenyl, o-methoxyphenyl, m-methoxyphenyl, p-methoxyphenyl, etc.); (3)(lower)alkoxy-carbonyl (e.g., methoxycarbonyl, etc.); (4) cyano; (5) carbamoyl optionally mono- or di-substituted with (lower)alkyl (e.g., carbamoyl, N,N-dimethylcarbamoyl, N-isopropylcarbamoyl, etc.); (6) halogen (e.g., chloro, bromo, etc.); (7) (lower)alkyl-carbonyl (e.g., acetyl, etc.); (8) arylcarbonyl (e.g., benzoyl, etc.); (9) cyclo(lower)alkyl (e.g., cyclohexyl, etc.), etc.

In the above formulas, suitable substituent represented by $R^{10}$ is hydrogen or a group such as (1) (lower)alkylcarbamoyl (e.g., N-methylcarbamoyl, etc.); (2) di(lower)alkylcarbamoyl (e.g., N,N-dimethylcarbamoyl, etc.); (3) aryl optionally substituted with halogen (e.g., phenyl, p-chlorophenyl, p-fluorophenyl, etc.); (4) (lower)alkoxy-carbonyl (e.g., methoxycarbonyl, ethoxycarbonyl, etc.); (5) carboxy; (6) non-aromatic heterocycle carbonyl (e.g., piperidinylcarbonyl, etc.); (7) halogen (e.g., chloro, etc.); (8) (lower)alkyl optionally substituted with hydroxy or (lower)alkoxy, non-aromatic heterocycle, aryl, di(lower)alkylamino or halogen (e.g., hydroxymethyl, methoxymethyl, piperidinomethyl, morpholinomethyl, N,N-dimethylaminomethyl, trifluoromethyl, etc.); and (9) adamantyl, etc.

In the above formulas, suitable substituent represented by $R^{11}$ is hydrogen or aryl(lower)alkyl in which the aryl portion is substituted with lower alkoxy (e.g., p-methoxyphenylmethyl, etc.), etc.

In the above formulas, suitable substituent represented by $R^{12}$ is hydrogen or a group selected from lower alkyl (e.g., methyl, etc.), aryl optionally substituted with halogen (e.g., phenyl, p-chlorophenyl, etc.), etc.

In the above-formulas, suitable substituent represented by $R^{13}$ is hydrogen or a group selected from lower alkyl (e.g., methyl, etc.), aryl (e.g., phenyl, etc.), etc.

In the above formulas, suitable substituent represented by $R^{14}$ is hydrogen or lower alkyl (e.g., methyl, etc.), etc.

Suitable "n" of the "—$(CH_2)_n$—" for $L^1$ is an integer of 0 to 6, preferably 1 or 2. The "—$(CH_2)_n$—" is optionally substituted with one or more suitable substituent(s) such as lower alkyl (e.g. methyl, ethyl, propyl, butyl, pentyl, hexyl, etc.), lower alkoxy (e.g. methoxy, ethoxy, propoxy, butoxy, pentyloxy, hexyloxy, etc.), aryl(lower)alkyl (e.g. benzyl, etc.), etc. Furthermore, one or more methylenes (e.g., one methylene, etc.) may be replaced with suitable heteroatoms (e.g., oxygen atom, etc.).

Suitable "—$(CH_2)_n$—" for $L^1$ of the present invention includes, for example, —$CH_2$—, —$(CH_2)_2$—, —$CH(CH_3)$—, —$CH_2$—O—, —$(CH_2)_3$—, —$(CH_2)_3$—O—, —$(CH_2)_4$—O—,

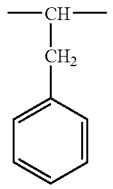

etc.

Suitable "hydroxy protecting group" is as follows:

lower alkyl (e.g., methyl, ethyl, propyl, isopropyl, butyl, isobutyl, t-butyl, pentyl, hexyl, etc.), preferably methyl;

lower alkoxy(lower)alkyl (e.g. methoxymethyl, etc.);

lower alkoxy(lower)alkoxy(lower)alkyl (e.g. 2-methoxyethoxymethyl, etc.);

ar(lower)alkyl in which the aryl portion is optionally substituted with one or more suitable substituent(s) (e.g. benzyl (Bn), p-methoxybenzyl, m,p-dimethoxybenzyl, etc.), preferably benzyl;

ar(lower)alkoxy(lower)alkyl in which the aryl portion is optionally substituted with one or more suitable substituent(s) (e.g. benzyloxymethyl, p-methoxybenzyloxymethyl, etc.);

(lower)alkylthio(lower)alkyl (e.g. methylthiomethyl, ethylthiomethyl, propylthiomethyl, isopropylthiomethyl, butylthiomethyl, isobutylthiomethyl, hexylthiomethyl, etc.), etc., preferably methylthiomethyl;

trisubstituted silyl such as tri(lower)alkylsilyl (e.g. trimethylsilyl, triethylsilyl, tributylsilyl, tert-butyldimethylsilyl, tri-tert-butylsilyl, etc.), lower alkyldiarylsilyl (e.g. methyldiphenylsilyl, ethyldiphenylsilyl, propyldiphenylsilyl, tert-butyldiphenylsilyl (TBDPS), etc.), etc., preferably tert-butyldimethylsilyl (TBDMS) and tert-butyldiphenylsilyl;

heterocyclic group (e.g. tetrahydropyranyl, etc.);

acyl as described below [e.g. aliphatic acyl such as lower alkanoyl (e.g. acetyl, propanoyl, pivaloyl, etc.); aromatic acyl (e.g. benzoyl (Bz), toluoyl, naphthoyl, fluorenylcarbonyl, etc.);

lower alkoxy-carbonyl (e.g. methoxycarbonyl, ethoxycarbonyl, propoxycarbonyl, isopropoxycarbonyl, butoxycarbonyl, isobutoxycarbonyl, t-butoxycarbonyl, pentyloxycarbonyl, hexyloxycarbonyl, etc.), etc.;

ar(lower)alkoxycarbonyl in which the aryl portion is optionally substituted with one or more suitable substituent(s) (e.g. benzyloxycarbonyl, bromobenzyloxycarbonyl, etc.);

lower alkylsulfonyl (e.g. methylsulfonyl, ethylsulfonyl, etc.);

lower alkoxysulfonyl (e.g. methoxysulfonyl, ethoxysulfonyl, etc.);

ar(lower)alkanoyl (e.g. phenylacetyl, phenylpropanoyl, phenylbutanoyl, phenylisobutanoyl, phenylpentanoyl, phenylhexanoyl, naphthylacetyl, naphthylpropanoyl, naphthylbutanoyl, naphthylisobutanoyl, naphthylpentanoyl, naphthylhexanoyl, etc.);

ar(lower)alkenoyl such as ar($C_3$–$C_6$)alkenoyl (e.g. phenylpropenoyl, phenylbutenoyl, phenylmethacryloyl, phenylpentenoyl, phenylhexenoyl, naphthylpropenoyl, naphthylbutenoyl, naphthylmethacryloyl, naphthylpentenoyl, naphthylhexenoyl, etc.), etc.];

lower alkenyl (e.g. vinyl, allyl, etc.); etc.

The preferable hydroxy protecting group for the present invention is, for example, tetrahydropyranyl, trimethylsilyl, t-butyldimethylsilyl, etc.

The following abbreviations are also used in the present-specification: Boc (t-butyloxycarbonyl); HOBT or HOBt (1-hydroxybenzotriazole); WSCD (1-ethyl-3-(3'-dimethylaminopropyl)-carbodiimide); DMF (N,N-dimethylformamide); aq. (aqueous solution); Me (methyl); MeOH (methanol); Et (ethyl); EtOH (ethanol); tBu (t-butyl); TsCl (p-toluenesulfonyl chloride); Ac (acetyl); AcOH (acetic acid); AcOEt (ethyl acetate); $AcONH_4$ (ammonium acetate); Ph (phenyl); DIEA (diisopropylethylamine); THP (tetrahydropyranyl); THF (tetrahydrofuran) and TFA or TFAOH (trifluoroacetic acid).

Test Method

In order to show the usefulness of the compound [I] of the invention, the pharmacological test result of the representative compound of the present invention is shown in the following.

Test 1: Determination of Histone Deacetylase Inhibitor Activity

The partial purification of human histone deacetylase, the preparation of [$^3$H] acetyl histones, and the assay for histone deacetylase activity were performed basically according to the method as proposed by Yoshida et al. as follows.

Partial Purification of Human Histone Deacetylase

The human histone deacetylase was partially purified from human T cell leukemia Jurkat cells. Jurkat cells ($5 \times 10^8$ cells) were suspended in 40 mL of the HDA buffer consisting of 15 mM potassium phosphate, pH 7.5, 5% glycerol and 0.2 mM EDTA. After homogenization, nuclei were collected by centrifugation (35,000×g, 10 min) and homogenized in 20 mL of the same buffer supplemented with 1 M $(NH_4)_2SO_4$. The viscous homogenate was sonicated and clarified by centrifugation (35,000×g, 10 min), and the deacetylase was precipitated by raising the concentration of $(NH_4)_2SO_4$ to 3.5 M. The precipitated protein was dissolved in 10 mL of the HDA buffer and dialyzed against 4 liters of the same buffer. The dialyzate was then loaded onto a DEAE-cellulose (Whatman DE52) column (25×85 mm) equilibrated with the same buffer and eluted with 300 mL of a linear gradient (0–0.6 M) of NaCl. A single peak of histone deacetylase activity appeared between 0.3 and 0.4 M NaCl.

Preparation of [$^3$H] Acetyl Histone

To obtain [$^3$H] acetyl-labeled histone as the substrate for the histone deacetylase assay, $1 \times 10^8$ cells of Jurkat in 20 mL of RPMI-1640 medium (supplemented with 10% FBS, penicillin (50 units/mL) and streptomycin (50 μg/mL)) were incubated with 300 MBq [$^3$H] sodium acetate in the presence of 5 mM sodium butyrate for 30 minutes in 5% $CO_2$-95% air atmosphere at 37° C. in a 75 $cm^2$ flask, harvested into a centrifuge tube (50 mL), collected by centrifugation at 1000 rpm for 10 minutes, and washed once with phosphate-buffered saline. The washed cells were suspended in 15 mL of ice-cold lysis buffer (10 mM Tris-HCl, 50 mM sodium bisulfite, 1% Triton X-100, 10 mM $MgCl_2$, 8.6% sucrose, pH 6.5). After Dounce homogenization (30 stroke), the nuclei were collected by centrifugation at 1000 rpm for 10 minutes, washed 3 times with 15 mL of the lysis buffer, and once with 15 mL of ice-cooled washing buffer (10 mM Tris-HCl, 13 mM EDTA, pH 7.4) successively. The pellet was suspended in 6 mL of ice-cooled water using a mixer, and 68 µl of $H_2SO_4$ was added to the suspension to give a concentration of 0.4 N. After incubation at 4° C. for 1 hour, the suspension was centrifuged for 5 minutes at 15,000 rpm, and the supernatant was taken and mixed with 60 mL of acetone. After overnight incubation at −20° C., the coagulated material was collected by microcentrifugation, air-dried, and stored at −80° C.

Assay for Histone Deacetylase Activity

For the standard assay, 10 µl of [$^3$H] acetyl-labeled histones were added to 90 µl of the enzyme fraction, and the mixture was incubated at 25° C. for 30 minutes. The reaction was stopped by addition of 10 µl of HCl. The released [$^3$H] acetic acid was extracted with 1 mL of ethyl acetate, and 0.9 mL of the solvent layer was taken into 10 mL of toluene scintillation solution for determination of radioactivity.

Test 2: Determination of T-Cell Growth Inhibitor Activity

The T lymphocyte blastogenesis test was performed in microtiter plates with each well containing $1.5 \times 10^5$ splenic cells of Lewis rats in 0.1 mL RPMI-1640 medium supplemented with 10% fetal bovine serum-(FBS), 50 mM 2-mercaptoethanol, penicilln (100 units/mL) and streptomycin (100 µg/mL), to which Concanavalin A (1 µl/mL) was added. The cells were incubated at 37° C. in a humidified atmosphere of 5% $CO_2$ for 72 hours. After the culture period, suppressive activities of the test compounds in T lymphocyte blastogenesis were quantified by AlamarBlue (trademark) Assay. The test samples were dissolved in DMSO and further diluted with RPMI-1640 medium and added to the culture. The activities of the test compounds were expressed as $IC_{50}$.

The results of those tests are shown in the Table 1.

TABLE 1

HDAC inhibitory activity and T-cell growth inhibitory activity of the compound of the present invention

| Examples | Test 1: HDAC inhibitory activity $IC_{50}$ (nM) | Test 2: T-cell growth inhibitory activity $IC_{50}$ (nM) |
| --- | --- | --- |
| Compound E1 | 28 | 69 |
| Compound E3 | 140 | 160 |
| Compound E5 | 96 | 310 |
| Compound E6 | 150 | 150 |

The pharmaceutical composition of the present invention comprising histone deacetylase inhibitor such as the compound [I] is useful as a therapeutic or prophylactic agent for diseases caused by abnormal gene expression, such as inflammatory disorders, diabetes, diabetic complications, homozygous thalassemia, fibrosis, cirrhosis, acute promyelocytic leukaemia (APL), protozoal infection, etc. Furthermore, it is useful as an antitumor agent or immunosuppressant, which prevents an organ transplant rejection and autoimmune diseases as exemplified below:

rejection reactions by transplantation of organs or tissues such as the heart, kidney, liver, bone marrow, skin, cornea, lung, pancreas, small intestine, limb, muscle, nerve, intervertebral disc, trachea, myoblast, cartilage, etc.;

graft-versus-host reactions following bone marrow transplantation;

autoimmune diseases such as rheumatoid arthritis, systemic lupus erythematosus, Hashimoto's thyroiditis, multiple sclerosis, myasthenia gravis, type I diabetes, etc.; and infections caused by pathogenic microorganisms (e.g. *Aspergillus fumigatus, Fusarium oxysporum, Trichophyton asteroides*, etc.).

Furthermore, pharmaceutical preparations of the histone deacetylase inhibitor, such as the compound [I], are useful for the therapy or prophylaxis of the following diseases.

Inflammatory or hyperproliferative skin diseases or cutaneous manifestations of immunologically-mediated diseases (e.g. psoriasis, atopic dermatitis, contact dermatitis, eczematoid dermatitis, seborrheic dermatitis, lichen planus, pemphigus, bullous pemphigoid, epidermolysis bullosa, urticaria, angioedema, vasculitides, erythema, dermal eosinophilia, lupus erythematosus, acne, alopecia greata, etc.);

autoimmune diseases of the eye (e.g. keratoconjunctivitis, vernal conjunctivitis, uveitis associated with Behcet's disease, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, etc.);

reversible obstructive airways diseases [asthma (e.g. bronchial asthma, allergic asthma, intrinsic asthma, extrinsic asthma, dust asthma, etc.), particularly chronic or inveterate asthma (e.g. late asthma, airway hyper-responsiveness, etc.), bronchitis, etc.];

mucosal or vascular inflammations (e.g. gastric ulcer, ischemic or thrombotic vascular injury, ischemic bowel diseases, enteritis, necrotizing enterocolitis, intestinal damages associated with thermal burns, leukotriene B4-mediated diseases, etc.);

intestinal inflammations/allergies (e.g. coeliac diseases, proctitis, eosinophilic gastroenteritis, mastocytosis, Crohn's disease, ulcerative colitis, etc.);

food-related allergic diseases with symptomatic manifestation remote from the gastrointestinal tract (e.g. migrain, rhinitis, eczema, etc.);

renal diseases (e.g. intestitial nephritis, Goodpasture's syndrome, hemolytic uremic syndrome, diabetic nephropathy, etc.);

nervous diseases (e.g. multiple myositis, Guillain-Barre syndrome, Meniere's disease, multiple neuritis, solitary neuritis, cerebral infarction, Alzheimer's disease, Parkinson's disease, amyotrophic lateral sclerosis (ALS), radiculopathy, etc.);

cerebral ischemic diseases (e.g., head injury, hemorrhage in brain (e.g., subarachnoid hemorrhage, intracerebral hemorrhage, etc.), cerebral thrombosis, cerebral embolism, cardiac arrest, stroke, transient ischemic attack (TIA), hypertensive encephalopathy, etc.);

endocrine diseases (e.g. hyperthyroidism, Basedow's disease, etc.);

hematic diseases (e.g. pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, etc.);

bone diseases (e.g. osteoporosis, etc.);

respiratory diseases (e.g. sarcoidosis, pulmonary fibrosis, idiopathic interstitial pneumonia, etc.);

skin diseases (e.g. dermatomyositis, leukoderma vulgaris, ichthyosis vulgaris, photosensitivity, cutaneous T-cell lymphoma, etc.);

circulatory diseases (e.g. arteriosclerosis, atherosclerosis, aortitis syndrome, polyarteritis nodosa, myocardosis, etc.);

collagen diseases (e.g. scleroderma, Wegener's granuloma, Sjögren's syndrome, etc.);
adiposis;
eosinophilic fasciitis;
periodontal diseases (e.g. damage to gingiva, periodontium, alveolar bone or substantia ossea dentis, etc.);
nephrotic syndrome (e.g. glomerulonephritis, etc.);
male pattern alopecia, alopecia senile;
muscular dystrophy;
pyoderma and Sezary syndrome;
chromosome abnormality-associated diseases (e.g. Down's syndrome, etc.);
Addison's disease;
active oxygen-mediated diseases {e.g. organ injury [e.g. ischemic circulation disorders of organs (e.g. heart, liver, kidney, digestive tract, etc.) associated with preservation, transplantation, ischemic diseases (e.g. thrombosis, cardial infarction, etc.), etc.];
intestinal diseases (e.g. endotoxin shock, pseudomembranous colitis, drug- or radiation-induced colitis, etc.);
renal diseases (e.g. ischemic acute renal insufficiency, chronic renal failure, etc.);
pulmonary diseases (e.g. toxicosis caused by pulmonary oxygen or drugs (e.g. paracort, bleomycin, etc.), lung cancer, pulmonary emphysema, etc.);
ocular diseases (e.g. cataracta, iron-storage disease (siderosis bulbi), retinitis, pigmentosa, senile plaques, vitreous scarring, corneal alkali burn, etc.);
dermatitis (e.g. erythema multiforme, linear immunoglobulin A bullous dermatitis, cement dermatitis, etc.); and
other diseases (e.g. gingivitis, periodontitis, sepsis, pancreatitis, diseases caused by environmental pollution (e.g. air pollution, etc.), aging, carcinogen, metastasis of carcinoma, hypobaropathy, etc.)};
diseases caused by histamine release or leukotriene C4 release;
restenosis of coronary artery following angioplasty and prevention of postsurgical adhesions;
autoimmune diseases and inflammatory conditions (e.g., primary mucosal edema, autoimmune atrophic gastritis, premature menopause, male sterility, juvenile diabetes mellitus, pemphigus vulgaris, pemphigoid, sympathetic ophthalmitis, lens-induced uveitis, idiopathic leukopenia, active chronic hepatitis, idiopathic cirrhosis, discoid lupus erythematosus, autoimmune orchitis, arthritis (e.g. arthritis deformans, etc.), polychondritis, etc.);
Human Immunodeficiency Virus (HIV) infection, AIDS;
allergic conjunctivitis;
hypertrophic cicatrix, keloid due to trauma, burn or surgery, etc.

Therefore, the pharmaceutical composition of the present invention is useful for the therapy and prophylaxis of liver diseases [e.g. immunogenic diseases (e.g. chronic autoimmune liver diseases such as autoimmune hepatic diseases, primary biliary cirrhosis, sclerosing cholangitis, etc.), partial liver resection, acute liver necrosis (e.g. necrosis caused by toxins, viral hepatitis, shock, anoxia, etc.), hepatitis B, non-A non-B hepatitis, hepatocirrhosis, hepatic failure (e.g. fulminant hepatitis, late-onset hepatitis, "acute-on-chronic" liver failure (acute liver failure on chronic liver diseases, etc.), etc.), etc.].

The pharmaceutical composition of the present invention can be used in the form of pharmaceutical preparation, for example, in a solid, semisolid or liquid form, which contains the histone deacetylase inhibitor, such as the compound [I], as an active ingredient in admixture with an organic or inorganic carrier or excipient suitable for external, enteral or parenteral administrations. The active ingredient may be compounded, for example, with the usual non-toxic, pharmaceutically acceptable carriers for tablets, pellets, capsules, suppositories, solutions, emulsions, suspensions, injections, ointments, liniments, eye drops, lotion, gel, cream, and any other form suitable for use.

The carriers those can be used for the present invention include water, glucose, lactose, gum acacia, gelatin, mannitol, starch paste, magnesium trisilicate, talc, corn starch, keratin, colloidal silica, potato starch, urea and other carriers suitable for use in manufacturing preparations in a solid, semisolid, or liquid form. Furthermore, auxiliary, stabilizing, thickening, solubilizing and coloring agents and perfumes may be used.

For applying the composition to human, it is preferable to apply it by intravenous, intramuscular, topical or oral administration, or by a vascular stent impregnated with the compound [I]. While the dosage of therapeutically effective amount of the histone deacetylase inhibitor, such as the compound [I], varies from and also depends upon the age and condition of each individual patient to be treated, when an individual patient is to be treated, in the case of intravenous administration, a daily dose of 0.01–10 mg of the histone deacetylase inhibitor, such as the compound [I], per kg weight of human being, in the case of intramuscular administration, a daily dose of 0.1–10 mg of the histone deacetylase inhibitor, such as the compound of the formula [I], per kg weight of human being, and in the case of oral administration, a daily dose of 0.5–50 mg of the histone deacetylase inhibitor, such as the compound [I], per kg weight of human being, is generally given for treatment.

During the preparation of the above-mentioned pharmaceutical administration forms, the compound [I] or a salt thereof can also be combined together with other immunosuppressive substances, for example repamycin, mycophenolic acid, cyclosporin A, tacrolimus or brequinar sodium.

Hereinafter the reactions in each Preparations and Examples for preparing the compound [I] of the present invention are explained in more detail. The invention should not be restricted by the following Preparations and Examples in any way.

Preparation 1

To a solution of 4-iodophenylacetic acid (1346 mg) in N,N-dimethylformamide (15 mL) was added tert-butyl 2-aminophenylcarbamate (1.07 g), 1-hydroxybenzotriazole (HOBT) (764 mg), 1-ethyl-3-(3'-dimethylaminopropyl)carbodiimide hydrochloride (1.08 g), and the mixture was stirred at ambient temperature for 3 hours. The mixture was poured into water and extracted with ethyl acetate. The organic phase was sequentially washed with saturated aqueous ammonium chloride solution, saturated aqueous sodium hydrogen carbonate solution and brine. The organic phase was dried over magnesium sulfate and evaporated in vacuo. The residue was purified by silica gel chromatography eluting with a mixture of hexane and ethyl acetate (4:1 to 2:1) to give Compound (1) as a pale yellow amorphous (2.03 g).

$^1$H-NMR (300 MHz, DMSO-d$_6$, δ): 1.50 (3×3H, s), 3.66 (2H, s), 6.62 (1H, brs), 7.07–7.20 (4H, m), 7.33 (1H, m), 7.47 (1H, m), 7.69 (2×1H, d, J=8.3 Hz), 8.00 (1H, brs); MASS (ES+): m/e 453.

Preparation 2

To a stirred solution of Compound (1) (25.6 g) in ethanol (300 mL) was added concentrated hydrochloric acid (30 mL), and the mixture was refluxed for 1 hour. The solvent was evaporated in vacuo azeotropically with toluene. The residual solid was collected with the mixture of ethanol and ethyl acetate (1:10) to give Compound (2) as an orange solid (20.0 g).

$^1$H-NMR (300 MHz, CDCl$_3$, δ): 4.52 (2H, s), 7.30 (2×1H, d, J=8.3 Hz), 7.49–7.57 (2H, m), 7.73–7.82 (4H, m); MASS (ES+): m/e 335.

Preparation 3

To a stirred solution of Compound (2) (114 mg) in dioxane (3 mL) and 1N-sodium hydroxide (0.8 mL) was added p-toluenesulfonyl chloride (70 mg) at 0° C. The mixture was allowed to warm to ambient temperature and stirred for 30 minutes. Additional p-toluenesulfonyl chloride (70 mg) was added, then 1N-sodium hydroxide (0.5 mL) was added so that the final pH was 9. The mixture was stirred at ambient temperature for 2 hours. The solvent was evaporated in vacuo and the resulting solution was extracted with ethyl acetate. The organic phase was washed with brine, dried over magnesium sulfate and evaporated in vacuo. The residue was purified by preparative thin layer chromatography (hexane:ethyl acetate=2:1) to give Compound (3) as a pale yellow amorphous (130 mg).

$^1$H-NMR (300 MHz, DMSO-d$_6$, δ): 2.35 (3H, s), 4.56 (2H, s), 7.05 (2×1H, d, J=8.5 Hz), 7.32–7.44 (4H, m), 7.63–7.70 (3H, m), 7.78 (2×1H, d, J=8.5 Hz), 7.94 (1H, d, J=6.5 Hz); MASS (ES+): m/e 489.

Preparation 4

To a stirred solution of Compound (3) (1,137 mg) in N,N-dimethylformamide (15 mL) was added acrylic acid (0.8 mL), palladium(II) acetate (26 mg), tris(2-methylphenyl)phosphine (142 mg) and N,N-diisopropylethylamine (1.25 ml). The mixture was stirred at 120° C. for 90 minutes. The resulting mixture was allowed to cool to ambient temperature, poured into water and extracted with ethyl acetate. The organic phase was washed with brine, dried over sodium sulfate and concentrated in vacuo. The residue was purified by silica column chromatography eluting with a mixture of chloroform and methanol (20:1) to give Compound (4) as a pale yellow amorphous (455 mg).

$^1$H-NMR (300 MHz, DMSO-d$_6$, δ): 2.32 (3H, s), 4.63 (2H, s), 6.51 (1H, d, J=16 Hz), 7.26–7.44 (6H, m), 7.54–7.69 (4H, m), 7.79 (2×1H, d, J=8.4 Hz), 7.94 (1H, m); MASS (ES+): m/e 433.

Preparation 5

To a stirred solution of Compound (4) (70 mg) in N,N-dimethylformamide (3 mL) was added 1-hydroxybenzotriazole (HOBT) (26 mg), 1-ethyl-3-(3'-dimethylaminopropyl) carbodiimide hydrochloride (37 mg) and O-(tetrahydro-2H-pyran-2-yl)hydroxylamine (23 mg), and the resulting mixture was stirred at ambient temperature for 14 hours. To the reaction mixture were added additional 1-hydroxybenzotriazole (13 mg), 1-ethyl-3-(3'-dimethylaminopropyl)carbodiimide hydrochloride (19 mg) and O-(tetrahydro-2H-pyran-2-yl)hydroxylamine (12 mg), and the mixture was stirred for 6 hours. The reaction mixture were diluted with ethyl acetate and washed succesively with water, saturated ammonium chloride solution, saturated sodium hydrogen carbonate solution and brine. The organic phase was dried over magnesium sulfate and concentrated in vacuo. The residue was purified by preparative thin layer chromatography (chloroform:methanol=10:1) to give Compound (5) as a white amorphous (503 mg). The Compound (5) was used in Example 1.

$^1$H-NMR (300 MHz, DMSO-d$_6$, δ): 1.44–1.76 (6H, m), 3.52 (1H, m), 3.95 (1H, m), 4.19 (1H, m), 4.90 (1H, m), 6.47 (1H, d, J=15.8 Hz), 7.09–7.19 (2H, m), 7.34–7.58 (7H, m), 11.23 (1H, s), 12.30 (1H, s); MASS (ES+): m/e 378.

Preparation 6

To a stirred solution of (4-bromophenyl)acetic acid (80.0 g, 372 mmol) in N,N-dimethylformamide (640 mL) was added acrylic acid t-butyl ester (95.4 g), palladium(II) acetate (1.67 g), triphenylphosphine (3.91 g) and N,N-diisopropylethylamine (162 mL). The mixture was stirred at 100° C. for 7 hours. The resulting mixture was allowed to cool to ambient temperature, poured into 1N-hydrochloric acid and extracted with ethyl acetate twice. The combined organic phase was extracted with saturated sodium hydrogen carbonate solution three times. The combined aqueous phase was acidified with concentrated hydrogen chloride to pH 2 and extracted with ethyl acetate. The organic phase was washed with brine, dried over magnesium sulfate and concentrated in vacuo to give Compound (6) as a pale yellow solid (78.1 g).

$^1$H-NMR (300 MHz, CDCl$_3$, δ): 1.53 (9H, s), 3.67 (2H, s), 6.35 (1H, d, J=16 Hz), 7.29 (2H, d, J=8 Hz), 7.47 (2H, d, J=8 Hz), 7.56 (1H, d, J=16 Hz).

Preparation 7

To a solution of Compound (6) (77.7 g), tert-butyl 2-aminophenylcarbamate (61.7 g) and 1-hydroxybenzotriazole (HOBT) (44.0 g) in N,N-dimethylformamide (777 mL) was added 1-(3-dimethylaminopropyl)-3-ethylcarbodiimide hydrochloride (62.5 g) at 4° C. The mixture was warmed to ambient temperature and stirred for 2 hours. The reaction mixture was added saturated aqueous sodium hydrogencarbonate (777 mL) and water (3.1 L), and extracted with ethyl acetate (1.5 L). The organic layer was washed with 5% aqueous potassium hydrogen sulfate (500 mL), saturated aqueous sodium hydrogencarbonate (500 mL) and brine (500 mL), dried over magnesium sulfate, filtered and evaporated in vacuo to give Compound (7) (135 g).

$^1$H-NMR (300 MHz, CDCl$_3$, δ): 1.49 (9H, s), 1.54 (9H, s), 3.74 (2H, s), 6.36 (1H, d, J=16 Hz), 6.66 (1H, brs), 7.10–7.20 (2H, m), 7.33–7.40 (3H, m), 7.44–7.54 (3H, m), 7.57 (1H, d, J=16 Hz), 7.98 (1H, brs).

Preparation 8

A solution of Compound (7) (47.6 g) in 1N-hydrogen chloride in acetic acid (60 mL) was heated at 120° C. for 1 hour. The resulting mixture was allowed to cool to ambient temperature and diluted with ethyl acetate. The resulted precipitate was filtered and the residue was washed with ethyl acetate to give Compound (8) (28.9 g).

$^1$H-NMR (300 MHz, DMSO-d$_6$, δ): 4.56 (2H, s), 6.56 (1H, d, J=16 Hz) 7.48–7.55 (4H, m), 7.59 (1H, d, J=16 Hz), 7.72–7.80 (4H, m).

Preparation 9

To a solution of Compound (8) (50.0 g), O-tetrahydro-2H-pyran-2-ylhydroxylamine (29.8 g) and 1-hydroxybenzotriazole (34.3 g) in N,N-dimethylformamide (795 mL) was added 1-(3-dimethylaminopropyl)-3-ethylcarbodiimide (39.5 g) at 9° C. The mixture was warmed to ambient temperature and stirred for 2 hours. The reaction mixture was added saturated aqueous sodium hydrogencarbonate (795 mL) and water (3.2 L). The resulting precipitate was collected by filtration, and washed with saturated aqueous sodium hydrogencarbonate (250×2 mL) and water (250×2 mL) to give Compound (9) (57.2 g).

$^1$H-NMR (300 MHz, DMSO-d$_6$, δ): 1.48–1.75 (6H, m), 3.48–3.57 (1H, m), 3.89–4.00 (1H, m), 4.20 (2H, s), 4.90 (1H, brs), 6.47 (1H, d, J=16 Hz), 7.07–7.16 (2H, m), 7.34–7.57 (7H, m), 11.2 (1H, brs), 12.3 (1H, brs).

Preparation 10

To a stirred solution of 2-(4-iodobenzyl)-1H-benzimidazole (451 mg) in dimethylformamide (5 ml) was added portionwise sodium hydride (81 mg, 60% oil dispersion) at 0° C. After 30 minutes, benzyl bromide (0.19 mL) was added dropwise to the mixture, and the mixture was stirred for 30 minutes. The resulting mixture was poured into saturated ammonium chloride solution and extracted with ethyl acetate. The organic phase was washed with brine, dried over sodium sulfate, and concentrated in vacuo. The residue was purified by preparative thin layer chromatography (chloroform:methanol=10:1) to give Compound (10) as a pale yellow oil (225 mg). In this preparation, a by-product (1-benzyl-2-[1-(4-iodophenyl)-2-phenylethyl]-1H-benzimidazole) (306 mg) was also obtained and was used in Preparation 23 described below.

$^1$H-NMR (300 MHz, CDCl$_3$, δ): 4.18 (2H, s), 5.19 (2H, s), 6.86–6.97 (4H, m), 7.19–7.32 (6H, m), 7.56 (2×1H, J=8.5 Hz), 7.81 (1H, d, J=7.5 Hz); MASS (ES+): m/e 425.

Preparation 11

Compound (11) was obtained from Compound (10) according to a manner similar to Preparation 4 as a pale yellow oil (142 mg).

$^1$H-NMR (300 MHz, CDCl$_3$, δ): 1.33 (3H, t, J=7 Hz), 4.26 (2H, s), 4.26 (2H, q, J=7 Hz), 5.21 (2H, s), 6.38 (1H, d, J=16 Hz), 6.88–6.96 (2H, m), 7.18–7.32 (8H, m), 7.41 (2×1H, d, J=8 Hz), 7.62 (1H, d, J=16 Hz), 7.81 (1H, d, J=8 Hz); MASS (ES+): m/e 397.

Preparation 12

To a stirred solution of Compound (11) (140 mg) in methanol (6 mL) was added 1N sodium hydroxide solution (0.71 mL). The mixture was stirred at ambient temperature for 7 hours. The solvent was evaporated in vacuo, and the residue was dissolved in water and washed with diethyl ether. The aqueous phase was acidified to pH 3 with hydrochloric acid, and extracted three times with ethyl acetate. The combined organic phase was washed with brine, dried over sodium sulfate and evaporated in vacuo to give Compound (12) as a pale yellow powder (111 mg).

$^1$H-NMR (300 MHz, CDCl$_3$, δ): 4.29 (2H, s), 5.23 (2H, s), 6.36 (1H, d, J=15.7 Hz), 6.88–6.96 (2H, m), 7.16–7.34 (8H, m), 7.41 (2×1H, d, J=8 Hz), 7.62 (1H, d, J=15.7 Hz), 7.81 (1H, d, J=7.5 Hz); MASS (ES+): m/e 368.

Preparation 13

Compound (13) was obtained from Compound (12) according to a manner similar to Preparation 9 as a white amorphous (111 mg).

$^1$H-NMR (300 MHz, CDCl$_3$, δ): 1.52–1.95 (6H, m), 3.61 (1H, m), 3.94 (1H, m), 4.25 (2H, s), 5.02 (1H, m), 5.20 (2H, s), 6.88–6.96 (2H, m), 7.12–7.41 (11H, m), 7.66 (1H, d, J=15.5 Hz), 7.82 (1H, d, J=8 Hz); MASS (ES+): m/e 468.

Preparation 14

To a stirred solution of 3-phenylpropanoic acid (7.51 g) in acetic acid (70 mL) were added periodic acid (2.39 g), iodine (5.08 g), concentrated sulfuric acid (1.5 mL) and water (10 mL), and the mixture was stirred at 70° C. for 7 hours. The solvent was evaporated in vacuo, and the residue was diluted with water and extracted with ethyl acetate. The organic phase was washed with 10% sodium thiosulfate solution twice, then washed with brine, dried over magnesium sulfate and evaporated in vacuo. The precipitate was crystallized from ethyl acetate and hexane to give Compound (14) (5.80 g).

$^1$H-NMR (300 MHz, CDCl$_3$, δ): 2.66 (2H, t, J=7 Hz), 2.90 (2H, t, J=7 Hz), 6.97 (2×1H, d, J=8.5 Hz), 7.61 (2×1H, d, J=8.5 Hz); MASS (ES-): m/e 275.

Preparation 15

Compound (15) was obtained from Compound (14) according to a manner similar to Preparation 1 (9.50 g).

$^1$H-NMR (300 MHz, CDCl$_3$, δ): 1.51 (3×3H, s), 2.64 (2H, t, J=7.5 Hz), 3.00 (2H, t, J=7.5 Hz), 6.69 (1H, s), 7.00 (2×1H, d, J=8.5 Hz), 7.12–7.20 (2H, m), 7.33 (1H, m), 7.45 (1H, m), 7.62 (2×1H, d, J=8.5 Hz), 7.97 (1H, brs); MASS (ES+): m/e 467.

Preparation 16

Compound (16) was obtained from Compound (15) according to a manner similar to Preparation 2 (1.55 g).

$^1$H-NMR (300 MHz, DMSO-d$_6$, δ): 3.20 (2H, t, J=7.5 Hz), 3.41 (2H, t, J=7.5 Hz), 7.10 (2×1H, d, J=8.5 Hz), 7.48–7.56 (2H, m), 7.66 (2×1H, d, J=8.5 Hz), 7.74–7.82 (2H, m); MASS (ES+): m/e 349.

Preparation 17

Compound (17) was obtained from Compound (16) according to a manner similar to Preparation 3 (7.10 g).

$^1$H-NMR (300 MHz, CDCl$_3$, δ): 2.38 (3H, s), 3.18 (2H, t, J=7 Hz), 3.43 (2H, t, J=7 Hz), 7.05 (2×1H, d, J=8.5 Hz), 7.25 (2×1H, d, J=8.5 Hz), 7.30–7.40 (2H, m), 7.61 (2×1H, d, J=8.5 Hz), 7.67 (1H, m), 7.71 (2×1H, d, J=8.5 Hz), 8.03 (1H, m); MASS (ES+): m/e 503.

Preparation 18

Compound (18) was obtained from Compound (17) according to a manner similar to Preparation 4 (3.59 g).

$^1$H-NMR (300 MHz, CDCl$_3$, δ): 2.38 (3H, s), 3.27 (2H, t, J=7 Hz), 3.47 (2H, t, J=7 Hz), 6.44 (1H, d, J=16 Hz), 7.25 (2×1H, d, J=8 Hz), 7.31–7.40 (4H, m), 7.50 (2×1H, d, J=8 Hz), 7.66–7.81 (4H, m), 8.04 (1H, m); MASS (ES+): m/e 447.

Preparation 19

Compound (19) was obtained from Compound (18) according to a manner similar to Preparation 5 (2.20 g). The Compound (19) was used in Example 3.

$^1$H-NMR (300 MHz, DMSO-d$_6$, δ): 1.46–1.76 (6H, m), 3.08–3.18 (4H, m), 3.53 (1H, m), 3.95 (1H, m), 4.90 (1H, m), 6.45 (1H, d, J=15.5 Hz), 7.08–7.16 (2H, m), 7.31 (2×1H, d, J=8 Hz), 7.40–7.54 (5H, m), 11.21 (1H, s), 12.28 (1H, br); MASS (ES+): m/e 392.

Preparation 20

To a stirred solution of 1H-benzimidazole (500 mg) in N,N-dimethylformamide (10 mL) was added sodium hydride (186 mg, 60% of oil suspension) at 0° C. After 90 minutes, 4-iodobenzyl bromide was added to the mixture and the mixture was stirred at ambient temperature for 1 hour. The reaction mixture was quenched with saturated ammonium chloride solution, diluted with water and extracted with ethyl acetate. The organic phase was washed with brine, dried over sodium sulfate and concentrated in vacuo. The residue was triturated with hexane to give Compound (20) as a white solid. (1.20 g).

$^1$H-NMR (300 MHz, CDCl$_3$, δ): 5.31 (2H, s), 6.92 (2×1H, d, J=8.5 Hz), 7.21–7.33 (3H, m), 7.67 (2×1H, d, J=8.5 Hz), 7.84 (1H, m), 7.95 (1H, s); MASS (ES+): m/e 335.

Preparation 21

Compound (21) was obtained from Compound (20) according to a manner similar to Preparation 4 (614 mg).

$^1$H-NMR (300 MHz, DMSO-d$_6$, δ): 5.53 (2H, s), 6.50 (1H, d, J=16 Hz), 7.15–7.24 (2H, m), 7.32 (2×1H, d, J=8.5

Hz), 7.51 (1H, m), 7.52 (1H, d, J=16 Hz), 7.61–7.70 (3H, m), 8.43 (1H, s); MASS (ES+): m/e 279.

Preparation 22

Compound (22) was obtained from Compound (21) according to a manner similar to Preparation 5 (536 mg). The obtained Compound (22) was used in Example 4.

$^1$H-NMR (300 MHz, DMSO-$d_6$, δ): 1.45–1.76 (6H, m), 3.52 (1H, m), 3.94 (1H, m), 4.89 (1H, m), 5.53 (2H, s), 6.46 (1H, d, J=16 Hz), 7.16–7.25 (2H, m), 7.33 (2×1H, d, J=8.5 Hz), 7.44 (1H, d, J=16 Hz), 7.51 (1H, m), 7.54 (2×1H, d, J=8.5 Hz), 7.67 (1H, m), 8.42 (1H, s), 11.24 (1H, s); MASS (ES+): m/e 378.

Preparation 23

Compound (23) was obtained from the by-product obtained in Preparation 10 according to a manner similar to Preparation 4 (150 mg).

$^1$H-NMR (300 MHz, CDCl$_3$, δ): 1.32 (3H, t, J=7 Hz), 3.35 (1H, dd, J=13.5, 7.5 Hz), 3.85 (1H, dd, J=13.5, 7.5 Hz), 4.25 (2H, q, J=7 Hz), 4.28 (1H, dd, J=7.5, 7.5 Hz), 5.05 (1H, d, J=16.5 Hz), 5.11 (1H, d, J=16.5 Hz), 6.35 (1H, d, J=16 Hz), 6.75 (2×1H, dd, J=7.5, 1 Hz), 6.93–7.00 (2H, m), 7.09–7.38 (13H, m), 7.59 (1H, d, J=16 Hz), 7.91 (1H, d, J=8 Hz); MASS (ES+): m/e 487.

Preparation 24

Compound (24) was obtained from Compound (23) according to a manner similar to Preparation 12 (135 mg).

$^1$H-NMR (300 MHz, CDCl$_3$, δ): 3.37 (1H, dd, J=13.5, 7.5 Hz), 3.86 (1H, dd, J=13.5, 7.5 Hz), 4.31 (1H, dd, J=7.5, 7.5 Hz), 5.06 (1H, d, J=15.7 Hz), 5.11 (1H, d, J=15.7 Hz), 6.39 (1H, d, J=15.7 Hz), 6.74 (2×1H, d, J=7 Hz), 6.93–7.02 (2H, m), 7.08–7.33 (11H, m), 7.36 (2×1H, d, J=8 Hz), 7.68 (1H, d, J=15.7 Hz), 7.94 (2×1H, d, J=7.5 Hz); MASS (ES+): m/e 459.

Preparation 25

Compound (25) was obtained from Compound (24) according to a manner similar to Preparation 9 (140 mg). The obtained Compound (25) was used in Example 5.

$^1$H-NMR (300 MHz, CDCl$_3$, δ): 1.55–1.92 (6H, m), 3.35 (1H, dd, J=13.5, 7.5 Hz), 3.64 (1H, m), 3.84 (1H, dd, J=13.5, 7.5 Hz), 3.95 (1H, m), 4.28 (1H, dd, J=7.5, 7.5 Hz), 5.00 (1H, m), 5.04 (1H, d, J=17 Hz), 5.11 (1H, d, J=17 Hz), 6.75 (2×1H, d, J=7 Hz), 6.92–7.00 (2H, m), 7.08–7.37 (14H, m), 7.64 (1H, d, J=15 Hz), 7.90 (1H, d, J=8 Hz); MASS (ES+): m/e 558.

Preparation 26

Compound (26) was obtained from (3-bromophenyl)acetic acid according to a manner similar to Preparation 6 (6.20 g).

$^1$H-NMR (300 MHz, CDCl$_3$, δ): 1.53 (3×3H, s), 3.06 (2H, s), 6.37 (1H, d, J=15.8 Hz), 7.25–7.46 (4H, m), 7.56 (1H, d, J=15.8 Hz); MASS (ES–): m/e 261.

Preparation 27

Compound (27) was obtained from Compound (26) according to a manner similar to Preparation 7 (6.96 g).

$^1$H-NMR (300 MHz, CDCl$_3$, δ): 1.48 (3×3H, s), 1.53 (3×3H, s), 3.74 (2H, s), 6.39 (1H, d, J=15.8 Hz), 6.70 (1H, brs), 7.09–7.20 (2H, m), 7.32–7.52 (6H, m), 7.56 (1H, d, J=15.8 Hz), 8.04 (1H, brs); MASS (ES+): m/e 453.

Preparation 28

Compound (28) was obtained from Compound (27) according to a manner similar to Preparation 8 (4.19 g).

$^1$H-NMR (300 MHz, DMSO-$d_6$, δ): 4.58 (2H, s), 6.58 (1H, d, J=16 Hz), 7.42–7.58 (5H, m), 7.58 (1H, d, J=16 Hz), 7.66 (1H, m), 7.74–7.82 (2H, m), 7.87 (1H, brs); MASS (ES+): m/e 279.

Preparation 29

Compound (29) was obtained from Compound (28) according to a manner similar to Preparation 9 (3.34 g). The obtained Compound (29) was used in Example 6.

$^1$H-NMR (300 MHz, DMSO-$d_6$, δ): 1.44–1.76 (6H, m), 3.53 (1H, m), 3.95 (1H, m), 4.20 (2H, s), 4.90 (1H, m), 6.50 (1H, d, J=16 Hz), 7.08–7.16 (2H, m), 7.32–7.60 (7H, m), 11.25 (1H, s), 12.31 (1H, brs); MASS (ES+): m/e 378.

Preparation 30

Compound (30) was obtained from {4-[(1E)-3-tert-butoxy-3-oxo-1-propenyl]phenyl}acetic acid according to a manner similar to Preparation 1 (324 mg).

$^1$H-NMR (300 MHz, DMSO-$d_6$, δ): 1.48 (3×3H, s), 3.176 (1H, s), 3.723 (1H, s), 5.00 (1H, s), 5.01 (1H, s), 6.51 (1H, d, J=15.7 Hz), 6.82 (1H, m), 7.19–7.60 (10H, m), 7.66 (2×1H, d, J=8 Hz), 9.45 (0.5H, s), 9.47 (0.5H, s); MASS (ES+): m/e 429.

Preparation 31

Compound (31) was obtained from Compound (30) according to a manner similar to Preparation 8 (216 mg).

$^1$H-NMR (300 MHz, DMSO-$d_6$, δ): 4.59 (2H, s), 6.57 (1H, d, J=16 Hz) 7.42 (1H, m), 7.51 (2×1H, d, J=7.5 Hz), 7.53 (2×1H, d, J=8.5 Hz), 7.60 (1H, d, J=16 Hz), 7.69–7.88 (6H, m), 7.96 (1H, s); MASS (ES+): m/e 355.

Preparation 32

Compound (32) was obtained from Compound (31) according to a manner similar to Preparation 9 (231 mg). The obtained Compound (32) was used in Example 7.

$^1$H-NMR (300 MHz, DMSO-$d_6$, δ): 1.46–1.78 (6H, m), 3.52 (1H, m), 3.95 (1H, m), 4.22 (2H, s), 4.90 (1H, m), 6.48 (1H, d, J=15 Hz), 7.30–7.81 (13H, m), 11.23 (1H, s), 12.38 (1/2H, s), 12.41 (1/2H, s); MASS (ES+): m/e 454.

Preparation 33

Compound (33) was obtained from Compound (6) according to manners similar to Preparations 7 and 8 (5.48 g).

$^1$H-NMR (300 MHz, DMSO-$d_6$, δ): 4.50 (2H, s), 6.55 (1H, d, J=16 Hz), 7.47 (2H, d, J=8 Hz), 7.59 (1H, d, J=16 Hz), 7.56–7.75 (4H, m), 7.97 (1H, s). MASS (ESI): m/z 357 (M+1).

Preparation 34

Compound (34) was obtained from Compound (33) according to a manner similar to Preparation 9 (557 mg). The Compound (34) was used in Example 8.

$^1$H-NMR (300 MHz, DMSO-$d_6$, δ): 1.48–1.74 (6H, m), 3.48–3.57 (1H, m), 3.89–4.00 (1H, m), 4.20 (2H, s), 4.90 (1H, brs), 6.47 (1H, d, J=16 Hz), 7.26 (1H, dd, J=2, 8 Hz), 7.34–7.56 (6H, m), 7.68 (1H, brs). MASS (ESI): m/z 456 (M+1).

Preparation 35

To a mixture of Compound (34) (200 mg), 4-acetylphenylboronic acid (167 mg) and dichlorobis(triphenylphosphine)palladium(II) (10.7 mg) in dioxane (10 mL) was added 2M sodium carbonate (2.5 mL), and the mixture was heated at 90° C. for 5 hours. After cooling, the reaction mixture was partitioned between ethyl acetate and water. The inorganic layer was separated and acidified with 1N hydrochloric acid. The resulting precipitate was collected by filtration, and washed with water and ethyl acetate to give Compound (35) (193 mg). The Compound (35) was used in Example 9.

$^1$H-NMR (300 MHz, DMSO-d$_6$, δ): 2.63 (3H, s), 4.57 (2H, s), 6.56 (1H, d, J=16 Hz), 7.52 (2H, d, J=8 Hz), 7.59 (1H, d, J=16 Hz), 7.74 (2H, d, J=8 Hz), 7.85–7.92 (4H, m), 8.03–8.10 (3H, m); MASS (ESI): m/z 397 (M+1).

Preparation 36

Compound (36) was obtained from Compound (34) according to a manner similar to Preparation 35 (163 mg). The Compound (36) was used in Example 10.

$^1$H-NMR (300 MHz, DMSO-d$_6$, δ): 4.37 (2H, s), 6.53 (1H, d, J=16 Hz), 7.12–7.16 (1H, m), 7.45–7.71 (9H, m), 7.81 (1H, s); MASS (ESI): m/z 361 (M+1).

Preparation 37

Compound (37) was obtained from Compound (34) according to a manner similar to Preparation 35 (183 mg). The Compound (37) was used in Example 11.

$^1$H-NMR (300 MHz, DMSO-d$_6$, δ): 4.55 (2H, s), 6.56 (1H, d, J=16 Hz), 7.40–8.01 (11H, m); MASS (ESI): m/z 361 (M+1).

Preparation 38

Compound (38) was obtained from Compound (6) according to manners similar to Preparations 7 and 8 (2.07 g).

$^1$H-NMR (300 MHz, DMSO-d$_6$, δ): 4.47 (2H, s), 6.54 (1H, d, J=16 Hz), 7.46 (2H, d, J=8 Hz), 7.58 (1H, d, J=16 Hz), 7.70 (2H, d, J=8 Hz), 7.77 (1H, d, J=8 Hz), 7.83 (1H, d, J=8 Hz), 8.26 (1H, s); MASS (ESI): m/z 304 (M+1).

Preparation 39

Compound (39) was obtained from Compound (38) according to a manner similar to Preparation 9 (2.14 g). The Compound (39) was used in Examples 12 and 18.

$^1$H-NMR (300 MHz, DMSO-d$_6$, δ): 1.49–1.72 (6H, m), 3.50–3.56 (1H, m), 3.91–3.99 (1H, m), 4.26 (2H, s), 4.91 (1H, brs), 6.47 (1H, d, J=16 Hz), 7.37 (2H, d, J=8 Hz), 7.46 (1H, d, J=16 Hz), 7.51–7.57 (3H, m), 7.65 (1H, d, J=8 Hz), 8.32 (1H, brs); MASS (ESI): m/z 401 (M−1).

Preparation 40

Compound (40) was obtained from Compound (6) according to manners similar to Preparations 7 and 8 (955 mg). The Compound (40) was used in Example 13.

$^1$H-NMR (300 MHz, DMSO-d$_6$, δ): 4.50 (2H, s), 6.55 (1H, d, J=16 Hz), 7.32–7.39 (1H, m), 7.47 (2H, d, J=8 Hz), 7.59 (1H, d, J=16 Hz), 7.62 (1H, dd, J=2, 8 Hz), 7.72 (2H, d, J=8 Hz), 7.74–7.79 (1H, m); MASS (ESI): m/z 297 (M+1).

Preparation 41

Compound (41) was obtained from Compound (6) according to manners similar to Preparations 7 and 8 (1.02 g).

$^1$H-NMR (300 MHz, DMSO-d$_6$, δ): 4.52 (2H, s), 6.55 (1H, d, J=16 Hz), 7.48 (2H, d, J=8 Hz), 7.50 (1H, dd, J=2, 8 Hz), 7.59 (1H, d, J=16 Hz), 7.72 (2H, d, J=8 Hz), 7.75 (1H, d, J=8 Hz), 7.85 (1H, J=2 Hz); MASS (ESI): m/z 313 (M+1).

Preparation 42

Compound (42) was obtained from Compound (41) according to a manner similar to Preparation 9 (839 mg). The Compound (42) was used in Example 14.

$^1$H-NMR (300 MHz, DMSO-d$_6$, δ): 1.49–1.71 (6H, m), 3.49–3.57 (1H, m), 3.88–4.02 (1H, m), 4.20 (2H, s), 4.88–4.93 (1H, m), 6.43–6.52 (1H, m), 7.12–7.18 (1H, m), 7.36 (2H, d, J=8 Hz), 7.46 (1H, d, J=16 Hz), 7.53 (2H, d, J=8 Hz), 7.53–7.60 (1H, m), 7.64 (1H, d, J=8 Hz); MASS (ESI): m/z 412 (M+1).

Preparation 43

Compound (43) was obtained from Compound (6) according to manners similar to Preparations 7 and 8 (411 mg).

$^1$H-NMR (300 MHz, DMSO-d$_6$, δ): 2.78–2.84 (4H, m), 3.13–3.20 (4H, m), 4.54 (2H, s), 6.55 (1H, d, J=16 Hz), 7.16–7.76 (8H, m); MASS (ESI): m/z 377 (M+1).

Preparation 44

Compound (44) was obtained from Compound (43) according to a manner similar to Preparation 9 (23 mg). The Compound (44) was used in Example 15.

$^1$H-NMR (300 MHz, DMSO-d$_6$, δ): 1.54–1.87 (6H, m), 2.36 (3H, s), 2.58–2.64 (4H, m), 3.12–3.20 (4H, m), 3.58–3.66 (1H, m), 3.92–4.04 (1H, m), 4.15 (2H, s), 5.02–5.10 (1H, m), 6.92–7.60 (9H, m); MASS (ESI): m/z 476 (M+1).

Preparation 45

Compound (45) was obtained from Compound (6) according to manners similar to Preparations 7 and 8 (358 mg).

$^1$H-NMR (300 MHz, DMSO-d$_6$, δ): 3.16–3.22 (4H, m), 3.76–3.83 (4H, m), 4.53 (2H, s), 6.56 (1H, d, J=16 Hz), 7.34–7.76 (8H, m); MASS (ESI): m/z 364 (M+1).

Preparation 46

Compound (46) was obtained from Compound (45) according to a manner similar to Preparation 9 (59 mg). The Compound (46) was used in Example 16.

$^1$H-NMR (300 MHz, CDCl$_3$, δ): 1.51–1.87 (6H, m), 3.05–3.13 (4H, m), 3.57–3.64 (1H, m), 3.83–3.91 (4H, m), 3.95–4.04 (1H, m), 4.15 (2H, s), 5.04–5.13 (1H, m), 6.91–7.61 (9H, m); MASS (ESI): m/z 463 (M+1).

Preparation 47

Compound (47) was obtained from Compound (6) according to manners similar to Preparations 7 and 8 (517 mg).

$^1$H-NMR (300 MHz, DMSO-d$_6$, δ): 1.57–1.69 (2H, m), 1.83–1.94 (4H, m), 3.37–3.50 (4H, m), 4.52 (2H, s), 6.48–6.58 (1H, m), 7.40–7.74 (8H, m); MASS (ESI): m/z 362 (M+1).

Preparation 48

Compound (48) was obtained from Compound (47) according to a manner similar to Preparation 9 (47 mg). The Compound (48) was used in Example 17.

$^1$H-NMR (300 MHz, CDCl$_3$, δ): 1.50–1.87 (12H, m), 3.05–3.11 (4H, m), 3.57–3.66 (1H, m), 3.94–4.05 (1H, m), 4.14 (2H, s), 5.02–5.12 (1H, m), 6.94–7.48 (9H, m); MASS (ESI): m/z 461 (M+1).

Preparation 49

Compound (49) was obtained from Compound (6) according to manners similar to Preparations 7 and 8 (1.17 g).

$^1$H-NMR (300 MHz, DMSO-d$_6$, δ): 3.90 (3H, s), 4.49 (2H, s), 6.54 (1H, d, J=16 Hz), 7.47 (2H, d, J=8 Hz), 7.59 (1H, d, J=16 Hz), 7.72 (2H, d, J=8 Hz), 7.78 (1H, d, J=8 Hz), 8.00 (1H, dd, J=2, 8 Hz), 8.24 (1H, brs); MASS (ESI): m/z 337 (M+1).

Preparation 50

Compound (50) was obtained from Compound (49) according to a manner similar to Preparation 9 (1.30 g). The Compound (50) was used in Example 19.

¹H-NMR (300 MHz, DMSO-d$_6$, δ): 1.48–1.74 (6H, m), 3.48–3.58 (1H, m), 3.85 (3H, s), 3.87–4.00 (1H, m), 4.25 (2H, brs), 4.90 (1H, brs), 6.47 (1H, d, J=16 Hz), 7.35–7.65 (6H, m), 7.74–8.16 (2H, m); MASS (ESI): m/z 436 (M+1).

Preparation 51

To a solution of Compound (50) (299 mg) in dioxane (7 mL) was added 1N sodium hydroxide (2.1 mL). After stirring at 80° C. for 1 hour, the reaction mixture was added water (25 mL) and acidified with 1N hydrochloric acid (to pH 3–4). A resulting precipitate was collected by filtration and washed with water to give Compound (51) (255 mg). The Compound (51) was used in Example 20.

¹H-NMR (300 MHz, DMSO-d$_6$, δ): 1.49–1.74 (6H, m), 3.47–3.59 (1H, m), 3.87–4.01 (1H, m), 4.24 (2H, s), 4.90 (1H, brs), 6.47 (1H, d, J=16 Hz), 7.38 (2H, d, J=8 Hz), 7.43–7.62 (4H, m), 7.73–8.14 (2H, m); MASS (ESI): m/z 422 (M+1).

Preparation 52

Compound (52) was obtained from Compound (6) according to manners similar to Preparations 7 and 8 (384 mg).

¹H-NMR (300 MHz, DMSO-d$_6$, δ): 2.68 (3H, s), 4.55 (2H, s), 6.55 (1H, d, J=16 Hz), 7.50 (2H, d, J=8 Hz), 7.59 (1H, d, J=16 Hz), 7.73 (2H, d, J=8 Hz), 7.81 (1H, d, J=8 Hz), 8.04 (1H, dd, J=2, 8 Hz), 8.27 (1H, s); MASS (ESI): m/z 321 (M+1).

Preparation 53

Compound (53) was obtained from Compound (52) according to a manner similar to Preparation 9 (394 mg). The Compound (53) was used in Example 21.

¹H-NMR (300 MHz, DMSO-d$_6$, δ): 1.47–1.73 (6H, m), 2.61 (3H, s), 3.48–3.57 (1H, m), 3.90–4.01 (1H, m), 4.25 (2H, brs), 4.90 (1H, brs), 6.47 (1H, d, J=16 Hz), 7.36–8.23 (8H, m); MASS (ESI): m/z 418 (M−1).

Preparation 54

Compound (54) was obtained from Compound (6) according to manners similar to Preparations 7 and 8 (335 mg).

¹H-NMR (300 MHz, DMSO-d$_6$, δ): 4.58 (2H, s), 6.53 (1H, d, J=16 Hz), 7.30–7.36 (1H, m), 7.47 (2H, d, J=8 Hz), 7.54–7.73 (5H, m); MASS (ESI): m/z 357 (M+1).

Preparation 55

Compound (55) was obtained from Compound (54) according to a manner similar to Preparation 9 (364 mg). The Compound (55) was used in Example 22.

¹H-NMR (300 MHz, DMSO-d$_6$, δ): 1.48–1.74 (6H, m), 3.48–3.58 (1H, m), 3.89–4.02 (1H, m), 4.24 (2H, s), 4.90 (1H, brs), 6.47 (1H, d, J=16 Hz), 7.05–7.12 (1H, m), 7.33–7.58 (7H, m); MASS (ESI): m/z 456 (M+1).

Preparation 56

Compound (56) was obtained from Compound (6) according to manners similar to Preparations 7 and 8 (805 mg).

¹H-NMR (300 MHz, DMSO-d$_6$, δ): 1.24 (3H, s), 1.27 (3H, s), 3.02–3.15 (1H, m), 4.54 (2H, s), 6.56 (1H, d, J=16 Hz), 7.33–7.75 (8H, m); MASS (ESI): m/z 321 (M+1).

Preparation 57

Compound (57) was obtained from Compound (56) according to a manner similar to Preparation 9 (70 mg). The Compound (57) was used in Example 23.

¹H-NMR (300 MHz, DMSO-d$_6$, δ): 1.22 (3H, s), 1.24 (3H, s), 1.48–1.73 (6H, m), 2.89–3.03 (1H, m), 3.48–3.57 (1H, m), 3.89–4.00 (1H, m), 4.17 (2H, s), 4.90 (1H, brs), 6.47 (1H, d, J=16 Hz), 7.01 (1H, d, J=8 Hz), 7.20–7.57 (7H, m); MASS (ESI): m/z 420 (M+1).

Preparation 58

Compound (58) was obtained from Compound (6) according to manners similar to Preparations 7 and 8 (925 mg).

¹H-NMR (300 MHz, DMSO-d$_6$, δ): 4.50 (2H, s), 5.37 (2H, s), 6.54 (1H, d, J=16 Hz), 7.13–7.75 (13H, m); MASS (ESI): m/z 385 (M+1).

Preparation 59

Compound (59) was obtained from Compound (58) according to a manner similar to Preparation 9. The Compound (59) was used in Example 24.

Preparation 60

Compound (60) was obtained according to a manner similar to Preparation 20 (1.25 g).

¹H-NMR (300 MHz, CDCl$_3$, δ): 2.56 (3H, s), 5.27 (2H, s), 6.79 (2×1H, d, J=8.4 Hz), 7.15–7.29 (3H, m), 7.63 (2×1H, d, J=8.4 Hz), 7.73 (1H, m); MASS (ES+): m/e 349.

Preparation 61

Compound (61) was obtained from Compound (60) according to a manner similar to Preparation 4 (625 mg).

¹H-NMR (300 MHz, CDCl$_3$, δ): 2.57 (3H, s), 5.36 (2H, s), 6.40 (1H, d, J=16.2 Hz), 7.07 (2×1H, d, J=8.5 Hz), 7.20–7.29 (3H, m), 7.48 (2×1H, d, J=8.5 Hz), 7.64 (1H, d, J=16.2 Hz), 7.71 (1H, m); MASS (ES+): m/e 293.

Preparation 62

Compound (62) was obtained from Compound (61) according to a manner similar to Preparation 9 (556 mg). The Compound (62) was used in Example 25.

¹H-NMR (300 MHz, DMSO-d$_6$, δ): 1.46–1.75 (6H, m), 2.52 (3H, s), 3.52 (1H, m), 3.94 (1H, m), 4.89 (1H, m), 5.50 (2H, s), 6.46 (1H, d, J=16 Hz), 7.11–7.20 (4H, m), 7.38–7.62 (5H, m); MASS (ES+): m/e 392.

Preparation 63

To a stirred solution of 1-phenylcyclopropanecarboxylic acid (3.25 g) in acetic acid (30 mL) was added periodic acid (959 mg), iodine (2.03 g), concentrated H$_2$SO$_4$ (0.6 mL) and water (4 mL), and the mixture was stirred at 70° C. for 12 hours. Water (100 mL) was added to the mixture and the precipitated solid was collected by filtration and washed with water to give Compound (63) (4.31 g).

¹H-NMR (300 MHz, CDCl$_3$, δ): 1.23 (2H, ddd, J=7, 4, 4 Hz), 1.67 (2H, ddd, J=7, 4, 4 Hz), 7.09 (2×1H, d, J=8.4 Hz), 7.63 (2×1H, d, J=8.4 Hz); MASS (ES−): m/e 287.

Preparation 64

Compound (64) was obtained from Compound (63) according to a manner similar to Preparation 6 (432 mg).

¹H-NMR (300 MHz, DMSO-d$_6$, δ): 1.16 (2H, ddd, J=7, 4, 4 Hz), 1.45 (2H, ddd, J=7, 4, 4 Hz), 1.48 (3×3H, s), 6.49 (1H, d, J=15.7 Hz), 7.35 (2×1H, d, J=8 Hz), 7.53 (1H, d, J=15.7 Hz), 7.61 (2×1H, d, J=8 Hz); MASS (ES−): m/e not determined.

Preparation 65

Compound (65) was obtained from Compound (64) according to a manner similar to Preparation 7 (1.67 g).

¹H-NMR (300 MHz, CDCl$_3$, δ): 1.20 (2H, m), 1.45 (3×3H, s), 1.51 (3×3H, s), 1.74 (2H, m), 6.40 (1H, d, J=15.7 Hz), 6.63 (1H, br-s), 6.98–7.62 (10H, m); MASS (ES+): m/e 479.

Preparation 66

Compound (66) was obtained from Compound (65) according to a manner similar to Preparation 8 (710 mg).

$^1$H-NMR (300 MHz, DMSO-d$_6$, δ): 1.71 (2H, m), 1.95 (2H, m), 6.59 (1H, d, J=15.8 Hz), 7.40–7.55 (4H, m), 7.63 (1H, d, J=15.8 Hz), 7.64–7.72 (2H, m), 7.76 (2×1H, d, J=8.4 Hz); MASS (ES+): m/e 305.

Preparation 67

Compound (67) was obtained from Compound (66) according to a manner similar to Preparation 9 (647 mg).

$^1$H-NMR (300 MHz, DMSO-d$_6$, δ): 1.39 (2H, m), 1.48–1.76 (8H, m), 3.34 (1H, m), 3.54 (1H, m), 3.96 (1H, m), 4.91 (2H, s), 6.51 (1H, d, J=16 Hz), 7.07–7.15 (2H, m), 7.31–7.43 (3H, m), 7.46–7.63 (4H, m); MASS (ES+): m/e 404.

Preparation 68

To a stirred solution of 4-bromo-2-nitroaniline (1.37 g) in dioxane (20 mL) was added 4-fluorophenylboronic acid (1.06 g), PdCl$_2$(PPh$_3$)$_2$ (133 mg), and 2M sodium carbonate solution (12.7 ml), and the mixture was stirred at 100° C. for 2 hours. The solvent was evaporated and the residue was partioned between ethyl acetate and water. The organic phase was washed with brine, dried over Na$_2$SO$_4$ and concentrated in vacuo. The resulting solid was recrystalized from toluene to give Compound (68) (1.13 g) as a white solid.

$^1$H-NMR (300 MHz, CDCl$_3$, δ): 6.18 (2H, br-s), 6.89 (1H, d, J=8.7 Hz), 7.12 (2×1H, dd, J=8.7, 8.7 Hz), 7.51 (2×1H, dd, J=8.7, 5 Hz), 7.59 (1H, dd, J=8.7, 2.2 Hz), 8.31 (1H, d, J=2.2 Hz); MASS (ES−) m/e 231.

Preparation 69

To a stirred solution of Compound (68) (1.08 g) in EtOH (15 mL) was added tin (II) chloride (1.32 g) The mixture was stirred at 100° C. for 6 hours. The solvent was evaporated to the half volume and the residue was basified with 1N-NaOH to pH 9 and extracted with ethyl acetate. The organic phase was washed with brine, dried over Na$_2$SO$_4$, and concentrated in vacuo. The residue was triturated with ethyl acetate to give Compound (69) (800 mg) as an orange powder.

$^1$H-NMR (300 MHz, CDCl$_3$, δ): 3.45 (2×2H, br-s), 6.76 (2×1H, d, J=8.3 Hz), 6.89 (1H, d, J=2.1 Hz), 6.91 (1H, dd, J=8.3, 2.1 Hz), 7.06 (2×1H, dd, J=8.8, 8.8 Hz), 7.46 (2×1H, dd, J=8.8, 5.4 Hz); MASS (ES+): m/e 203.

Preparation 70

Compound (70) was obtained from Compound (69) according to a manner similar to Preparation 7 (552 mg).

$^1$H-NMR (300 MHz, CDCl$_3$, δ): 1.54 (3×3H, s), 3.81 (2H, s), 6.39 (1H, sd, J=16 Hz), 6.80–7.62 (15H, m); MASS (ES+): m/e 446.

Preparation 71

Compound (71) was obtained from Compound (70) according to a manner similar to Preparation 8 (375 mg).

$^1$H-NMR (300 MHz, DMSO-d$_6$, δ): 4.58 (2H, s), 6.56 (1H, d, J=16 Hz), 7.23–7.86 (11H, m), 7.94 (1H, s); MASS (ES+): m/e 373.

Preparation 72

Compound (72) was obtained from Compound (71) according to a manner similar to Preparation 9 (321 mg). The Compound (71) was used in Example 26.

$^1$H-NMR (300 MHz, DMSO-d$_6$, δ): 1.45–1.75 (6H, m), 3.52 (1H, m), 3.95 (1H, m), 4.22 (2H, s), 4.90 (1H, m), 6.48 (1H, d, J=15.8 Hz), 7.22–7.80 (12H, m), 11.23 (1H, br-s), 12.40 (H, br-s); MASS (ES+): m/e 472.

Preparation 73

Compound (73) was obtained from Compound (6) according to a manner similar to Preparation 7 (228 mg).

$^1$H-NMR (300 MHz, DMSO-d$_6$, δ): 1.53 (3×3H, s), 3.75–3.87 (4H, br), 6.41 (1H, d, J=15.7 Hz), 6.81–7.54 (13H, m), 7.58 (1H, d, J=15.7 Hz); MASS (ES+): m/e 429.

Preparation 74

Compound (74) was obtained from Compound (73) according to a manner similar to Preparation 8 (165 mg).

$^1$H-NMR (300 MHz, DMSO-d$_6$, δ): 4.59 (2H, s), 6.59 (1H, d, J=16 Hz), 7.38–7.55 (5H, m), 7.59 (1H, d, J=16 Hz), 7.67 (1H, m), 7.73 (2×1H, d, J=7.5 Hz), 7.78–7.85 (2H, m), 7.87 (1H, br), 7.96 (1H, br-s); MASS (ES+): m/e 355.

Preparation 75

Compound (75) was obtained from Compound (74) according to a manner similar to Preparation 9 (185 mg). The Compound (75) was used in Example 27.

$^1$H-NMR (300 MHz, DMSO-d$_6$, δ): 1.46–1.76 (6H, m), 3.53 (1H, m), 3.94 (1H, m), 4.23 (2H, s), 4.90 (1H, m), 6.50 (1H, d, J=16 Hz), 7.28–7.52 (10H, m), 7.57 (1H, m), 7.66 (2×1H, d, J=7.5 Hz), 11.25 (1H, br), 12.38 (1H, br); MASS (ES+): m/e 454.

Preparation 76

Compound (76) was obtained according to a manner similar to Preparation 35 (320 mg).

$^1$H-NMR (300 MHz, DMSO-d$_6$, δ): 3.24 (3H, s), 7.16 (1H, d, J=8.8 Hz), 7.68 (2H, s), 7.85–8.07 (5H, m), 8.34 (1H, d, J=2.5 Hz); MASS (ES−): m/e 291.

Preparation 77

To a stirred solution of 4'-(methylsulfonyl)-3-nitro-1,1'-biphenyl-4-ylamine (305 g) in EtOH (15 mL) was added iron powder (583 mg), NH$_4$Cl (56 mg) and water (1 mL). The mixture was refluxed for 5 hours. The iron powder was filtered off and the filtrate was evaporated in vacuo. The residue was partioned between CHCl$_3$ and saturated NaHCO$_3$ solution. The organic phase was washed with brine, dried over Na$_2$SO$_4$, and concentrated in vacuo to give Compound (77) (150 mg) as an orange powder.

$^1$H-NMR (300 MHz, DMSO-d$_6$, δ): 3.44 (3H, s), 4.45–5.20 (4H, m), 6.65 (1H, br), 6.82–7.22 (2H, m), 7.62–8.22 (4H, m); MASS (ES+): m/e 263.

Preparation 78

Compound (78) was obtained from Compound (77) according to a manner similar to Preparation 7 (200 mg).

$^1$H-NMR (300 MHz, CDCl$_3$, δ): 1.54 (3×3H, s), 3.07 (3×1/2H, s), 3.08 (3×1/2H, s), 3.83 (2H, br-s), 6.39 (1H, d, J=16 Hz), 6.84–7.10 (2H, m), 7.29 (1H, m), 7.42 (2H, m), 7.53–7.73 (5H, m), 7.95 (2H, m); MASS (ES+): m/e 507.

Preparation 79

Compound (79) was obtained from Compound (78) according to a manner similar to Preparation 8 (162 mg).

$^1$H-NMR (300 MHz, DMSO-d$_6$, δ): 3.28 (3H, s), 4.59 (2H, s), 6.57 (1H, d, J=15.8 Hz), 7.52 (2×1H, d, J=8.2 Hz), 7.59 (1H, d, J=15.8 Hz), 7.74 (2×1H, d, J=8.2 Hz), 7.86–7.90 (2H, m), 7.95–8.10 (5H, m); MASS (ES+): m/e 432.

Preparation 80

Compound (80) was obtained from Compound (79) according to a manner similar to Preparation 9 (190 mg). The Compound (80) was used for Example 28.

$^1$H-NMR (300 MHz, DMSO-d$_6$, δ): 1.46–1.76 (6H, m), 3.25 (3H, s), 3.53 (1H, m), 3.94 (1H, m), 4.24 (2H, m), 4.90

(1H, m), 6.48 (1H, d, J=16 Hz), 7.39 (2×1H, d, J=8 Hz), 7.42–8.02 (10H, m), 11.23 (0.5H, br), 12.50 (0.5H, br); MASS (ES+): m/e 532.

Preparation 81

Compound (81) was obtained from Compound (6) according to a manner similar to Preparation 7 (137 mg).

$^1$H-NMR (300 MHz, CDCl$_3$, δ): 1.33 (3H, t, J=7.5 Hz), 4.26 (2H, q, J=7.5 Hz), 4.38 (2H, s), 6.41 (1H, d, J=16 Hz), 7.18 (1H, dd, J=8, 4.5 Hz), 7.38 (2×1H, d, J=8 Hz), 7.51 (2×1H, d, J=8 Hz), 7.65 (1H, d, J=16 Hz), 7.99–8.10 (2H, m); MASS (ES+): m/e 308.

Preparation 82

Compound (82) was obtained from Compound (81) according to a manner similar to Preparation 12 (362 mg).

$^1$H-NMR (300 MHz, DMSO-d$_6$, δ): 4.23 (2H, s), 6.50 (1H, d, J=16 Hz) 7.17 (1H, dd, J=8, 5 Hz), 7.38 (2×1H, d, J=8 Hz), 7.56 (1H, d, J=16 Hz), 7.65 (2×1H, d, J=8 Hz), 7.91 (1H, br), 8.25 (1H, br); MASS (ES+): m/e 280.

Preparation 83

Compound (83) was obtained from Compound (82) according to a manner similar to Preparation 9 (312 mg). The Compound (83) was used in Example 29.

$^1$H-NMR (300 MHz, DMSO-d$_6$, δ): 1.46–1.76 (6H, m), 3.53 (1H, m), 3.95 (1H, m), 4.21 (2H, br-s), 4.90 (1H, m), 6.48 (1H, d, J=15.5 Hz), 7.17 (1H, dd, J=8, 4.5 Hz), 7.39 (2×1H, d, J=8 Hz), 7.46 (1H, d, J=15.5 Hz), 7.54 (2×1H, br-d, J=8 Hz), 7.88 (1H, m), 8.27 (1H, m), 11.24 (1H, br-s), 12.58 (0.5H, br), 13.00 (0.5H, br); MASS (ES+): m/e 379.

Preparation 84

Compound (84) was obtained from Compound (6) according to a manner similar to Preparation 7 (9.77 g).

$^1$H-NMR (300 MHz, DMSO-d$_6$, δ): 1.26 (3H, t, J=7 Hz), 3.74 (2H, s), 4.19 (2H, q, J=7 Hz), 6.54 (2H, s), 6.62 (1H, d, J=16 Hz), 6.77 (1H, d, J=8.8 Hz), 7.41 (2×1H, d, J=8 Hz), 7.65 (1H, d, J=16 Hz), 7.70 (2×1H, d, J=8 Hz), 7.85 (1H, dd, J=8.8, 2.5 Hz), 8.20 (1H, d, J=2.5 Hz), 9.46 (1H, s); MASS (ES+):: m/e 370.

Preparation 85

Compound (85) was obtained from Compound (84) according to a manner similar to Preparation 8 (6.83 g).

$^1$H-NMR (300 MHz, DMSO-d$_6$, δ): 1.25 (3H, t, J=7 Hz), 4.18 (2H, q, J=7 Hz), 4.44 (2H, s), 6.64 (1H, d, J=16 Hz), 7.46 (2×1H, d, J=8 Hz), 7.64 (1H, d, J=16 Hz), 7.73 (2×1H, d, J=8 Hz), 7.80 (1H, d, J=9 Hz), 8.20 (1H, dd, J=9, 2.2 Hz), 8.50 (1H, d, J=2.2 Hz); MASS (ES+): m/e 352.

Preparation 86

Compound (86) was obtained from Compound (85) according to a manner similar to Preparation 77 (872 mg).

$^1$H-NMR (300 MHz, CDCl$_3$, δ): 1.31 (3H, br-t, J=7 Hz), 4.15–4.36 (4H, m), 6.26 (1H, br-d, J=16 Hz), 6.64 (1H, m), 6.78 (1H, m), 7.20–7.40 (5H, m), 7.49 (1H, br-d, J=16 Hz); MASS (ES+): m/e 322.

Preparation 87

To a stirred suspension of Compound (86) (303 mg) in dioxane (10 mL) was added di-tert-butyldicarbonate (618 mg) in dioxane (3 mL) and then 1N-NaOH (2.8 mL), and the mixture was stirred at ambient temperature for 12 hours. The solvent was evaporated in vacuo and the residue was partioned between ethyl acetate and water. The organic phase was washed with brine, dried over Na$_2$SO$_4$, and concentrated in vacuo. The residue was purified by preparative thin layer chromatography (hexane:ethyl acetate=1:1) to give Compound (87) (379 mg) as a pale brown amorphous (379 mg).

$^1$H-NMR (300 MHz, CDCl$_3$, δ): 1.33 (3H, t, J=7 Hz), 1.52 (4.5H, s), 1.53 (4.5H, s), 1.58 (4.5H, s), 1.60 (4.5H, s), 4.25 (2H, q, J=7 Hz), 4.61 (2H, s), 6.39 (1H, d, J=16 Hz), 6.58 (1H, br-d, J=6 Hz), 7.09 (0.5H, dd, J=8.8, 2.2 Hz), 7.23–7.30 (2H, m), 7.42–7.48 (2.5H, m), 7.567.68 (2H, m), 7.77 (0.5H, d, J=8.8 Hz), 8.24 (0.5H, br); MASS (ES+): m/e 522.

Preparation 88

To a stirred solution of Compound (87) (360 mg) in methanol (5 mL) was added 1N-NaOH solution (1.4 mL). The mixture was stirred at ambient temperature for 2.5 hours. The reaction mixture was neutralized by 1N—HCl solution, and the solvent was evaporated in vacuo. The residue was partioned between ethyl acetate and water. The oraganic phase was washed with brine, dried over Na$_2$SO$_4$, and concentrated in vacuo. The residue was purified by preparative thin layer chromatography (chloroform:methanol=10:1) to give Compound (88) (57 mg) as an orange powder and a methyl ester of Compound (88) as a by-product.

$^1$H-NMR (300 MHz, DMSO-d$_6$, δ): 1.48 (3×3H, s), 4.16 (2H, s), 6.49 (1H, d, J=16 Hz), 7.12 (1H, br), 7.31–7.42 (3H, m), 7.55 (1H, d, J=16 Hz), 7.60–7.72 (3H, m), 9.25 (1H, br), 12.12 (1H, br); MASS (ES+): m/e 394.

Preparation 89

Compound (89) was obtained from the metyl ester of Compound (88) according to a manner similar to Preparation 12 (245 mg). [The Compound (89) is similar to Compound (88).]

$^1$H-NMR (300 MHz, DMSO-d$_6$, δ): 1.48 (3×3H, s), 4.22 (2H, s), 6.50 (1H, d, J=16 Hz), 7.19 (1H, br-d, J=8.5 Hz), 7.34–7.42 (3H, m), 7.56 (1H, d, J=16 Hz), 7.65 (2×1H, d, J=8.5 Hz), 7.72 (1H, br-s), 9.30 (1H, br-s), 12.38 (1H, br); MASS (ES+): m/e 394.

Preparation 90

Compound (90) was obtained from Compound (88) according to a manner similar to Preparation 9 (230 mg). The Compound (90) was used for Example 30.

$^1$H-NMR (300 MHz, DMSO-d$_6$, δ): 1.48 (3×3H, s), 1.48–1.75 (6H, m), 3.53 (1H, m), 3.94 (1H, m), 4.15 (2H, s), 4.90 (1H, m), 6.47 (1H, br-d, J=16 Hz), 7.06–7.414 (4H, m), 7.46 (1H, d, J=16 Hz), 7.53 (2×1H, br-d, J=8.5 Hz), 7.67 (1H, m), 9.15 (1/3H, br-s), 9.26 (2/3H, br-s), 11.22 (1H, br-s), 12.10 (2/3H, br-s), 12.13 (1/3H, br-s); MASS (ES+): m/e 493.

Preparation 91

To a stirred solution of Compound (86) (150 mg) in DMF (2 mL) was added butyric acid (49 mg), HOBT (76 mg), and EDCI hydrochloride (107 mg), and the resulting mixture was stirred at ambient temperature for 12 hours. The reaction mixture was diluted with ethyl acetate and washed successively with water, saturated NaHCO$_3$ solution and brine. The organic phase was dried over Na$_2$SO$_4$ and concentrated in vacuo. The residue was purified by preparative thin layer chromatography (chloroform:methanol=10:1) to give Compound (91) (30 mg) as a pale yellow amorphous.

$^1$H-NMR (300 MHz, CDCl$_3$, δ): 0.98 (3H, t, J=7.3 Hz), 1.33 (3H, t, J=7 Hz), 1.73 (2H, tq, J=7.3, 7.3 Hz), 2.33 (2H, t, J=7.3 Hz), 4.09 (2H, s), 4.24 (2H, q, J=7 Hz), 6.31 (1H, d, J=16 Hz), 7.05 (1H, br-d, J=8 Hz), 7.15 (2×1H, d, J=8 Hz), 7.32 (2×1H, d, J=8 Hz), 7.36 (1H, d, J=8 Hz), 7.53 (1H, s), 7.58 (1H, s); MASS (ES+): m/e 392.

Preparation 92

Compound (92) was obtained from Compound (91) according to a manner similar to Preparation 11 (28 mg).

$^1$H-NMR (300 MHz, CD$_3$OD, δ): 1.00 (3H, t, J=7.3 Hz), 1.73 (2H, tq, J=7.3, 7.3 Hz), 2.42 (2H, t, J=7.3 Hz), 4.58 (2H, s), 6.52 (1H, d, J=16 Hz), 7.47–7.58 (3H, m), 7.64–7.74 (4H, m), 8.29 (1H, s); MASS (ES+): m/e 364.

Preparation 93

Compound (93) was obtained from Compound (92) according to a manner similar to Preparation 9 (19 mg). The Compound (93) was used in Example 31.

$^1$H-NMR (300 MHz, CD$_3$OD-CDCl$_3$, δ): 1.00 (3H, t, J=7.4 Hz), 1.52–1.96 (8H, m), 2.35 (2H, t, J=7.5 Hz), 3.65 (1H, m), 4.03 (1H, m), 4.11 (2H, s), 5.03 (1H, m), 6.24 (1H, m), 7.06–7.29 (4H, m), 7.38 (2×1H, d, J=8.5 Hz), 7.48 (1H, m), 7.82 (1H, s); MASS (ES+): m/e 463.

Preparation 94

Compound (94) was obtained from Compound (6) according to a manner similar to Preparation 7 (641 mg).

$^1$H-NMR (300 MHz, DMSO-d$_6$, δ): 1.26 (3H, t, J=7 Hz), 3.76 (2H, s), 4.19 (2H, q, J=7 Hz), 6.62 (1H, d, J=16 Hz), 6.64 (1H, dd, J=8.5, 8.5 Hz), 7.12 (2H, s), 7.40 (2×1H, d, J=8.5 Hz), 7.45 (1H, dd, J=8.5, 1 Hz), 7.65 (1H, d, J=16 Hz), 7.69 (2×1H, d, J=8.5 Hz), 7.91 (1H, dd, J=8.5, 1 Hz), 9.57 (1H, s); MASS (ES+): m/e 370.

Preparation 95

Compound (95) was obtained from Compound (94) according to a manner similar to Preparation 8 (512 mg).

$^1$H-NMR (300 MHz, DMSO-d$_6$, δ): 1.25 (3H, t, J=7 Hz), 4.18 (2H, q, J=7 Hz), 4.45 (2H, s), 6.62 (1H, d, J=16 Hz), 7.46 (2×1H, d, J=8.3 Hz), 7.49 (1H, dd, J=8, 8 Hz), 7.63 (1H, d, J=16 Hz), 7.71 (2×1H, d, J=8.3 Hz), 8.11 (1H, d, J=8 Hz), 8.20 (1H, d, J=8 Hz); MASS (ES+): m/e 352.

Preparation 96

Compound (96) was obtained from Compound (95) according to a manner similar to Preparation 12 (119 mg).

$^1$H-NMR (300 MHz, DMSO-d$_6$, δ): 4.34 (2H, s), 6.49 (1H, d, J=16 Hz), 7.36 (1H, dd, J=8, 8 Hz), 7.41 (2×1H, d, J=8 Hz), 7.55 (1H, d, J=16 Hz), 7.64 (2×1H, d, J=8 Hz), 8.04 (1H, d, J=8 Hz), 8.09 (1H, d, J=8 Hz), 13.26 (1H, br-s); MASS (ES+): m/e 324.

Preparation 97

Compound (97) was obtained from Compound (96) according to a manner similar to Preparation 9 (70 mg). The Compound (97) was used in Example 32.

$^1$H-NMR (300 MHz, DMSO-d$_6$, δ): 1.45–1.77 (6H, m), 3.53 (1H, m) 3.95 (1H, m), 4.34 (2H, s), 4.90 (1H, m), 6.47 (1H, d, J=16 Hz), 7.37 (1H, dd, J=8, 8 Hz), 7.42 (2×1H, d, J=8 Hz), 7.46 (1H, d, J=16 Hz), 7.53 (2×1H, d, J=8 Hz), 8.05 (1H, d, J=8 Hz), 8.10 (1H, d, J=8 Hz); MASS (ES+): m/e 423.

Preparation 98

Compound (98) was obtained from Compound (6) according to a manner similar to Preparation 7 (160 mg).

$^1$H-NMR (300 MHz, DMSO-d$_6$, δ): 1.26 (3H, t, J=7 Hz), 3.75 (2H, s), 4.19 (2H, q, J=7 Hz), 6.47 (2H, br-s), 6.62 (1H, d, J=16 Hz), 6.70 (1H, d, J=6 Hz), 7.40 (2×1H, d, J=8 Hz), 7.65 (1H, d, J=16 Hz), 7.69 (2×1H, d, J=8 Hz), 7.91 (1H, d, J=6 Hz), 8.18 (1H, s), 9.61 (1H, s); MASS (ES+): m/e 326.

Preparation 99

Compound (99) was obtained from Compound (6) according to a manner similar to Preparation 8 (91 mg).

$^1$H-NMR (300 MHz, DMSO-d$_6$, δ): 4.26 (2H, s), 6.50 (1H, d, J=16 Hz), 7.38 (2×1H, d, J=8 Hz), 7.48 (1H, m), 7.56 (1H, d, J=16 Hz), 7.65 (2×1H, d, J=8 Hz), 8.25 (1H, d, J=3 Hz), 8.81 (1H, s), 12.75 (1H, br); MASS (ES+): m/e 280.

Preparation 100

Compound (100) was obtained from Compound (99) according to a manner similar to Preparation 9 (33 mg). The Compound (100) was used for Example 33.

$^1$H-NMR (300 MHz, DMSO-d$_6$, δ): 1.40–1.80 (6H, m), 3.52 (1H, m), 3.96 (1H, m), 4.26 (2H, s), 4.91 (1H, m), 6.50 (1H, br-d, J=15.5 Hz), 7.35–7.60 (6H, m), 8.22 (1H, d, J=5.5 Hz), 8.81 (1H, s); MASS (ES+) m/e 379.

Preparation 101

Compound (101) was obtained from Compound (6) according to a manner similar to Preparation 7 (520 mg).

$^1$H-NMR (300 MHz, DMSO-d$_6$, δ): 1.26 (3H, t, J=7 Hz), 3.11 (3H, s), 3.31 (3H, s), 3.62 (2H, s), 4.19 (2H, q, J=7 Hz), 6.54–6.68 (3H, m), 7.41 (2×1H, d, J=8 Hz), 7.58–7.70 (3H, m), 8.66 (1H, s); MASS (ES+): m/e 387.

Preparation 102

Compound (102) was obtained from Compound (101) according to a manner similar to Preparation 8 (416 mg).

$^1$H-NMR (300 MHz, DMSO-d$_6$, δ): 3.22 (3H, s), 3.40 (3H, s), 4.08 (2H, s), 6.49 (1H, d, J=16 Hz), 7.33 (2×1H, d, J=8.3 Hz), 7.55 (1H, d, J=16 Hz), 7.64 (2×1H, d, J=8.3 Hz), 12.39 (1H, s), 13.48 (1H, s); MASS (ES+): m/e 341.

Preparation 103

Compound (103) was obtained from Compound (102) according to a manner similar to Preparation 9 (254 mg). The Compound (103) was used in Example 34.

$^1$H-NMR (300 MHz, DMSO-d$_6$, δ): 1.46–1.76 (6H, m), 3.22 (3H, s), 3.40 (3H, s), 3.53 (1H, m), 3.95 (1H, m), 4.07 (2H, s), 4.90 (1H, m), 6.47 (1H, d, J=16 Hz), 7.33 (2×1H, d, J=7.5 Hz), 7.46 (1H, d, J=16 Hz), 7.53 (2×1H, d, J=7.5 Hz), 11.23 (1H, br-s), 13.47 (1H, br-s); MASS (ES−): m/e 438.

Preparation 104

Compound (104) was obtained from Compound (85) according to a manner similar to Preparation 12 (1.54 g).

$^1$H-NMR (300 MHz, DMSO-d$_6$, δ): 4.38 (2H, s), 6.52 (1H, d, J=16.2 Hz), 7.42 (2×1H, d, J=8 Hz), 7.57 (1H, d, J=16.2 Hz), 7.68 (2×1H, d, J=8 Hz), 7.74 (1H, d, J=8.8 Hz), 8.14 (1H, dd, J=8.8, 2.2 Hz), 8.46 (1H, d, J=2.2 Hz); MASS (ES+): m/e 324.

Preparation 105

Compound (105) was obtained from Compound (104) according to a manner similar to Preparation 9 (1.42 g). The Compound (105) was used in Example 35.

$^1$H-NMR (300 MHz, DMSO-d$_6$, δ): 1.45–1.76 (6H, m), 3.53 (1H, m), 3.95 (1H, m), 4.30 (2H, s), 4.90 (1H, m), 6.48 (1H, d, J=15.8 Hz), 7.39 (2×1H, d, J=8.5 Hz), 7.47 (1H, d, J=15.8 Hz), 7.55 (2×1H, d, J=8.5 Hz), 7.67 (1H, d, J=8.8 Hz), 8.08 (2×1H, d, J=8.8 Hz), 8.41 (1H, d, J=2.2 Hz), 11.25 (1H, br), 13.02 (1H, br); MASS (ES+): m/e 423.

Preparation 106

Thionyl chloride (1.75 mL) was dropwise added under stirring to methanol at 0° C. After 30 minutes 4-hydroxycinnamic acid (3.29 g) was added and the mixture was refluxed for 1.5 h. The solvent was evaporated in vacuo and the residue was crystalized from diisopropyl ether and hexane to give Compound (106) (2.41 g) as a white crystal.

¹H-NMR (300 MHz, CDCl₃, δ): 3.80 (3H, s), 5.44 (1H, s), 6.31 (1H, d, J=16 Hz), 6.85 (2×1H, d, J=8.5 Hz), 7.43 (2×1H, d, J=8.5 Hz), 7.64 (1H, d, J=16 Hz); MASS (ES−): m/e 177.

Preparation 107

To a stirred solution of Compound (106) (609 mg) in dimethylformamide (15 mL) was added sodium hydride (164 mg, 60% oil dispersion) at 0° C. After 30 minutes, tert-butyl bromoacetate (733 mg) was added dropwise, and the mixture was stirred at ambient temperature for 2 hours. The resulting mixture was poured into 10% citric acid solution and extracted with ethyl acetate. The organic phase was washed with saturated NaHCO₃ solution and brine, dried over sodium sulfate, and concentrated in vacuo. The residue was purified by chromatography (hexane:ethyl acetate=4:1) to give Compound (107) (962 mg) as a solid.

¹H-NMR (300 MHz, CDCl₃, δ): 1.49 (3×3H, s), 3.80 (3H, s), 4.55 (2H, s), 6.32 (1H, d, J=15.8 Hz), 6.90 (2×1H, d, J=8.8 Hz), 7.47 (2×1H, d, J=8.8 Hz), 7.65 (1H, d, J=15.8 Hz); MASS (ES+): m/e not detected.

Preparation 108

A solution of Compound (107) (906 mg) in 0.5 N-hydrogen chloride in acetic acid (10 mL) was heated at 60° C. for 2 hours. The solvent was evaporated in vacuo and the residue was triturated with diisopropyl ether to give Compound (108) (645 mg) as a white solid.

¹H-NMR (300 MHz, DMSO-d₆, δ): 3.71 (3H, s), 4.74 (2H, s), 6.51 (1H, d, J=16 Hz), 6.96 (2×1H, d, J=8.5 Hz), 7.62 (1H, d, J=16 Hz), 7.67 (2×1H, d, J=8.5 Hz), 13.07 (1H, br-s); MASS (ES−): m/e 235.

Preparation 109

Compound (109) was obtained from Compound (108) according to a manner similar to Preparation 7 (950 mg).

¹H-NMR (300 MHz, DMSO-d₆, δ): 1.45 (3×3H, s), 3.71 (3H, s), 4.79 (2H, s), 6.53 (1H, d, J=16 Hz), 7.07 (2×1H, d, J=8.8 Hz), 7.08–7.20 (2H, m), 7.46 (1H, m), 7.56 (1H, m), 7.63 (1H, d, J=16 Hz), 7.72 (2×1H, d, J=8.8 Hz), 8.73 (1H, br-s), 9.55 (1H, br-s); MASS (ES+): m/e 427.

Preparation 110

Compound (110) was obtained from Compound (109) according to a manner similar to Preparation 8 (800 mg).

¹H-NMR (300 MHz, DMSO-d₆, δ): 3.71 (3H, s), 5.69 (2H, s), 6.56 (1H, d, J=16 Hz), 7.20 (2×1H, d, J=8.8 Hz), 7.49–7.57 (2H, m), 7.65 (1H, d, J=16 Hz), 7.73–7.85 (4H, m); MASS (ES+): m/e 309.

Preparation 111

Compound (111) was obtained from Compound (110) according to a manner similar to Preparation 12 (580 mg).

¹H-NMR (300 MHz, DMSO-d₆, δ): 5.45 (2H, s), 6.41 (1H, d, J=16 Hz), 7.14 (2×1H, d, J=8.8 Hz), 7.23–7.32 (2H, m), 7.55 (1H, d, J=16 Hz), 7.56–7.66 (2H, m), 7.68 (2×1H, d, J=8.8 Hz), 12.28 (1H, br); MASS (ES+): m/e 295.

Preparation 112

Compound (112) was obtained from Compound (111) according to a manner similar to Preparation 9 (503 mg). The Compound (112) was used in Example 36.

¹H-NMR (300 MHz, DMSO-d₆, δ): 1.47–1.76 (6H, m), 3.53 (1H, m), 3.95 (1H, m), 4.89 (1H, m), 5.37 (2H, s), 6.37 (1H, d, J=16 Hz), 7.10–7.25 (4H, m), 7.39–7.67 (5H, m), 11.16 (1H, s), 12.68 (1H, s); MASS (ES+): m/e 394.

Preparation 113

To a stirred solution of Compound (86) (165 mg) in methanol (3 mL) were added cyclopentanone (52 mg) and sodium cyanoborohydride (39 mg). To the mixture was added acetic acid so that final pH was set to 5. The mixture was stirred at ambient temperature for 2 hours. The resulting mixture was poured into water and extracted with ethyl acetate. The organic phase was washed with brine, dried over magnesium sulfate, and concentrated in vacuo. The residue was purified by preparative thin layer chromatography (chloroform:methanol=10:1) to give Compound (113) (140 mg) as a brown oil.

¹H-NMR (300 MHz, CDCl₃, δ): 1.34 (3H, t, J=7.3 Hz), 1.40–1.77 (6H, m), 1.95–2.08 (2H, m), 3.76 (1H, m), 4.24 (2H, s), 4.26 (2H, q, J=7.3 Hz), 6.41 (1H, d, J=16 Hz), 6.56 (1H, dd, J=7, 2.2 Hz), 6.64 (1H, s), 7.31 (2×1H, d, J=8 Hz), 7.36 (1H, d, J=8.8 Hz), 7.48 (2×1H, d, J=8 Hz), 7.65 (1H, d, J=16 Hz); MASS (ES+): m/e 390.

Preparation 114

Compound (114) was obtained from Compound (113) according to a manner similar to Preparation 12 (91 mg).

¹H-NMR (300 MHz, DMSO-d₆, δ): 1.36–1.76 (6H, m), 1.89 (2H, m), 4.08 (2H, s), 6.44–6.56 (3H, m), 7.17 (1H, m), 7.34 (2×1H, d, J=8 Hz), 7.55 (1H, d, J=16 Hz), 7.62 (2×1H, d, J=8 Hz), 11.72 (1H, br); MASS (ES+): m/e 362.

Preparation 115

Compound (115) was obtained from Compound (114) according to a manner similar to Preparation 9 (40 mg). The Compound (115) was used in Example 37.

¹H-NMR (300 MHz, CDCl₃, δ): 1.38–2.08 (14H, m), 3.62 (1H, m), 3.75 (1H, m), 4.00 (1H, m), 4.11 (2H, s), 5.08 (1H, m), 6.20 (1H, br), 6.56 (1H, d, J=8 Hz), 6.68 (1H, s), 6.94–7.55 (6H, m); MASS (ES+): m/e 461.

Preparation 116

Compound (116) was obtained according to a manner similar to Preparation 106 (1.77 g).

¹H-NMR (300 MHz, DMSO-d₆, δ): 3.72 (3H, s), 6.53 (1H, d, J=16 Hz), 6.84 (1H, br-dd, J=8, 2 Hz), 7.04 (1H, br-d, J=2 Hz), 7.14 (1H, br-d, J=8 Hz), 7.22 (1H, dd, J=8, 8 Hz), 7.57 (1H, d, J=16 Hz), 9.63 (1H, s); MASS (ES−): m/e 177.

Preparation 117

Compound (117) was obtained from Compound (116) according to a manner similar to Preparation 107 (1.61 g).

¹H-NMR (300 MHz, CDCl₃, δ): 1.49 (3×3H, s), 3.81 (3H, s), 4.54 (2H, s), 6.41 (1H, d, J=16 Hz), 6.92 (1H, dd, J=8, 2.5 Hz), 7.04 (1H, dd, J=2.5, 2.5 Hz), 7.15 (1H, br-d, J=8 Hz), 7.31 (1H, dd, J=8, 8 Hz), 7.64 (1H, d, J=16 Hz); MASS (ES+): m/e not detected.

Preparation 118

Compound (118) was obtained from Compound (117) according to a manner similar to Preparation 8 (1.25 g).

¹H-NMR (300 MHz, CDCl₃, δ): 3.82 (3H, s), 4.72 (2H, s), 6.43 (1H, d, J=16 Hz), 6.96 (1H, dd, J=8, 2.5 Hz), 7.07 (1H, br-s), 7.20 (1H, br-d, J=8 Hz), 7.34 (1H, dd, J=8, 8 Hz), 7.65 (1H, d, J=16 Hz); MASS (ES−): m/e 235.

Preparation 119

Compound (119) was obtained from Compound (118) according to a manner similar to Preparation 7 (1.92 g).

¹H-NMR (300 MHz, CDCl₃, δ): 1.49 (3×3H, s), 3.82 (3H, s), 4.69 (2H, s), 6.45 (1H, d, J=16 Hz), 6.69 (1H, br-s), 7.03 (1H, dd, J=8, 2.5 Hz), 7.15–7.26 (4H, m), 7.37 (1H, dd, J=8, 8 Hz), 7.41 (1H, m), 7.63 (1H, m), 7.66 (1H, d, J=16 Hz), 9.00 (1H, br-s); MASS (ES+): m/e 427.

Preparation 120

Compound (120) was obtained from Compound (119) according to a manner similar to Preparation 8 (1.67 g).

$^1$H-NMR (300 MHz, DMSO-d$_6$, δ): 3.74 (3H, s), 5.68 (2H, s), 6.74 (1H, d, J=16 Hz), 7.21 (1H, m), 7.40–7.46 (2H, m), 7.49–7.59 (3H, m), 7.68 (1H, d, J=16 Hz), 7.77–7.85 (2H, m); MASS (ES+): m/e 309.

Preparation 121

Compound (121) was obtained from Compound (120) according to a manner similar to Preparation 12 (1.24 g).

$^1$H-NMR (300 MHz, DMSO-d$_6$, δ): 5.37 (2H, s), 6.58 (1H, d, J=16 Hz), 7.11–7.26 (3H, m), 7.27–7.40 (2H, m), 7.45 (1H, br-s), 7.50 (1H, m), 7.57 (1H, d, J=16 Hz), 7.63 (1H, m), 12.69 (1H, s); MASS (ES+): m/e 295.

Preparation 122

Compound (122) was obtained from Compound (120) according to a manner similar to Preparation 9 (1662 mg). The Compound (122) was used in Example 38.

$^1$H-NMR (300 MHz, DMSO-d$_6$, δ): 1.46–1.78 (6H, m), 3.54 (1H, m), 3.96 (1H, m), 4.91 (1H, m), 5.36 (2H, s), 6.53 (1H, d, J=16 Hz), 7.12 (1H, dd, J=8, 2.5 Hz), 7.15–7.26 (3H, m), 7.32 (1H, br-s), 7.36 (1H, dd, J=8, 8 Hz), 7.46–7.68 (2H, m), 7.47 (1H, d, J=16 Hz), 11.27 (1H, br-s), 12.69 (1H, br-s); MASS (ES+): m/e 394.

Preparation 123

Compound (123) was obtained from Compound (86) according to a manner similar to Preparation 113 (415 mg).

$^1$H-NMR (300 MHz, CDCl$_3$, δ): 1.12 (2×3H, t, J=7 Hz), 1.34 (3H, t, J=7 Hz), 3.34 (2×2H, q, J=7 Hz), 4.23 (2H, s), 4.26 (2H, q, J=7 Hz), 6.39 (1H, d, J=16 Hz), 6.79 (1H, dd, J=9, 2 Hz), 6.91 (1H, d, J=2 Hz), 7.30 (2×1H, d, J=8 Hz), 7.44 (1H, d, J=9 Hz), 7.45 (2×1H, d, J=8 Hz), 7.63 (1H, d, J=16 Hz); MASS (ES+): m/e 378.

Preparation 124

Compound (124) was obtained from Compound (123) according to a manner similar to Preparation 12 (227 mg).

$^1$H-NMR (300 MHz, DMSO-d$_6$, δ): 1.05 (2×3H, t, J=7 Hz), 3.28 (2×2H, q, J=7 Hz), 4.12 (2H, s), 6.49 (1H, d, J=16 Hz), 6.61–6.72 (2H, m), 7.28 (1H, br-d, J=8 Hz), 7.35 (2×1H, d, J=8 Hz), 7.56 (1H, d, J=16 Hz), 7.63 (2×1H, d, J=8 Hz), 11.82 (1H, br-s); MASS (ES+): m/e 350.

Preparation 125

Compound (125) was obtained from Compound (124) according to a manner similar to Preparation 9 (132 mg). The Compound (125) was used in Example 39.

$^1$H-NMR (300 MHz, CDCl$_3$, δ): 1.12 (2×3H, t, J=7 Hz), 1.50–1.92 (6H, m), 3.32 (2×3H, q, J=7 Hz), 3.62 (1H, m), 4.00 (1H, m), 4.15 (2H, br-s), 5.07 (1H, m), 6.22 (1H, br), 6.71–6.83 (2H, m), 6.96–7.28 (3H, m), 7.38–7.54 (3H, m); MASS (ES+): m/e 449.

Preparation 126

Compound (126) was obtained according to a manner similar to Preparation 106 (4.19 g).

$^1$H-NMR (300 MHz, CDCl$_3$, δ): 3.80 (3H, s), 3.93 (3H, s), 5.85 (1H, br-s), 6.30 (1H, d, J=16 Hz), 6.92 (1H, d, J=8 Hz), 7.03 (1H, d, J=2 Hz), 7.08 (1H, dd, J=8, 2 Hz), 7.63 (1H, d, J=16 Hz); MASS (ES+): m/e not detected.

Preparation 127

Compound (127) was obtained from Compound (126) according to a manner similar to Preparation 107 (5.16 g).

$^1$H-NMR (300 MHz, CDCl$_3$, δ): 1.47 (3×3H, s), 3.80 (3H, s), 3.92 (3H, s), 4.62 (2H, s), 6.32 (1H, d, J=16 Hz), 6.76 (1H, d, J=8.7 Hz), 7.04–7.09 (2H, m), 7.63 (1H, d, J=16 Hz); MASS (ES+): m/e not detected.

Preparation 128

Compound (128) was obtained from Compound (127) according to a manner similar to Preparation 8 (4.28 g).

$^1$H-NMR (300 MHz, CDCl$_3$, δ): 3.81 (3H, s), 3.93 (3H, s), 4.74 (2H, s), 6.35 (1H, d, J=16 Hz), 6.89 (1H, d, J=9 Hz), 7.07–7.12 (2H, m), 7.63 (1H, d, J=16 Hz); MASS (ES–): m/e 265.

Preparation 129

Compound (129) was obtained from Compound (128) according to a manner similar to Preparation 7 (5.43 g).

$^1$H-NMR (300 MHz, DMSO-d$_6$, δ): 1.42 (3×3H, s), 3.72 (3H, s), 3.86 (3H, s), 4.76 (2H, s), 6.61 (1H, d, J=16 Hz), 7.02 (1H, d, J=8.5 Hz), 7.08–7.19 (2H, m), 7.25 (1H, dd, J=8.5, 2 Hz), 7.40–7.48 (2H, m), 7.57–7.66 (2H, m), 8.71 (1H, s), 9.46 (1H, s); MASS (ES+): m/e 457.

Preparation 130

Compound (130) was obtained from Compound (129) according to a manner similar to Preparation 8 (4.35 g).

$^1$H-NMR (300 MHz, DMSO-d$_6$, δ): 3.72 (3H, s), 3.85 (3H, s), 5.67 (2H, s), 6.65 (1H, d, J=16 Hz), 7.20–7.32 (2H, m), 7.49 (1H, s), 7.54–7.62 (2H, m), 7.63 (1H, d, J=16 Hz), 7.80–7.88 (2H, m); MASS (ES+): m/e 339.

Preparation 131

Compound (131) was obtained from Compound (130) according to a manner similar to Preparation. 12 (1.63 g).

$^1$H-NMR (300 MHz, DMSO-d$_6$, δ): 3.83 (3H, s), 5.33 (2H, s), 6.47 (1H, d, J=16 Hz), 7.14–7.26 (4H, m), 7.36 (1H, s), 7.50 (1H, m), 7.52 (1H, d, J=16 Hz), 7.63 (1H, m), 12.70 (1H, s); MASS (ES+): m/e 325.

Preparation 132

Compound (132) was obtained from Compound (131) according to a manner similar to Preparation 9 (1.93 g). The Compound (132) was used in Example 40.

$^1$H-NMR (300 MHz, DMSO-d$_6$, δ): 1.45–1.77 (6H, m), 3.53 (1H, m), 3.82 (3H, s), 3.95 (1H, m), 4.90 (1H, m), 5.32 (2H, s), 6.41 (1H, d, J=16 Hz), 7.10–7.28 (5H, m), 7.43 (1H, d, J=16 Hz), 7.50 (1H, m), 7.62 (1H, m), 11.13 (1H, s), 12.69 (1H, s); MASS (ES+): m/e 424.

Preparation 133

Compound (133) was obtained from Compound (86) according to a manner similar to Preparation 113 (437 mg).

$^1$H-NMR (300 MHz, CDCl$_3$, δ): 1.34 (3H, t, J=7 Hz), 2.92 (2×3H, s), 4.21 (2H, s), 4.26 (2H, q, J=7 Hz), 6.39 (1H, d, J=16 Hz),6.75–6.84 (2H, m), 7.24–7.32 (2H, m), 7.42–7.50 (3H, m), 7.63 (1H, d, J=16 Hz); MASS (ES+): m/e 350.

Preparation 134

The ethylcarbonyl group of Compound (133) was deprotected according to a manner similar to Preparation 12. The obtained compound (300 mg) was suspended in dioxane (10 mL). To the suspension was added 1N-NaOH (3 mL) di-tert-butyldicarbonate (407 mg) in dioxane (4 mL) and the mixture was stirred at ambient temperature for 12 hours. Additional di-tert-butyldicarbonate (407 mg) and 1N-NaOH (3 mL) was added and the mixture was stirred at ambient temperature for 6 hours. The solvent was evaporated in vacuo and the residue was partioned between diisopropyl ether and water. The aqueous phase was acidified with hydrochloric acid to pH 5 and the precipitate was collected and washed with water to give Compound (134) (326 mg) as a pale brown powder. The obtained compound (134) was used in Example 41.

$^1$H-NMR (300 MHz, CDCl$_3$, δ): 1.45–1.95 (15H, m), 2.94–3.03 (6H, m), 3.65 (1H, m), 3.96 (1H, m), 4.54–4.64 (2H, m), 5.00 (1H, m), 6.30–7.80 (9H, m); MASS (ES+) m/e 521.

Preparation 135

Compound (135) was obtained according to a manner similar to Preparation 106 (2.11 g).

$^1$H-NMR (300 MHz, CDCl$_3$, δ): 3.79 (3H, s), 3.93 (3H, s), 6.30 (1H, d, J=16 Hz), 6.85 (1H, d, J=8 Hz), 7.03 (1H, dd, J=8, 2 Hz), 7.14 (1H, d, J=2 Hz), 7.60 (1H, d, J=16 Hz); MASS (ES+): m/e 209.

Preparation 136

Compound (136) was obtained from Compound (135) according to a manner similar to Preparation 107 (3.12 g).

$^1$H-NMR (300 MHz, CDCl$_3$, δ): 1.48 (3×3H, s), 3.79 (3H, s), 3.91 (3H, s), 4.61 (2H, s), 6.26 (1H, d, J=16 Hz), 6.89 (1H, d, J=8.3 Hz), 6.97 (1H, d, J=2 Hz), 7.14 (1H, dd, J=8.3, 2 Hz), 7.60 (1H, d, J=16 Hz); MASS (ES+): m/e 323.

Preparation 137

Compound (137) was obtained from Compound (136) according to a manner similar to Preparation 8 (2.03 g).

$^1$H-NMR (300 MHz, DMSO-d$_6$, δ): 3.71 (3H, s), 3.81 (3H, s), 4.75 (2H, s), 6.54 (1H, d, J=16 Hz), 7.01 (1H, d, J=8 Hz), 7.27 (1H, dd, J=8, 2 Hz), 7.31 (1H, d, J=2 Hz), 7.57 (1H, d, J=16 Hz), 12.87 (1H, br); MASS (ES+): m/e 267.

Preparation 138

Compound (138) was obtained from Compound (137) according to a manner similar to Preparation 8 (2.97 g).

$^1$H-NMR (300 MHz, CDCl$_3$, δ): 1.47 (3×3H, s), 3.80 (3H, s), 3.93 (3H, s), 4.72 (2H, s), 6.33 (1H, d, J=16 Hz), 6.95 (1H, d, J=8 Hz), 6.96 (1H, br), 7.12–7.29 (4H, m), 7.47 (1H, br-d, J=7.5 Hz), 7.62 (1H, d, J=16 Hz), 7.64 (1H, br-d, J=7.5 Hz), 9.02 (1H, s); MASS (ES+) m/e 457.

Preparation 139

Compound (139) was obtained from Compound (138) according to a manner similar to Preparation 7 (2.29 g).

$^1$H-NMR (300 MHz, DMSO-d$_6$, δ): 3.71 (3H, s), 3.83 (3H, s), 5.63 (2H, s), 6.61 (1H, d, J=16 Hz), 7.11 (1H, d, J=8.4 Hz), 7.42 (1H, dd, J=8.4, 2 Hz), 7.50–7.58 (2H, m), 7.61 (1H, d, J=16 Hz), 7.65 (1H, d, J=2 Hz), 7.78–7.96 (2H, m); MASS (ES+) m/e 339.

Preparation 140

Compound (140) was obtained from Compound (139) according to a manner similar to Preparation 12 (1.84 g).

$^1$H-NMR (300 MHz, DMSO-d$_6$, δ): 3.81 (3H, s), 5.36 (2H, s), 6.45 (1H, d, J=16 Hz), 7.04 (1H, d, J=8.8 Hz), 7.20–7.28 (2H, m), 7.28 (1H, dd, J=8.8, 2 Hz), 7.52 (1H, d, J=16 Hz), 7.55–7.64 (2H, m), 7.57 (1H, d, J=2 Hz), 12.26 (1H, br-s); MASS (ES+) m/e 325.

Preparation 141

Compound (141) was obtained from Compound (140) according to a manner similar to Preparation 9 (609 mg). The Compound (141) was used in Example 42.

$^1$H-NMR (300 MHz, DMSO-d$_6$, δ): 1.42–1.78 (6H, m), 3.53 (1H, m) 3.81 (3H, s), 3.96 (1H, m), 4.90 (1H, m), 5.32 (2H, s), 6.40 (1H, br-d, J=16 Hz), 7.05 (1H, d, J=8.4 Hz), 7.16–7.26 (3H, m), 7.36–7.47 (2H, m), 7.50–7.66 (2H, m), 11.18 (1H, br), 12.69 (1H, br); MASS (ES+) m/e 424.

Preparation 142

Compound (142) was obtained from Compound (6) according to a manner similar to Preparation 7 (400 mg).

$^1$H-NMR (300 MHz, CDCl$_3$, δ): 1.54 (9H, s), 3.76 (2H, s), 5.86 (2H, s), 6.33 (1H, s), 6.38 (1H, d, J=16.1 Hz), 6.77 (1H, s), 7.37 (2H, d, J=8.1 Hz), 7.54 (2H, d, J=8.1 Hz), 7.58 (1H, d, J=16.5 Hz); MASS (ES+): m/e 397 (M+1).

Preparation 143

Compound (143) was obtained from Compound (142) according to a manner similar to Preparation 8 (305 mg).

$^1$H-NMR (300 MHz, DMSO-d$_6$, δ): 4.44 (2H, s); 6.15 (2H, s), 6.55 (1H, d, J=16.2 Hz), 7.29 (2H, s), 7.42 (2H, d, J=8.1 Hz), 7.58 (1H, d, J=15.7 Hz), 7.72 (2H, d, J=8.4 Hz); MASS (ES+): m/e 323 (M+1).

Preparation 144

Compound (144) was obtained from Compound (143) according to a manner similar to Preparation 9 (196 mg). The Compound (144) was used in Example 43.

$^1$H-NMR (300 MHz, DMSO-d$_6$, δ): 1.53 (3H, br), 1.69 (3H, br), 3.53 (1H, m), 3.95 (1H, m), 4.11 (2H, s), 4.90 (1H, s), 5.95 (2H, s), 6.46 (1H, d, J=15.4 Hz), 6.96 (1H, s), 7.03 (1H, s), 7.34 (2H, d, J=8.1 Hz), 7.46 (1H, d, J=15.8 Hz), 7.52 (2H, d, J=8.1 Hz); MASS (ES+): m/e 422 (M+1).

Preparation 145

Compound (145) was obtained from Compound (6) according to a manner similar to Preparation 7 (460 mg).

$^1$H-NMR (300 MHz, CDCl$_3$, δ): (1:1 mixture) 1.54 (9H, s), 3.71 (3H, s), 3.82 (2H, s), 6.30 (1H, d, J=8.1 Hz), 6.39 (1H, d, J=16.1 Hz), 6.41 (1H, d, J=8.0 Hz), 6.98 (1H, t, J=8.4 Hz), 7.40 (2H, d, J=8.4 Hz), 7.54 (2H, d, J=8.4 Hz), 7.59 (1H, d, J=15.7 Hz), 1.54 (9H, s), 3.77 (2H, s), 3.83 (3H, s), 6.37 (1H, d, J=15.8 Hz), 6.65–6.74 (sH, m), 6.80 (1H, dd, J=7.7, 1.8 Hz), 7.37 (2H, d, J=8.4 Hz), 7.53 (2H, d, J=8.4 Hz), 7.57 (1H, d, J=17.2 Hz); MASS (ES+): m/e 383 (M+1).

Preparation 146

Compound (146) was obtained from Compound (145) according to a manner similar to Preparation 8 (326 mg).

$^1$H-NMR (300 MHz, DMSO-d, 6): 4.00 (3H, s), 4.44 (2H, s), 6.54 (1H, d, J=15.7 Hz), 7.06 (1H, d, J=8.7 Hz), 7.24 (1H, d, J=8.1 Hz), 7.40 (1H, t, J=8.1 Hz), 7.44 (2H, d, J=8.4 Hz), 7.58 (1H, d, J=16.0 Hz), 7.71 (2H, d, J=8.2 Hz); MASS (ES+): m/e 309 (M+1).

Preparation 147

Compound (147) was obtained from Compound (146) according to a manner similar to Preparation 9 (308 mg). The Compound (147) was used in Example 44.

$^1$H-NMR (300 MHz, CDCl$_3$, δ): 1.53 (3H, br), 1.69 (3H, br), 3.52 (1H, m), 3.90 (3H, s), 3.95 (1H, m), 4.15 (2H, s), 4.90 (1H, s), 6.46 (1H, d, J=16.2 Hz), 6.68 (1H, br), 7.04 (2H, m), 7.35 (2H, d, J=8.0 Hz), 7.45 (1H, d, J=16.4 Hz), 7.52 (2H, d, J=8.0 Hz); MASS (ES+): m/e 408 (M+1).

Preparation 148

Compound (148) was obtained according to a manner similar to Preparation 6 (929 mg).

$^1$H-NMR (300 MHz, CDCl$_3$, δ): 1.50 (3H, d, J=6.9 Hz); 1.53 (9H, s), 3.75 (1H, q, J=7.1 Hz), 6.33 (1H, d, J=16.1 Hz), 7.32 (2H, d, J=8.5 Hz), 7.45 (2H, d, J=8.1 Hz), 7.55 (1H, d, J=16.1 Hz); MASS (ES+): not detected.

Preparation 149

Compound (149) was obtained from Compound (148) according to a manner similar to Preparation 7 (1.09 g).

$^1$H-NMR (300 MHz, CDCl$_3$, δ): 1.54 (9H, s), 1.60 (3H, d, J=7.0 Hz), 3.79 (1H, q, J=7.0 Hz), 6.36 (1H, d, J=16.0 Hz), 6.70–6.78 (2H, m), 6.98–7.04 (1H, m), 7.08–7.15 (1H, m), 7.40 (2H, d, J=8.6 Hz), 7.51 (2H, d, J=8.4 Hz), 7.56 (1H, d, J=16.0 Hz); MASS (ES+): m/e 367 (M+1).

Preparation 150

Compound (150) was obtained from Compound (149) according to a manner similar to Preparation 8 (567 mg).

$^1$H-NMR (300 MHz, DMSO-d$_6$, δ): 1.86 (3H, d, J=7.0 Hz), 4.83 (1H, q, J=7.0 Hz), 6.55 (1H, d, J=15.8 Hz), 7.49 (2H, d, J=8.1 Hz), 7.52–7.55 (2H, m), 7.58 (1H, d, J=16.4 Hz), 7.73 (2H, d, J=8.1 Hz), 7.76–7.79 (2H, m); MASS (ES+): m/e 293 (M+1).

Preparation 151

Compound (151) was obtained from Compound (150) according to a manner similar to Preparation 9 (598 mg). The Compound (151) was used in Example 45.

$^1$H-NMR (300 MHz, DMSO-d$_6$, δ): 1.53 (3H, br), 1.68 (3H, br), 1.70 (3H, d, J=7.3 Hz), 3.52 (1H, m), 3.93 (1H, m), 4.41 (1H, q, J=7.0 Hz), 4.89 (1H, s), 6.47 (1H, d, J=16.5 Hz), 7.08–7.15 (2H, m), 7.34–7.40 (2H, m), 7.37 (2H, d, J=8.3 Hz), 7.44 (1H, d, J=16.5 Hz), 7.52 (2H, d, J=8.0 Hz); MASS (ES+): m/e 392 (M+1).

Preparation 152

Compound (152) was obtained according to a manner similar to Preparation 6 (1.2 g).

$^1$H-NMR (300 MHz, CDCl$_3$, δ): 1.51 (3H, d, J=6.9 Hz), 1.53 (9H, s), 3.76 (1H, q, J=7.1 Hz), 6.34 (1H, d, J=16.0 Hz), 7.33 (2H, d, J=8.5 Hz), 7.47 (2H, d, J=81 Hz), 7.56 (1H, d, J=16.0 Hz); MASS (ES+): not detected.

Preparation 153

Compound (153) was obtained from Compound (152) according to a manner similar to Preparation 7 (1.298 g).

$^1$H-NMR (300 MHz, CDCl$_3$, δ): 1.54 (9H, s), 1.61 (3H, d, J=7.0 Hz), 3.79 (1H, q, J=7.0 Hz), 6.36 (1H, d, J=16.0 Hz), 6.70–6.75 (2H, m), 6.97–7.05 (1H, m), 7.09–7.14 (1H, m), 7.24 (2H, d, J=8.4 Hz), 7.51 (2H, d, J=8.5 Hz), 7.56 (1H, d, J=16.2 Hz); MASS (ES+): m/e 367 (M+1)

Preparation 154

Compound (154) was obtained from Compound (153) according to a manner similar to Preparation 8 (611 mg).

$^1$H-NMR (300 MHz, DMSO-d$_6$, δ): 1.86 (3H, d, J=7.4 Hz), 4.83 (1H, q, J=7.1 Hz), 6.55 (1H, d, J=15.7 Hz), 7.49 (2H, d, J=8.0 Hz), 7.52–7.55 (2H, m), 7.58 (1H, d, J=16.2 Hz), 7.74 (2H, d, J=8.4 Hz), 7.76–7.79 (2H, m); MASS (ES+): m/e 293 (M+1).

Preparation 155

Compound (155) was obtained from Compound (154) according to a manner similar to Preparation 9 (700 mg). The Compound (155) was used in Example 46.

$^1$H-NMR (300 MHz, DMSO-d$_6$, δ): 1.52 (3H, br), 1.68 (3H, br), 1.70 (3H, d, J=6.9 Hz), 3.50 (1H, m), 3.93 (1H, m), 4.41 (1H, q, J=7.1 Hz), 4.89 (1H, s), 6.48 (1H, d, J=16.1 Hz), 7.08–7.14 (2H, m), 7.34–7.40 (2H, m), 7.37 (2H, d, J=8.3 Hz), 7.47 (2H, d, J=16.1 Hz), 7.51 (2H, d, J=8.9 Hz); MASS (ES+): m/e 392 (M+1).

Preparation 156

Compound (156) was obtained according to a manner similar to Preparation 7 (536 mg).

$^1$H-NMR (300 MHz, CDCl$_3$, δ): 1.34 (3H, t, J=7.0 Hz), 1.46 (9H, s), 1.48 (9H, s), 4.05 (2H, q, J=7.0 Hz), 6.50 (1H, d, J=16.1 Hz), 6.98 (2H, d, J=8.4 Hz), 7.01 (1H, d, J=7.7 Hz), 7.40 (2H, d, J=7.7 Hz), 7.50 (2H, d, J=8.8 Hz), 7.52 (1H, d, J=8.4 Hz), 7.55 (1H, d, J=16.3 Hz), 7.66 (2H, d, J=8.1 Hz), 7.68 (1H, s); MASS (ES+): m/e 573 (M+1).

Preparation 157

Compound (157) was obtained from Compound (156) according to a manner similar to Preparation 8 (345 mg).

$^1$H-NMR (300 MHz, DMSO-d$_6$, δ): 1.36 (3H, t, J=7.0 Hz), 4.08 (2H, q, J=7.0 Hz), 4.55 (2H, s), 6.56 (1H, d, J=16.1 Hz), 7.05 (2H, d, J=8.8 Hz), 7.49 (2H, d, J=8.4 Hz), 7.60 (1H, d, J=16.1 Hz), 7.65 (2H, d, J=9.1 Hz), 7.74 (2H, d, J=8.4 Hz), 7.77 (2H, m), 7.88 (1H, s); MASS (ES+): m/e 399 (M+1).

Preparation 158

Compound (158) was obtained from Compound (157) according to a manner similar to Preparation 9 (370 mg). The Compound (158) was used in Example 47.

$^1$H-NMR (300 MHz, DMSO-d$_6$, δ): 1.35 (3H, t, J=7.0 Hz), 1.54 (3H, br), 1.68 (3H, br), 3.53 (1H, m), 3.94 (1H, m), 4.06 (2H, q, J=7.0 Hz), 4.21 (2H, s), 4.90 (1H, s), 6.48 (1H, d, J=16.1 Hz), 7.00 (2H, dd, J=8.8, 2.2 Hz), 7.38 (3H, m), 7.44 (1H, s), 7.50 (1H, m), 7.53–7.60 (5H, m), 7.72 (1H, s); MASS (ES+): m/e 498 (M+1).

Preparation 159

Compound (159) was obtained from Compound (6) according to a manner similar to Preparation 7 (652 mg).

$^1$H-NMR (300 MHz, DMSO-d$_6$, δ): 1.47 (9H, s), 1.49 (9H, s), 3.77 (2H, s), 6.50 (1H, d, J=16.1 Hz), 7.40 (2H, d, J=7.9 Hz), 7.49 (1H, d, J=7.9 Hz), 7.50 (1H, m), 7.60 (1H, m), 7.67 (2H, d, J=8.1 Hz), 8.00 (1H, m), 8.51 (1H, m), 8.55 (1H, m), 8.83 (1H, m), 9.76 (1H, d, J=7.7 Hz); MASS (ES+): m/e 530 (M+1).

Preparation 160

Compound (160) was obtained from Compound (159) according to a manner similar to Preparation 8 (458 mg).

$^1$H-NMR (300 MHz, DMSO-d$_6$, δ): 4.58 (2H, s), 6.56 (1H, d, J=16.1 Hz), 7.51 (2H, d, J=8.1 Hz), 7.59 (1H, d, J=16.1 Hz), 7.74 (2H, d, J=8.4 Hz), 7.90 (2H, s), 8.14 (1H, s), 8.53 (1H, d, J=7.7 Hz), 8.76 (1H, d, J=5.1 Hz), 9.15 (1H, s); MASS (ES+): m/e 356 (M+1).

Preparation 161

Compound (161) was obtained from Compound (160) according to a manner similar to Preparation 9 (316 mg). The Compound (161) was used in Example 48.

$^1$H-NMR (300 MHz, DMSO-d$_6$, δ): 1.53 (3H, br), 1.69 (3H, br), 3.53 (1H, m), 3.95 (1H, m), 4.23 (2H, s), 4.90 (1H, s), 6.48 (1H, d, J=15.7 Hz), 7.39 (2H, d, J=8.1 Hz), 7.44–7.52 (4H, m), 7.54 (2H, d, J=8.4 Hz), 7.80 (1H, br), 8.08 (1H, m), 8.53 (1H, m), 8.90 (1H, m); MASS (ES+): m/e 455 (M+1).

Preparation 162

Compound (162) was obtained according to a manner similar to Preparation 7 (748 mg).

$^1$H-NMR (300 MHz, CDCl$_3$, δ): 1.54 (9H, s), 3.80 (2H, s), 6.38 (1H, d, J=16.1 Hz), 6.76 (1H, d, J=8.1 Hz), 7.11 (sH,), 7.38 (2H, d, J=7.7 Hz), 7.47 (2H, d, J=7.7 Hz), 7.52–7.60 (5H, m), 7.71 (2H, d, J=7.0 Hz); MASS (ES+): m/e 457 (M+1).

Preparation 163

Compound (163) was obtained from Compound (162) according to a manner similar to Preparation 8 (521 mg).

$^1$H-NMR (300 MHz, DMSO-d$_6$, δ): 4.49 (2H, s), 6.54 (1H, d, J=16.1 Hz), 7.47 (2H, d, J=7.7 Hz), 7.56–7.62 (3H, m), 7.67–7.77 (3H, m), 7.81 (2H, s), 7.98 (1H, s); MASS (ES+): m/e 383 (M+1)

Preparation 164

Compound (164) was obtained from Compound (163) according to a manner similar to Preparation 9 (185 mg). The Compound (164) was used in Example 49.

$^1$H-NMR (300 MHz, DMSO-d$_6$, δ): 1.53 (3H, br), 1.69 (3H, br), 3.53 (1H, m), 3.95 (1H, m), 4.27 (2H, s), 4.90 (1H, s), 6.48 (1H, d, J=16.1 Hz), 7.39 (2H, d, J=8.0 Hz), 7.46 (1H, d, J=15.7 Hz), 7.56 (5H, m), 7.62 (2H, s), 7.67 (3H, m), 7.73 (2H, d, J=7.0 Hz), 7.86 (1H, s) MASS (ES+): m/e 482 (M+1).

Preparation 165

To a solution of Compound (60) in EtOH (3 mL) was added sodium borohydride (28 mg) at 5° C. and the mixture was allowed to warm to ambient temperature. After stirred for 0.5 hr, sodium borohydride (14 mg) was added to the mixture, and sodium borohydride (14 mg) was then additionally added three times to the mixture before Compound (60) was disappeared. The mixture was poured into water and washed with ether. The aqueous phase was acidified with 1N hydrochloric acid to pH 4 and extracted with ethyl acetate, washed with brine. The organic phase was dried over Na$_2$SO$_4$ and the solvent was removed in vacuo to give Compound (165) (120 mg) as colorless form.

$^1$H-NMR (300 MHz, DMSO-d$_6$, δ): 4.44 (2H, s), 5.86 (1H, s), 6.06 (1H, br), 6.53 (1H, d, J=16.1 Hz), 7.19 (1H, t, J=7.3 Hz), 7.29 (2H, t, J=7.3 Hz), 7.38 (3H, d, J=7.0 Hz), 7.42 (2H, d, J=8.1 Hz), 7.56 (1H, d, J=5.5 Hz), 7.60 (1H, d, J=1.8 Hz), 7.67 (1H, s), 7.70 (2H, d, J=8.4 Hz); MASS (ES+): m/e 385 (M+1).

Preparation 166

Compound (166) was obtained from Compound (165) according to a manner similar to Preparation 9 (104 mg). The Compound (166) was used in Example 50.

$^1$H-NMR (300 MHz, DMSO-d$_6$, δ): 1.53 (3H, br), 1.68 (3H, br), 3.50 (1H, m), 3.93 (1H, m), 4.16 (2H, s), 4.90 (1H, s), 5.77 (1H, s), 5.82 (1H, br), 6.45 (1H, d, J=16.5 Hz), 7.12 (1H, m), 7.18 (1H, d, J=6.6 Hz), 7.27 (2H, d, J=7.5 Hz), 7.32 (2H, t, J=7.3 Hz), 7.34 (1H, s), 7.36 (2H, d, J=7.4 Hz), 7.42 (2H, m), 7.51 (2H, d, J=8.1 Hz) MASS (ES+): m/e 484 (M+1).

Preparation 167

Compound (167) was obtained from Compound (6) according to a manner similar to Preparation 7 (234 mg).

$^1$H-NMR (300 MHz, CDCl$_3$, δ): 2.96 (3H, s), 2.98 (3H, s), 3.80 (2H, s), 6.38 (1H, d, J=16.8 Hz), 6.75 (2H, d, J=8.5 Hz), 6.95 (1H, s), 6.99 (1H, d, J=7.3 Hz), 7.14 (1H, d, J=7.3 Hz), 7.40 (2H, d, J=7.0 Hz), 7.43 (2H, d, J=7.0 Hz), 7.54 (2H, d, J=7.3 Hz), 7.59 (1H, d, J=15.0 Hz); MASS (ES+): m/e 472 (M+1).

Preparation 168

Compound (168) was obtained from Compound (167) according to a manner similar to Preparation 8 (263 mg).

$^1$H-NMR (300 MHz, DMSO-d$_6$, δ): 3.04 (6H, s), 4.60 (2H, s), 6.57 (1H, d, J=16.1 Hz), 7.42 (1H, d, J=8.1 Hz), 7.60 (1H, d, J=16.1 Hz), 7.61–7.72 (2H, m), 7.74 (2H, d, J=8.4 Hz), 7.80 (2H, s), 7.90 (1H, s); MASS (ES+): m/e 398 (M+1).

Preparation 169

Compound (169) was obtained from Compound (168) according to a manner similar to Preparation 9 (116 mg). The Compound (169) was used in Example 51.

$^1$H-NMR (300 MHz, DMSO-d$_6$, δ): 1.54 (3H, br), 1.69 (3H, br), 2.93 (6H, s), 3.53 (1H, m), 3.94 (1H, m), 4.20 (2H, s), 4.90 (1H, m), 6.47 (1H, d, J=15.8 Hz), 6.81 (2H, d, J=9.1 Hz), 7.38 (4H, d, J=8.4 Hz), 7.43 (1H, m), 7.50 (2H, m), 7.54 (2H, d, J=8.4 Hz), 7.69 (1H, s); MASS (ES+): m/e 497 (M+1).

Preparation 170

Compound (170) was obtained from Compound (6) according to a manner similar to Preparation 7 (334 mg).

$^1$H-NMR (300 MHz, CDCl$_3$, δ): 1.54 (9H, s), 3.81 (2H, s), 4.02 (2H, br), 6.39 (1H, d, J=16.1 Hz), 7.03 (1H, br), 7.29 (1H, br), 7.38 (2H, d, J=8.0 Hz), 7.44 (1H, br), 7.55 (2H, dd, J=8.0 Hz), 7.58 (1H, d, J=16.2 Hz); MASS (ES+): m/e 421 (M+1)

Preparation 171

Compound (171) was obtained from Compound (170) according to a manner similar to Preparation 8 (247 mg).

$^1$H-NMR (300 MHz, DMSO-d$_6$, δ): 4.39. (2H, s), 6.52 (1H, d, J=15.6 Hz), 7.42 (2H, d, J=7.7 Hz), 7.58 (1H, d, J=15.8 Hz), 7.61 (1H, d, J=8.8 Hz), 7.69 (2H, d, J=8.1 Hz), 7.79 (1H, d, J=9.5 Hz), 7.97 (1H, s); MASS (ES+): m/e 347 (M+1).

Preparation 172

Compound (172) was obtained from Compound (171) according to a manner similar to Preparation 9 (308 mg). The Compound (172) was used in Example 52.

$^1$H-NMR (300 MHz, DMSO-d$_6$, δ): 1.53 (3H, br), 1.76 (3H, br), 3.52 (1H, m), 3.96 (1H, m), 4.27 (2H, s), 4.90 (1H, s), 6.48 (1H, d, J=16.4 Hz), 7.38 (2H, d, J=8.5 Hz), 7.46 (1H, d, J=8.4 Hz), 7.47 (1H, d, J=16.0 Hz), 7.55 (2H, d, J=7.9 Hz), 7.69 (1H, d, J=8.1 Hz), 7.85 (1H, s); MASS (ES+): m/e 346 (M+1).

Preparation 173

Compound (173) was obtained from Compound (6) according to a manner similar to Preparation 7 (617 mg).

$^1$H-NMR (300 MHz, CDCl$_3$, δ): 1.48 (9H, s), 3.69 (2H, s), 5.25 (2H, br), 6.50 (1H, d, J=15.7 Hz), 6.49–6.55 (1H, m), 6.95–7.00 (1H, m), 7.37 (2H, d, J=8.1 Hz), 7.54 (1H, d, J=16.1 Hz), 7.65 (2H, d, J=8.4 Hz); MASS (ES+): m/e 389 (M+1).

Preparation 174

Compound (174) was obtained from Compound (173) according to a manner similar to Preparation 8 (466 mg).

$^1$H-NMR (300 MHz, DMSO-d$_6$, δ): 4.36 (2H, s), 6.52 (1H, d, J=16.1 Hz), 7.31–7.40 (2H, m), 7.43 (2H, d, J=8.1 Hz), 7.57 (1H, d, J=15.7 Hz), 7.69 (2H, d, J=8.1 Hz); MASS (ES+): m/e 315 (M+1).

Preparation 175

Compound (175) was obtained from Compound (174) according to a manner similar to Preparation 9 (542 mg). The Compound (175) was used in Example 53.

$^1$H-NMR (300 MHz, DMSO-d$_6$, δ): 1.53 (3H, br), 1.69 (3H, br), 3.52 (1H, m), 3.96 (1H, m), 4.22 (2H, s), 4.90 (1H, s), 6.47 (1H, d, J=16.1 Hz), 7.13–7.22 (2H, m), 7.37 (2H, d, J=8.0 Hz), 7.47 (1H, d, J=15.7 Hz), 7.54 (2H, d, J=8.0 Hz); MASS (ES+): m/e 414 (M+1).

Preparation 176

Compound (176) was obtained from Compound (6) according to a manner similar to Preparation 7 (555 mg).

$^1$H-NMR (300 MHz, CDCl$_3$, δ): 0.93 (6H, d, J=6.6 Hz), 1.54 (9H, s), 1.62 (2H, dt, J=7.0, 7.0 Hz), 1.79 (1H, hept, J=6.8 Hz), 3.76 (2H, s), 3.90 (2H, t, J=6.5 Hz), 6.30 (2H, m), 6.38 (1H, d, J=16.1 Hz), 6.91 (1H, d, J=9.5 Hz), 7.53 (2H, d, J=8.7 Hz), 7.55 (1H, d, J=16.6 Hz); MASS (ES+): m/e 439 (M+1).

Preparation 177

Compound (177) was obtained from Compound (176) according to a manner similar to Preparation 8 (398 mg).

$^1$H-NMR (300 MHz, DMSO-d$_6$, δ): 0.94 (6H, d, J=6.7 Hz), 1.64 (2H, dt, J=6.7, 6.7 Hz), 1.79 (1H, hept, J=6.7 Hz), 4.07 (2H, t, J=6.7 Hz), 4.50 (2H, s), 6.55 (1H, d, J=16.3 Hz), 7.10 (1H, dd, J=8.4, 2.2 Hz), 7.21 (1H, d, J=2.2 Hz), 7.46 (2H, d, J=8.4 Hz), 7.59 (1H, d, J=16.1 Hz), 7.62 (1H, d, J=8.7 Hz), 7.73 (2H, d, J=8.6 Hz); MASS (ES+): m/e 365 (M+1).

Preparation 178

Compound (178) was obtained from Compound (177) according to a manner similar to Preparation 9 (176 mg). The Compound (178) was used in Example 54.

$^1$H-NMR (300 MHz, CDCl$_3$, δ): 0.92 (6H, d, J=6.7 Hz), 1.42–1.87 (6H, m), 1.64 (2H, dt, J=6.7 Hz), 1.80 (1H, hept, J=6.7 Hz), 3.52 (1H, m), 3.94 (2H, t, J=6.7 Hz), 3.97 (1H, m), 4.11 (2H, s), 5.13 (1H, s), 6.18 (1H, br.s), 6.84 (1H, dd, J=8.8, 2.5 Hz), 6.90 (4H, br.s), 7.04 (1H, br.s), 7.29 (1H, br.d), 7.45 (1H, d, J=8.8 Hz); MASS (ES+): m/e 464 (M+1).

Preparation 179

Compound (179) was obtained from Compound (6) according to a manner similar to Preparation 7 (414 mg).

$^1$H-NMR (300 MHz, CDCl$_3$, δ): 1.28 (6H, d, J=6.3 Hz), 3.76 (2H, s), 4.44 (1H, hept, J=6.3 Hz), 6.28 (2H, m), 6.37 (1H, d, J=15.8 Hz), 6.91 (1H, d, J=9.0 Hz), 7.37 (2H, d, J=8.1 Hz), 7.52 (2H, d, J=8.1 Hz), 7.57 (1H, d, J=15.7 Hz); MASS (ES+): m/e 411 (M+1).

Preparation 180

Compound (180) was obtained from Compound (179) according to a manner similar to Preparation 8 (330 mg).

$^1$H-NMR (300 MHz, DMSO-d$_6$, δ): 1.29 (6H, d, J=6.1 Hz), 4.69 (1H, hept, J=6.1 Hz), 6.55 (1H, d, J=16.2 Hz), 7.08 (1H, dd, J=2.6, 9.2 Hz), 7.19 (1H, d, J=2.6 Hz), 7.59 (1H, d, J=16.1 Hz), 7.62 (1H, d, J=9.2 Hz), 7.73 (2H, d, J=8.2 Hz); MASS (ES+): m/e 337 (M+1).

Preparation 181

Compound (181) was obtained from Compound (180) according to a manner similar to Preparation 9 (281 mg). The obtained Compound (181) was used in Example 55.

$^1$H-NMR (300 MHz, CDCl$_3$, δ): 1.31 (6H, d, J=6.0 Hz), 1.53 (3H, br), 1.69 (3H, br), 3.64 (1H, m), 4.01 (1H, m), 4.22 (2H, s), 4.47 (1H, hept, J=6.0 Hz), 5.05 (1H, m), 6.30 (1H, br), 6.85 (1H, d, J=9.0 Hz), 7.00 (1H, s), 707–7.20 (2H, br), 7.26–7.35 (1H, br), 7.42 (2H, d, J=8.8 Hz); MASS (ES+): m/e 436 (M+1).

Preparation 182

Compound (182) was obtained from Compound (6) according to a manner similar to Preparation 7 (546 mg).

$^1$H-NMR (300 MHz, DMSO-d$_6$, δ): 3.78 (2H, s), 6.38 (1H, d, J=16.1 Hz), 6.40 (2H, m), 6.89 (1H, s), 7.00 (2H, m), 7.09 (1H, t, J=7.3 Hz), 7.31 (2H, dd, J=8.7, 7.6 Hz), 7.38 (2H, d, J=8.5 Hz), 7.54 (2H, d, J=7.4 Hz), 7.58 (1H, d, J=16.2 Hz); MASS (ES+): m/e 445 (M+1).

Preparation 183

Compound (183) was obtained from Compound (182) according to a manner similar to Preparation 8 (417 mg).

$^1$H-NMR (300 MHz, DMSO-d$_6$, δ): 4.52 (2H, s), 6.56 (1H, d, J=16.1 Hz), 7.17 (1H, t, J=7.3 Hz), 7.21 (1H, dd, J=9.1, 2.3 Hz), 7.30 (1H, d, J=2.3 Hz), 7.41 (2H, t, J=8.1 Hz), 7.48 (2H, d, J=8.5 Hz), 7.59 (1H, d, J=16.3 Hz), 7.73 (2H, d, J=8.8 Hz), 7.76 (1H, d, J=9.1 Hz); MASS (ES+): m/e 371 (M+1).

Preparation 184

Compound (184) was obtained from Compound (183) according to a manner similar to Preparation 9 (442 mg). The Compound (184) was used in Example 56.

$^1$H-NMR (300 MHz, DMSO-d$_6$, δ): 1.54 (3H, br), 1.69 (3H, br), 3.52 (1H, m), 3.95 (1H, m), 4.19 (2H, s), 4.90 (1H, s), 6.47 (1H, d, J=16.5 Hz), 6.88 (1H, m), 6.94 (2H, m), 7.06 (2H, m), 7.35 (2H, m), 7.37 (3H, m), 7.46 (1H, d, J=16.4 Hz), 7.54 (2H, m); MASS (ES+): m/e 470 (M+1).

Preparation 185

Compound (185) was obtained from Compound (6) according to a manner similar to Preparation 7 (163 mg). 1-NMR (300 MHz, CDCl$_3$, δ): 3.74 (3H, s), 3.78 (2H, s), 6.31 (2H, m), 6.38 (1H, d, J=16.1 Hz), 6.93 (1H, d, J=10.0 Hz), 7.38 (2H, d, J=8.0 Hz), 7.54 (2H, d, J=8.4 Hz), 7.58 (1H, d, J=16.1 Hz); MASS (ES+): m/e 383 (M+1).

Preparation 186

Compound (186) was obtained from Compound (185) according to a manner similar to Preparation 8 (127 mg).

$^1$H-NMR (300 MHz, DMSO-d$_6$, δ): 3.84 (3H, s), 4.52 (2H, s), 6.55 (1H, d, J=16.1 Hz), 7.12 (1H, dd, J=8.8, 2.2 Hz), 7.20 (1H., d, J=2.6 Hz), 7.47 (2H, d, J=8.1 Hz), 7.59 (1H, d, J=16.1 Hz), 7.65 (1H, d, J=9.2 Hz), 7.73 (2H, d, J=8.1 Hz); MASS (ES+): m/e 309 (M+1).

Preparation 187

Compound (187) was obtained from Compound (186) according to a manner similar to Preparation 9 (127 mg). The Compound (187) was used in Example 57.

$^1$H-NMR (300 MHz, DMSO-d$_6$, δ): 1.53 (3H, br), 1.69 (3H, br), 3.53 (1H, m), 3.75 (3H, s), 3.95 (1H, m), 4.15 (2H, s), 6.48 (1H, d, J=15.7 Hz), 6.75 (1H, dd, J=8.8, 2.6 Hz), 6.98 (1H, s), 7.35 (3H, d, J=8.4 Hz), 7.46 (1H, d, J=15.7 Hz), 7.53 (2H, d, J=8.0 Hz); MASS (ES+): m/e 408 (M+1).

Preparation 188

To a stirred solution of Compound (247) (described in Preparation 247 below, 1.75 g) in dichloromethane (20 mL) was added trifluoroacetic acid (20 mL) and the resulting mixture was stirred at ambient temperature for 3 hrs. The mixture was concentrated in vacuo and the residue was dissolved in N,N-dimethylformamide (25 mL). To this solution were successively added 1-hydroxybenzotriazole (731 mg), O-(tetrahydro-2H-pyran-2-yl)hydroxylamine (588 mg) and 1-[3-(dimethylamino)propyl]-3-ethylcarbodiimide (840 mg) in an ice bath, and the resulting mixture was stirred at ambient temperature. After 16 hrs, additional 1-hydroxybenzotriazole (157 mg), O-(tetrahydro-2H-pyran-2-yl)hydroxylamine (136 mg) and 1-[3-(dimethylamino)propyl]-3-ethylcarbodiimide (180 mg) were added to the mixture and the mixture was stirred for additional 4 hrs. The mixture was extracted with ethyl acetate (300 mL) and successively washed with 5% aqueous potassium hydrogen sulfate (100 mL), saturated aqueous sodium bicarbonate (100 mL) and brine (100 mL). The organic layer was dried over anhydrous sodium sulfate and concentrated in vacuo. The residue was purified by flash chromatography eluting with ethyl acetate to afford Compound (188) (1.82 g) as a colorless amorphous solid. The Compound (188) was used in Example 60.

$^1$H-NMR (300 MHz, CDCl$_3$, δ): 1.50–1.91 (6H, m), 3.58–3.71 (1H, m), 3.82 (3H, s), 3.88–4.21 (1H, m), 4.87–5.09 (3H, m), 6.17–6.40 (1H, m), 7.03–7.61 (5H, m), 7.74–7.87 (4H, m); MASS (ES+): m/z 496 (M+1)

Preparation 189

Compound (189) was obtained from Compound (249) described later according to a manner similar to Preparation 188 (142 mg). The Compound (189) was used in Example 64.

$^1$H-NMR (300 MHz, CDCl$_3$, δ): 1.46–1.92 (6H, m), 3.56–3.69 (1H, m), 3.89–4.18 (2H, m), 4.96–5.12 (2H, m), 6.11–6.37 (1H, m), 7.00–7.36 (7H, m), 7.64 (2H, d, J=8.4 Hz); MASS (ES+): m/z 438 (M+1)

Preparation 190

Compound (190) was obtained from Compound (250) described later according to a manner similar to Preparation 188 (110 mg). The Compound (190) was used in Example 68.

$^1$H-NMR (300 MHz, CDCl$_3$, δ): 1.43–1.90 (6H, m), 3.58–3.71 (1H, m), 3.91–4.12 (3H, m), 5.03 (1H, br.s), 5.95–6.21 (1H, m), 7.00–7.42 (9H, m), 7.67–7.76 (2H, m); MASS (ES+): m/z 404 (M+1).

Preparation 191

Compound (191) was obtained from Compound (226) described later according to a manner similar to Preparation 188 (78 mg). The Compound (191) was used in Example 69.

$^1$H-NMR (300 MHz, CDCl$_3$, δ): 1.41–2.05 (6H, m), 3.54–3.69 (1H, m), 3.89–4.05 (3H, m), 4.93 (1H, br.s), 6.04–6.28 (1H, m), 6.95–7.53 (8H, m), 7.73 (2H, d, J=7.0 Hz); MASS (ES+): m/z 438 (M+1).

Preparation 192

Compound (192) was obtained obtained from Compound (242) described later according to a manner similar to Preparation 188 (638 mg). The Compound (192) was used in Example 86.

$^1$H-NMR (300 MHz, DMSO-d$_6$, δ): 1.26 (3H, t, J=7.0 Hz), 1.54 (3H, br.), 1.69 (3H, br.), 3.53 (1H, m), 3.95 (1H, m), 4.07 (2H, s), 4.24 (2H, q, J=7.0 Hz), 4.90 (1H, s), 6.46 (1H, d, J=16.1 Hz), 7.36 (5H, m), 7.52 (3H, m), 7.85 (2H, d, J=7.3 Hz); MASS (ES+): m/e 476 (M+1).

Preparation 193

To a stirred solution of Compound (326) (200 mg, described later in Preparation 326) in N,N-dimethylformamide (2 mL) were added 1-[3-(dimethylamino)propyl]-3-ethylcarbodiimide (90 mg) and 1-hydroxybenzotriazole (79 mg) at ambient temperature, and the resulting mixture was stirred at the same temperature for 2 hrs. To this mixture was added 28% ammonium hydroxide solution in water (0.08 mL), and the mixture was stirred at ambient temperature for 16 hrs. The mixture was extracted with ethyl acetate (50 mL), and successively washed with saturated aqueous sodium bicarbonate (25 mL) and brine (25 mL). The organic layer was dried over anhydrous sodium sulfate and concentrated in vacuo. The residue was purified by preparative thin-layer chromatography eluting with methanol-chloroform (10:90 v/v) to afford Compound (193) (141 mg) as a colorless amorphous solid. The Compound (193) was used in Example 61.

$^1$H-NMR (300 MHz, CDCl$_3$—CD$_3$OD (9:1 v/v), δ): 1.51–1.94 (6H, m), 3.59–3.72 (3H, m), 3.95–4.12 (1H, m), 4.99 (2H, br.s), 6.23–6.47 (1H, m), 7.22–7.30 (2H, m), 7.32–7.47 (4H, m), 7.55–7.69 (4H, m); MASS (ES+): m/z 447 (M+1).

Preparation 194

To a stirred solution of Compound (193) (138 mg) in pyridine (2 mL) was added trifluoroacetic anhydride (84 mg) in an ice bath. The resulting mixture was stirred at the same temperature for 2 hrs and then allowed to warm to ambient temperature. After 2 hrs, additional trifluoroacetic anhydride (84 mg) was added to the reaction mixture at ambient temperature, and the mixture was stirred at the same temperature for an hour. The mixture was concentrated in vacuo and the residue was extracted with chloroform (50 mL), and successively washed with saturated aqueous sodium bicarbonate (25 mL) and brine (25 mL). The organic layer was dried over anhydrous sodium sulfate and evaporated. The residue was purified by preparative thin-layer chromatography eluting with ethyl acetate to afford Compound (194) (55 mg) as a colorless amorphous solid. The Compound (194) was used in Example 62.

$^1$H-NMR (300 MHz, CDCl$_3$, δ): 1.32–2.01 (6H, m), 3.48–4.10 (3H, m) 4.16 (2H, br.s), 4.86–5.06 (1H, m), 6.97–7.52 (8H, m), 7.81–7.92 (2H, m); MASS (ES+): m/z 429 (M+1).

Preparation 195

To a stirred solution of Compound (6) (500 mg) in N,N-dimethylformamide (8 mL) were successively added 2,2-diethoxyethanamine (305 mg), 1-[3-(dimethylamino)propyl]-3-ethylcarbodiimide hydrochloride (439 mg) and 1-hydroxybenzotriazole (309 mg) in an ice bath, and the resulting solution was stirred at the same temperature for 15 min. The mixture was then allowed to warm to ambient temperature and stirred at the same temperature for 16 hrs. The mixture was extracted with ethyl acetate (50 mL), and successively washed with 5% aqueous potassium sulfate (25 mL), saturated aqueous sodium bicarbonate (25 mL) and brine (25 mL). The organic layer was dried over anhydrous sodium sulfate and evaporated to give crude Compound (195) (861 mg) as a colorless oil, which was used in the next step without further purification.

$^1$H-NMR (300 MHz, CDCl$_3$, δ): 1.13 (3H, t, J=7.3 Hz), 1.54 (9H, s), 3.36 (2H, t, J=5.5 Hz), 3.40–3.52 (1H, m), 3.58 (2H, s), 3.59–3.70 (1H, m), 4.42 (1H, t, J=5.5 Hz), 5.62 (1H, br.s), 6.36 (1H, d, J=16.1 Hz), 7.28 (2H, d, J=8.1 Hz), 7.49 (2H, d, J=8.1 Hz), 7.57 (1H, d, J=16.1 Hz); MASS (ES+): m/z 378 (M+1)

Preparation 196

A mixture of Compound (195) (603 mg), ammonium acetate (616 mg) and acetic acid (1.9 g) in xylene (12 mL) was heated at 170° C. for five days, during which time additional same amounts of ammonium acetate and acetic acid were added to the mixture every 12 hrs. The mixture was concentrated in vacuo and extracted with chloroform (100 mL). The organic phase was successively washed with saturated aqueous sodium bicarbonate (25 mL) and brine (25 mL). The organic layer was dried over anhydrous sodium sulfate and evaporated. The residue was triturated with acetonitrile to afford Compound (196) (200 mg) as a pale tan amorphous solid.

$^1$H-NMR (300 MHz, CDCl$_3$, δ): 1.47 (9H, s), 3.98 (2H, s), 6.46 (1H, d, J=16.1 Hz), 6.78 (1H, br.s), 7.00 (1H, br.s), 7.25 (2H, d, J=8.1 Hz), 7.51 (1H, d, J=16.1 Hz), 7.61 (2H, d, J=8.1 Hz); MASS (ES+): m/z 285 (M+1).

Preparation 197

Compound (197) was obtained according to a manner similar to Preparation 188 (51 mg). The obtained Compound (197) was used in Example 112.

$^1$H-NMR (300 MHz, CDCl$_3$, δ): 1.18–2.23 (6H, m), 3.48–4.20 (5H, m), 5.02–5.12 (1H, m), 6.90–7.53 (7H, m); MASS (ES+): m/z 328 (M+1)

Preparation 198

Compound (198) was obtained from Compound (242) described later according to a manner similar to Preparation 188 (638 mg). The obtained Compound (198) was used in Example 86.

(Compound (198) is the same compound as Compound (192).)

$^1$H-NMR (300 MHz, DMSO-$d_6$, δ): 1.26 (3H, t, J=7.0 Hz), 1.54 (3H, br.), 1.69 (3H, br.), 3.53 (1H, m), 3.95 (1H, m), 4.07 (2H, s), 4.24 (2H, q, J=7.0 Hz), 4.90 (1H, s), 6.46 (1H, d, J=16.1 Hz), 7.36 (5H, m), 7.52 (3H, m), 7.85 (2H, d, J=7.3 Hz); MASS (ES+): m/e 476 (M+1).

Preparation 199

A solution of Compound (248) (427 mg, described later in Preparation 248) in 1N-hydrogen chloride in acetic acid (10 mL) was heated at 60° C. for 2 hrs. The solvent was evaporated in vacuo, and the residue was triturated with the mixture of ethyl acetate and acetic acid (10:1 (v/v)) to give Compound (199) (353 mg) as an off-white solid.

$^1$H-NMR (300 MHz, DMSO-$d_6$, δ): 4.41 (2H, s), 6.55 (1H, d, J=16 Hz), 7.39 (2×1H, dd, J=8.8, 8.8 Hz), 7.47 (2×1H, d, J=8.2 Hz), 7.58 (1H, d, J=16 Hz), 7.71 (2×1H, d, J=8.2 Hz), 7.91 (2×1H, dd, J=8.8, 5 Hz), 8.05 (1H, s); MASS (ES+): m/z 323.

Preparation 200

Compound (200) was obtained from Compound (207) described later according to a manner similar to Preparation 199 (361 mg).

$^1$H-NMR. (300 MHz, DMSO-$d_6$, δ): 2.51 (3H, s), 2.53 (3H, s), 4.28 (2H, s); MASS (ES+): m/z 285.

Preparation 201

Compound (201) was obtained from Compound (206) described later according to a manner similar to Preparation 199 (433 mg).

$^1$H-NMR (300 MHz, DMSO-$d_6$, δ): 2.25 (3H, s), 4.31 (2H, s), 6.55 (1H, d, J=16 Hz), 7.45 (2×1H, d, J=8 Hz), 7.54–7.63 (3H, m), 7.67–7.75 (3H, m), 7.86 (2×1H, d, J=8 Hz); MASS (ES+): m/z 347.

Preparation 202

Compound (202) was obtained from Compound (256) described later according to a manner similar to Preparation 199 (181 mg).

$^1$H-NMR (300 MHz, DMSO-$d_6$, δ): 1.65–1.79 (6H, m), 1.85–1.91 (6H, m), 2.00–2.07 (3H, m), 4.32 (2H, s), 6.54 (1H, d, J=16 Hz), 7.25 (1H, s), 7.40 (2H, d, J=8 Hz), 7.57 (1H, d, J=16 Hz), 7.70 (2H, d, J=8 Hz). MASS (ES+): m/z 363 (M+1).

Preparation 203

To a stirred solution of Compound (199) (316 mg) in N,N-dimethylformamide (5 mL) were added O-(tetrahydro-2H-pyran-2-yl)hydroxylamine (206 mg), 1-hydroxybenzotriazole (238 mg) and 1-ethyl-3-(3'-dimethylaminopropyl) carbodiimide hydrochloride (338 mg), and the resulting mixture was stirred at ambient temperature for 5 hrs. The reaction mixture was diluted with ethyl acetate and washed successively with water, saturated sodium hydrogen carbonate solution and brine. The organic phase was dried over sodium sulfate and concentrated in vacuo. The residue was purified by preparative thin-layer chromatography (chloroform:methanol=10:1) to give Compound (203) (341 mg) as a pale yellow powder.

$^1$H-NMR (300 MHz, DMSO-$d_6$, δ): 1.45–1.75 (6H, m), 3.53 (1H, m), 3.95 (1H, m), 4.03 (2H, m), 4.90 (1H, m), 6.46 (1H, d, J=16 Hz), 7.14 (2×1H, dd, J=8.8, 8.8 Hz), 7.32 (2×1H, d, J=8.5 Hz), 7.42–7.57 (4H, m), 7.76 (2×1H, dd, J=8.8, 6.0 Hz), 11.22 (1H, s), 11.98 (1H, br-s); MASS (ES+): m/z 422.

Preparation 204

To a suspension of p-iodo-phenylalanine (1.20 g) in n-BuOH (15 mL) was added 1-phenyl-1,2,3-butanetrione-2-oxime (788 mg). The resulting mixture was refluxed for 2 days and cooled, then concentrated in vacuo. The residue was triturated with ethyl acetate to give Compound (204) (870 mg) as a pale yellow solid.

$^1$H-NMR (300 MHz, DMSO-$d_6$, δ): 2.48 (3H, s), 3.96 (2H, s), 7.08 (2×1H, d, J=8.5 Hz), 7.44–7.60 (3H, m), 7.67 (2×1H, d, J=8.5 Hz), 8.18 (2×1H, d, J=8 Hz), 12.44 (1H, s); MASS (ES+): m/z 403.

Preparation 205

Compound (205) was obtained from p-iodophenylalanine according to a manner similar to Preparation 204 (402 mg).

$^1$H-NMR (300 MHz, DMSO-$d_6$, δ): 2.35 (3H, s), 2.38 (3H, s), 3.91 (2H, s), 7.07 (2×1H, d, J=8 Hz), 7.67 (2×1H, d, J=8 Hz); MASS (ES+): m/z 341.

Preparation 206

To a stirred solution of Compound (204) (661 mg) in DMF (10 mL) were added tert-butyl acrylate (0.72 mL), palladium(II) acetate (18 mg), tris(2-methylphenyl)phosphine (100 mg) and N,N-diisopropylethylamine (0.86 mL). The mixture was stirred at 90° C. for 4 hrs. The resulting mixture was allowed to cool to ambient temperature, poured into water and extracted with ethyl acetate. The organic phase was washed with brine, dried over $Na_2SO_4$ and concentrated in vacuo. The residue was purified by silica gel column chromatography eluting with a mixture of hexane and ethyl acetate (1:1 v/v) to give Compound (206) (707 mg) as a pale yellow foam.

$^1$H-NMR (300 MHz, DMSO-$d_6$, δ): 1.47 (3×3H, s), 2.48 (3H, s), 4.02 (2H, s), 6.48 (1H, d, J=16 Hz), 7.30 (2×1H, d, J=8.5 Hz), 7.44–7.58 (4H, m), 7.64 (2×1H, d, J=8.5 Hz), 8.19 (2×1H, d, J=7.5 Hz), 12.49 (1H, s); MASS (ES+): m/z 403.

Preparation 207

Compound (207) was obtained from Compound (205) according to a manner similar to Preparation 206 (370 mg).

$^1$H-NMR (300 MHz, CDCl$_3$, δ): 1.54 (3×3H, s), 2.45 (3H, s), 2.54 (3H, s), 4.08 (2H, s), 6.36 (1H, d, J=16 Hz), 7.25 (2×1H, d, J=8 Hz), 7.48 (2×1H, d, J=8 Hz), 7.56 (1H, d, J=16 Hz); MASS (ES+): m/z 341.

Preparation 208

Compound (208) was obtained from Compound (201) according to a manner similar to Preparation 188 (461 mg). The Compound (208) was used in Example 66.

$^1$H-NMR (300 MHz, DMSO-$d_6$, δ): 1.46–1.76 (6H, m), 3.53 (1H, m), 3.95 (1H, m), 4.02 (2H, s), 4.90 (1H, m), 6.47 (1H, d, J=16 Hz), 7.31 (2×1H, d, J=8.5 Hz), 7.42–7.68 (6H, m), 8.19 (2×1H, d, J=7 Hz), 11.22 (1H, s), 11.48 (1H, s); MASS (ES+): m/z 446.

Preparation 209

Compound (209) was obtained from Compound (200) according to a manner similar to Preparation 188 (268 mg). The Compound (209) was used in Example 65.

$^1$H-NMR (300 MHz, DMSO-$d_6$, δ): 1.46–1.78 (6H, m), 2.36 (3H, s), 2.39 (3H, s), 3.53 (1H, m), 3.96 (1H, m), 3.97 (2H, s), 4.90 (1H, m), 6.47 (1H, d, J=16 Hz), 7.29 (2×1H, d, J=8 Hz), 7.47 (1H, d, J=16 Hz), 7.53 (2×1H, d, J=8 Hz), 11.2.2 (1H, s), 12.31 (1H, br-s); MASS (ES+): m/z 384.

Preparation 210

Compound (210) was obtained from Compound (340) described later according to a manner similar to Preparation 188 (107 mg). The Compound (210) was used in Example 96.

$^1$H-NMR (300 MHz, DMSO-$d_6$, δ): 1.48–1.73 (6H, m), 1.92–2.00 (4H, m), 3.18–3.24 (4H, m), 3.48–3.57 (1H, m), 3.88–4.01 (1H, m), 4.10 (2H, s), 4.87–4.93 (1H, m), 6.42–6.52 (3H, m), 7.25–7.37 (3H, m), 7.46 (1H, d, J=16 Hz), 7.52 (2H, d, J=8 Hz); MASS (ES+): m/z 447 (M+1).

Preparation 211

To a mixture of methyl (2E)-3-[4-(hydroxymethyl)phenyl]acrylate (1.0 g) and triethylamine (1.26 g) in dichloromethane (10 mL) was dropwise added methanesulfonyl chloride (715 mg) in dichloromethane (5 mL) in an ice bath. The resulting mixture was stirred at the same temperature for 1 hr and then allowed to warm to ambient temperature. After stirring at ambient temperature for 3 hrs, the mixture was concentrated in vacuo. The residue was extracted with ethyl acetate (100 mL), and washed with 10% aqueous citric acid (25 mL), saturated aqueous sodium bicarbonate (25 mL) and brine (25 mL). The organic phase was separated, dried over anhydrous sodium sulfate and evaporated in vacuo to give Compound (211) (655 mg) as a colorless amorphous solid, which was used in the next step without further purification.

$^1$H-NMR (300 MHz, CDCl$_3$, δ): 3.82 (3H, s), 4.59 (2H, s), 6.45 (1H, d, J=15.8 Hz), 7.41 (2H, d, J=8.4 Hz), 7.52 (2H, d, J=8.4 Hz), 7.69 (1H, d, J=15.8 Hz).

Preparation 212

To a stirred solution of 4-phenyl-1H-imidazole (115 mg) in N,N-dimethylformamide (0.5 mL) was added sodium hydride (60% oil dispersion, 31 mg) in an ice bath. The mixture was stirred at the same temperature for 15 min and then allowed to warm to ambient temperature. After stirring at ambient temperature for 15 min, the mixture was cooled in an ice bath. To this mixture was dropwise added Compound (211) (180 mg) in N,N-dimethylformamide (1.5 mL), and the mixture was stirred at the same temperature for 2 hrs. The mixture was extracted with ethyl acetate (50 mL), and washed with saturated aqueous sodium bicarbonate (25 mL) and brine (25 mL). The organic layer was dried over anhydrous sodium sulfate, filtered and concentrated in vacuo. The residue was purified by preparative thin-layer chromatography eluting with a mixture of ethyl acetate and hexane (3:1 v/v) to afford Compound (212) (135 mg) as a colorless oil.

$^1$H-NMR (300 MHz, CDCl$_3$, δ): 3.81 (3H, s), 5.17 (2H, s), 6.44 (1H, d, J=15.8 Hz), 7.17–7.29 (4H, m), 7.33–7.41 (2H, m), 7.53 (2H, d, J=8.4 Hz), 7.63 (1H, d, J=15.8 Hz), 7.68 (1H, s), 7.76 (2H, d, J=8.4 Hz); MASS (ES+): m/z 319 (M+1).

Preparation 213

Compound (213) was obtained from Compound (211) according to a manner similar to Preparation 212 (457 mg).

$^1$H-NMR (300 MHz, CDCl$_3$, δ): 2.40 (3H, s), 3.81 (3H, s), 5.10 (2H, s), 6.43 (1H, d, J=16.1 Hz), 7.13 (2H, d, J=6.7 Hz), 7.14 (1H, s), 7.22 (1H, t, J=7.0 Hz), 7.36 (2H, t, J=8.1 Hz), 7.51 (2H, d, J=8.1 Hz), 7.67 (1H, d, J=16.1 Hz), 7.74 (2H, d, J=7.0 Hz); MASS (ES+): m/e 333 (M+1).

Preparation 214

Compound (214) was obtained from Compound (211) according to a manner similar to Preparation 212 (723 mg).

$^1$H-NMR (300 MHz, DMSO-$d_6$, δ): 2.25 (3H, s), 3.72 (3H, s), 5.28 (2H, s), 6.64 (1H, d, J=16.1 Hz), 7.20 (2H, d, J=8.4 Hz), 7.42 (2H, d, J=8.4 Hz), 7.64 (2H, d, J=8.4 Hz), 7.65 (1H, d, J=16.1 Hz), 7.74 (2H, d, J=8.1 Hz), 7.84 (1H, s); MASS (ES+): m/z 367 (M+1)

Preparation 215

Compound (215) was obtained from tert-butyl (2E)-3-[3-chloromethylphenyl]acrylate according to a manner similar to Preparation 212 (308 mg).

$^1$H-NMR (300 MHz, CDCl$_3$, δ): 1.53 (9H, s), 5.16 (2H, s), 6.36 (1H, d, J=15.8 Hz), 7.18 (1H, d, J=1.1 Hz), 7.20 (1H, m), 7.23 (1H, t, J=7.4 Hz), 7.34–7.41 (4H, m), 7.48 (1H, d, J=7.7 Hz), 7.54 (1H, d, J=16.1 Hz), 7.61 (1H, d, J=1.1 Hz), 7.76 (2H, dd, J=8.4, 1.5 Hz); MASS (ES+): m/z 361 (M+1).

Preparation 216

Compound (216) was obtained from tert-butyl (2E)-3-[3-chloromethylphenyl]acrylate according to a manner similar to Preparation 212 (418 mg).

$^1$H-NMR (300 MHz, CDCl$_3$, δ): 1.53 (9H, s), 2.27 (3H, s), 5.12 (2H, s), 6.34 (1H, d, J=16.1 Hz), 7.08 (1H, br.d, J=7.7 Hz), 7.24 (1H, s), 7.37 (2H, d, J=8.38 Hz), 7.38 (1H, t, J=7.8 Hz), 7.47 (1H, d, J=8.1 Hz), 7.54 (1H, d, J=15.8 Hz), 7.60 (2H, d, J=8.8 Hz); MASS (ES+): m/z 409 (M+1).

Preparation 217

Compound (217) was obtained from Compound (211) according to a manner similar to Preparation 212 (354 mg).

$^1$H-NMR (300 MHz, CDCl$_3$, δ): 3.81 (3H, s), 5.24 (2H, s), 6.43 (1H, d, J=16.1 Hz), 6.98 (1H, s), 7.06–7.14 (3H, m), 7.20–7.23 (1H, m), 7.36–7.46 (3H, m), 7.47–7.57 (3H, m), 7.67 (1H, d, J=16.1 Hz); MASS (ES+): m/z 319 (M+1).

Preparation 218

Compound (218) was obtained as a mixture of two regioisomers from Compound (211) according to a manner similar to Preparation 212 (291 mg).

$^1$H-NMR (300 MHz, CDCl$_3$, δ): (for a mixture of two regioisomers) 2.09 (1.2H, s), 2.22 (1.8H, s), 3.81 (3H, s), 5.06 (1.2H, s), 5.08 (0.8H, s), 6.43 (1H, d, J=16.1 Hz), 6.60 (0.6H, s), 6.85 (0.4H, s), 7.05 (0.8H, d, J=8.1 Hz), 7.16 (1.2H, d, J=8.1 Hz), 7.44–7.55 (3H, m), 7.66 (1H, d, J=16.1 Hz); MASS (ES+): (for a mixture of two regioisomers) m/z 257 (M+1).

Preparation 219

To a stirred solution of Compound (212) (185 mg) in a mixture of methanol (1 mL) and 1,4-dioxane (1 mL) was added 1N sodium hydroxide (0.87 mL) at ambient temperature. The resulting solution was stirred at the same temperature for 2 hrs. The mixture was cooled in an ice bath and to this mixture was added concentrated hydrochloric acid to acidify the mixture. The precipitate was filtered and washed with 50% aqueous methanol (1 mL) to afford Compound (219) (130 mg) as a white amorphous solid.

$^1$H-NMR (300 MHz, DMSO-$d_6$, δ): 5.47 (2H, s), 6.58 (1H, d, J=16.1 Hz), 7.38–7.55 (5H, m), 7.60 (1H, d, J=16.1 Hz), 7.77 (2H, d, J=8.4 Hz), 7.84 (2H, d, J=7.0 Hz), 8.25 (1H, s), 9.35 (1H, s); MASS (ES+): m/z 305 (M+1).

Preparation 220

Compound (220) was obtained from Compound (213) according to a manner similar to Preparation 219 (357 mg).

$^1$H-NMR (300 MHz, DMSO-$d_6$, δ): 2.68 (3H, s), 5.42 (2H, s), 6.58 (1H, d, J=16.1 Hz), 7.42 (1H, t, J=7.7 Hz), 7.43 (2H, d, J=8.4 Hz), 7.51 (2H, t, J=7.5 Hz), 7.60 (1H, d, J=16.1 Hz), 7.75 (2H, d, J=8.4 Hz), 7.83 (2H, d, J=7.3 Hz), 8.14 (1H, s); MASS (EI+) 319 (M+1).

Preparation 221

Compound (221) was obtained from Compound (214) according to a manner similar to Preparation 219 (564 mg).

$^1$H-NMR (300 MHz, DMSO-d$_6$, δ): 2.25 (3H, s), 5.30 (2H, s), 6.52 (1H, d, J=16.1 Hz), 7.21 (2H, d, J=8.1 Hz), 7.43 (2H, d, J=8.4 Hz), 7.57 (1H, d, J=15.8 Hz), 7.64 (2H, d, J=8.1 Hz), 7.70 (2H, d, J=8.1 Hz), 7.94 (1H, s); MASS (ES+): m/z 353 (M+1)

Preparation 222

To a stirred solution of Compound (219) (105 mg) in N,N-dimethylformamide (1.5 mL) were successively added 1-hydroxybenztriazole (61 mg), O-(tetrahydro-2H-pyran-2-yl)hydroxylamine (49 mg) and 1-[3-(dimethylamino)propyl]-3-ethylcarbodiimide hydrochloride (86 mg) in an ice bath, and the resulting mixture was stirred at ambient temperature for three days. The mixture was extracted with ethyl acetate (50 mL), and washed with saturated aqueous sodium bicarbonate (25 mL) and brine (25 mL). The organic layer was dried over anhydrous sodium sulfate, and concentrated in vacuo. The residue was purified by preparative thin-layer chromatography eluting with a mixture of methanol and chloroform (10:90 v/v) to afford Compound (222) (120 mg) as a colorless viscous oil. The Compound (222) was used in Example 67.

$^1$H-NMR (300 MHz, CDCl$_3$, δ): 1.50–1.97 (6H, m), 3.60–3.72 (1H, m), 3.90–4.05 (1H, m), 5.02 (1H, br.s), 5.17 (2H, s), 7.14–7.30 (6H, m), 7.32–7.42 (2H, m), 7.44–7.56 (2H, m), 7.62–7.82 (3H, m); MASS (ES+): m/z 404 (M+1)

Preparation 223

Compound (223) was obtained from Compound (220) according to a manner similar to Preparation 203 (431 mg). The Compound (223) was used in Example 78.

$^1$H-NMR (300 MHz, DMSO-d$_6$, δ): 1.54 (3H, br.), 1.69 (3H, br.), 2.29 (3H, s), 3.52 (1H, m), 3.94 (1H, m), 4.90 (1H, s), 5.21 (2H, s), 6.49 (1H, d, J=16.8 Hz), 7.16 (1H, t, J=7.5 Hz), 7.24 (2H, d, J=8.1 Hz), 7.32 (2H, t, J=7.9 Hz), 7.47 (1H, d, J=16.8 Hz), 7.58 (2H, d, J=8.1 Hz), 7.63 (1H, s), 7.71 (2H, d, J=7.0 Hz); MASS (ES+): m/e 418 (M+1).

Preparation 224

Compound (224) was obtained from Compound (221) according to a manner similar to Preparation 203 (569 mg). The Compound (224) was used in Example 79.

$^1$H-NMR (300 MHz, DMSO-d$_6$, δ): 1.54 (3H, br.), 1.69 (3H, br.), 2.25 (3H, s), 3.53 (1H, m), 3.95 (1H, m), 4.90 (1H, s), 5.27 (2H, s), 6.48 (1H, d, J=15.8 Hz), 7.21 (2H, d, J=8.1 Hz), 7.42 (2H, d, J=8.4 Hz), 7.47 (1H, d, J=15.8 Hz), 7.58 (2H, d, J=8.1 Hz), 7.65 (2H, d, J=8.4 Hz), 7.84 (1H, s); MASS (ES+): m/z 452 (M+1).

Preparation 225

Compound (225) was obtained from (2E)-3-[4-(1H-imidazol-1-ylmethyl)phenyl]acrylic acid according to a manner similar to Preparation 203 (388 mg). The Compound (225) was used in Example 95.

$^1$H-NMR (300 MHz, DMSO-d$_6$, δ): 1.42–1.78 (6H, m), 3.53 (1H, m), 3.95 (1H, m), 4.90 (1H, s), 5.23 (2H, s), 6.49 (1H, d, J=16 Hz), 6.93 (1H, s), 7.21 (1H, s), 7.27 (2×1H, d, J=8 Hz), 7.47 (1H, d, J=16 Hz), 7.56 (2×1H, d, J=8 Hz), 7.80 (1H, s), 11.25 (1H, s); MASS (ES+): m/e 328.

Preparation 226

To a stirred solution of Compound (250) (125 mg, described later in Preparation 250) in acetonitrile (2 mL) was added N-chlorosuccinimide (70 mg) in an ice bath. The mixture was stirred at ambient temperature for 2 days. The mixture was concentrated in vacuo and the residue was purified by preparative thin-layer chromatography eluting with a mixture of methanol and chloroform (4:96 v/v) to afford Compound (226) (100 mg) as a yellow oil.

$^1$H-NMR (300 MHz, CDCl$_3$, δ): 1.52 (9H, s), 4.09 (2H, s), 6.33 (1H, d, J=16.1 Hz), 7.21–7.44 (7H, m), 7.51 (1H, d, J=16.1 Hz), 7.59 (2H, d, J=7.3 Hz); MASS (ES+): m/z 395 (M+1).

Preparation 227

Compound (227) was obtained from Compound (245) described later according to a manner similar to Preparation 226 (230 mg).

$^1$H-NMR (300 MHz, CDCl$_3$, δ): 1.53 (9H, s), 4.09 (2H, s), 6.32 (1H, d, J=15.8 Hz), 7.27 (2H, d, J=7.7 Hz), 7.29 (1H, t, J=7.7 Hz), 7.40 (2H, t, J=7.4 Hz), 7.45 (2H, d, J=8.1 Hz), 7.53 (1H, d, J=16.1 Hz), 7.57 (2H, d, J=8.1 Hz); MASS (ES+): m/e 395 (M+1).

Preparation 228

Compound (228) was obtained from Compound (251) described later according to a manner similar to Preparation 226 (157 mg).

$^1$H-NMR (300 MHz, CDCl$_3$, δ): 3.80 (3H, s), 3.97 (2H, s), 6.25 (1H, d, J=16.1 Hz), 6.90 (2H, d, J=8.8 Hz), 7.15 (2H, d, J=8.1 Hz), 7.32 (2H, d, J=8.1 Hz), 7.44 (1H, d, J=16.1 Hz), 7.54 (2H, d, J=8.8 Hz); MASS (ES+): m/e 425 (M+1)

Preparation 229

To a solution of Compound (6) (4.1 g) in DMF (41 mL) were added HOBt (2.75 g) and 1-ethyl-3-(3'-dimethylaminopropyl)carbodiimide (EDCI, 3.15 g) at 5° C. To the mixture was slowly added 2-amino-1-phenylethanone hydrochloride (2.82 g) at 5° C. The mixture was allowed to warm to ambient temperature and stirred for 2 hrs at the same temperature. The resulting mixture was poured into water (100 mL) and extracted with AcOEt. The organic phase was sequentially washed with NH$_4$Cl, NaHCO$_3$ and brine, and dried over NaSO$_4$. The solvent was removed in vacuo, and the residue was purified by silica gel flash column chromatography eluting with CHCl$_3$: MeOH=95:5 to give pale yellow solid. The resulting solid was triturated with isopropyl ether to give Compound (229) (5.425 g) as pale yellow powder.

$^1$H-NMR (300 MHz, DMSO-d$_6$, δ): 1.54 (9H, s), 3.69 (2H, s), 4.75 (2H, d, J=4.0 Hz), 6.38 (1H, d, J=16.1 Hz), 7.35 (2H, d, J=8.1 Hz), 7.47–7.56 (1+1+2+2H, m), 7.61 (1H, m), 7.95 (2H, d, J=8.4 Hz); MASS (ES+): m/e 380 (M+1).

Preparation 230

Compound (230) was obtained from Compound (26) according to a manner similar to Preparation 229 (1.73 g).

$^1$H-NMR (300 MHz, CDCl$_3$, δ): 1.53 (9H, s), 3.67 (2H, s), 3.70 (3H, s), 6.19 (1H, d, J=7.3 Hz), 6.38 (1H, d, J=16.1 Hz), 6.85 (1H, br.d, J=7.3 Hz), 7.25–7.59 (7H, m), 7.60–7.68 (1H, m), 8.06–8.13 (2H, m); MASS (ES−): m/z 436(M−1).

Preparation 231

Compound (231) was obtained from Compound (6) according to a manner similar to Preparation 229 (5.69 g).

$^1$H-NMR (300 MHz, CDCl$_3$, δ): 1.54 (9H, s), 3.67 (2H, s), 3.70 (3H, s), 6.12 (1H, d, J=7.0 Hz), 6.36 (1H, d, J=16.1 Hz), 6.82 (1H, br.d, J=7.0 Hz), 7.30 (2H, d, J=8.1 Hz), 7.44–7.53 (4H, m), 7.57 (1H, d, J=16.1 Hz), 8.03 (2H, d, J=8.8 Hz); MASS (ES+): m/z 472 (M+1).

Preparation 232

Compound (232) was obtained from Compound (6) according to a manner similar to Preparation 229 (3.22 g).

$^1$H-NMR (300 MHz, DMSO-d$_6$, δ): 1.48 (3×3H, s), 3.57 (2H, s), 4.61 (2H, d, J=5.5 Hz), 6.49 (1H, d, J=16 Hz), 7.30–7.42 (4H, m), 7.53 (1H, d, J=16 Hz), 7.63 (2×1H, d, J=8.5 Hz), 8.02–8.11 (2H, m), 8.48 (1H, t, J=5.5 Hz); MASS (ES−): m/z 442 (M+HCO$_2$H−1).

Preparation 233

Compound (233) was obtained from Compound (6) according to a manner similar to Preparation 229 (1.74 g).

$^1$H-NMR (300 MHz, CDCl$_3$, δ): 1.54 (9H, s), 3.68 (2H, s), 4.71 (2H, d, J=5.5 Hz), 6.37 (2H, d, J=16.1 Hz), 6.50 (1H, br.s), 7.34 (2H, d, J=8.1 Hz), 7.47 (2H, d, J=8.4 Hz), 7.52 (2H, d, J=8.1 Hz), 7.58 (1H, d, J=16.1 Hz), 7.89 (2H, d, J=8.4 Hz); MASS (ES+): m/z 414 (M+1).

Preparation 234

Compound (234) was obtained from Compound (26) according to a manner similar to Preparation 229 (1.95 g).

$^1$H-NMR (300 MHz, CDCl$_3$, δ): 1.53 (9H, s), 3.68 (2H, s), 4.75 (2H, d, J=4.4 Hz), 6.40 (1H, d, J=16.1 Hz), 6.56 (1H, br.s), 7.25–7.70 (8H, m), 7.91–8.02 (2H, m); MASS (ES+): m/z 380 (M+1).

Preparation 235

Compound (235) was obtained from Compound (6) according to a manner similar to Preparation 229 (2.74 g).

$^1$H-NMR (300 MHz, CDCl$_3$, δ): 1.54 (9H, s), 3.68 (2H, s), 3.88 (3H, s), 4.68 (2H, d, J=4.4 Hz), 6.37 (1H, d, J=15.8 Hz), 6.95 (2H, d, J=9.1 Hz), 7.34 (2H, d, J=8.1 Hz), 7.52 (2H, d, J=8.1 Hz), 7.58 (1H, d, J=16.1 Hz), 7.92 (2H, d, J=8.8 Hz); MASS (ES+): m/e 410 (M+1)

Preparation 236

Compound (236) was obtained from Compound (6) according to a manner similar to Preparation 229 (2.86 g).

$^1$H-NMR (300 MHz, CDCl$_3$, δ): 1.54 (9H, s), 3.69 (2H, s), 3.85 (3H, s), 4.73 (2H, d, J=4.4 Hz), 6.73 (2H, d, J=15.8 Hz), 7.16 (1H, dd, J=8.1, 2.6 Hz), 7.34 (2H, d, J=8.1 Hz), 7.39 (1H, t, J=8.1 Hz), 7.45 (1H, m), 7.52 (2H, d, J=8.4 Hz), 7.58 (1H, d, J=16.1 Hz); MASS (ES+): m/e 410 (M+1).

Preparation 237

Compound (237) was obtained from Compound (6) according to a manner similar to Preparation 229 (1.82 g).

$^1$H-NMR (300 MHz, CDCl$_3$, δ): 1.54 (9H, s), 3.66 (2H, s), 3.93 (3H, s), 4.69 (2H, d, J=4.4 Hz), 6.37 (1H, d, J=16.1 Hz), 6.63 (1H, br), 7.00 (1H, t, J=8.4 Hz), 7.03 (1H, t, J=7.7 Hz), 7.35 (2H, d, J=8.4 Hz), 7.51 (2H, d, J=8.1 Hz), 7.58 (1H, d, J=16.1 Hz), 7.90 (1H, dd, J=7.7, 1.8 Hz); MASS (ES+): m/e 410 (M+1).

Preparation 238

Compound (238) was obtained from 4-iodophenylacetic acid according to a manner similar to Preparation 229 (4.20 g).

$^1$H-NMR (300 MHz, CDCl$_3$, δ): 3.61 (2H, s), 4.74 (2H, d, J=4.4 Hz), 7.09 (2H, d, J=8.4 Hz), 7.49 (2H, t, J=7.4 Hz), 7.63 (1H, t, J=7.4 Hz), 7.70 (2H, d, J=8.4 Hz), 7.95 (2H, d, J=7.4 Hz); MASS (ES+): m/e 380 (M+1).

Preparation 239

Compound (239) was obtained from Compound (6) according to a manner similar to Preparation 229 (600 mg).

$^1$H-NMR (300 MHz, DMSO-d$_6$, δ): 1.54 (9H, s), 1.58–1.84 (12H, m), 1.99–2.10 (3H, m), 3.61 (2H, s), 4.21 (2H, d, J=4.4 Hz), 6.35 (1H, d, J=16.1 Hz), 7.30 (2H, d, J=8.1 Hz), 7.50 (2H, d, J=8.1 Hz), 7.56 (1H, d, J=16.1 Hz); MASS (ES+): m/z 438 (M+1).

Preparation 240

Compound (240) was obtained from Compound (6) according to a manner similar to Preparation 229 (231 mg).

$^1$H-NMR (300 MHz, CDCl$_3$, δ): 1.54 (9H, s), 3.68 (2H, s), 3.69 (3H, s), 6.18 (1H, d, J=7.3 Hz), 6.36 (1H, d, J=15.8 Hz), 7.30 (2H, d, J=8.1 Hz), 7.51 (4H, m), 7.62 (2H, m), 8.08 (2H, d, J=7.0 Hz); MASS (ES+): m/e 438 (M+1).

Preparation 241

Compound (241) was obtained according to a manner similar to Preparation 229 (1.33 g).

$^1$H-NMR (300 MHz, CDCl$_3$, δ): 1.17 (9H, s), 1.54 (9H, s), 3.62 (2H, s), 4.25 (2H, d, J=4.4 Hz), 6.36 (1H, d, J=15.8 Hz), 7.31 (2H, d, J=8.4 Hz), 7.51 (2H, d, J=8.1 Hz), 7.57 (1H, d, J=16.1 Hz); MASS (ES+): m/e 360 (M+1)

Preparation 242

Compound (242) was obtained from Compound (6) according to a manner similar to Preparation 229 (1.58 g).

$^1$H-NMR (300 MHz, CDCl$_3$, δ): 1.12 (3H, t, J=7.0 Hz), 1.53 (9H, s), 3.67 (2H, s), 4.13 (2H, q, J=7.4 Hz), 6.15 (1H, d, J=7.3 Hz), 6.36 (1H, d, J=15.8 Hz), 6.86 (1H, br.d, J=6.6 Hz), 7.31 (2H, d, J=8.1 Hz), 7.48 (2H, t, J=7.4 Hz), 7.50 (2H, d, J=8.1 Hz), 7.57 (1H, d, J=16.1 Hz), 7.63 (1H, t, J=7.4 Hz), 8.08 (2H, d, J=8.1 Hz); MASS (ES+): m/z 452 (M+1).

Preparation 243

Compound (243) was obtained from Compound (6) according to a manner similar to Preparation 229 (200 mg).

$^1$H-NMR (300 MHz, CDCl$_3$, δ): 1.30 (4H, m), 1.53 (9H, s), 1.64 (2H, m), 1.80 (4H, m), 2.36 (1H, m), 3.62 (2H, s), 4.17 (2H, d, J=4.4 Hz), 6.35 (1H, d, J=16.1 Hz), 7.30 (2H, d, J=8.4 Hz), 7.49 (2H, d, J=8.1 Hz), 7.56 (1H, d, J=15.8 Hz); MASS (ES+): m/z 386 (M+1).

Preparation 244

Compound (244) was obtained from Compound (6) according to a manner similar to Preparation 229 (866 mg).

$^1$H-NMR (300 MHz, CDCl$_3$, δ): 1.34 (3H, t, J=7 Hz), 3.60 (2H, s), 3.71 (2H, s), 4.16 (2H, d, J=5 Hz), 4.27 (2H, q, J=7 Hz), 6.42 (1H, d, J=16 Hz), 7.16–7.37 (7H, m), 7.50 (2H, d, J=8 Hz), 7.66 (1H, d, J=16 Hz); MASS (ES+): m/z 366 (M+1)

Preparation 245

To a suspension of Compound (229) (5.42 g) in xylene (50 mL) were added AcONH$_4$ and AcOH, and the mixture was refluxed for 3 hrs with azeotropic removal of water. The resulting solution was cooled to ambient temperature and poured into saturated aqueous NaHCO$_3$ solution (100 mL) and extracted with AcOEt. The organic layer was washed with saturated aqueous NaHCO$_3$, water and brine, and dried over Na$_2$SO$_4$. The solvent was removed in vacuo, and the residual solid was triturated with isopropyl ether to give Compound (245) (4.56 g) as pale yellow powder.

$^1$H-NMR (300 MHz, CDCl$_3$, δ): 1.53 (9H, s), 4.19 (2H, s), 6.35 (1H, d, J=15.7 Hz), 7.21 (1H, s), 7.25 (1H, t, J=7.0 Hz), 7.29 (2H, d, J=8.4 Hz), 7.38 (2H, t, J=7.0 Hz), 7.48 (2H, d, J=7.7 Hz), 7.56 (1H, d, J=15.4 Hz), 7.69 (2H, br.d); MASS (ES+): m/e 361 (M+1).

Preparation 246

Compound (246) was obtained from Compound (230) according to a manner similar to Preparation 245 (1.10 g).

$^1$H-NMR (300 MHz, CDCl$_3$, δ): 1.53 (9H, s), 3.82 (3H, s), 4.17 (2H, s), 6.36 (1H, d, J=16.1 Hz), 7.22–7.48 (9H, m), 7.54 (1H, d, J=16.1 Hz), 7.74–7.87 (1H, m); MASS (ES+): m/z 419 (M+1).

Preparation 247

Compound (247) was obtained from Compound (231) according to a manner similar to Preparation 245 (3.8 g).

¹H-NMR (300 MHz, CDCl₃, δ): 1.54 (9H, s), 3.82 (3H, s), 4.17 (2H, s), 6.36 (1H, d, J=16.1 Hz), 7.29 (2H, d, J=8.1 Hz), 7.38 (2H, d, J=8.1 Hz), 7.49 (2H, d, J=8.1 Hz), 7.55 (1H, d, J=16.1 Hz), 7.78–7.90 (2H, m); MASS (ES+): m/z 453 (M+1).

Preparation 248

Compound (248) was obtained from Compound (232) according to a manner similar to Preparation 245 (2.08 g).

¹H-NMR (300 MHz, CDCl₃, δ): 1.54 (3×3H, s), 4.16 (2H, s), 6.36 (1H, d, J=16.2 Hz), 7.06 (2×1H, dd, J=8.8, 8.7 Hz), 7.14 (1H, s), 7.27 (2×1H, d, J=8 Hz), 7.46 (2×1H, d, J=8 Hz), 7.54 (1H, d, J=16.2 Hz), 7.73 (2H, m), 8.84 (1H, br); MASS (ES+): m/z 379.

Preparation 249

Compound (249) was obtained from Compound (233) according to a manner similar to Preparation 245 (1.12 g).

¹H-NMR (300 MHz, CDCl₃, δ): 1.54 (9H, s), 4.17 (2H, s), 6.33 (1H, d, J=16.1 Hz), 7.17 (1H, s), 7.27 (2H, d, J=8.1 Hz), 7.33 (2H, d, J=8.4 Hz), 7.46 (2H, d, J=8.1 Hz), 7.53 (2H, d, J=16.1 Hz), 7.64 (2H, d, J=8.4 Hz); MASS (ES+): m/z 395 (M+1)

Preparation 250

Compound (250) was obtained from Compound (234) according to a manner similar to Preparation 245 (1.28 g).

¹H-NMR (300 MHz, CDCl₃, δ): 1.52 (9H, s), 4.16 (2H, s), 6.33 (1H, d, J=16.1 Hz), 7.17–7.44 (8H, m), 7.52 (1H, d, J=16.1 Hz), 7.64–7.73 (2H, m); MASS (ES+): m/z 361 (M+1).

Preparation 251

Compound (251) was obtained from Compound (235) according to a manner similar to Preparation 245 (2.00 g).

¹H-NMR (300 MHz, CDCl₃, δ): 1.54 (9H, s), 3.82 (3H, s), 4.16 (2H, s), 6.34 (1H, d, J=15.8 Hz), 6.91 (2H, d, J=8.8 Hz), 7.10 (1H, s), 7.27 (2H, d, J=8.4 Hz), 7.47 (2H, d, J=8.4 Hz), 7.55 (1H, d, J=16.1 Hz), 7.60 (2H, br.d); MASS (ES+): m/z 391 (M+1)

Preparation 252

Compound (252) was obtained from Compound (236) according to a manner similar to Preparation 245 (2.72 g).

¹H-NMR (300 MHz, CDCl₃, δ): 1.53 (9H, s), 3.78 (3H, s), 4.05 (2H, s), 6.28 (1H, d, J=16.1 Hz), 6.78 (1H, m), 7.17 (2H, d, J=8.1 Hz), 7.18 (1H, s), 7.247 (2H, d, J=5.17 Hz), 7.37 (2H, d, J=8.4 Hz), 7.49 (1H, d, J=15.7 Hz); MASS (ES+): m/e 391 (M+1).

Preparation 253

Compound (253) was obtained from Compound (237) according to a manner similar to Preparation 245 (1.56 g).

¹H-NMR (300 MHz, CDCl₃, δ): 1.54 (9H, s), 3.85 (3H, s), 4.19 (2H, s, J=16.1 Hz), 6.34 (1H, d, J=8.4 Hz), 6.76 (1H, d, J=7.5 Hz), 7.00 (1H, t, J=7.5 Hz), 7.22 (1H, t, J=8.1 Hz), 7.30 (2H, d), 7.41 (1H, s, J=8.4 Hz), 7.48 (2H, d, J=16.1 Hz), 7.72 (1H, d, J=8.4 Hz), 7.76 (1H, br.d); MASS (ES+): m/e 391 (M+1).

Preparation 254

Compound (254) was obtained from Compound (238) according to a manner similar to Preparation 245 (4.00 g).

¹H-NMR (300 MHz, CDCl₃, δ): 4.08 (2H, s), 7.03 (2H, d, J=8.4 Hz), 7.24 (1H, t, J=7.4 Hz), 7.37 (2H, t, J=7.7 Hz), 7.65 (2+2H, d, J=8.4 Hz); MASS (ES+): m/e 361 (M+1).

Preparation 255

Compound (255) was obtained from N-(2-oxo-2-phenylethyl)acetamide according to a manner similar to Preparation 245 (803 mg).

¹H-NMR (300 MHz, DMSO-d₆, δ): 2.48 (3H, s), 7.20 (1H, s), 7.23 (1H, t, J=8.1 Hz), 7.37 (2H, t, J=7.7 Hz), 7.69 (2H, d, J=8.1 Hz).

Preparation 256

Compound (256) was obtained from Compound (239) according to a manner similar to Preparation 245 (460 mg).

¹H-NMR (300 MHz, CDCl₃, δ): 1.53 (9H, s), 1.69–1.81 (6H, m), 1.83–1.91 (6H, m), 1.99–2.08 (3H, m), 4.09 (2H, s), 6.34 (1H, d, J=16.1 Hz), 6.57 (1H, s), 7.23 (2H, d, J=8.2 Hz), 7.45 (2H, d, J=8.2 Hz), 7.55 (1H, d, J=16.1 Hz); MASS (ES+): m/z 419 (M+1).

Preparation 257

Compound (257) was obtained from Compound (240) according to a manner similar to Preparation 245 (58 mg).

¹H-NMR (300 MHz, CDCl₃, δ): 1.54 (9H, s), 3.82 (3H, s), 4.17 (2H, s), 6.35 (1H, d, J=16.1 Hz), 7.28 (2H, d, J=7.7 Hz), 7.39 (3H, m), 7.48 (2H, d, J=7.7 Hz), 7.55 (1H, d, J=16.1 Hz), 7.87 (2H, br.); MASS (ES+): m/e 419 (M+1).

Preparation 258

Compound (258) was obtained from Compound (241) according to a manner similar to Preparation 245 (1.06 g).

¹H-NMR (300 MHz, CDCl₃, δ): 1.28 (9H, s), 1.53 (9H, s), 4.07 (2H, s), 6.31 (1H, d, J=16.1 Hz), 6.60 (1H, s), 7.21 (2H, d, J=8.1 Hz), 7.43 (2H, d, J=8.4 Hz), 7.52 (1H, d, J=15.8 Hz); MASS (ES+): m/e 341 (M+1).

Preparation 259

Compound (259) was obtained from Compound (243) according to a manner similar to Preparation 245 (80 mg).

¹H-NMR (300 MHz, CDCl₃, δ): 1.32 (4H, m), 1.53 (9H, s), 1.73 (4H, m), 1.98 (2H, m), 2.50 (1H, m), 4.04 (2H, s), 6.31 (1H, d, J=16.1 Hz), 6.58 (1H, s), 7.20 (2H, d, J=8.1 Hz), 7.42 (2H, d, J=8.1 Hz), 7.52 (1H, d, J=16.1 Hz); MASS (ES+): m/z 367 (M+1).

Preparation 260

Compound (260) was obtained from Compound (244) according to a manner similar to Preparation 245 (232 mg).

¹H-NMR (300 MHz, CDCl₃, δ): 1.39 (3H, t, J=7 Hz), 3.92 (2H, s), 4.09 (2H, s), 4.26 (2H, q, J=7 Hz), 6.41 (1H, d, J=16 Hz), 7.21–7.33 (7H, m), 7.48 (2H, d, J=8 Hz), 7.65 (1H, d, J=16 Hz); MASS (ES+): m/z 347 (M+1).

Preparation 261

To a solution of Compound (297) (2.56 g, described later in Preparation 297 in dichloromethane) (17 mL) was added trifluoroacetic acid (2.74 mL), and the mixture was stirred for 1 hr. The solvent was removed in vacuo, and the residue was triturated with isopropyl ether to give Compound (261) (2.83 g) as colorless powder.

¹H-NMR (300 MHz, DMSO-d₆, δ): 4.37 (2H, s), 6.54 (1H, d, J=15.8 Hz), 7.39 (2H, d, J=8.1 Hz), 7.43 (1H, t, J=7.7 Hz), 7.53 (2H, t, J=8.1 Hz), 7.58 (1H, d, J=15.8 Hz), 7.72 (2H, d, J=8.4 Hz), 7.77 (2H, d, J=8.1 Hz), 8.05 (1H, s); MASS (ES+): m/e 305 (M+1).

Preparation 262

Compound (262) was obtained from Compound (246) according to a manner similar to Preparation 261 (1.55 g).

¹H-NMR (300 MHz, CDCl₃—CD₃OD (10:1), δ): 3.87 (3H, s), 4.35 (2H, s), 6.46 (1H, d, J=16.2 Hz), 7.10–7.76 (10H, m); MASS (ES+): m/z 369 (M+1, free).

Preparation 263

Compound (263) was obtained from Compound (251) according to a manner similar to Preparation 261 (2.32 g).

¹H-NMR (300 MHz, DMSO-d₆, δ): 3.81 (3H, s), 4.37 (2H, s), 6.55 (1H, d, J=16.1 Hz), 7.10 (2H, d, J=8.8 Hz), 7.40

Preparation 264

Compound (264) was obtained from Compound (252) according to a manner similar to Preparation 261 (1.27 g).

$^1$H-NMR (300 MHz, DMSO-$d_6$, δ): 3.83 (3H, s), 4.39 (2H, s), 6.55 (1H, d, J=15.8 Hz), 7.02 (1H, d, J=8.1 Hz), 7.33–7.47 (5H, m), 7.60 (1H, d, J=15.8 Hz), 7.73 (2H, d, J=8.1 Hz), 8.11 (1H, s); MASS: Not Detected.

Preparation 265

Compound (265) was obtained from Compound (253) according to a manner similar to Preparation 261 (1.24 g).

$^1$H-NMR (300 MHz, DMSO-$d_6$, δ): 3.93 (3H, s), 4.40 (2H, s), 6.54 (1H, d, J=16.1 Hz), 7.12 (1H, t, J=7.3 Hz), 7.22 (1H, d, J=7.7 Hz), 7.39 (2H, d, J=8.1 Hz), 7.46 (1H, t, J=7.9 Hz), 7.58 (1H, d, J=16.1 Hz), 7.72 (2H, d, J=8.1 Hz), 7.89 (1H, s); MASS (ES+): m/e 335 (M+1)

Preparation 266

Compound (266) was obtained from Compound (293) described later according to a manner similar to Preparation 261 (208 mg).

$^1$H-NMR (300 MHz, DMSO-$d_6$, δ): 4.08 (2H, s), 6.05 (1H, d, J=16.1 Hz), 7.35 (2H, d, J=8.4 Hz), 7.37 (1H, t, J=7.4 Hz), 7.49 (2H, d, J=7.4 Hz), 7.57 (1H, d, J=16.1 Hz), 7.66 (2H, d, J=8.1 Hz), 7.71 (1H, d, J=7.0 Hz); MASS (ES+): m/e 383 (M+1).

Preparation 267

Compound (267) was obtained from Compound (227) according to a manner similar to Preparation 261 (234 mg).

$^1$H-NMR (300 MHz, DMSO-$d_6$, δ): 4.03 (2H, s), 6.49 (1H, d, J=15.8 Hz), 7.32 (1H, t, J=7.3 Hz), 7.34 (2H, d, J=8.4 Hz), 7.47 (2H, t, J=7.3 Hz), 7.57 (1H, d, J=16.1 Hz), 7.65 (2H, d, J=8.4 Hz), 7.70 (2H, d, J=7.3 Hz); MASS (ES+): m/e 339 (M+1).

Preparation 268

Compound (268) was obtained from Compound (294) described later according to a manner similar to Preparation 261 (1.32 g).

$^1$H-NMR (300 MHz, DMSO-$d_6$, δ): 2.72 (6H, s), 4.21 (2H, s), 4.39 (2H, s), 6.52 (1H, d, J=15.8 Hz), 7.38 (2H, d, J=8.1 Hz), 7.47 (1H, m), 7.54 (4H, m), 7.58 (1H, d, J=15.4 Hz), 7.68 (2H, d, J=8.4 Hz); MASS (ES+): m/e 362 (M+1).

Preparation 269

Compound (269) was obtained from Compound (295) described later according to a manner similar to Preparation 261 (412 mg).

$^1$H-NMR (300 MHz, DMSO-$d_6$, δ): 1.48 (2H, br.), 1.69 (4H, br.), 2.91 (2H, br.), 3.27 (2H, br.), 4.24 (2H, s), 4.38 (2H, s), 6.53 (1H, d, J=16.1 Hz), 7.38 (2H, d, J=8.1 Hz), 7.47–7.61 (6H, m), 7.69 (2H, d, J=8.1 Hz); MASS (ES+): m/e 402 (M+1).

Preparation 270

Compound (270) was obtained from Compound (296) described later according to a manner similar to Preparation 261 (407 mg).

$^1$H-NMR (300 MHz, DMSO-$d_6$, δ): 3.07 (4H, br.), 3.75 (4H, br.), 4.22 (2H, s), 4.29 (2H, s), 6.52 (1H, d, J=15.7 Hz), 7.39 (2H, d, J=8.1 Hz), 7.46 (1H, t, J=7.0 Hz), 7.53 (2H, t, J=7.0 Hz), 7.58 (1H, d, J=16.1 Hz), 7.59 (2H, d, J=7.3 Hz), 7.68 (2H, d, J=8.1 Hz); MASS (ES+): m/e 404 (M+1).

Preparation 271

Compound (271) was obtained from Compound (228) according to a manner similar to Preparation 261 (171 mg).

$^1$H-NMR (300 MHz, DMSO-$d_6$, δ): 3.79 (3H, s), 4.03 (2H, s), 6.50 (1H, d, J=16.1 Hz), 7.05 (2H, d, J=8.8 Hz), 7.34 (2H, d, J=8.1 Hz), 7.57 (1H, d, J=15.8 Hz), 7.62 (2H, d, J=8.8 Hz), 7.65 (2H, d, J=8.1 Hz); MASS (ES+): m/e 369 (M+1).

Preparation 272

Compound (272) was obtained from Compound (215) according to a manner similar to Preparation 261 (339 mg).

$^1$H-NMR (300 MHz, DMSO-$d_6$, δ): 5.46 (2H, s), 6.60 (1H, d, J=16.1 Hz), 7.43 (1H, t, J=7.0 Hz), 7.46–7.54 (4H, m), 7.61 (1H, d, J=16.1 Hz), 7.72 (1H, m), 7.78 (2H, d, J=7.0 Hz), 7.84 (1H, s), 8.25 (1H, s), 9.29 (1H, s); MASS (ES+): m/e 305 (M+1).

Preparation 273

Compound (273) was obtained from Compound (218) according to a manner similar to Preparation 261 (491 mg).

$^1$H-NMR (300 MHz, DMSO-$d_6$, δ): 2.30 (3H, s), 5.48 (2H, s), 6.57 (1H, d, J=16.1 Hz), 7.34–7.52 (3H, m), 7.58 (1H, d, J=15.8 Hz), 7.60 (4H, s), 7.71 (1H, s), 9.26 (1H, s); MASS (ES+): m/e 353 (M+1).

Preparation 274

Compound (274) was obtained from Compound (257) according to a manner similar to Preparation 261 (65 mg).

$^1$H-NMR (300 MHz, DMSO-$d_6$, δ): 3.78 (3H, s), 4.20 (2H, s), 6.51 (1H, d, J=15.8 Hz), 7.38 (2H, d, J=7.7 Hz), 7.47 (3H, m), 7.57 (1H, d, J=15.8 Hz), 7.67 (2H, d, J=8.4 Hz), 7.76 (2H, m); MASS (ES+): m/e 363 (M+1).

Preparation 275

Compound (275) was obtained from Compound (258) according to a manner similar to Preparation 261 (454 mg).

$^1$H-NMR (300 MHz, DMSO-$d_6$, δ): 1.21 (9H, s), 4.32 (2H, s), 6.55 (1H, d, J=16.1 Hz), 7.34 (2H, d, J=8.4 Hz), 7.58 (1H, d, J=16.1 Hz), 7.71 (2H, d, J=8.1 Hz); MASS (ES+): m/e 285 (M+1).

Preparation 276

Compound (276) was obtained from Compound (259) according to a manner similar to Preparation 261 (98.5 mg).

$^1$H-NMR (300 MHz, DMSO-$d_6$, δ): 1.32 (4H, m), 1.72 (4H, m), 1.94 (2H, m), 2.47 (1H, m), 4.28 (2H, s), 6.54 (1H, d, J=15.8 Hz), 7.31 (1H, s), 7.33 (2H, d, J=8.1 Hz), 7.58 (1H, d, J=15.4 Hz), 7.71 (2H, d, J=8.1 Hz); MASS (ES+): m/z 311 (M+1) 0.116

Preparation 277

To a solution of Compound (261) (2.46 g) in DMF (30 mL) were added O-(tetrahydro-2H-pyran-2-yl)hydroxylamine (1.66 g), HOBt (2.74 g) and EDCI (3.15 g) at ambient temperature, and the mixture was stirred for 3 hrs. The resulting mixture was diluted with saturated aqueous NaHCO$_3$ solution and the precipitate was collected by filtration. The obtained powder was washed with water and dried to give Compound (277) (2.46 g) as pale yellow powder. The obtained Compound (277) was used in Example 58.

$^1$H-NMR (300 MHz, DMSO-$d_6$, δ): 1.54 (3H, br.), 1.70 (3H, br.), 3.51 (1H, m), 3.96 (1H, m), 4.04 (2H, s), 4.90 (1H, s), 6.46 (1H, d, J=16.1 Hz), 7.16 (1H, m), 7.31 (4H, m), 7.46 (1H, d, J=15.7 Hz), 7.51 (3H, m), 7.73 (2H, d, J=7.3 Hz); MASS (ES+): m/e 304 (M+1)

Preparation 278

Compound (278) was obtained from Compound (262) according to a manner similar to Preparation 277 (896 mg). The obtained Compound (278) was used in Example 59.

$^1$H-NMR (300 MHz, CDCl$_3$, δ): 1.48–1.86 (6H, m), 3.58–3.69 (1H, m) 3.81 (3H, s), 3.91–4.09 (3H, m), 4.95 (1H, br.s), 6.09–6.30 (1H, m), 7.17–7.31 (6H, m), 7.33–7.43 (4H, m), 7.74–7.84 (2H, m); MASS (ES+): m/z 462 (M+1).

Preparation 279

Compound (279) was obtained from Compound (263) according to a manner similar to Preparation 277 (1.67 g). The obtained Compound (278) was used in Example 70.

$^1$H-NMR (300 MHz, DMSO-d$_6$, δ): 1.54 (3H, br.), 1.69 (3H, br.), 3.53 (1H, m), 3.76 (3H, s), 3.94 (1H, m), 4.08 (2H, s), 4.91 (1H, s), 6.47 (1H, d, J=15.8 Hz), 6.94 (2H, d, J=8.8 Hz), 7.33 (2H, d, J=8.1 Hz), 7.43 (1H, s), 7.46 (1H, d, J=15.8 Hz), 7.54 (2H, d, J=7.7 Hz), 7.64 (2H, d, J=8.8 Hz); MASS (ES+): m/z 434 (M+1).

Preparation 280

Compound (280) was obtained from Compound (264) according to a manner similar to Preparation 277 (758 mg). The obtained Compound (280) was used in Example 71.

$^1$H-NMR (300 MHz, DMSO-d$_6$, δ): 1.54 (3H, br.), 1.69 (3H, br.), 3.52 (1H, m), 3.78 (3H, s), 3.95 (1H, m), 4.04 (2H, s), 4.90 (1H, s), 6.46 (1H, d, J=16.1 Hz), 6.74 (1H, d, J=8.1 Hz), 7.20–7.33 (5H, m), 7.46 (1H, d, J=15.8 Hz), 7.51 (1H, s), 7.52 (2H, d, J=8.1 Hz); MASS (ES+): m/e 434 (M+1).

Preparation 281

Compound (281) was obtained from Compound (265) according to a manner similar to Preparation 277 (729 mg). The obtained Compound (281) was used in Example 72.

$^1$H-NMR (300 MHz, DMSO-d$_6$, δ): 1.53 (3H, br.s), 1.69 (3H, br.s), 3.53 (1H, m), 3.88 (3H, s), 3.95 (1H, m), 4.05 (2H, s), 4.90 (1H, s), 6.46 (1H, d, J=16.3 Hz), 6.96 (1H, t, J=7.3 Hz), 7.03 (1H, d, J=8.1 Hz), 7.17 (1H, t, J=8.1 Hz), 7.32 (2H, d, J=8.1 Hz), 7.42 (1H, br.s), 7.46 (1H, d, J=16.1 Hz), 7.52 (2H, d, J=8.1 Hz); MASS (ES+): m/z 434 (M+1).

Preparation 282

Compound (282) was obtained from Compound (266) according to a manner similar to Preparation 277 (148 mg). The obtained Compound (282) was used in Example 73.

$^1$H-NMR (300 MHz, DMSO-d$_6$, δ): 1.54 (3H, br.), 1.69 (3H, br.), 3.55 (1H, m), 3.95 (1H, m), 4.02 (2H, s), 4.91 (1H, s), 6.48 (1H, d, J=16.1 Hz), 7.32 (1H, t, J=7.0 Hz), 7.34 (2H, d, J=8.1 Hz), 7.46 (2H, t, J=7.3 Hz), 7.46 (1H, d, J=15.4 Hz), 7.54 (2H, d, J=8.1 Hz), 7.71 (2H, d, J=7.3 Hz); MASS (ES+): m/e 482 (M+1)

Preparation 283

Compound (283) was obtained from Compound (267) according to a manner similar to Preparation 277 (166 mg). The obtained Compound (283) was used in Example 74.

$^1$H-NMR (300 MHz, DMSO-d$_6$, δ): 1.54 (3H, br.), 1.69 (3H, br.), 3.53 (1H, m), 3.69 (1H, m), 4.02 (2H, s), 4.90 (1H, s), 6.47 (1H, d, J=16.1 Hz), 7.32 (1H, t, J=8.1 Hz), 7.33 (2H, d, J=8.1 Hz), 7.47 (2H, t, J=15.8 Hz), 7.47 (1H, d, J=8.1 Hz), 7.54 (2H, d, J=8.4 Hz), 7.70 (2H, d, J=8.1 Hz); MASS (ES+): m/e 438 (M+1).

Preparation 284

Compound (284) was obtained from Compound (268) according to a manner similar to Preparation 277 (811 mg). The obtained Compound (284) was used in Examples 90 and 111.

$^1$H-NMR (300 MHz, CDCl$_3$, δ): 1.51–1.67 (6H, br), 2.28 (6H, s), 3.60 (1H, m), 3.94 (1H, m), 4.12 (2H, s), 4.71 (1H, s), 7.39 (3H, m), 7.59 (2H, d, J=6.6 Hz), 7.61 (1H, d, J=16.8 Hz); MASS (ES+): m/e 461 (M+1).

Preparation 285

Compound (285) was obtained from Compound (269) according to a manner similar to Preparation 277 (105 mg). The obtained Compound (285) was used in Example 75.

$^1$H-NMR (300 MHz, CDCl$_3$, δ): 1.45 (3H, br.), 1.59 (3+4H, br.), 1.84 (2H, br.), 2.48 (4H, br.), 3.64 (1H, m), 3.71 (2H, s), 3.97 (1H, m), 4.12 (2H, s), 5.01 (1H, s), 6.32 (1H, d, J=16.1 Hz), 7.26 (1+2H, m), 7.39 (2+2H, m), 7.49 (1H, d, J=16.5 Hz), 7.59 (2H, d, J=7.0 Hz); MASS (ES+): m/e 501 (M+1).

Preparation 286

Compound (286) was obtained from Compound (270) according to a manner similar to Preparation 277 (129 mg). The obtained Compound (286) was used in Example 76.

$^1$H-NMR (300 MHz, DMSO-d$_6$, δ): 1.53 (3H, br.), 1.69 (3H, br.), 2.40 (4H, br.), 3.52 (1H, m), 3.57 (4H, br.), 3.95 (1H, m), 4.00 (2H, s), 4.90 (1H, s), 6.46 (1H, d, J=15.8 Hz), 7.23 (1H, br.), 7.33 (2H, d, J=8.4 Hz), 7.36 (2H, br.), 7.46 (1H, d, J=15.8 Hz), 7.51 (2H, d, J=8.1 Hz), 7.70 (2H, br.); MASS (ES+): m/e 503 (M+1)

Preparation 287

Compound (287) was obtained from Compound (271) according to a manner similar to Preparation 277 (108 mg). The obtained Compound (287) was used in Example 77.

$^1$H-NMR (300 MHz, DMSO-d$_6$, δ): 1.53 (3H, br.), 1.69 (3H, br.), 3.54 (1H, m), 3.79 (3H, s), 3.94 (1H, m), 3.98 (2H, s), 4.90 (1H, s), 6.47 (1H, d, J=16.1 Hz), 7.04 (2H, d, J=8.8 Hz), 7.33 (2H, d, J=7.7 Hz), 7.47 (1H, d, J=15.4 Hz), 7.53 (2H, d, J=7.7 Hz), 7.61 (2H, d, J=8.8 Hz); MASS (ES+): m/e 468 (M+1).

Preparation 288

Compound (288) was obtained from Compound (272) according to a manner similar to Preparation 277 (215 mg). The obtained Compound (288) was used in Example 80.

$^1$H-NMR (300 MHz, DMSO-d$_6$, δ): 1.53 (3H, br.), 1.69 (3H, br.), 3.53 (1H, m), 3.94 (1H, m), 4.90 (1H, s), 5.25 (2H, s), 6.50 (1H, d, J=16.1 Hz), 7.18 (1H, t, J=7.3 Hz), 7.32 (3H, m), 7.38 (1H, d, J=15.4 Hz), 7.44 (1H, d, J=7.3 Hz), 7.52 (1H, s), 7.56 (1H, s), 7.73 (3H, m), 7.86 (1H, s); MASS (ES+): m/e 404 (M+1).

Preparation 289

Compound (289) was obtained from Compound (273) according to a manner similar to Preparation 277 (419 mg). The obtained Compound (289) was used in Example 81.

$^1$H-NMR (300 MHz, DMSO-d$_6$, δ): 1.53 (3H, br.), 1.69 (3H, br.), 3.52 (1H, m), 3.95 (1H, m), 4.91 (1H, s), 5.26 (2H, s), 6.48 (1H, d, J=15.8 Hz), 7.19 (1H, d, J=7.7 Hz), 7.43 (5H, m), 7.51 (1H, s), 7.65 (2H, d, J=8.8 Hz), 7.86 (1H, s); MASS (ES+): m/e 452 (M+1).

Preparation 290

Compound (290) was obtained from Compound (274) according to a manner similar to Preparation 277 (43 mg). The obtained Compound (290) was used in Example 84.

$^1$H-NMR (300 MHz, CDCl$_3$, δ): 1.60 (3H, br.), 1.81 (3H, br.), 6.64 (1H, m), 3.82 (3H, s), 3.97 (1H, s), 4.03 (2H, s), 5.00 (1H, br.), 6.28 (1H, br.), 7.12 (2H, br.), 7.32 (2H, br.), 7.39 (3H, m), 7.54 (1H, br.), 7.79 (2H, br.); MASS (ES+): m/e 462 (M+1).

Preparation 291

Compound (291) was obtained from Compound (275) according to a manner similar to Preparation 277 (85 mg). The obtained Compound (291) was used in Example 85.

$^1$H-NMR (300 MHz, DMSO-d$_6$, δ): 1.54 (3H, br.), 1.69 (3H, br.), 3.53 (1H, m), 3.94 (2H, s), 3.97 (1H, m), 4.91 (1H, s), 6.45 (1H, d, J=15.3 Hz), 6.56 (1H, s), 7.27 (2H, d, J=8.1 Hz), 7.47 (1H, d, J=16.1 Hz), 7.50 (2H, d, J=8.8 Hz); MASS (ES+): m/e 384 (M+1).

Preparation 292

Compound (292) was obtained from Compound (276) according to a manner similar to Preparation 277 (42 mg). The obtained Compound (292) was used in Example 110.

$^1$H-NMR (300 MHz, CDCl$_3$, δ): 1.30 (6H, m), 1.62–2.00 (10H, m), 2.51 (1H, m), 3.67 (1H, m), 4.02 (1H, m), 4.02 (2H, s), 5.01 (1H, s), 6.37 (1H, br.), 6.58 (1H, s, J=8.0 Hz), 7.23 (2H, d, J=7.7 Hz), 7.43 (2H, d, J=16.1 Hz), 7.62 (1H, d); MASS (ES+): m/z 410 (M+1)

Preparation 293

To a suspension of Compound (245) (2.0 g) in MeCN (20 mL) was added N-bromosuccinimide (988 mg) at 5° C. and the mixture was stirred for 0.5 hr at 5° C. The mixture was poured into 5% aqueous NaHSO$_3$ solution (100 mL), and the mixture was extracted with AcOEt. The organic layer was washed with saturated aqueous NaHCO$_3$ solution and brine, and dried over Na$_2$SO$_4$. The solvent was removed in vacuo and the residual brown oil was purified by Silica gel flash column chromatography eluting with Hexane: AcOEt=1:1 to give Compound (293) (1.68 g) as orange form.

$^1$H-NMR (300 MHz, CDCl$_3$, δ): 1.53 (9H, s), 4.13 (2H, s), 6.34 (1H, d, J=16.1 Hz), 7.28 (2H, d, J=8.1 Hz), 7.31 (1H, t, J=7.4 Hz), 7.40 (2H, t, J=7.4 Hz), 7.47 (2H, d, J=8.1 Hz), 7.54 (1H, d, J=16.1 Hz), 7.57 (2H, d, J=7.4 Hz); MASS (ES+): m/e 439 (M+1)

Preparation 294

To a solution of Compound (245) (1.0 g) were added N,N-dimethylamine hydrochloride (339 mg) and paraformaldehyde (125 mg), and the mixture was heated at 90° C. for 1 hr. The reaction mixture was poured into saturated aqueous NaHCO$_3$ solution and extracted with AcOEt. The organic phase was washed with saturated aqueous NaHCO$_3$ solution, water and brine, and dried over Na$_2$SO$_4$. The solvent was removed in vacuo to give Compound (294) (742 mg) as yellow form.

$^1$H-NMR (300 MHz, CDCl$_3$, δ): 1.53 (9H, s), 2.23 (6H, s), 3.58 (2H, s), 4.16 (2H, s), 6.35 (1H, d, J=15.8 Hz), 7.29 (1H, t, J=8.1 Hz), 7.30 (2H, d, J=8.1 Hz), 7.39 (2H, t, J=8.1 Hz), 7.48 (2H, t, J=8.1 Hz), 7.57 (1H, d, J=16.1 Hz), 7.58 (1H, br.); MASS (ES+): m/e 418 (M+1).

Preparation 295

Compound (295) was obtained from Compound (245) according to a manner similar to Preparation 294 (243 mg).

$^1$H-NMR (300 MHz, CDCl$_3$, δ): 1.44 (2H, br.), 1.53 (9+4H, br.), 2.42 (4H, br.), 3.63 (2H, s), 4.11 (2H, s), 6.34 (1H, d, J=15.8 Hz), 7.27 (1H, t, J=8.1 Hz), 7.28 (2H, d, J=8.1 Hz), 7.37 (2H, t, J=8.1 Hz), 7.45 (2H, d, J=8.4 Hz), 7.55 (1H, d, J=15.7 Hz), 7.58 (2H, d, J=8.1 Hz); MASS (ES+): m/e 458 (M+1).

Preparation 296

Compound (296) was obtained from Compound (245) according to a manner similar to Preparation 294 (297 mg).

$^1$H-NMR (300 MHz, CDCl$_3$, δ): 1.53 (9H, s), 2.48 (4H, br.), 3.64 (2H, s), 3.68 (4H, br.), 4.15 (2H, s), 6.35 (1H, d, J=16.1 Hz), 7.28 (1H, t, J=8.1 Hz), 7.29 (2H, d, J=8.1 Hz), 7.39 (2H, t, J=7.5 Hz), 7.48 (2H, d, J=8.4 Hz), 7.56 (2H, br.), 7.56 (1H, d, J=16.1 Hz); MASS (ES+): m/e 460 (M+1).

Preparation 297

To a stirred solution of Compound (254) (4.0 g) in DMF (40 mL) were added acrylic acid t-butyl ester (8.13 mL), palladium(II) acetate (125 mg), triphenylphosphine (583 mg) and N,N-diisopropylethylamine (3.2 mL). The mixture was stirred at 100° C. for 1 hr. The resulting mixture was poured into saturated aqueous NaHCO$_3$ solution and extracted with AcOEt. The organic phase was washed with saturated aqueous NaHCO$_3$ solution and brine, and dried over Na$_2$SO$_4$. The solvent was removed in vacuo and purified by silica gel column chromatography eluted with AcOEt to give Compound (297) (2.56 g) as colorless solid.

$^1$H-NMR (300 MHz, CDCl$_3$, δ): 1.53 (9H, s), 4.18 (2H, s), 6.34 (1H, d, J=16.1 Hz), 7.21 (1H, s), 7.25 (1H, m), 7.28 (2H, d, J=8.4 Hz), 7.37 (2H, t, J=7.4 Hz), 7.47 (2H, d, J=8.4 Hz), 7.55 (1H, d, J=16.1 Hz); MASS (ES+): m/e 361 (M+1).

Preparation 298

To a solution of 4-iodophenol (1.0 g) in DMF (10 mL) was added K$_2$CO$_3$ (powder 325 mesh, manufactured by Aldrich, 691 mg) was added, and the mixture was stirred for 15 min. To the mixture was added ethyl 4-bromobutanoate (0.722 mL), and the mixture was stirred for 65 hrs at ambient temperature. The resulting mixture was poured into saturated aqueous ammonium chloride solution and extracted with AcOEt. The organic phase was sequentially washed with water, saturated aqueous ammonium chloride solution, water and brine, and dried over Na$_2$SO$_4$. The solvent was removed in vacuo, and residual colorless oil was purified by silica gel column chromatography eluting with AcOEt and hexane (1:4) to give Compound (298) (1.32 g) as colorless oil.

$^1$H-NMR (300 MHz, CDCl$_3$, δ): 1.26 (3H, t, J=7.1 Hz), 2.10 (2H, quint., J=6.7 Hz), 2.50 (2H, t, J=7.3 Hz), 3.97 (2H, t, J=6.0 Hz), 4.14 (2H, q, J=7.1 Hz), 6.66 (2H, d, J=9.2 Hz), 7.54 (2H, d, J=9.2 Hz); MASS: Not Detected.

Preparation 299

Compound (299) was obtained from 4-iodophenol according to a manner similar to Preparation 298 (1.70 g).

$^1$H-NMR (300 MHz, CDCl$_3$, δ): 1.26 (3H, t, J=7.1 Hz), 1.81 (4H, m), 2.38 (2H, m), 3.94 (2H, m), 4.14 (2H, q, J=7.2 Hz), 6.66 (2H, d, J=9.2 Hz), 7.54 (2H, d, J=9.2 Hz); MASS: Not Detected.

Preparation 300

To a solution of Compound (298) (1.32 g) in dioxane 13 mL was added 1N NaOH aq solution (11.9 mL) and the mixture was stirred for 15 hrs. The organic solvent was removed in vacuo, and the pH value of residual aqueous phase was adjusted to 3 with 1N HCl. The precipitate was collected by filtration and dried in vacuo to give Compound (300) (1.047 g) as colorless powder.

$^1$H-NMR (300 MHz, DMSO-d$_6$, δ): 1.91 (2H, quint., J=6.8 Hz), 2.36 (2H, t, J=7.3 Hz), 3.95 (2H, t, J=6.4 Hz), 6.78 (2H, d, J=8.9 Hz), 7.58 (2H, d, J=9.2 Hz); MASS (ES+): Not Detected.

Preparation 301

Compound (301) was obtained from Compound (299) according to a manner similar to Preparation 300 (883 mg).

$^1$H-NMR (300 MHz, DMSO-d$_6$, δ): 1.56–1.76 (4H, m), 2.26 (2H, t, J=7.1 Hz), 3.94 (2H, t, J=6.2 Hz), 6.78 (2H, d, J=8.8 Hz), 7.57 (2H, d, J=8.8 Hz); MASS: Not Detected.

Preparation 302

Compound (302) was obtained from Compound (300) according to a manner similar to Preparation 297 (1.026 g).

$^1$H-NMR (300 MHz, CDCl$_3$, δ): 1.53 (9H, s), 2.13 (2H, quint., J=6.6 Hz), 2.58 (2H, t, J=7.2 Hz), 4.05 (2H, t, J=6.0 Hz), 6.24 (1H, d, J=15.8 Hz), 6.87 (2H, d, J=8.8 Hz), 7.44 (2H, d, J=8.8 Hz), 7.53 (2H, d, J=16.1 Hz); MASS Not Detected.

Preparation 303

Compound (303) was obtained from Compound (301) according to a manner similar to Preparation 297 (635 mg).

$^1$H-NMR (300 MHz, CDCl$_3$, δ): 1.53 (9H, s), 1.85 (4H, m), 2.45 (2H, t, J=5.9 Hz), 4.00 (2H, t, J=5.9 Hz), 6.24 (1H, d, J=16.1 Hz), 6.87 (2H, d, J=8.8 Hz), 7.44 (2H, d, J=8.8 Hz), 7.54 (1H, d, J=15.8 Hz); MASS: Not Detected.

Preparation 304

Compound (304) was obtained from 4-(4-iodophenyl)butanoic acid according to a manner similar to Preparation 297 (1.68 mg).

$^1$H-NMR (300 MHz, CDCl$_3$, δ): 1.53 (9H, s), 1.97 (2H, quint., J=7.5 Hz), 2.38 (2H, t, J=7.3 Hz), 2.69 (2H, t, J=7.5 Hz), 6.33 (1H, d, J=15.8 Hz), 7.19 (2H, d, J=8.1 Hz), 7.44 (2H, d, J=8.1 Hz), 7.56 (2H, d, J=15.8 Hz); MASS: Not Detected.

Preparation 305

Compound (305) was obtained from Compound (318) described later according to a manner similar to Preparation 297 (2.45 g).

$^1$H-NMR (300 MHz, CDCl$_3$, δ): 1.43 (1H, s), 1.53 (9H, s), 1.69 (1H, s), 1.93 (1H, s), 2.59 (1H, s), 6.33 (1H, d, J=16.4 Hz), 7.10 (2H, d, J=8.1 Hz), 7.43 (2H, d, J=8.1 Hz), 7.55 (1H, d, J=15.8 Hz); MASS (ES−): m/e 287 (M−1).

Preparation 306

To a solution of Compound (302) in DMF (3 mL) were added tert-butyl 2-aminophenylcarbamate (224 mg), HOBt (172 mg) and N-ethyl-N'-(3-dimethylaminopropyl)carbodiimide hydrochloride (EDCI.HCl, 224 mg), and the mixture was stirred at ambient temperature for 2 hrs. The mixture was poured into saturated aqueous NaHCO$_3$ solution and extracted with ethyl acetate. The organic phase was sequentially washed with saturated NH$_4$Cl solution, saturated NaHCO$_3$ solution and brine, and dried over Na$_2$SO$_4$. The solvent was removed in vacuo and the residue was purified by preparative thin layer chromatography (chloroform:methanol=10:1) to give Compound (306) (379 mg) as pale yellow form.

$^1$H-NMR (300 MHz, CDCl$_3$, δ): 1.50 (9H, s), 1.53 (9H, s), 2.23 (2H, quint., J=6.6 Hz), 2.60 (2H, t, J=7.0 Hz), 4.09 (2H, t, J=6.0 Hz), 6.24 (1H, d, J=15.8 Hz), 6.88 (2H, d, J=8.8 Hz), 7.16 (2H, m), 7.36 (1H, m), 7.44 (2H, d, J=8.8 Hz), 7.50 (1H, m), 7.53 (1H, d, J=15.8 Hz); MASS (ES+): m/e 497 (M+1).

Preparation 307

Compound (307) was obtained from Compound (303) according to a manner similar to Preparation 306 (395 mg).

$^1$H-NMR (300 MHz, CDCl$_3$, δ): 1.50 (9H, s), 1.53 (9H, s), 1.92 (4H, m), 2.47 (2H, m), 4.03 (2H, m), 6.24 (1H, d, J=16.1 Hz), 6.87 (2H, d, J=8.8 Hz), 7.17 (2H, m), 7.35 (1H, m), 7.44 (2H, d, J=8.8 Hz), 7.50 (1H, m), 7.53 (1H, d, J=16.1 Hz); MASS (ES+): m/e 511 (M+1).

Preparation 308

Compound (308) was obtained from Compound (304) according to a manner similar to Preparation 306 (294 mg).

$^1$H-NMR (300 MHz, CDCl$_3$, δ): 1.48 (9H, s), 1.53 (9H, s), 2.07 (2H, quint., J=7.7 Hz), 2.40 (2H, t, J=7.9 Hz), 2.73 (2H, t, J=7.9 Hz), 6.33 (1H, d, J=7.9 Hz), 7.18 (2H, m, J=16.1 Hz), 7.21 (2H, d), 7.35 (1H, m, J=8.1 Hz), 7.44 (2H, d), 7.50 (1H, m, J=8.1 Hz), 7.56 (1H, d, J=16.1 Hz); MASS (ES+): m/e 481 (M+1).

Preparation 309

To a stirred solution of Compound (306) (379 mg) in ACOH (4 mL) was added 1N HCl in AcOH (3.82 mL), and the mixture was heated at 120° C. for 2 hrs. The reaction mixture was cooled to ambient temperature and diluted with AcOEt. The precipitate was collected by filtration to give Compound (309) (199 mg) as pale yellow powder.

$^1$H-NMR (300 MHz, DMSO-d$_6$, δ): 2.36 (2H, quint., J=6.5 Hz), 3.30 (2H, t, J=7.5 Hz), 4.16 (2H, t, J=5.9 Hz), 6.37 (1H, d, J=16.1 Hz), 6.79 (2H, d, J=8.4 Hz), 7.52 (1H, d, J=16.5 Hz), 7.55 (2H, m), 7.59 (2H, d, J=8.8 Hz), 7.79 (2H, m); MASS (ES+): m/e 323 (M+1)

Preparation 310

Compound (310) was obtained from Compound (307) according to a manner similar to Preparation 309 (205 mg).

$^1$H-NMR (300 MHz, DMSO-d$_6$, δ): 1.84 (2H, m), 2.03 (2H, m), 3.21 (2H, t, J=7.6 Hz), 4.08 (2H, t, J=5.9 Hz), 6.38 (1H, d, J=16.1 Hz), 6.96 (2H, d, J=8.8 Hz), 7.53 (2H, m), 7.54 (1H, d, J=15.8 Hz), 7.63 (2H, d, J=9.1 Hz), 7.78 (2H, m); MASS (ES+): m/e 337 (M+1).

Preparation 311

Compound (311) was obtained from Compound (308) according to a manner similar to Preparation 309 (174 mg).

$^1$H-NMR (300 MHz, DMSO-d$_6$, δ): 2.19 (2H, quint., J=7.1 Hz), 2.75 (2H, t, J=7.3 Hz), 3.12 (2H, t, J=7.5 Hz), 6.48 (1H, d, J=16.1 Hz), 7.30 (2H, d, J=7.7 Hz), 7.52 (2H, m), 7.56 (1H, d, J=15.0 Hz), 7.62 (2H, d, J=8.4 Hz), 7.76 (2H, m); MASS (ES+): m/e 307 (M+1).

Preparation 312

To a stirred solution of Compound (309) (234 mg) in DMF (2 mL) was added O-(tetrahydro-2H-pyran-2-yl)hydroxylamine (71.5 mg), HOBt (97.4 mg) and EDCI (112 mg), and the resulting mixture was stirred at ambient temperature for 16 hrs. To the reaction mixture was added saturated aqueous NaHCO$_3$ solution, and the precipitate was collected by filtration and washed with water. The obtained powder was dried in vacuo to give Compound (312) (161 mg) as colorless powder. The obtained compound (312) was used in Example 103.

$^1$H-NMR (300 MHz, CDCl$_3$, δ): 1.62 (3H, br.), 1.84 (3H, br.), 2.38 (2H, quint., J=7.1 Hz), 3.13 (2H, t, J=7.1 Hz), 3.65 (1H, m), 3.98 (1H, m), 4.05 (2H, t, J=6.0 Hz), 5.02 (1H, s), 6.78 (2H, d, J=8.8 Hz), 7.23 (2H, m), 7.37 (2H, d, J=8.4 Hz), 7.56 (2H, br.), 7.63 (1H, d, J=16.1 Hz); MASS (ES+): m/e 422 (M+1).

Preparation 313

Compound (313) was obtained from Compound (310) according to a manner similar to Preparation 312 (197 mg). The obtained compound (313) was used in Example 104.

$^1$H-NMR (300 MHz, CDCl$_3$, δ): 1.64 (3H, br.), 1.84 (3H, br.), 1.91 (2H, m), 2.07 (2H, m), 3.01 (2H, t, J=7.7 Hz), 3.65 (1H, m), 3.97 (1H, m), 3.99 (2H, t, J=6.3 Hz), 5.02 (1H, s), 6.81 (2H, d, J=8.8 Hz), 7.22 (2H, m), 7.40 (2H, d, J=8.1 Hz), 7.53 (2H, br.m), 7.67 (2H, d, J=15.0 Hz); MASS (ES+): m/e 436 (M+1).

Preparation 314

Compound (314) was obtained from Compound (311) according to a manner similar to Preparation 312 (177 mg). The obtained compound (314) was used in Example 105.

$^1$H-NMR (300 MHz, DMSO-d$_6$, δ): 1.53 (3H, br.), 1.69 (3H, br.), 2.09 (2H, quint., J=7.7 Hz), 2.69 (2H, t, J=7.7 Hz), 2.81 (2H, t, J=7.4 Hz), 3.55 (1H, m), 3.96 (1H, m), 4.91 (1H, s), 6.47 (1H, d, J=16.1 Hz), 7.10 (2H, m), 7.29 (2H, d, J=8.1 Hz), 7.46 (1H, d, J=15.8 Hz), 7.47 (2H, m), 7.51 (2H, d, J=7.7 Hz); MASS (ES+): m/e 406 (M+1).

Preparation 315

Compound (315) was obtained from Compound (320) described later according to a manner similar to Preparation 312 (287 mg).

$^1$H-NMR (300 MHz, DMSO-d$_6$, δ): 1.52 (3H, br.), 1.66 (1H, m), 1.69 (3H, br.), 1.82 (1H, m), 2.40 (1H, m), 2.56 (1H, m), 3.50 (1H, m), 3.95 (1H, m), 4.90 (1H, s), 6.47 (1H, d, J=15.8 Hz), 7.11 (2H, m) 7.25 (2H, d, J=8.1 Hz), 7.41 (1H, d, J=16.1 Hz), 7.44 (2H, m), 7.50 (2H, d, J=8.8 Hz); MASS (ES+): m/e 404 (M+1).

Preparation 316

Compound (316) was obtained from Compound (335) described later according to a manner similar to Preparation 312 (55 mg). The obtained compound (316) was used in Example 100.

$^1$H-NMR (300 MHz, CDCl$_3$, δ): 1.60–1.90 (6H, m), 3.64–3.73 (1H, m), 3.80 (3H, s), 3.94–4.04 (1H, m), 4.13 (2H, s), 4.82 (2H, s), 4.97–5.07 (1H, m), 6.81–7.31 (8H, m), 7.45 (2H, d, J=8 Hz), 7.71 (1H, d, J=16 Hz); MASS (ES+): m/z 516 (M+1).

Preparation 317

Compound (317) was obtained from Compound (202) according to a manner similar to Preparation 312 (177 mg). The obtained compound (317) was used in Example 101.

$^1$H-NMR (300 MHz, DMSO-d$_6$, δ): 1.49–2.02 (21H, m), 3.49–3.58 (1H, m), 3.88–4.01 (3H, m), 4.87–4.93 (1H, m), 6.45 (1H, d, J=16 Hz), 7.18 (1H, d, J=8 Hz), 7.26 (2H, d, J=8 Hz), 7.41–7.53 (3H, m). MASS (ES+): m/z 462 (M+1)

Preparation 318

To a stirred solution of trans-2-phenylcyclopropanecarboxylic acid (5.0 g) in acetic acid (30 mL) were added periodic acid (3.13 g), iodine (3.13 g) and concentrated sulfuric acid (3.62 mL), and the mixture was stirred at 75° C. for 5 hrs. The resulting mixture was poured into 5% aqueous NaHSO$_3$ solution (100 mL), and the precipitate was collected by filtration. The filtrate was extracted with AcOEt, and the organic phase was sequentially washed with 5% aqueous NaHSO$_3$ solution, saturated aqueous NH$_4$Cl solution and brine, and dried over Na$_2$SO$_4$. The solvent was removed in vacuo, and the residual solid was combined with the powder obtained by filtration, and dissolved in AcOEt. The precipitate was filtered off, and the filtrate was concentrated and crystallized from ethyl acetate and hexane (20 mL:40 mL) to give Compound (318) (3.88 g).

$^1$H-NMR (300 MHz, CDCl$_3$, δ): 1.36 (1H, m), 1.66 (1H, m), 1.87 (1H, m), 2.53 (1H, m), 6.86 (2H, d, J=8.4 Hz), 7.60 (2H, d, J=8.4 Hz); MASS (ES−): m/e 287 (M−1).

Preparation 319

To a solution of Compound (305) (500 mg) in DMF (5 mL) were added 1,2-benzenediamine (206 mg), HOBt (305 mg) and EDCI.HCl (432 mg), and the mixture was stirred for 2 hrs at ambient temperature. The mixture was poured into saturated aqueous NaHCO$_3$ solution and extracted with AcOEt. The organic phase was sequentially washed with saturated aqueous NaHCO$_3$ solution, water and brine, and dried over Na$_2$SO$_4$. The solvent was removed in vacuo, and the residue was purified by preparative thin layer chromatography (chloroform:methanol=10:1). The obtained amorphous solid was triturated with isopropyl ether to give Compound (319) (341 mg) as colorless powder.

$^1$H-NMR (300 MHz, CDCl$_3$, δ): 1.40 (1H, m), 1.53 (9H, s), 1.77 (1H, m), 1.84 (1H, m), 2.62 (1H, m), 3.85 (1H, br.), 6.34 (1H, d, J=15.8 Hz), 6.80 (2H, m), 7.07 (2H, m), 7.13 (2H, d, J=8.4 Hz), 7.34 (2H, s), 7.45 (2H, d, J=8.4 Hz), 7.56 (1H, d, J=16.1 Hz); MASS (ES+): m/e 379 (M+1).

Preparation 320

A solution of Compound (319) (341 mg) in AcOH (3.5 mL) was added 1N-hydrogen chloride in AcOH (3.6 mL) was heated at 110° C. for 2 hr. The resulting mixture was allowed to cool to ambient temperature, diluted with ethyl acetate. The precipitate was collected by filtration and dried to give Compound (320) (242 mg).

$^1$H-NMR (300 MHz, DMSO-d$_6$, δ): 2.03 (1H, m), 2.14 (1H, m), 2.70 (1H, m), 2.92 (1H, m), 6.53 (1H, d, J=15.8 Hz), 7.35 (2H, d, J=8.4 Hz), 7.49 (2H, m), 7.58 (1H, d, J=16.1 Hz), 7.68 (2H, d, J=8.1 Hz), 7.73 (2H, m); MASS (ES+): m/e 305 (M+1).

Preparation 321

To a stirred solution of Compound (217) (350 mg) in methanol (3 mL) was added 1N sodium hydroxide (1.65 mL) in an ice bath. After 1 hr, the mixture was allowed to warm to ambient temperature and stirred at the same temperature for 16 hrs. To this mixture was added concentrated hydrochloric acid to acidify the mixture, and the resulting mixture was concentrated in vacuo. The residue was dissolved in N,N-dimethylformamide (5 mL), and to this solution were successively added O-(tetrahydro-2H-pyran-2-yl)hydroxylamine (167 mg), 1-[3-(dimethylamino)propyl]-3-ethylcarbodiimide (222 mg) and 1-hydroxybenzotriazole (193 mg) at ambient temperature. The resulting mixture was stirred at the same temperature for two days, extracted with ethyl acetate (100 mL), and successively washed with saturated aqueous sodium bicarbonate (25 mL) and brine (25 mL). The organic layer was dried over anhydrous sodium sulfate and concentrated in vacuo. The residue was purified by silica gel flash chromatography eluting with a mixture of methanol and ethyl acetate (5:95 v/v) to afford Compound (321) (387 mg) as a colorless amorphous solid. The obtained Compound (321) was used in Example 82.

$^1$H-NMR (300 MHz, CDCl$_3$, δ): 1.43–1.82 (6H, m), 3.43–3.59 (1H, m), 3.84–4.07 (1H, m), 4.89 (1H, br.s), 5.36 (2H, s), 6.47 (1H, d, J=16.1 Hz), 7.00–7.09 (3H, m), 7.33–7.59 (10H, m); MASS (ES+): m/z 404 (M+1)

Preparation 322

Compound (322) was obtained as a mixture of two regioisomers from Compound (218) according to a manner similar to Preparation 321 (316 mg in total). The obtained Compound (322) was used in Example 115.

$^1$H-NMR (300 MHz, DMSO-d$_6$, δ): (for a mixture of two regioisomers) 1.34–1.78 (6H, m), 2.03 (1.2H, s), 2.06 (1.8H, s), 3.47–3.59 (1H, m), 3.85–4.04 (1H, m), 4.83–4.95 (1H, m), 5.13 (1.2H, s), 5.19 (0.8H, s), 6.49 (1H, d, J=16.4 Hz), 6.67 (0.4H, s), 6.85 (0.6H, s), 7.13 (0.8H, d, J=8.1 Hz), 7.26 (1.2H, d, J=8.1 Hz), 7.39–7.72 (4H, m); MASS (ES+): (for a mixture of two regioisomers) m/z 342 (M+1).

Preparation 323

To a stirred solution of Compound (326) (100 mg, described later in Preparation 326) in N,N-dimethylformamide (2 mL) were added methylamine hydrochloride (23 mg), 1-[3-(dimethylamino)propyl]-3-ethylcarbodiimide (56 mg) and 1-hydroxybenzotriazole (48 mg) at ambient temperature, and the resulting mixture was stirred at the same temperature for 20 hrs. The mixture was extracted with ethyl acetate (50 mL), and successively washed with saturated aqueous sodium bicarbonate (25 mL) and brine (25 mL). The organic layer was dried over anhydrous sodium sulfate and concentrated in vacuo to afford crude Compound (324) (86 mg) as a colorless amorphous solid. The Compound (324) was used in Example 83.

$^1$H-NMR (300 MHz, CDCl$_3$, δ): 1.42–1.97 (6H, m), 2.85 (3H, br.d, J=4.4 Hz), 3.54–3.68 (1H, m), 3.89–4.07 (2H, m), 4.98 (2H, br.s), 6.05–6.34 (1H, m), 6.95–7.73 (10H, m); MASS (ES+): m/z 461 (M+1).

Preparation 324

To a solution of Compound (326) (60 mg, described later in Preparation 326) in DMF (1 mL) were added piperidine (0.015 mL), HOBt (23.6 mg) and EDCI HCl (33.4 mg), and the mixture was stirred for 2 hrs at ambient temperature. The mixture was poured into water and extracted with AcOEt, and the organic phase was sequentially washed with saturated aqueous NH$_4$Cl solution, saturated aqueous NaHCO$_3$ solution and brine, and dried over Na$_2$SO$_4$. The solvent was removed in vacuo, and the residue was purified by preparative thin layer chromatography (chloroform:methanol=10:1) to give Compound (324) (44 mg) as colorless amorphous solid. The obtained Compound (324) was used in Example 88.

$^1$H-NMR (300 MHz, DMSO-d$_6$, δ): 1.25 (2H, br.), 1.53 (7H, br.), 1.69 (3H, br.), 3.25 (4H, br.), 3.53 (1H, m), 3.94 (1H, m), 4.03 (2H, s), 4.90 (1H, s), 6.46 (1H, d, J=15.4 Hz), 7.26 (1H, t, J=7.3 Hz), 7.36 (4H, m), 7.43 (1H, d, J=15.8 Hz), 7.53 (4H, m); MASS (ES+): m/e 515 (M+1).

Preparation 325

Compound (325) was obtained from Compound (326) described later according to a manner similar to Preparation 325 (57 g). The obtained compound (325) was used in Example 89.

$^1$H-NMR (300 MHz, CDCl$_3$, δ): 1.18 (6H, br.), 1.60 (3H, br.), 1.84 (3H, br.), 3.65 (1H, m), 3.98 (1H, m), 4.09 (2H, s), 4.18 (1H, m), 5.00 (1H, s), 7.22 (1H, m), 7.39 (6H, m), 7.67 (3H, m); MASS (ES+): m/e 489 (M+1).

Preparation 326

To a solution of Compound (290) (200 mg) in dioxane (2 mL) was added 1N NaOH aqueous solution (1.3 mL) and the mixture was heated at 70° C. for 6 hrs. The organic solvent was removed in vacuo and the pH value of aqueous base adjusted to 3 with 1N HCl. The precipitate was collected by filtration and dried to give Compound (326) (145 mg) as pale yellow powder. The obtained Compound (326) was used in Example 91.

$^1$H-NMR (300 MHz, DMSO-d$_6$, δ): 1.54 (3H, br.), 1.69 (3H, br.), 3.53 (1H, m), 3.95 (1H, m), 4.05 (2H, s), 4.90 (1H, s), 6.46 (1H, d, J=16.4 Hz), 7.32–7.40 (5H, m), 7.46 (1H, d, J=16.1 Hz), 7.53 (2H, d, J=7.7 Hz), 7.86 (2H, br); MASS (ES+): m/e 448 (M+1).

Preparation 327

To a suspension of lithium aluminum hydride in THF (5 mL) was added a solution of Compound (290) (500 mg) in THF (5 mL) and the mixture was refluxed for 6 hrs. To the resulting solution was added water (50 mL) at ambient temperature, and the mixture was stirred for 1 hr. The precipitate was collected by filtration, and the obtained powder was purified by silica gel column chromatography eluting with a mixture of chloroform and methanol (10:1) to give Compound (327) (110 mg).

$^1$H-NMR (300 MHz, CDCl$_3$, δ): 1.54 (9H, s), 3.68 (2H, s), 3.88 (3H, s), 4.69 (2H, d, J=4.0 Hz), 6.37 (1H, d, J=15.8 Hz), 6.60 (1H, br), 6.95 (2H, d, J=8.8 Hz), 7.33 (2H, d, J=8.1 Hz), 7.52 (2H, d, J=8.1 Hz), 7.58 (1H, d, J=16.1 Hz), 7.91 (2H, d, J=9.2 Hz); MASS (ES+): m/e 434 (M+1).

Preparation 328

Compound (328) was obtained from Compound (50) according to a manner similar to Preparation 327 (493 mg). The obtained compound (328) was used in Example 97.

$^1$H-NMR (300 MHz, DMSO-d$_6$, δ): 1.48–1.72 (6H, m), 3.49–3.57 (1H, m), 3.90–4.01 (1H, m), 4.18 (2H, s), 4.51–4.58 (2H, m), 4.87–4.92 (1H, m), 6.47 (1H, d, J=16 Hz), 7.33–7.57 (8H, m); MASS (ES+): m/z 408 (M+1).

Preparation 329

To a suspension of Compound (327) (400 mg) in dichloromethane (3 mL) was added triethylamine (0.154 mL) and methanesulfonyl chloride (0.079 mL) at 5° C., and the mixture was stirred for 1 hr. The solvent was removed in vacuo, and the obtained benzyl chloride was dissolved in MeOH. To the solution was added sodium methoxide in MeOH (5 equivalent) at ambient temperature, and the mixture was stirred for 0.5 hr. The resulting mixture was poured into saturated aqueous NH$_4$Cl solution and extracted with AcOEt. The organic phase was washed with water and brine, and dried over Na$_2$SO$_4$. The solvent was removed in vacuo, and the residue was purified by preparative thin layer chromatography (chloroform:methanol=10:1) to give Compound (329) (110 mg). The obtained compound (329) was used in Example 93.

$^1$H-NMR (300 MHz, DMSO-d$_6$, δ): 1.54 (3H, br.), 1.69 (3H, br.), 3.29 (3H, s), 3.53 (1H, m), 3.97 (1H, m), 4.05 (2H, s), 4.39 (2H, s), 4.90 (1H, s), 6.47 (1H, d, J=15.8 Hz), 7.25–7.61 (10H, m); MASS (ES+): m/e 448 (M+1).

Preparation 330

To a solution of Compound (323) (1 g) in DMF (5 mL) were added N,O-dimethylhydroxylamine hydrochloride (240 mg) and HOBt (393 mg) and EDCI (451 mg), and the mixture was stirred at ambient temperature. To the resulting mixture was added saturated aqueous NaHCO$_3$ solution, and the precipitate was collected by filtration. The obtained powder was washed with water and Et$_2$O to give Compound (330) (817 mg) as pale yellow powder.

$^1$H-NMR (300 MHz, DMSO-d$_6$, δ): 1.53 (3H, br.), 1.69 (3H, br.), 3.21 (3H, s), 3.53 (1H, m), 3.63 (3H, s), 3.95 (1H, m), 4.05 (2H, s), 4.90 (1H, s), 6.46 (1H, d, J=16.1 Hz), 7.30–7.60 (10H, m); MASS (ES+): m/z 491 (M+1).

Preparation 331

To a solution of Compound (330) (300 mg) in THF (5 mL) was added methyl magnesium iodide in Et$_2$O (3.64 mL, 0.84 mol/L, Kanto Chemical, Co., Inc.) and the mixture was heated at 70° C. for 3 hrs. Methylmagnesium iodide in Et$_2$O (0.84 mol/L, 3.64 mL) was then added thereto, and the mixture was additionally heated at 70° C. for 2 hrs. The mixture was cooled, poured into water and extracted with AcOEt. The organic phase was successively washed with saturated aqueous NaHCO$_3$ solution, water and brine, and dried over Na$_2$SO$_4$. The solvent was removed in vacuo, and the residue was purified by preparative thin layer chromatography (chloroform:methanol=10:1) to give Compound (331) (67 mg) as orange form. The obtained Compound (331) was used in Example 94.

$^1$H-NMR (300 MHz, DMSO-d$_6$, δ): 1.54 (3H, br.), 1.69 (3H, br.), 2.36 (3H, s), 3.55 (1H, m), 3.95 (1H, m), 4.22 (2H, s), 4.90 (1H, s), 6.48 (1H, d, J=15.8 Hz), 7.31–7.57 (10H, m); MASS (ES+): m/z 446 (M+1).

Preparation 332

Compound (332) was obtained from Compound (326) according to a manner similar to Preparation 330 (124 mg). The obtained compound (332) was used in Example 87.

Preparation 333

To a solution of Compound (51) (120 mg), pyrrolidine (0.029 mL) and 1-hydroxybenzotriazole (46.2 mg) in N,N-dimethylformamide (2.6 mL) was added 1-(3-dimethylaminopropyl)-3-ethylcarbodiimide (65.5 mg) at 4° C. The mixture was warmed to ambient temperature and stirred for 8 hrs. The reaction mixture was added saturated $NaHCO_3$ (3 mL) and water (12 mL). A resulting precipitate was collected by filtration, and washed with water to give Compound (333) (95 mg).

$^1$H-NMR (300 MHz, DMSO-$d_6$, δ): 1.47–1.93 (10H, m), 3.39–3.57 (5H, m), 3.87–4.01 (1H, m), 4.22 (2H, s), 4.88–4.93 (1H, m), 6.47 (1H, d, J=16 Hz), 7.28–7.70 (8H, m); MASS (ES+): m/z 475 (M+1)

Preparation 334

To a mixture of Compound (328) (170 mg), N,N-diisopropylethylamine (0.16 mL) and THF (8.4 mL) was added methanesulfonyl chloride (0.068 mL) at 4° C. The reaction mixture was stirred for 3 hrs and diethylamine (0.432 mL) was added thereto. After stirring for 15 hrs at room temperature, the resulting mixture was partitioned between ethyl acetate and $H_2O$. The organic layer was washed with saturated $NaHCO_3$ and brine, dried over $MgSO_4$, filtered and evaporated in vacuo to give Compound (334) (38 mg).

$^1$H-NMR (300 MHz, DMSO-$d_6$, δ): 1.03–1.22 (6H, m), 1.48–1.72 (6H, m) 3.31–3.44 (4H, m), 3.49–3.57 (1H, m), 3.88–4.03 (1H, m), 4.10–4.41 (4H, m), 4.87–4.95 (1H, m), 6.48 (1H, d, J=16 Hz), 7.22–7.87 (8H, m). MASS (ES+): m/z 463 (M+1).

Preparation 335

Compound (335) was obtained from Compound (6) according to manners similar to Preparations 199 and 229 (2.89 g).

$^1$H-NMR (300 MHz, $CDCl_3$, δ): 1.34 (3H, t, J=7 Hz), 3.64–4.08 (7H, m), 4.27 (2H, q, J=7 Hz), 4.53–4.64 (2H, m), 6.42 (1H, d, J=16 Hz), 6.81–6.92 (2H, m), 7.01 (1H, d, J=8 Hz), 7.27–7.35 (3H, m), 7.45–7.53 (2H, m), 7.66 (1H, d, J=16 Hz); MASS (ES–): m/z 410 (M–1)

Preparation 336

To a mixture of Compound (335) (1.44 g) in chloroform (12 mL) was added trifluoroacetic anhydride (1.48 mL) at 4° C. After stirring for 3 hrs at room temperature, the reaction mixture was evaporated in vacuo. To a mixture of the above product in N,N-dimethylformamide (18 mL) was added ammonium acetate (405 mg) at 4° C. After stirring at 70° C. for 2 hrs, the resulting mixture was partitioned between ethyl acetate and $H_2O$. The organic layer was washed with $H_2O$ and brine, dried over $MgSO_4$, filtered and evaporated in vacuo. To a mixture of the above product in pyridine (1 mL) was added phosphorus oxychloride (0.3 mL) at 4° C. After stirring at 90° C. for 2 hrs, the resulting mixture was partitioned between ethyl acetate and $H_2O$. The organic layer was washed with $H_2O$ and brine, dried over $MgSO_4$, filtered and evaporated in vacuo. The residue was purified by column chromatography on silica gel to give Compound (336) (313 mg).

$^1$H-NMR (300 MHz, $CDCl_3$, δ): 1.34 (3H, t, J=7 Hz), 3.79 (3H, s) 4.12 (2H, s), 4.19 (2H, q, J=7 Hz), 4.81 (2H, s), 6.41 (1H, d, J=16 Hz), 6.81–6.90 (4H, m), 7.11–7.19 (3H, m), 7.45 (2H, d, J=8 Hz), 7.65 (1H, d, J=16 Hz); MASS (ES+): m/z 445 (M+1).

Preparation 337

To a mixture of Compound (336) (175 mg) in dioxane (4 mL) was added 1N sodium hydroxide (1.18 mL). After stirring at 80° C. for 1 hr, the reaction mixture was added $H_2O$ (20 mL) and acidified with 1N hydrochloric acid (to pH 3–4). The resulting precipitate was collected by filtration and washed with $H_2O$ to give Compound (337) (153 mg).

$^1$H-NMR (300 MHz, $CDCl_3$, δ): 3.79 (3H, s), 4.14 (2H, s), 4.82 (2H, s), 6.42 (1H, d, J=16 Hz), 6.81–6.91 (4H, m), 7.11–7.21 (3H, m), 7.48 (2H, d, J=8 Hz), 7.73 (1H, d, J=16 Hz); MASS (ES–): m/z 415 (M–1)

Preparation 338

To a mixture of (1Z)-2-(4-iodophenyl)-N'-hydroxyethaneimidamide (2.17 g) in EtOH (40 mL) was added ethyl propiolate (0.803 mL), and the mixture was heated under reflux for 6 hrs. The reaction mixture was evaporated in vacuo. The residue was added diphenylether (20 mL) and stirred at 200° C. for 2 hrs. After cooling, the resulting mixture was purified by column chromatography on silica gel (eluting with $CHCl_3$: MeOH=50:1) to give Compound (338) (845 mg).

$^1$H-NMR (300 MHz, $CDCl_3$, δ): 1.30–1.43 (3H, m), 4.06–4.13 (2H, m), 4.26–4.43 (2H, m), 6.97–7.06 (2H, m), 7.61 (1H, s), 7.65–7.72 (2H, m); MASS (ES+): m/z 357 (M+1).

Preparation 339

To a solution of Compound (338) (400 mg), palladium(II) acetate (12.6 mg) and triphenylphosphine (29.5 mg) in DMF (11 mL) were added acrylic acid (0.154 mL) and N,N-diisopropylethylamine (0.49 mL), and the mixture was stirred at 70° C. for 6 hrs. The reaction mixture was partitioned between ethyl acetate and $H_2O$, and the inorganic layer was evaporated in vacuo. To a mixture of the obtained reaction product, O-tetrahydro-2H-pyran-2-ylhydroxylamine (1.5 eq.) and 1-hydroxybenzotriazole (1.5 eq.) in N,N-dimethylformamide (6 mL) was added 1-(3-dimethylaminopropyl)-3-ethylcarbodiimide (1.5 eq.) at 4° C. The mixture was warmed to ambient temperature and stirred for 6 hrs. To the reaction mixture were added saturated $NaHCO_3$ (6 mL) and water (24 mL), and the mixture was extracted with ethyl acetate. The organic layer was washed with $H_2O$ and brine, dried over $MgSO_4$, filtered and evaporated in vacuo. The residue was purified by column chromatography on silica gel to give Compound (339) (98 mg).

$^1$H-NMR (300 MHz, DMSO-$d_6$, δ): 1.25 (3H, t, J=7 Hz), 1.44–1.75 (6H, m), 3.45–3.59 (1H, m), 3.88–4.01 (1H, m) 4.01 (2H, s), 4.18 (2H, q, J=7 Hz), 4.87–4.93 (1H, m), 6.46 (1H, d, J=16 Hz), 7.24–7.78 (5H, m), 8.32 (1H, s); MASS (ES+): m/z 400 (M+1)

Preparation 340

Compound (340) was obtained according to manners similar to Preparations 319 and 320 (184 mg).

$^1$H-NMR (300 MHz, DMSO-$d_6$, δ): 1.95–2.08 (4H, m), 3.22–3.34 (4H, m), 4.50 (2H, s), 6.55 (1H, d, J=16 Hz), 6.62 (1H, s), 6.84 (1H, dd, J=2, 8 Hz), 7.48–7.75 (6H, m); MASS (ES+): m/z 348 (M+1).

EXAMPLE 1

To a stirred solution of Compound (5) (125 mg) in methanol (5 mL) was added hydrogen chloride methanol reagent 10 (0.5 mL, manufactured by Tokyo Kasei Kogyo Co., Ltd.), and the mixture was stirred at ambient temperature for 30 minutes. The solvent was evaporated in vacuo and the residue was triturated with the mixture of methanol and ethyl acetate (1:2) to give Compound E1 as a white solid (81 mg).

$^1$H-NMR (300 MHz, DMSO-$d_6$, δ): 4.57 (2H, s), 6.50 (1H, d, J=15.7 Hz), 7.41–7.56 (5H, m), 7.60 (2×1H, d, J=8 Hz), 7.73–7.81 (2H, m), 10.84 (1H, br); MASS (ES+): m/e 294.

EXAMPLE 2

Compound E2 was obtained from Compound (13) according to a manner similar to Example 1 (79 mg).

$^1$H-NMR (300 MHz, DMSO-$d_6$, δ): 4.76 (2H, s), 5.82 (2H, s), 6.49 (1H, d, J=16 Hz), 7.12–7.21 (2H, m), 7.26–7.34 (3H, m), 7.38–7.62 (7H, m), 7.73 (1H, dd, J=7, 1.5 Hz), 7.83 (1H, dd, J=7, 1.5 Hz); MASS (ES+): m/e 384.

EXAMPLE 3

Compound E3 was obtained from Compound (19) according to a manner similar to Example 1 (1.74 mg).

$^1$H-NMR (300 MHz, DMSO-$d_6$, δ): 3.28 (2×1H, t, J=7.5 Hz), 3.47 (2×1H, t, J=7.5 Hz), 6.45 (1H, d, J=16 Hz), 7.32 (2×1H, d, J=8 Hz), 7.41 (1H, d, J=16 Hz), 7.46–7.60 (4H, m), 7.73–7.83 (2H, m), 10.80 (1H, s), 15.10 (1H, br); MASS (ES+): m/e 308.

EXAMPLE 4

Compound E4 was obtained from Compound (22) according to a manner similar to Example 1 (377 mg).

$^1$H-NMR (300 MHz, DMSO-$d_6$, δ): 5.79 (2H, s), 6.50 (1H, d, J=16 Hz), 7.43 (1H, d, J=16 Hz), 7.48–7.64 (6H, m), 7.86–7.94 (2H, m), 9.84 (1H, s); MASS (ES+): m/e 294.

EXAMPLE 5

Compound E5 was obtained from Compound (25) according to a manner similar to Example 1 (102 mg).

$^1$H-NMR (300 MHz, DMSO-$d_6$, δ): 3.31 (1H, m), 3.70 (1H, dd, J=13, 8 Hz), 4.74 (1H, br-t, J=8 Hz), 5.34 (1H, d, J=17 Hz), 5.41 (1H, d, J=17 Hz), 6.37 (1H, d, J=15.5 Hz), 6.73 (2×1H, d, J=6.5 Hz), 7.07–7.45 (16H, m), 7.71 (1H, d, J=7.5 Hz), 9.02 (1H, brs), 10.73 (1H, brs); MASS (ES+): m/e 474.

EXAMPLE 6

Compound E6 was obtained from Compound (29) according to a manner similar to Example 1 (1.88 mg).

$^1$H-NMR (300 MHz, DMSO-$d_6$, δ): 4.57 (2H, s), 6.51 (1H, d, J=16 Hz), 7.40–7.56 (6H, m), 7.68 (1H, s), 7.73–7.81 (2H, m), 10.88 (1H, s); MASS (ES+): m/e 294.

EXAMPLE 7

Compound E7 was obtained from Compound (32) according to a manner similar to Example 1 (162 mg).

$^1$H-NMR (300 MHz, DMSO-$d_6$, δ): 4.58 (2H, s), 6.50 (1H, d, J=15.7 Hz), 7.38–7.56 (6H, m), 7.61 (2×1H, d, J=8 Hz), 7.73 (2×1H, d, J=7 Hz), 7.78–7.88 (2H, m), 7.96 (1H, s), 10.84 (1H, s); MASS (ES+): m/e 370.

EXAMPLE 8

Compound E8 was obtained from Compound (34) according to a manner similar to Example 1 (75 mg).

$^1$H-NMR (300 MHz, DMSO-$d_6$, δ): 4.50 (2H, s), 6.48 (1H, d, J=16 Hz), 7.42–7.48 (3H, m), 7.56–7.71 (4H, m), 7.97 (1H, d, J=2 Hz); MASS (ESI): m/z 372 (M+1)

EXAMPLE 9

Compound E9 was obtained from Compound (35) according to manners similar to Preparation 9 and Example 1 (152 mg).

$^1$H-NMR (300 MHz, DMSO-$d_6$, δ): 2.63 (3H, s), 4.58 (2H, s), 6.49 (1H, d, J=16 Hz), 7.46 (1H, d, J=16 Hz), 7.50 (2H, d, J=8 Hz), 7.61 (2H, d, J=8 Hz), 7.85–7.93 (4H, m), 8.04–8.10 (3H, m); MASS (ESI): m/z 412 (M+1)

EXAMPLE 10

Compound E10 was obtained from Compound (36) according to manners similar to Preparation 9 and Example 1 (138 mg).

$^1$H-NMR (300 MHz, DMSO-$d_6$, δ): 4.58 (2H, s), 6.50 (1H, d, J=16 Hz), 7.17–7.21 (1H, m), 7.46 (1H, d, J=16 Hz), 7.51 (2H, d, J=8 Hz), 7.59–7.65 (4H, m), 7.80–7.83 (2H, m), 7.95 (1H, s); MASS (ESI): m/z 376 (M+1).

EXAMPLE 11

Compound E11 was obtained from Compound (37) according to manners similar to Preparation 9 and Example 1 (120 mg).

$^1$H-NMR (300 MHz, DMSO-$d_6$, δ): 4.58 (2H, s), 6.49 (1H, d, J=16 Hz), 7.46 (1H, d, J=16 Hz), 7.51 (2H, d, J=8 Hz), 7.61 (2H, d, J=8 Hz), 7.64–7.73 (2H, m), 7.79 (1H, d, J=8 Hz), 7.90 (1H, dd, J=2, 8 Hz), 8.00–8.05 (2H, m); MASS (ESI): m/z 376 (M+1).

EXAMPLE 12

Compound E12 was obtained from Compound (39) according to a manner similar to Example 1 (142 mg).

$^1$H-NMR (300 MHz, DMSO-$d_6$, δ): 4.42 (2H, s), 6.46 (1H, d, J=16 Hz), 7.41–7.47 (3H, m), 7.56 (2H, d, J=8 Hz), 7.73 (1H, d, J=8 Hz), 7.80 (1H, d, J=8 Hz), 8.22 (1H, s); MASS (ESI): m/z 317 (M−1).

EXAMPLE 13

Compound E13 was obtained from Compound (40) according to manners similar to Preparation 9 and Example 1 (710 mg).

$^1$H-NMR (300 MHz, DMSO-$d_6$, δ): 4.55 (2H, s), 6.50 (1H, d, J=16 Hz), 7.36–7.44 (1H, m), 7.45 (1H, d, J=16 Hz), 7.50 (2H, d, J=8 Hz), 7.59 (2H, d, J=8 Hz), 7.66 (1H, dd, J=2, 8 Hz), 7.77–7.83 (1H, MASS (ESI): m/z 312 (M+1].

EXAMPLE 14

Compound E14 was obtained from Compound (42) according to a manner similar to Example 1 (504 mg).

$^1$H-NMR (300 MHz, DMSO-$d_6$, δ): 4.51 (2H, s), 6.48 (1H, d, J=16 Hz), 7.45 (1H, d, J=16 Hz), 7.47 (2H, d, J=8 Hz), 7.52 (1H, dd, J=2, 8 Hz), 7.59 (2H, d, J=8 Hz), 7.76 (1H, d, J=8 Hz), 7.86 (1H, J=2 Hz); MASS (ESI): m/z 328 (M+1)

EXAMPLE 15

Compound E15 was obtained from Compound (44) according to a manner similar to Example 1 (14 mg).
$^1$H-NMR (300 MHz, DMSO-d$_6$, δ): 2.79–2.85 (4H, m), 3.11–3.22 (4H, m), 4.52 (2H, s), 6.48 (1H, d, J=16 Hz), 7.15–7.67 (8H, m); MASS (ESI): m/z 392 (M+1)

EXAMPLE 16

Compound E16 was obtained from Compound (46) according to a manner similar to Example 1 (45 mg).
$^1$H-NMR (300 MHz, DMSO-d$_6$, δ): 3.15–3.21 (4H, m), 3.75–3.81 (4H, m), 4.52 (2H, s), 6.49 (1H, d, J=16 Hz), 7.10 (1H, d, J=2 Hz), 7.29 (1H, dd, J=2, 8 Hz), 7.42–7.50 (3H, m), 7.57–7.64 (3H, m); MASS (ESI): m/z 379 (M+1).

EXAMPLE 17

Compound E17 was obtained from Compound (48) according to a manner similar to Example 1 (27 mg).
$^1$H-NMR (300 MHz, DMSO-d$_6$, δ): 1.60–1.70 (2H, m), 1.83–2.00 (4H, m), 3.39–3.54 (4H, m), 4.54 (2H, s), 6.49 (1H, d, J=16 Hz), 7.40–7.86 (8H, m); MASS (ESI): m/z 377 (M+1)

EXAMPLE 18

A mixture of Compound (39), sodium azide (485 mg) and triethylamine hydrochloride (1.54 g) in N,N-dimethylformamide (7.5 mL) was heated at 130° C. for 6 hours. After cooling, the reaction mixture was partitioned between ethyl acetate (20 mL) and water (40 mL). The organic layer was washed with brine, dried over MgSO$_4$, filtered, and evaporated in vacuo. The crude product was triturated with ethyl acetate-water. The product was treated according to a manner similar to Example 1 to give Compound E18 (18 mg).
$^1$H-NMR (300 MHz, DMSO-d$_6$, δ): 4.30 (2H, s), 6.44 (1H, d, J=16 Hz), 7.40 (2H, d, J=8 Hz), 7.44 (1H, d, J=16 Hz), 7.55 (2H, d, J=8 Hz), 7.72 (1H, d, J=8 Hz), 7.90 (1H, d, J=8 Hz), 8.21 (1H, s); MASS (ESI): m/z 362 (M+1)

EXAMPLE 19

Compound E19 was obtained from Compound (50) according to a manner similar to Example 1 (101 mg).
$^1$H-NMR (300 MHz, DMSO-d$_6$, δ): 3.91 (3H, s), 4.55 (2H, s), 6.49 (1H, d, J=16 Hz), 7.46 (1H, d, J=16 Hz), 7.50 (2H, d, J=8 Hz), 7.60 (2H, d, J=8 Hz), 7.84 (1H, d, J=8 Hz), 8.05 (1H, d, J=8 Hz), 8.27 (1H, s); MASS (ESI): m/z 352 (M+1).

EXAMPLE 20

Compound E20 was obtained from Compound (51) according to a manner similar to Example 1 (72 mg).
$^1$H-NMR (300 MHz, DMSO-d$_6$, δ): 4.55 (2H, s), 6.49 (1H, d, J=16 Hz), 7.45 (1H, d, J=16 Hz), 7.49 (2H, d, J=8 Hz), 7.60 (2H, d, J=8 Hz), 7.81 (1H, d, J=8 Hz), 8.04 (1H, dd, J=2, 8 Hz), 8.25 (1H, s); MASS (ESI): m/z 338 (M+1)

EXAMPLE 21

Compound E21 was obtained from Compound (53) according to a manner similar to Example 1 (55 mg).
$^1$H-NMR (300 MHz, DMSO-d$_6$, δ): 2.68 (3H, s), 4.56 (2H, s), 6.49 (1H, d, J=16 Hz), 7.45 (1H, d, J=16 Hz), 7.50 (2H, d, J=8 Hz), 7.59 (2H, d, J=8 Hz), 7.83 (1H, d, J=8 Hz), 8.06 (1H, dd, J=2, 8 Hz), 8.28 (1H, s); MASS (ESI): m/z 336 (M+1).

EXAMPLE 22

Compound E22 was obtained from Compound (55) according to a manner similar to Example 1 (279 mg).
$^1$H-NMR (300 MHz, DMSO-d$_6$, δ): 4.48 (2H, s), 6.47 (1H, d, J=16 Hz), 7.33–7.49 (4H, m), 7.57 (2H, d, J=8 Hz), 7.65–7.72 (4H, m); MASS (ESI): m/z 372 (M+1).

EXAMPLE 23

Compound E23 was obtained from Compound (57) according to a manner similar to Example 1 (50 mg).
$^1$H-NMR (300 MHz, DMSO-d$_6$, δ): 1.25 (3H, s), 1.27 (3H, s), 3.04–3.16 (1H, m), 4.55 (2H, s), 6.49 (1H, d, J=16 Hz), 7.42–7.52 (4H, m), 7.56–7.62 (3H, m), 7.68 (1H, d, J=8 Hz); MASS (ESI): m/z 336 (M+1).

EXAMPLE 24

Compound E24 was obtained from Compound (59) according to manners similar to Preparation 9 and Example 1 (249 mg).
$^1$H-NMR (300 MHz, DMSO-d$_6$, δ): 4.42 (2H, s), 5.35 (2H, s), 6.45 (1H, d, J=16 Hz), 7.10–7.61 (13H, m); MASS (ESI): m/z 400 (M+1).

EXAMPLE 25

Compound E25 was obtained from Compound (62) according to a manner similar to Example 1 (417 mg).
$^1$H-NMR (300 MHz, DMSO-d$_6$, δ): 4.58 (2H, s), 6.50 (1H, d, J=15.7 Hz), 7.38–7.56 (6H, m), 7.61 (2×1H, d, J=8 Hz), 7.73 (2×1H, d, J=7 Hz), 7.78–7.88 (2H, m), 7.96 (1H, s), 10.84 (1H, s); MASS (ES+): m/e 370.

EXAMPLE 26

Compound E26 was obtained from Compound (72) according to a manner similar to Example 1 (207 mg).
$^1$H-NMR (300 MHz, DMSO-d$_6$, δ): 4.57 (2H, s), 6.50 (1H, d, J=15.7 Hz), 7.35 (2×1H, dd, J=8.8, 8.8 Hz), 7.46 (1H, d, J=15.7 Hz), 7.50 (2×1H, d, J=8 Hz), 7.61 (2×1H, d, J=8 Hz), 7.74–7.86 (4H, m), 7.94 (1H, s); MASS (ES+): m/e 388.

EXAMPLE 27

Compound E27 was obtained from Compound (75) according to a manner similar to Example 1 (123 mg).
$^1$H-NMR (300 MHz, DMSO-d$_6$, δ): 4.58 (2H, s), 6.51 (1H, d, J=15.8 Hz), 7.38–7.59 (7H, m), 7.65–7.87 (5H, m), 7.96 (1H, s), 10.86 (1H, br); MASS (ES+): m/e 370.

EXAMPLE 28

Compound E28 was obtained from Compound (80) according to a manner similar to Example 1 (103 mg).
$^1$H-NMR (300 MHz, DMSO-d$_6$, δ): 3.28 (3H, s), 4.59 (2H, s), 6.49 (1H, d, J=16 Hz), 7.42–7.65 (5H, m), 7.87–7.92 (2H, m), 7.98–8.10 (5H, m); MASS (ES+): m/e 447.

EXAMPLE 29

Compound E29 was obtained from Compound (83) according to a manner similar to Example 1 (200 mg).
$^1$H-NMR (300 MHz, DMSO-d$_6$, δ): 4.49 (2H, s), 6.49 (1H, d, J=16 Hz), 7.44 (1H, d, J=16 Hz), 7.47 (2×1H, d, J=8 Hz), 7.57 (2×1H, d, J=8 Hz), 7.57 (1H, dd, J=8, 5 Hz), 8.34 (1H, d, J=8 Hz), 8.58 (1H, d, J=5 Hz); MASS (ES+): m/e 295.

EXAMPLE 30

Compound E30 was obtained from Compound (90) according to a manner similar to Example 1 (175 mg).
$^1$H-NMR (300 MHz, DMSO-d$_6$, δ): 4.52 (2H, s), 6.50 (1H, d, J=16 Hz), 7.23 (1H, br-d, J=8.5 Hz), 7.41–7.53 (4H, m), 7.59 (2×1H, d, J=8 Hz), 7.69 (1H, d, J=8.5 Hz); MASS (ES+): m/e 309.

EXAMPLE 31

Compound E31 was obtained from Compound (93) according to a manner similar to Example 1 (14 mg).
$^1$H-NMR (300 MHz, DMSO-d$_6$, δ): 0.92 (3H, t, J=7.5 Hz), 1.63 (2H, tq, J=7.5, 7.5 Hz), 2.34 (2H, t, J=7.5 Hz), 4.54 (2H, s), 6.49 (1H, d, J=15.7 Hz), 7.41–7.51 (3H, m), 7.55 (1H, dd, J=9, 2 Hz), 7.60 (2×1H, d, J=8.5 Hz), 7.69 (1H, d, J=9 Hz), 8.31 (1H, d, J=2 Hz); MASS (ES+): m/e 379.

EXAMPLE 32

Compound E32 was obtained from Compound (97) according to a manner similar to Example 1 (73 mg).
$^1$H-NMR (300 MHz, DMSO-d$_6$, δ): 4.45 (2H, s), 6.45 (1H, d, J=16 Hz), 7.43 (1H, d, J=16 Hz), 7.45 (2×1H, d, J=8 Hz), 7.50 (2×1H, dd, J=8, 8 Hz), 7.54 (2×1H, d, J=8 Hz), 8.11 (1H, d, J=8 Hz), 8.21 (1H, d, J=8 Hz); MASS (ES+): m/e 339.

EXAMPLE 33

Compound E33 was obtained from Compound (100) according to a manner similar to Example 1 (15 mg).
$^1$H-NMR (300 MHz, DMSO-d$_6$, δ): 4.43 (2H, s), 6.48 (1H, d, J=16 Hz), 7.39–7.60 (5H, m), 8.08 (1H, d, J=6.5 Hz), 8.55 (1H, d, J=6.5 Hz), 9.35 (1H, s); MASS (ES+): m/e 295.

EXAMPLE 34

Compound E34 was obtained from Compound (103) according to a manner similar to Example 1 (240 mg).
$^1$H-NMR (300 MHz, DMSO-d$_6$, δ): 3.22 (3H, s), 3.40 (3H, s), 4.08 (2H, s), 6.44 (1H, d, J=15.8 Hz), 7.32 (2×1H, d, J=8 Hz), 7.42 (1H, d, J=15.8 Hz), 7.51 (2×1H, d, J=8 Hz); MASS (ES+): m/e 356.

EXAMPLE 35

Compound E35 was obtained from Compound (105) according to a manner similar to Example 1 (160 mg).
$^1$H-NMR (300 MHz, DMSO-d$_6$, δ): 4.42 (2H, s), 6.47 (1H, d, J=16 Hz), 7.44 (1H, d, J=16 Hz), 7.44 (2×1H, d, J=8 Hz), 7.56 (2×1H, d, J=8 Hz), 7.80 (1H, d, J=9 Hz), 8.19 (1H, dd, J=9, 2.2 Hz), 8.50 (1H, d, J=2.2 Hz); MASS (ES+): m/e 339.

EXAMPLE 36

Compound E36 was obtained from Compound (112) according to a manner similar to Example 1 (375 mg).
$^1$H-NMR (300 MHz, CDCl$_3$, δ): 5.66 (2H, s), 6.38 (1H, d, J=15.7 Hz), 7.19 (2×1H, d, J=8.8 Hz), 7.43 (1H, d, J=15.7 Hz), 7.48–7.56 (2H, m), 7.58 (2×1H, d, J=8.8 Hz), 7.76–7.84 (2H, m), 10.75 (1H, br-s); MASS (ES+): m/e 310.

EXAMPLE 37

Compound E37 was obtained from Compound (115) according to a manner similar to Example 1 (40 mg).
$^1$H-NMR (300 MHz, DMSO-d$_6$, δ): 1.40–1.94 (8H, m), 3.85 (1H, m), 4.54 (2H, s), 6.51 (1H, d, J=15.8 Hz), 7.28–7.80 (8H, m); MASS (ES+): m/e 377.

EXAMPLE 38

Compound E38 was obtained from Compound (122) according to a manner similar to Example 1 (1.19 g).
$^1$H-NMR (300 MHz, DMSO-d$_6$, δ): 5.67 (2H, s), 6.53 (1H, d, J=16 Hz), 7.14 (1H, m), 7.27 (1H, m), 7.35 (1H, s), 7.41 (1H, dd, J=8, 8 Hz), 7.46 (1H, d, J=16 Hz), 7.47–7.79 (2H, m), 7.77–7.87 (2H, m), 10.90 (1H, br); MASS (ES+): m/e 310.

EXAMPLE 39

Compound E39 was obtained from Compound (125) according to a manner similar to Example 1 (110 mg).
$^1$H-NMR (300 MHz, DMSO-d$_6$, δ): 1.05 (2×3H, t, J=7 Hz), 3.52 (4H, m), 4.51 (2H, s), 6.49 (1H, d, J=15.8 Hz), 7.41–7.53 (5H, m), 7.56–7.64 (3H, m); MASS (ES+): m/e 365.

EXAMPLE 40

Compound E40 was obtained from Compound (132) according to a manner similar to Example 1 (1472 mg).
$^1$H-NMR (300 MHz, DMSO-d$_6$, δ): 3.84 (3H, s), 5.62 (2H, s), 6.43 (1H, d, J=15.8 Hz), 7.14 (1H, d, J=8 Hz), 7.21 (1H, d, J=8 Hz), 7.28 (1H, s), 7.42 (1H, d, J=15.8 Hz), 7.50–7.58 (2H, m), 7.78–7.86 (2H, m); MASS (ES+): m/e 340.

EXAMPLE 41

Compound E41 was obtained from Compound (134) according to manners similar to Preparation 9 and Example 1 (115 mg).
$^1$H-NMR (300 MHz, DMSO-d$_6$, δ): 3.02 (2×3H, s), 4.52 (2H, s), 6.50 (1H, d, J=16 Hz), 6.90–7.70 (8H, m); MASS (ES+) m/e 337.

EXAMPLE 42

Compound E42 was obtained from Compound (141) according to a manner similar to Example 1 (450 mg).
$^1$H-NMR (300 MHz, DMSO-d$_6$, δ): 3.82 (3H, s), 5.61 (2H, s), 6.40 (1H, d, J=15.8 Hz), 7.11 (1H, d, J=8.8 Hz), 7.28 (1H, dd, J=8.8, 1.7 Hz), 7.40 (1H, d, J=15.8 Hz), 7.43 (1H, d, J=1.7 Hz), 7.50–7.58 (2H, m), 7.78–7.86 (2H, m); MASS (ES+): m/e 340.

EXAMPLE 43

Compound E43 was obtained from Compound (144) according to a manner similar to Example 1 (160.8 mg).
$^1$H-NMR (300 MHz, DMSO-$d_6$, δ): 4.45 (2H, s), 6.16 (2H, s), 6.47 (1H, d, J=15.8 Hz), 7.43 (1H, d, J=8.1 Hz), 7.46 (1H, d, J=16.0 Hz), 7.59 (2H, d, J=8.1 Hz); MASS (ES+): m/e 338 (M+1)

EXAMPLE 44

Compound E44 was obtained from Compound (147) according to a manner similar to Example 1 (160.8 mg).
$^1$H-NMR (300 MHz, DMSO-$d_6$, δ): 4.00 (3H, s), 4.42 (2H, s), 6.44 (1H, d, J=16.2 Hz), 7.04 (1H, d, J=8.0 Hz), 7.27 (1H, d, J=8.4 Hz), 7.41 (1H, t, J=8.2 Hz), 7.42 (2H, d, J=8.0 Hz), 7.45 (1H, d, J=16.0 Hz), 7.57 (2H, d, J=8.0 Hz); MASS (ES+): m/e 324 (M+1).

EXAMPLE 45

Compound E45 was obtained from Compound (151) according to a manner similar to Example 1 (481.2 mg).
$^1$H-NMR (300 MHz, DMSO-$d_6$, δ): 1.87 (3H, d, J=7.4 Hz), 4.85 (1H, q, J=7.4 Hz), 6.49 (1H, d, J=16.1 Hz), 7.43 (1H, d, J=15.7 Hz), 7.49–7.52 (2H, m), 7.51 (2H, d, J=8.5 Hz), 7.58 (2H, d, J=8.5 Hz), 7.74–7.77 (2H, m); MASS (ES+): m/e 308 (M+1)

EXAMPLE 46

Compound E46 was obtained from Compound (155) according to a manner similar to Example 1 (576.3 mg).
$^1$H-NMR (300 MHz, DMSO-$d_6$, δ): 1.88 (3H, d, J=7.3 Hz), 4.83 (1H, q, J=7.4 Hz), 6.50 (1H, d, J=15.7 Hz), 7.43 (1H, d, J=15.4 Hz), 7.48–7.51 (2H, m), 7.53 (2H, d, J=8.2 Hz), 7.58 (2H, d, J=8.4 Hz), 7.74–7.77 (2H, m); MASS (ES+): m/e 308 (M+1).

EXAMPLE 47

Compound E47 was obtained from Compound (158) according to a manner similar to Example 1 (274.9 mg).
$^1$H-NMR (300 MHz, DMSO-$d_6$, δ) 1.36 (3H, t, J=7.0 Hz), 4.08 (2H, q, J=7.0 Hz), 4.58 (2H, s), 6.49 (1H, d, J=15.7 Hz), 7.05 (2H, d, J=8.8 Hz), 7.46 (1H, d, J=17.0 Hz), 7.50 (2H, d, J=8.4 Hz), 7.61 (2H, d, J=8.4 Hz), 7.66 (2H, d, J=8.8 Hz), 7.77 (1H, dd, J=8.8, 1.5 Hz), 7.81 (1H, d, J=8.4 Hz), 7.90 (1H, s); MASS (ES+): m/e 414 (M+1).

EXAMPLE 48

Compound E48 was obtained from Compound (161) according to a manner similar to Example 1 (231.1 mg).
$^1$H-NMR (300 MHz, DMSO-$d_6$, δ): 4.60 (2H, s), 6.49 (1H, d, J=15.8 Hz), 7.46 (1H, d, J=16.1 Hz), 7.52 (2H, d, J=8.4 Hz), 7.60 (2H, d, J=8.4 Hz), 7.93 (2H, s), 8.19 (1H, s), 8.66 (1H, d, J=9.0 Hz), 8.81. (1H, dd, J=5.5, 1.5 Hz), 9.21 (1H, d, J=1.8 Hz); MASS (ES+): m/e 371 (M+1).

EXAMPLE 49

Compound E49 was obtained from Compound (164) according to a manner similar to Example 1 (130.9 mg).
$^1$H-NMR (300 MHz, DMSO-$d_6$, δ): 4.54 (2H, s), 6.48 (1H, d, J=15.8 Hz), 7.46 (1H, d, J=15.8 Hz), 7.47 (2H, d, J=8.1 Hz), 7.58 (2H, t, J=7.0 Hz), 7.60 (2H, d, J=8.1 Hz), 7.71 (1H, t, J=7.7 Hz), 7.76 (2H, d, J=7.4 Hz), 7.83 (1H, dd, J=8.8, 1.5 Hz), 7.87 (2H, d, J=8.4 Hz), 8.01 (1H, s); MASS (ES+): m/e 398 (M+1).

EXAMPLE 50

Compound E50 was obtained from Compound (166) according to a manner similar to Example 1 (69.3 mg).
$^1$H-NMR (300 MHz, DMSO-$d_6$, δ): 4.51 (2H, s), 5.89 (1H, s), 6.46 (1H, d, J=45.8 Hz), 7.20 (1H, t, J=7.0 Hz), 7.30 (2H, t, J=7.3 Hz), 7.39 (2H, d, J=7.3 Hz), 7.46 (4H, m), 7.59 (2H, d, J=8.4 Hz), 7.65 (1H, d, J=8.4 Hz), 7.74 (1H, s); MASS (ES+): m/e 398 (M+1).

EXAMPLE 51

Compound E51 was obtained from Compound (169) according to a manner similar to Example 1 (103.9 mg).
$^1$H-NMR (300 MHz, DMSO-$d_6$, δ): 3.00 (6H, s), 4.57 (2H, s), 6.48 (1H, d, J=15.8 Hz), 7.47 (1H, d, J=15.0 Hz), 7.50 (1H, d, J=8.1 Hz), 7.61 (2H, d, J=8.4 Hz), 7.65 (2H, d, J=9.1 Hz), 7.79 (2H, s), 7.87 (1H, s); MASS (ES+): m/e 413 (M+1)

EXAMPLE 52

Compound E52 was obtained from Compound (172) according to a manner similar to Example 1 (203.9 mg).
$^1$H-NMR (300 MHz, DMSO-$d_6$, δ): 4.46 (2H, s), 6.46 (1H, d, J=16.1 Hz), 7.44 (2H, d, J=8.5 Hz), 7.45 (1H, d, J=16.0 Hz), 7.57 (2H, d, J=8.5 Hz), 7.69 (1H, d, J=8.5 Hz), 7.85 (1H, d, J=7.8 Hz), 8.03 (1H, s); MASS (ES+): m/e 361 (M+1).

EXAMPLE 53

Compound E53 was obtained from Compound (175) according to a manner similar to Example 1 (419.6 mg).
$^1$H-NMR (300 MHz, DMSO-$d_6$, δ): 4.35 (2H, s), 6.46 (1H, d, J=15.7 Hz), 7.31–7.40 (2H, m), 7.42 (2H, d, J=8.0 Hz), 7.43 (1H, d, J=16.0 Hz), 7.56 (2H, d, J=8.0 Hz); MASS (ES+): m/e 330 (M+1).

EXAMPLE 54

Compound E54 was obtained from Compound (178) according to a manner similar to Example 1 (90.7 mg).
$^1$H-NMR (300 MHz, DMSO-$d_6$, δ): 0.94 (6H, d, J=6.6 Hz), 1.64 (2H, dt, J=6.6, 6.6 Hz), 1.80 (1H, hept, J=6.6 Hz), 4.07 (2H, t, J=6.6 Hz), 4.51 (2H, s), 6.48 (1H, d, J=16.2 Hz), 7.11 (1H, dd, J=2.1,9.0 Hz), 7.21 (1H, d, J=2.1 Hz), 7.44 (2H, d, J=8.4 Hz), 7.45 (1H, d, J=16.2 Hz), 7.59 (2H, d, J=8.5 Hz), 7.63 (1H, d, J=9.0 Hz); MASS (ES+): m/e 380 (M+1).

EXAMPLE 55

Compound E55 was obtained from Compound (181) according to a manner similar to Example 1 (215.8 mg).
$^1$H-NMR (300 MHz, DMSO-$d_6$, δ): 1.29 (6H, d, J=6.1 Hz), 4.51 (2H, s), 4.70 (1H, hept, J=6.1 Hz), 6.48 (1H, d, J=16.0 Hz), 7.09 (1H, dd, J=2.2, 8.9 Hz), 7.20 (1H, d, J=2.2 Hz), 7.45 (1H, d, J=16.0 Hz), 7.47 (2H, d, J=8.5 Hz), 7.59 (2H, d, J=8.1 Hz), 7.63 (1H, d, J=8.9 Hz); MASS (ES+): m/e 352 (M+1)

EXAMPLE 56

Compound E56 was obtained from Compound (184) according to a manner similar to Example 1 (387.8 mg).
$^1$H-NMR (300 MHz, DMSO-$d_6$, δ): 4.52 (2H, s), 6.48 (1H, d, J=16.1 Hz), 7.04 (2H, d, J=7.7 Hz), 7.18 (1H, t, J=7.7 Hz), 7.22 (1H, dd, J=8.8,2.2 Hz), 7.30 (1H, d, J=2.2 Hz), 7.41 (2H, t, J=8.0 Hz), 7.46 (1H, d, J=16.0 Hz), 7.47 (2H, d, J=8.1 Hz), 7.57 (2H, d, J=7.7 Hz), 7.77 (1H, d, J=9.2 Hz); MASS (ES+): m/e 386 (M+1)

EXAMPLE 57

Compound E57 was obtained from Compound (187) according to a manner similar to Example 1 (78.2 mg).
$^1$H-NMR (300 MHz, DMSO-$d_6$, δ): 3.85 (3H, s), 4.52 (2H, s), 6.48 (1H, d, J=15.7 Hz), 7.12 (1H, dd, J=8.8, 2.2 Hz), 7.20 (1H, d, J=2.2 Hz), 7.45 (1H, d, J=15.0 Hz), 7.46 (2H, d, J=8.4 Hz), 7.60 (2H, d, J=8.4 Hz), 7.65 (1H, d, J=9.2 Hz); MASS (ES+): m/e 324 (M+1).

EXAMPLE 58

To a solution of Compound (277) (2.46 g) in MeOH (12 mL) was added hydrogen chloride methanol reagent 10 (15 mL, Tokyo Kasei Kogyo Co., Ltd.), and the mixture was stirred at ambient temperature for 2 hrs. The reaction mixture was diluted with isopropyl ether (50 mL) and the precipitate was collected by filtration. The obtained pale yellow powder was crystallized with a mixed solvent (EtOH: $H_2O$=6:4, 100 mL) to give Compound E58 (1.23 g) as colorless powder.
$^1$H-NMR (300 MHz, DMSO-$d_6$, δ): 4.39 (2H, s), 6.46 (1H, d, J=15.7 Hz), 7.43 (3H, m), 7.50 (1H, t, J=6.6 Hz), 7.52 (2H, t, J=7.0 Hz), 7.58 (2H, d, J=8.0 Hz), 7.82 (2H, d, J=7.4 Hz), 8.06 (1H, s); MASS (ES+): m/e 320 (M+1).

EXAMPLE 59

Compound E59 was obtained from Compound (278) according to a manner similar to Example 58 (274 mg).
$^1$H-NMR (300 MHz, DMSO-$d_6$, δ): 3.81 (3H, s), 4.33 (2H, s), 6.49 (1H, d, J=16.1 Hz), 7.36–7.65 (8H, m), 7.74–7.85 (2H, m); MASS (ES+): m/z 378 (M+1, free).

EXAMPLE 60

Compound E60 was obtained from Compound (188) according to a manner similar to Example 58 (1.36 g).
$^1$H-NMR (300 MHz, DMSO-$d_6$, δ): 3.80 (3H, s), 4.26 (2H, s), 6.45 (1H, d, J=15.8 Hz), 7.38–7.48 (3H, m), 7.52–7.61 (4H, m), 7.82 (2H, d); MASS (ES+): m/z 412 (M+1, free).

EXAMPLE 61

Compound E61 was obtained from Compound (193) according to a manner similar to Example 58 (68 mg).
$^1$H-NMR (300 MHz, DMSO-$d_6$, δ): 4.32 (2H, s), 6.47 (1H, d, J=16.1 Hz), 7.39–7.61 (6H, m), 7.62–7.89 (4H, m); MASS (ES+): m/z 363 (M+1, free).

EXAMPLE 62

Compound E61 was obtained from Compound (194) according to a manner similar to Example 58 (40 mg).
$^1$H-NMR (300 MHz, DMSO-$d_6$, δ): 4.10 (2H, s), 6.44 (1H, d, J=15.8 Hz), 7.31–7.64 (8H, m), 7.76–7.86 (2H, m); MASS (ES+): m/z 345 (M+1, free).

EXAMPLE 63

Compound E63 was obtained from Compound (203) according to a manner similar to Example 58 (212 mg).
$^1$H-NMR (300 MHz, DMSO-$d_6$, δ): 4.40 (2H, s), 6.47 (1H, d, J=16 Hz), 7.34–7.50 (5H, m), 7.58 (2×1H, d, J=8 Hz), 7.87–7.96 (2H, m), 8.05 (1H, s), 10.81 (1H, s); MASS (ES+): m/z 338.

EXAMPLE 64

Compound E64 was obtained from Compound (189) according to a manner similar to Example 58 (81 mg).
$^1$H-NMR (300 MHz, DMSO-$d_6$, δ): 4.40 (2H, s), 6.47 (1H, d, J=15.2 Hz), 7.44 (1H, d, J=15.2 Hz), 7.45 (2H, d, J=8.4 Hz), 7.55–7.66 (4H, m, J=8.4 Hz), 7.89 (2H, d, J=8.8 Hz), 8.11 (1H, s); MASS (ES+): m/z 354 (M+1, free).

EXAMPLE 65

Compound E65 was obtained from Compound (209) according to a manner similar to Example 58 (145 mg).
$^1$H-NMR (300 MHz, DMSO-$d_6$, δ): 2.52 (3H, s), 2.53 (3H, s), 4.27 (2H, s), 6.47 (1H, d, J=16 Hz), 7.41 (2×1H, d, J=8 Hz), 7.44 (1H, d, J=16 Hz), 7.56 (2×1H, d, J=8 Hz), 10.82 (1H, br-s); MASS: not detected.

EXAMPLE 66

Compound E66 was obtained from Compound (208) according to a manner similar to Example 58 (364 mg).
$^1$H-NMR (300 MHz, DMSO-$d_6$, δ): 2.25 (3H, s), 4.29 (2H, s), 6.48 (1H, d, J=16 Hz), 7.39–7.50 (3H, m), 7.53–7.63 (4H, m), 7.71 (1H, m), 7.87 (2×1H, d, J=7.5 Hz), 10.81 (1H, br-s); MASS (ES+): m/z 362.

EXAMPLE 67

Compound E67 was obtained from Compound (222) according to a manner similar to Example 58 (90 mg).
$^1$H-NMR (300 MHz, DMSO-$d_6$, δ): 6.52 (1H, d, J=16.1 Hz), 7.40–7.57 (6H, m), 7.63 (2H, d, J=8.1 Hz), 7.86 (2H, d, J=7.0 Hz), 8.29 (1H, s), 9.47 (1H, s); MASS (ES+): m/z 320 (M+1, free).

EXAMPLE 68

Compound E68 was obtained from Compound (190) according to a manner similar to Example 58 (80 mg).
$^1$H-NMR (300 MHz, DMSO-$d_6$, δ): 4.43 (2H, s), 6.49 (1H, d, J=16.1 Hz), 7.38–7.57 (7H, m), 7.64 (1H, s), 7.87 (2H, d, J=7.0 Hz), 8.09 (1H, s); MASS (ES+): m/z 320 (M+1, free).

EXAMPLE 69

Compound E69 was obtained from Compound (191) according to a manner similar to Example 58 (47 mg).
$^1$H-NMR (300 MHz, DMSO-$d_6$, δ): 4.09 (2H, s), 6.47 (1H, d, J=16.1 Hz), 7.29–7.59 (8H, m), 7.70–7.77 (2H, m); MASS (ES+): m/z 354 (M+1, free).

EXAMPLE 70

Compound E70 was obtained from Compound (279) according to a manner similar to Example 58 (1.34 mg).

$^1$H-NMR (300 MHz, DMSO-d$_6$, δ): 3.81-(3H, s), 4.38 (2H, s), 6.47 (1H, d, J=16.1 Hz), 7.08 (2H, d, J=8.8 Hz), 7.44 (2H, d, J=8.4 Hz), 7.45 (1H, d, J=15.1 Hz), 7.58 (2H, d, J=8.4 Hz), 7.77 (2H, d, J=8.8 Hz), 7.94 (1H, s); MASS (ES+): m/e 350 (M+1).

EXAMPLE 71

Compound E71 was obtained from Compound (280) according to a manner similar to Example 58 (482 mg).

$^1$H-NMR (300 MHz, DMSO-d$_6$, δ): 3.83 (3H, s), 4.40 (2H, s), 6.47 (1H, d, J=15.8 Hz), 7.00 (1H, m), 7.39–7.47 (6H, m), 7.58 (2H, d, J=8.1 Hz), 8.09 (1H, s); MASS (ES+): m/e 350 (M+1).

EXAMPLE 72

Compound E72 was obtained from Compound (281) according to a manner similar to Example 58 (498 mg).

$^1$H-NMR (300 MHz, DMSO-d$_6$, δ): 3.93 (3H, s), 4.40 (2H, s), 6.46 (1H, d, J=15.7 Hz), 7.11 (1H, t, J=8.1 Hz), 7.21 (1H, d, J=8.1 Hz), 7.43 (2+1+1H, d, J=8.1 Hz), 7.58 (2H, d, J=8.1 Hz), 7.80 (1H, dd, J=8.1, 1.6 Hz), 7.88 (1H, s); MASS (ES+): m/z 350 (M+1).

EXAMPLE 73

Compound E73 was obtained from Compound (282) according to a manner similar to Example 58 (94.8 mg).

$^1$H-NMR (300 MHz, DMSO-d$_6$, δ): 4.13 (2H, s), 6.44 (1H, d, J=15.8 Hz), 7.37 (2H, d, J=8.4 Hz), 7.38 (2H, t, J=8.1 Hz), 7.43 (1H, d, J=15.4 Hz), 7.50 (2H, t, J=8.1 Hz), 7.54 (2H, d, J=8.4 Hz), 7.74 (2H, d, J=8.1 Hz); MASS (ES+): m/e 398 (M+1).

EXAMPLE 74

Compound E74 was obtained from Compound (283) according to a manner similar to Example 58 (76 mg).

$^1$H-NMR (300 MHz, DMSO-d$_6$, δ): 4.03 (2H, s), 6.43 (1H, d, J=16.1 Hz), 7.32 (1H, t, J=7.4 Hz), 7.34 (2H, d, J=7.4 Hz), 7.43 (1H, d, J=15.4 Hz), 7.47 (2H, t, J=7.7 Hz), 7.52 (2H, d, J=8.4 Hz), 7.70 (2H, d, J=8.1 Hz); MASS (ES+): m/e 354 (M+1).

EXAMPLE 75

Compound E75 was obtained from Compound (285) according to a manner similar to Example 58 (74.3 mg).

$^1$H-NMR (300 MHz, DMSO-d$_6$, δ): 1.64 (2H, br.), 1.72 (4H, br.), 2.88 (2H, br.), 3.27 (2H, br.), 4.35 (2H, s), 4.43 (2H, s), 6.47 (1H, d, J=15.7 Hz), 7.45 (1H, d, J=15.7 Hz), 7.49 (2+1H, m), 7.56 (2+2H, m)., 7.67 (2H, d, J=7.4 Hz); MASS (ES+): m/e 417 (M+1).

EXAMPLE 76

Compound E76 was obtained from Compound (286) according to a manner similar to Example 58 (76.8 mg).

$^1$H-NMR (300 MHz, DMSO-d$_6$, δ): 3.15 (4H, br.), 3.81 (4H, br.), 4.36 (2H, s), 4.46 (2H, s), 6.48 (1H, d, J=15.8 Hz), 7.45 (1H, d, J=16.1 Hz), 7.49 (2+1H, m), 7.55 (2+2H, m), 7.71 (2H, d, J=7.3 Hz); MASS (ES+): m/e 419 (M+1).

EXAMPLE 77

Compound E77 was obtained from Compound (287) according to a manner similar to Example 58 (76 mg).

$^1$H-NMR (300 MHz, DMSO-d$_6$, δ): 3.79 (3H, s), 4.05 (2H, s), 6.44 (1H, d, J=15.8 Hz), 7.05 (2H, d, J=8.1 Hz), 7.34 (2H, d, J=8.4 Hz), 7.43 (1H, d, J=16.1 Hz), 7.52 (2H, d, J=8.1 Hz), 7.64 (2H, d, J=8.1 Hz); MASS (ES+): m/e 384 (M+1).

EXAMPLE 78

Compound E78 was obtained from Compound (223) according to a manner similar to Example 58 (280 mg).

$^1$H-NMR (300 MHz, DMSO-d$_6$, δ): 2.69 (3H, s), 5.43 (2H, s), 6.49 (1H, d, J=15.8 Hz), 7.44 (3H, m), 7.47 (1H, d, J=15.8 Hz), 7.53 (2H, t, J=7.3 Hz), 7.62 (2H, d, J=8.4 Hz), 7.81 (2H, d, J=7.0 Hz), 8.16 (1H, s) MASS (ES+): m/e 334 (M+1).

EXAMPLE 79

Compound E79 was obtained from Compound (224) according to a manner similar to Example 58 (432.4 mg).

$^1$H-NMR (300 MHz, DMSO-d$_6$, δ): 2.31 (3H, s), 5.53 (2H, s), 6.50 (1H, d, J=15.8 Hz), 7.40 (2H, d, J=8.1 Hz), 7.47 (1H, d, J=15.8 Hz), 7.63 (2H, d, J=8.1 Hz), 7.64 (4H, s), 9.36 (1H, s); MASS (ES+): m/z 368 (M+1).

EXAMPLE 80

Compound E80 was obtained from Compound (288) according to a manner similar to Example 58 (176 mg).

$^1$H-NMR (300 MHz, DMSO-d$_6$, δ): 5.47 (2H, s), 6.52 (1H, d, J=15.8 Hz), 7.41–7.53 (6H, m), 7.60 (1H, d, J=6.2 Hz), 7.68 (1H, s), 7.84 (2H, d, J=7.0 Hz), 8.26 (1H, s), 9.34 (1H, s); MASS (ES+): m/e 319 (M+1).

EXAMPLE 81

Compound E81 was obtained from Compound (289) according to a manner similar to Example 58 (268 mg).

$^1$H-NMR (300 MHz, DMSO-d$_6$, δ): 2.33 (3H, s), 5.54 (2H, s), 6.53 (1H, d, J=16.1 Hz), 7.369–7.54 (4H, m), 7.58 (1H, s), 7.63 (2H, d, J=8.4 Hz), 7.68 (2H, d, J=8.4 Hz), 9.42 (1H, s); MASS (ES+): m/e 368 (M+1).

EXAMPLE 82

Compound E82 was obtained from Compound (321) according to a manner similar to Example 58 (220 mg).

$^1$H-NMR (300 MHz, DMSO-d$_6$, δ): 5.50 (2H, s), 6.48 (1H, d, J=16.1 Hz), 7.15 (2H, d, J=8.1 Hz), 7.41 (1H, d, J=16.1 Hz), 7.53 (2H, d, J=8.1 Hz), 7.59–7.78 (5H, m), 7.88–7.97 (2H, m); MASS (ES+): m/z 320 (M+1, free).

EXAMPLE 83

Compound E83 was obtained from Compound (323) according to a manner similar to Example 58 (60 mg).

$^1$H-NMR (300 MHz, DMSO-d$_6$, δ): 2.73 (3H, d, J=4.8 Hz), 4.28 (2H, s), 6.46 (1H, d, J=15.8 Hz), 7.35–7.61 (7H, m), 7.70–7.80 (2H, m), 8.24–8.37 (1H, m); MASS (ES+): m/z 377 (M+1, free).

EXAMPLE 84

Compound E84 was obtained from Compound (290) according to a manner similar to Example 58 (22.2 mg).
$^1$H-NMR (300 MHz, DMSO-$d_6$, δ): 3.78 (3H, s), 4.22 (2H, s), 6.44 (1H, d, J=15.8 Hz), 7.39 (2H, d, J=8.1 Hz), 7.43 (1H, d, J=15.8 Hz), 7.48 (3H, m), 7.54 (2H, d, J=8.4 Hz), 7.76 (2H, m); MASS (ES+): m/e 378 (M+1).

EXAMPLE 85

Compound E85 was obtained from Compound (291) according to a manner similar to Example 58 (13.5 mg).
$^1$H-NMR (300 MHz, DMSO-$d_6$, δ): 1.29 (9H, s), 4.32 (2H, s), 6.46 (1H, d, J=15.8 Hz), 7.29 (1H, s), 7.39 (2H, d, J=8.4 Hz), 7.44 (1H, d, J=16.1 Hz), 7.57 (2H, d, J=8.1 Hz); MASS (ES+): m/z 300 (M+1).

EXAMPLE 86

Compound E86 was obtained from Compound (198) according to a manner similar to Example 58 (491 mg).
$^1$H-NMR (300 MHz, DMSO-$d_6$, δ): 1.23 (3H, t, J=7.0 Hz), 4.24 (2H, s), 4.26 (2H, q, J=7.0 Hz), 6.44 (1H, d, J=15.8 Hz), 7.41 (2H, d, J=8.0 Hz), 7.43 (1H, d, J=15.4 Hz), 7.48 (3H, m), 7.55 (2H, d, J=8.1 Hz), 7.75 (2H, m); MASS (ES+): m/e 392 (M+1).

EXAMPLE 87

Compound E87 was obtained from Compound (332) according to a manner similar to Example 58 (86.7 mg).
$^1$H-NMR (300 MHz, DMSO-$d_6$, δ): 2.71 (3H, s), 2.98 (3H, s), 4.32 (2H, s), 6.46 (1H, d, J=16.1 Hz), 7.41–7.60 (10H, m); MASS: Not Detected.

EXAMPLE 88

Compound E88 was obtained from Compound (325) according to a manner similar to Example 58 (35.8 mg).
$^1$H-NMR (300 MHz, DMSO-$d_6$, δ): 1.09 (2H, br.), 1.49 (4H, br.), 3.12 (4H, br.), 4.34 (2H, s), 6.47 (1H, d, J=15.8 Hz), 7.42–7.60 (10H, m); MASS (ES+): m/e 431 (M+1).

EXAMPLE 89

Compound E89 was obtained from Compound (326) according to a manner similar to Example 58 (40.5 mg).
$^1$H-NMR (300 MHz, DMSO-$d_6$, δ): 1.11 (6H, d, J=6.6 Hz), 4.02 (1H, m), 4.23 (2H, s), 6.44 (1H, d, J=15.8 Hz), 7.40 (2H, d, J=7.7 Hz), 7.48 (4H, m), 7.56 (2H, d, J=8.1 Hz), 7.73 (2H, d, J=8.1 Hz); MASS (ES+): m/e 405 (M+1).

EXAMPLE 90

Compound E90 was obtained from Compound (284) according to a manner similar to Example 58 (11.1 mg).
$^1$H-NMR (300 MHz, DMSO-$d_6$, δ): 2.71 (6H, s), 4.21 (2H, s), 4.38 (2H, s), 6.44 (1H, d, J=16.1 Hz), 7.40 (3H, m), 7.48 (2H, m), 7.55 (5H, m); MASS (ES+): m/e 377 (M+1).

EXAMPLE 91

Compound E91 was obtained from Compound (323) according to a manner similar to Example 58 (40.1 mg).
$^1$H-NMR (300 MHz, DMSO-$d_6$, δ): 4.27 (2H, s), 6.45 (1H, d, J=15.8 Hz), 7.41–7.58 (8H, m), 7.78 (2H, m); MASS: Not Detected.

EXAMPLE 92

Compound E92 was obtained from Compound (327) according to a manner similar to Example 58 (14.8 mg).
$^1$H-NMR (300 MHz, DMSO-$d_6$, δ): 4.37 (2H, s), 4.60 (2H, s), 6.47 (1H, d, J=15.0 Hz), 7.42–7.60 (8H, m), 7.67 (2H, d, J=7.0 Hz); MASS (ES+): m/e 350 (M+1).

EXAMPLE 93

Compound E93 was obtained from Compound (329) according to a manner similar to Example 58 (145 mg).
$^1$H-NMR (300 MHz, DMSO-$d_6$, δ): 3.34 (3H, s), 4.37 (2H, s), 4.51 (2H, s), 6.46 (1H, d, J=15.8 Hz), 7.43–7.65 (10H, m); MASS (ES+): m/e 364 (M+1).

EXAMPLE 94

Compound E94 was obtained from Compound (330) according to a manner similar to Example 58 (42.4 mg).
$^1$H-NMR (300 MHz, DMSO-$d_6$, δ): 2.17 (3H, s), 4.41 (2H, s), 6.46 (1H, d, J=16.1 Hz), 7.37–7.44 (2H, m), 7.45 (1H, d, J=15.8 Hz), 7.52–7.60 (6H, m), 7.71 (1H, m); MASS (ES+): m/z 362 (M+1).

EXAMPLE 95

Compound E95 was obtained from Compound (225) according to a manner similar to Example 58 (176 mg).
$^1$H-NMR (300 MHz, DMSO-$d_6$, δ): 5.47 (2H, s), 6.53 (1H, d, J=16 Hz), 7.44 (1H, d, J=16 Hz), 7.45 (2×1H, d, J=8.5 Hz), 7.60 (2×1H, d, J=8.5 Hz), 7.72 (1H, dd, J=1.7, 1.5 Hz), 7.81 (1H, dd, J=1.7, 1.3 Hz), 9.34 (1H, dd, J=1.5, 1.3 Hz), 10.89 (1H, br-s), 14.73 (1H, br-s); MASS (ES+): m/e 244.

EXAMPLE 96

Compound E96 was obtained from Compound (210) according to a manner similar to Example 58 (21 mg).
$^1$H-NMR (300 MHz, DMSO-$d_6$, δ): 1.96–2.03 (4H, m), 3.24–3.31 (4H, m), 4.49 (2H, s), 6.49 (1H, d, J=16 Hz), 6.60 (1H, s), 6.83 (1H, dd, J=2, 8 Hz), 7.42–7.62 (6H, m); MASS (ES+): m/z 363 (M+1).

EXAMPLE 97

Compound E97 was obtained from Compound (328) according to a manner similar to Example 58 (7.9 mg).
$^1$H-NMR (300 MHz, DMSO-$d_6$, δ): 4.55 (2H, s), 4.66 (2H, s), 6.48 (1H, d, J=16 Hz), 7.43–7.51 (4H, m), 7.60 (2H, d, J=8 Hz), 7.71 (2H, d, J=8 Hz); MASS (ES+): m/z 324 (M+1).

EXAMPLE 98

Compound E98 was obtained from Compound (333) according to a manner similar to Example 58 (72 mg).
$^1$H-NMR (300 MHz, DMSO-$d_6$, δ): 1.77–1.92 (4H, m), 3.33–3.54 (4H, m), 4.57 (2H, s), 6.50 (1H, d, J=16 Hz), 7.45 (1H, d, J=16 Hz), 7.50 (2H, d, J=8 Hz), 7.60 (2H, d, J=8 Hz), 7.64 (1H, dd, J=2, 8 Hz), 7.80 (1H, d, J=8 Hz), 7.88 (1H, s); MASS (ES+): m/z 391 (M+1)

EXAMPLE 99

Compound E99 was obtained from Compound (334) according to a manner similar to Example 58 (12 mg).
$^1$H-NMR (300 MHz, DMSO-d$_6$, δ): 1.24 (6H, t, J=7 Hz), 2.93–3.09 (4H, m), 4.25 (2H, s), 4.32–4.39 (2H, m), 6.78 (1H, d, J=16 Hz), 7.38–7.65 (7H, m), 7.82 (1H, s); MASS (ES+): m/z 379 (M+1).

EXAMPLE 100

Compound E100 was obtained from Compound (316) according to a manner similar to Example 58 (40 mg).
$^1$H-NMR (300 MHz, DMSO-d$_6$, δ): 3.71 (3H, s), 4.10 (2H, s), 5.11 (2H, s), 6.41 (1H, d, J=16 Hz), 6.86 (2H, d, J=8 Hz), 7.09 (2H, d, J=8 Hz), 7.16 (2H, d, J=8 Hz), 7.36–7.52 (3H, m), 7.80 (1H, s); MASS (ES–): m/z 430 (M–1).

EXAMPLE 101

Compound E101 was obtained from Compound (317) according to a manner similar to Example 58 (164 mg).
$^1$H-NMR (300 MHz, DMSO-d$_6$, δ): 1.65–1.79 (6H, m), 1.84–1.93 (6H, m), 2.00–2.07 (3H, m), 4.32 (2H, s), 6.47 (1H, d, J=16 Hz), 7.25 (1H, s), 7.38–7.48 (3H, m), 7.56 (2H, d, J=8 Hz); MASS (ES+): m/z 378 (M+1).

EXAMPLE 102

Compound E102 was obtained from Compound (338) according to a manner similar to Example 58 (35 mg).
$^1$H-NMR (300 MHz, DMSO-d$_6$, δ): 1.31 (3H, t, J=7 Hz), 4.28 (2H, s), 4.33 (2H, q, J=7 Hz), 6.47 (1H, d, J=16 Hz), 7.37 (2H, d, J=8 Hz), 7.43 (1H, d, J=16 Hz), 7.55 (2H, d, J=8 Hz), 8.23 (1H, s); MASS (ES+): m/z 316 (M+1).

EXAMPLE 103

Compound E103 was obtained from Compound (312) according to a manner similar to Example 58 (138 mg).
$^1$H-NMR (300 MHz, DMSO-d$_6$, δ): 2.36 (2H, m), 3.30 (2H, t, J=7.4 Hz), 4.15 (2H, t, J=5.8 Hz), 6.30 (1H, d, J=16.1 Hz), 6.79 (2H, d, J=8.8 Hz), 7.38 (1H, d, J=15.8 Hz), 7.45 (2H, d, J=8.8 Hz), 7.54 (2H, m), 7.78 (2H, m); MASS (ES+): m/e 338 (M+1).

EXAMPLE 104

Compound E104 was obtained from Compound (313) according to a manner similar to Example 58 (174 mg).
$^1$H-NMR (300 MHz, DMSO-d$_6$, δ): 1.84 (2H, m), 2.03 (2H, m), 3.21 (2H, t, J=7.4 Hz), 4.07 (2H, t, J=6.4 Hz), 6.31 (1H, d, J=15.4 Hz), 6.96 (2H, d, J=8.8 Hz), 7.40 (1H, d, J=15.8 Hz), 7.49 (2H, d, J=8.1 Hz), 7.53 (2H, m), 7.78 (2H, m); MASS (ES+): m/e 352 (M+1).

EXAMPLE 105

Compound E105 was obtained from Compound (314) according to a manner similar to Example 58 (153 mg).
$^1$H-NMR (300 MHz, DMSO-d$_6$, δ): 2.21 (2H, quint., J=7.3 Hz), 2.74 (2H, t, J=7.3 Hz), 3.14 (2H, t, J=7.7 Hz), 6.42 (1H, d, J=16.1 Hz), 7.29 (2H, d, J=8.0 Hz), 7.41 (1H, d, J=15.8 Hz), 7.48 (2H, d, J=7.7 Hz), 7.52 (2H, m), 7.76 (2H, m); MASS (ES+): m/e 322 (M+1).

EXAMPLE 106

A suspension of Compound E116 (1.23 g, described later in Example 116) and benzenesulfonic acid (732 mg) in 80% aqueous ethanol (20 mL) was dissolved at 90° C. The insoluble materials were removed by filtration and the filtrate was evaporated in vacuo to give a crude solid. This solid was recrystallized from 80% aqueous ethanol to give Compound E106 as a pale yellow crystal (820 mg).
$^1$H-NMR (300 MHz, DMSO-d$_6$, δ): 4.53 (2H, s), 6.47 (1H, d, J=16 Hz), 7.28–7.36 (3H, m), 7.41–7.56 (5H, m), 7.57–7.66 (4H, m), 7.72–7.81 (2H, m), 10.78 (1H, s); MASS (ES+): m/z 294.

EXAMPLE 107

A suspension of Compound E116 (1.80 g, described later in Example 116) and (1R)-(–)-10-camphorsulfonic acid (855 mg) in 80% aqueous ethanol (20 mL) was dissolved at 90° C. The insoluble materials were removed by filtration, and the filtrate was evaporated in vacuo to give a crude solid. This solid was recrystallized from 80% aqueous ethanol to give Compound E107 as a white crystal (1.30 g).
$^1$H-NMR (300 MHz, DMSO-d$_6$, δ): 0.74 (3H, s), 1.05 (3H, s), 1.20–1.35 (2H, m), 1.74–1.96 (3H, m), 2.24 (1H, m), 2.39 (1H, d, J=14.7 Hz), 2.69 (1H, m), 2.89 (1H, d, J=14.7 Hz), 4.55 (2H, s), 6.48 (1H, d, J=15.7 Hz), 7.42–7.58 (5H, m), 7.61 (2×1H, d, J=8 Hz), 7.74–7.82 (2H, m), 10.79 (1H, s); MASS (ES+): m/z 294.

EXAMPLE 108

To a stirred suspension of Compound E116 (1.0 g, described later in Example 116) in ethanol (20 mL) was added 4-methylbenzenesulfonic acid monohydrate (713 mg) at ambient temperature. The resulting suspension was stirred at 70° C. for 1 hr, during which time water (0.1 mL) was added to the mixture in order to dissolve some insoluble materials. The mixture was allowed to cool to ambient temperature and the stirring was continued for additional 1 hr. The precipitate was filtered, washed with ethanol (5 mL, 2 times) and dried to afford crude Compound E108 (1.58 g) as a pale tan solid. The Compound E110 was used without further purification.

EXAMPLE 109

A suspension of crude Compound E108 (salt, 710 mg) in 80% aqueous acetonitrile (20 mL) was heated at 90° C. for 15 min. The insoluble materials were removed by filtration and the resulting filtrate was allowed to cool to ambient temperature. The solution was stirred at ambient temperature for 1 hr and then in an ice bath for 0.5 hr. The precipitate formed was filtered, washed with acetonitrile (5 mL, 2 times) and dried to afford Compound E111 (370 mg) as a pale tan solid.
m.p. 228.5–230.5° C. $^1$H-NMR (300 MHz, DMSO-d$_6$, δ): 2.29 (3H, s), 4.54 (2H, s), 6.47 (1H, d, J=15.8 Hz), 7.11 (2H, d, J=7.7 Hz), 7.42–7.57 (7H, m), 7.61 (2H, d, J=8.4 Hz), 7.72–7.82 (2H, m); MASS (ES+): m/z 294 (M+1, free).

EXAMPLE 110

To a solution of Compound (292) (42 mg) in MeOH (1 mL) was added hydrogen chloride methanol reagent 10 (0.8 mL, manufactured by Tokyo Kasei Kogyo Co., Ltd.), and the mixture was stirred at ambient temperature for 2 hrs. To the reaction mixture was added saturated aqueous NaHCO$_3$ solution and extracted with AcOEt. The organic phase was sequentially washed with saturated aqueous NaHCO$_3$ solution, water and brine, and the solvent was removed in vacuo. The obtained colorless solid was triturated with MeCN to give Compound E110 (4.8 mg) as colorless powder.

$^1$H-NMR (300 MHz, DMSO-d$_6$, δ): 1.28 (4H, m), 1.69 (4H, m), 1.90 (2H, m), 2.37 (1H, m), 3.91 (2H, s), 6.41 (1H, d, J=15.8 Hz), 6.62 (1H, s), 7.26 (2H, d, J=8.1 Hz), 7.41 (1H, d, J=15.8 Hz), 7.47 (2H, d, J=7.7 Hz); MASS (ES+): m/z 326 (M+1)

EXAMPLE 111

Compound E111 was obtained from Compound (284) according to a manner similar to Example 110 (289 mg).

$^1$H-NMR (300 MHz, DMSO-d$_6$, δ): 2.16 (6H, s), 3.44 (2H, s), 4.00 (2H, s), 6.41 (1H, d, J=16.5 Hz), 7.18 (1H, t, J=7.0 Hz), 7.32 (2H, d, J=7.3 Hz), 7.33 (2H, t, J=7.3 Hz), 7.41 (1H, d, J=15.8 Hz), 7.50 (2H, d, J=7.7 Hz), 7.70 (2H, d, J=7.3 Hz); MASS (ES+): m/z 377 (M+1).

EXAMPLE 112

Compound E112 was obtained from Compound (197) according to a manner similar to Example 58 (22.5 mg).

m.p. 235–239° C. $^1$H-NMR (300 MHz, DMSO-d$_6$, δ): 4.34 (2H, s), 6.47 (1H, d, J=15.8 Hz), 7.37 (2H, d, J=8.1 Hz), 7.44 (1H, d, J=15.8 Hz), 7.57 (2H, d, J=8.1 Hz), 7.60 (2H, s); MASS (ES+) m/z 243 (M+1, free).

EXAMPLE 113

To a stirred solution of [(1S,4R)-7,7-dimethyl-2-oxobicyclo[2.2.1]hept-1-yl]methanesulfonic acid (832 mg, described later in Example 116) in ethanol (10 mL) was added Compound E116 (1.0 g, described later in Example 118) at ambient temperature. The resulting suspension was heated at 60° C. for 1 hr and then allowed to cool to ambient temperature. The suspension was further stirred at ambient temperature for 1 hr. The precipitate was filtered, washed with ethanol (2 mL, 3 times) and dried to afford Compound E113 (1.73 g) as a pale tan solid. The Compound E113 was used in the following Example 114 without further purification.

EXAMPLE 114

A suspension of crude Compound E113 (salt, 700 mg) in 90% aqueous acetonitrile (20 mL) was heated at 90° C. for 5 min. The insoluble materials were removed by filtration and the resulting filtrate was heated at 90° C. again. The solution was allowed to cool to ambient temperature and stirred at the same temperature for 1 hr. The precipitate was filtered, washed with acetonitrile (2 mL, 2 times) and dried to afford Compound E114 (522 mg) as a pale tan solid.

m.p. 185.5–194.5° C. $^1$H-NMR (300 MHz, DMSO-d$_6$, δ): 0.74 (3H, s), 1.05 (3H, s), 1.20–1.35 (2H, m), 1.79 (1H, d, J=18.0 Hz), 1.80–1.90 (1H, m), 1.93 (1H, t, J=4.2 Hz), 2.23 (1H, dt, J=18.0, 4.2 Hz), 2.39 (1H, d, J=14.7 Hz), 2.61–2.76 (1H, m), 2.89 (1H, d, J=14.7 Hz), 4.54 (2H, s), 6.48 (1H, d, J=16.1 Hz), 7.41–7.57 (5H, m), 7.61 (2H, d, J=8.1 Hz), 7.73–7.82 (2H, m), 10.79 (1H, br.s); MASS (ES+): m/z 294 (M+1, free).

EXAMPLE 115

To a mixture of Compound (322) (as a mixture of two regioisomers, 310 mg in total) in methanol (1 mL) was added 10% hydrogen chloride in methanol (3 mL) at ambient temperature for 20 min. The mixture was concentrated in vacuo, and the residue was purified by preparative high performance liquid chromatography (column; Mightysil RP-18 GP 250-20 Kanto Chemical Co., Inc.) eluting with a gradient solvent system from acetonitrile in water (10:90 v/v) to acetonitrile in water (50:50 v/v). The residue was lyophilized to give a mixture of Compound E115 as a mixture of two regioisomers (85 mg in total) as a pale red viscous oil.

$^1$H-NMR (300 MHz, DMSO-d$_6$, δ):(for a mixture of two regioisomers) 2.17 (1.2H, s), 2.25 (1.8H, s), 5.39 (1.2H, s), 5.47 (0.8H, s), 6.52 (1H, d, J=15.8 Hz), 7.18–7.37 (1.2H, m), 7.39–7.54 (2.8H, m), 7.60 (1.2H, d, J=8.1 Hz), 7.75 (0.8H, d, J=8.1 Hz), 9.20 (0.6H, s), 9.25 (0.4H, s); MASS (ES+): (for a mixture of two regioisomers) m/z 258 (M+1).

EXAMPLE 116

To a suspension of Compound E1 (990 mg) in ethanol (10 mL) was added 1N sodium hydroxide solution (3.0 mL), and the mixture was stirred at 70° C. for 2 hrs. The resulting precipitate was collected by filtration and washed with ethanol and H$_2$O to give Compound E116 (810 mg) as a white powder.

$^1$H-NMR (300 MHz, DMSO-d$_6$, δ): 4.19 (2H, s), 6.41 (1H, d, J=16 Hz), 7.07–7.16 (2H, m), 7.33–7.55 (7H, m).

EXAMPLE 117

To a suspension of Compound E116 (147 mg) in ethanol (5 mL) was added 1N sodium hydroxide solution (0.501 mL), and the mixture was stirred at room temperature for 1 hour. The resulting mixture was evaporated in vacuo and triturated with isopropyl ether to give Compound E117 (162 mg) as a pale green powder.

$^1$H-NMR (300 MHz, DMSO-d$_6$, δ): 4.13 (2H, s), 6.32 (1H, d, J=16 Hz), 6.89 (1H, d, J=16 Hz), 7.07–7.14 (2H, m), 7.24 (2H, d, J=8 Hz), 7.36 (2H, d, J=8 Hz), 7.43–7.50 (2H, m).

EXAMPLE 118

To a suspension of Compound E116 (147 mg) in ethanol (5 mL) was added 1N methanesulfonic acid solution (0.501 mL), and the mixture was stirred at room temperature for 2 hrs. The resulting precipitate was collected by filtration and washed with ethanol to give Compound E118 (91 mg) as a white powder.

$^1$H-NMR (300 MHz, DMSO-d$_6$, δ): 2.32 (3H, s), 4.54 (2H, s), 6.47 (1H, d, J=16 Hz), 7.46. (2H, d, J=8 Hz), 7.48–7.56 (3H, m), 7.61 (2H, d, J=8 Hz), 7.74–7.81 (2H, m).

EXAMPLE 119

To a suspension of Compound E116 (147 mg) in ethanol (5 mL) was added 1N sulfuric acid (1.0 mL), and the mixture was stirred at 70° C. for 2 hours. The resulting precipitate was collected by filtration and washed with ethanol to give Compound E119 (177 mg) as a white powder.

$^1$H-NMR (300 MHz, DMSO-d$_6$, δ): 4.44 (2H, s), 6.46 (1H, d, J=16 Hz), 7.39–7.49 (5H, m), 7.59 (2H, d, J=8 Hz), 7.67–7.71 (2H, m).

EXAMPLE 120

To a solution of Compound (6) (1.0 g), 3-(benzyloxy)-1,2-benzenediamine (817 mg) and 1-hydroxybenzotriazole (567 mg) in N,N-dimethylformamide (19 mL) was added 1-(3-dimethylaminopropyl)-3-ethylcarbodiimide hydrochloride (804 mg). After stirring for 6 hrs, saturated aqueous NaHCO$_3$ (20 mL) and water (80 mL) were added to the reaction mixture. The resulting precipitate was collected by filtration and washed with water. To a mixture of this product in acetic acid (7 mL) was added a solution of hydrogen chloride in acetic acid (13 mL). After stirring at 100° C. for 1 hour, the resulting mixture was cooled to 4° C. and diluted with ethyl acetate (40 mL). The resulting precipitate was collected by filtration and washed with ethyl acetate. To a solution of this product, O-tetrahydro-2H-pyran-2-ylhydroxylamine (1.5 eq.) and 1-hydroxybenzotriazole (1.5 eq.) in N,N-dimethylformamide (11 mL) was added 1-(3-dimethylaminopropyl)-3-ethylcarbodiimide (1.5 eq.) at 4° C. The mixture was warmed to ambient temperature and stirred for 8 hrs. The reaction mixture was added saturated NaHCO$_3$ (11 mL) and water (44 mL). A resulting precipitate was filtered and the filtrate was extracted with ethyl acetate. The organic layer was washed with H$_2$O and brine, dried over MgSO$_4$, filtered and evaporated in vacuo. The crude product was treated with trifluoroacetic acid to give Compound E120 (52 mg).

$^1$H-NMR (300 MHz, DMSO-d$_6$, δ): 4.43 (2H, s), 6.46 (1H, d, J=16 Hz) 6.86 (1H, d, J=8 Hz), 7.12(1H, d, J=8 Hz), 7.23–7.30 (1H, m), 7.39–7.62 (5H, m); MASS (ES+): m/z 310 (M+1).

EXAMPLE 121

To a solution of Compound (6) (1.0 g), 4-(benzyloxy)-1,2-benzenediamine (817 mg) and 1-hydroxybenzotriazole (567 mg) in N,N-dimethylformamide (19 mL) was added 1-(3-dimethylaminopropyl)-3-ethylcarbodiimide hydrochloride (804 mg). After stirring for 6 hours, the reaction mixture were added saturated NaHCO$_3$ (20 mL) and water (80 mL) The resulting precipitate was collected by filtration and washed with water. To a solution of this product in acetic acid (7 mL) was added hydrogen chloride in acetic acid (13 mL). After stirring at 100° C. for 1 hour, the resulting mixture was cooled to 4° C. and diluted with ethyl acetate (40 mL). A resulting precipitate was collected by filtration and washed with ethyl acetate. This product, O-tetrahydro-2H-pyran-2-ylhydroxylamine (1.5 eq.) and 1-hydroxybenzotriazole (1.5 eq.) were dissolved in N,N-dimethylformamide (9 mL), and 1-(3-dimethylaminopropyl)-3-ethylcarbodiimide (1.5 eq.) was added thereto at 4° C. The mixture was warmed to ambient temperature and stirred for 8 hours. To the reaction mixture were added saturated NaHCO$_3$ (10 mL) and water (40 mL). The resulting precipitate was collected by filtration and washed with water. The crude product was treated with hydrogen chloride in methanol to give Compound E121 (35 mg).

$^1$H-NMR (300 MHz, DMSO-d$_6$, δ): 4.52 (2H, s), 5.22 (2H, s), 6.49 (1H, d, J=16 Hz), 7.21 (1H, dd, J=2, 8 Hz), 7.30 (1H, d, J=2 Hz), 7.34–7.50 (8H, m), 7.59 (2H, d, J=8 Hz), 7.67 (1H, d, J=8 Hz); MASS (ES+): m/z 400 (M+1)

EXAMPLE 122

To a solution of Compound (51) (70 mg) in N,N-dimethylformamide (1.5 mL) was added N,N'-carbonyldiimidazole (40 mg). The mixture was stirred for 30 min, and methanesulfonamide (24 mg) and 1,8-diazabicyclo[5.4.0]-7-undecene (0.037 mL) were added thereto. The reaction mixture was stirred for 8 hrs at 80° C. The resulting mixture was acidified with 1 N hydrochloric acid at 0° C., and water (7.5 mL) was added thereto. The resulting precipitate was collected by filtration and washed with water. The crude product was treated with hydrogen chloride in methanol to give Compound E122 (7.9 mg).

$^1$H-NMR (300 MHz, DMSO-d$_6$, δ): 3.40 (3H, s), 4.46 (2H, s), 6.47 (1H, d, J=16 Hz), 7.41–7.49 (3H, m), 7.58 (2H, d, J=8 Hz), 7.76 (1H, d, J=8 Hz), 7.95 (1H, d, J=8 Hz), 8.29 (1H, s); MASS (ES+): m/z 415 (M+1).

EXAMPLE 123

To a suspension of Compound E116 (500 mg) in ethanol (5 mL) was added maleic acid (198 mg), and the mixture was stirred at 70° C. for 2 hrs. The resulting precipitate was collected by filtration and washed with ethanol and water. The solid was recrystallized from 50% aqueous EtOH to give Compound E123 (374 mg) as a pale yellow powder.

$^1$H-NMR (300 MHz, DMSO-$_6$, δ): 4.33 (2H, s), 6.17 (2H, s), 6.44 (1H, d, J=16 Hz), 7.24–7.32 (2H, m), 7.38–7.48 (3H, m), 7.53–7.62 (4H, m).

EXAMPLE 124

Compound E124 was obtained from Compound (260) according to manners similar to Preparations 337 and 208 and Example 58 (7 mg).

$^1$H-NMR (300 MHz, DMSO-d$_6$, δ): 3.93 (2H, s), 4.18 (2H, s), 6.45 (1H, d, J=16 Hz), 7.13 (1H, s), 7.23–7.38 (7H, m), 7.43 (1H, d, J=16 Hz), 7.54 (2H, d, J=8 Hz); MASS (ES+): m/z 334 (M+1).

The compounds obtained in the above-mentioned Preparations are shown in the following Table 2 (including Tables 2-1 to 2-44) and the above-mentioned Examples are shown in the following Table 3 (including Tables 3-1 to 3-17).

TABLE 2
Compound (1)
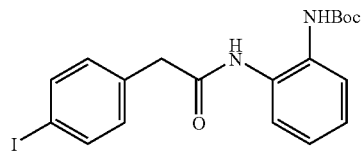
Compound (2)
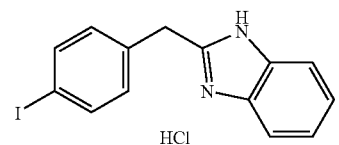
HCl
Compound (3)
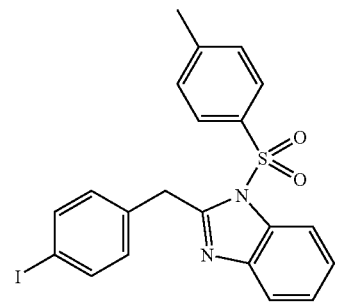
Compound (4)
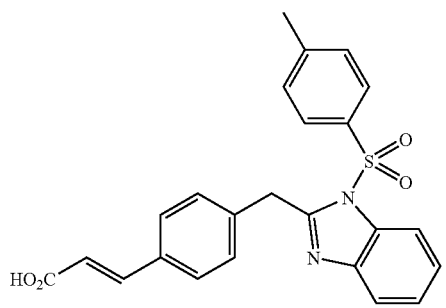
Compound (5)
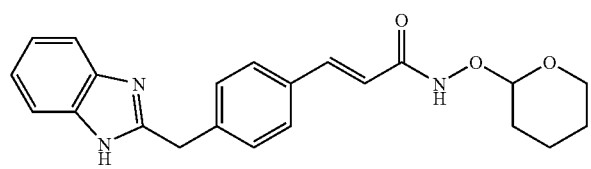
Compound (6)
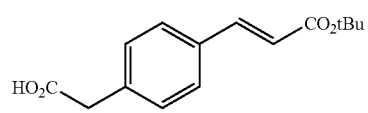

TABLE 2-continued
Compound (7)
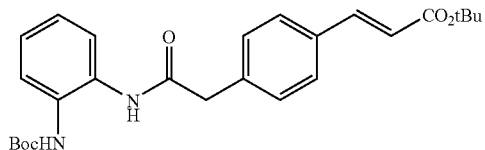
Compound (8)
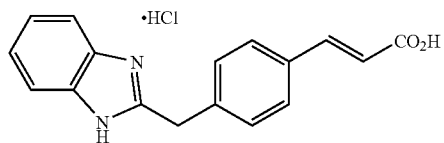
Compound (9)
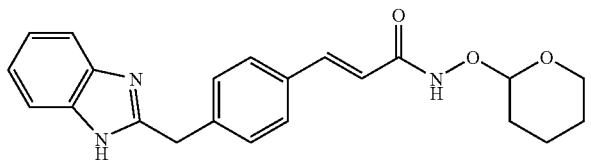
Compound (10)
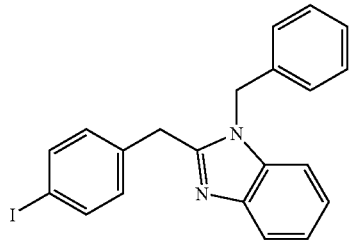  ← Compound (10)
Compound (11)
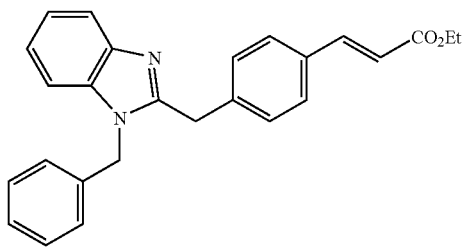
Compound (12)
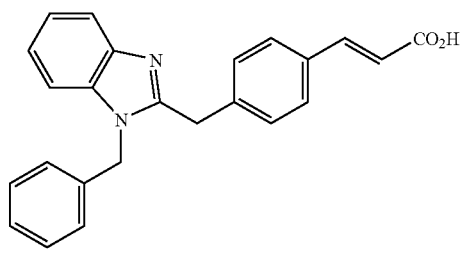

TABLE 2-continued
Compound (13)
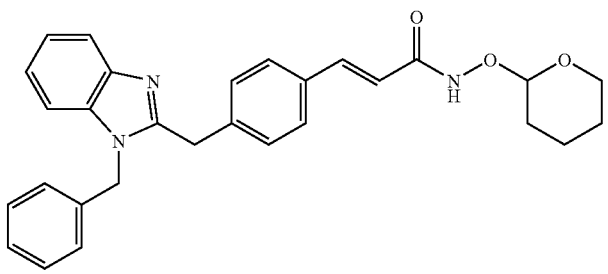
Compound (14)
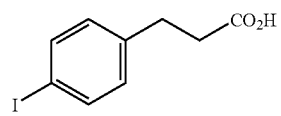
Compound (15)
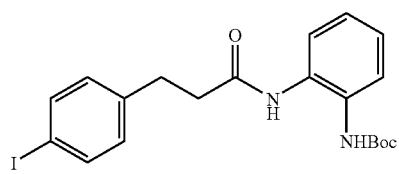
Compound (16)
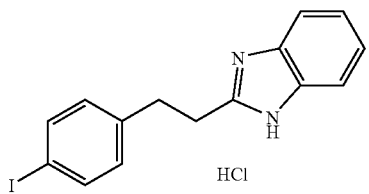
Compound (17)
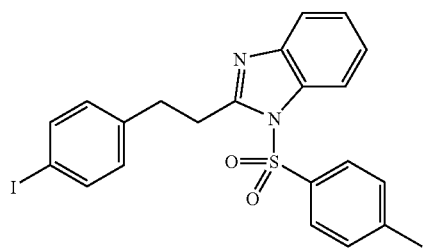
Compound (18)
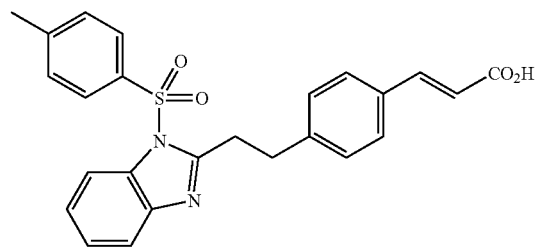

TABLE 2-continued
Compound (19)
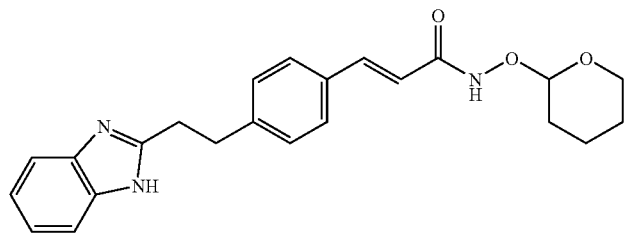
Compound (20)
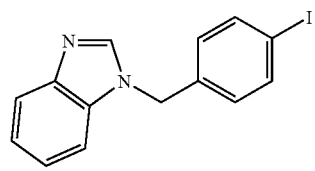
Compound (21)
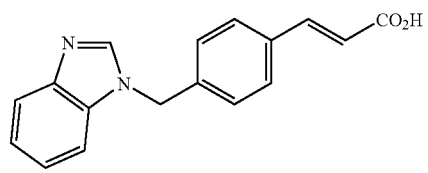
Compound (22)
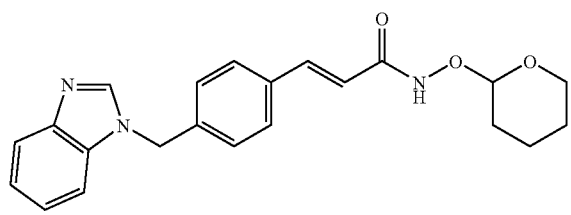
Compound (23)
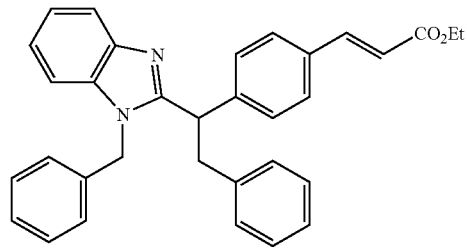
Compound (24)
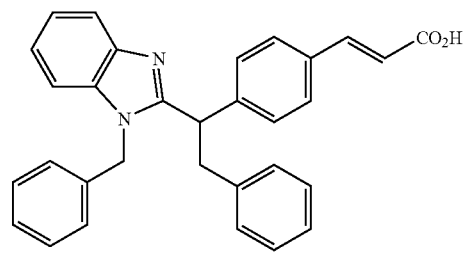

TABLE 2-continued
Compound (25)
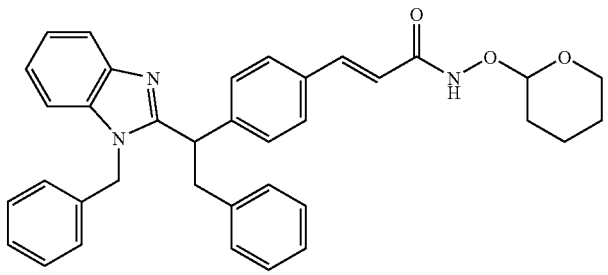
Compound (26)
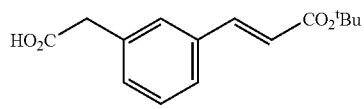
Compound (27)
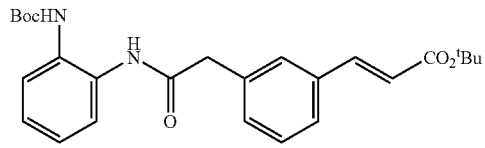
Compound (28)
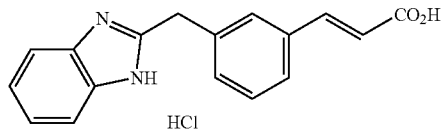
Compound (29)
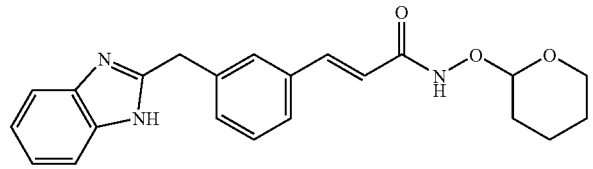
Compound (30)
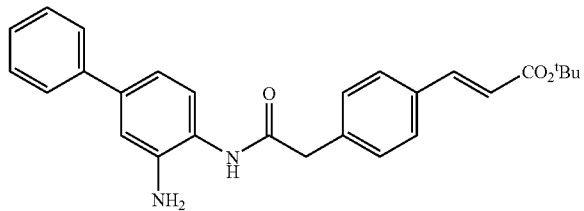

TABLE 2-continued
Compound (31)
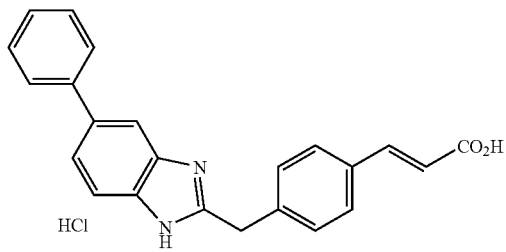
Compound (32)
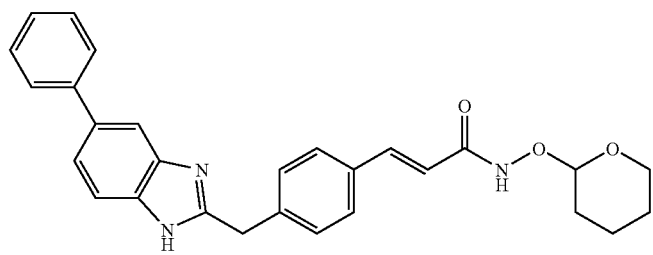
Compound (33)
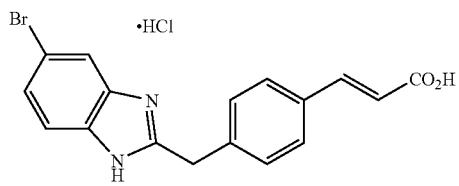
Compound (34)
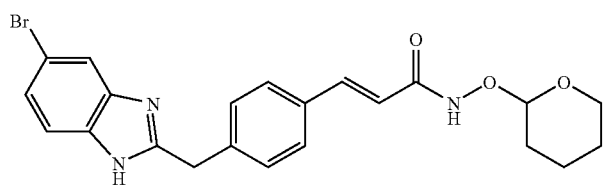
Compound (35)
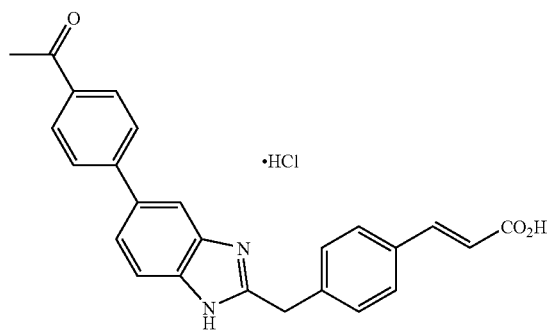

TABLE 2-continued
Compound (36)
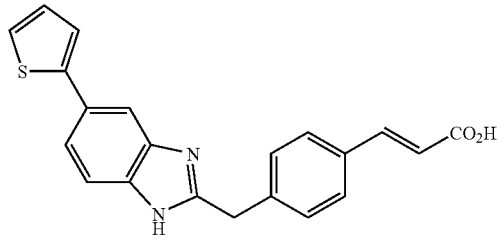
Compound (37)
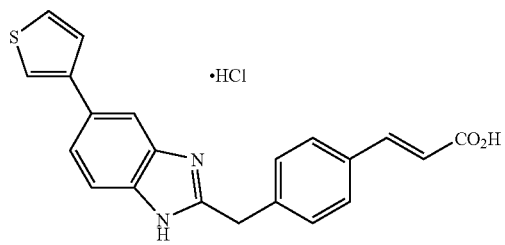
Compound (38)
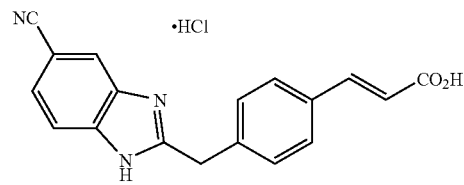
Compound (39)
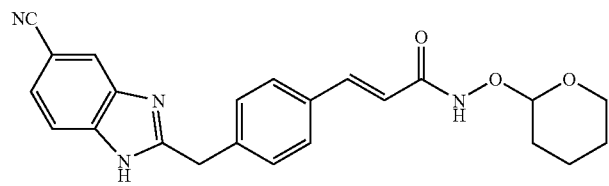
Compound (40)
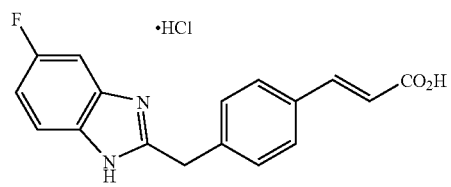
Compound (41)
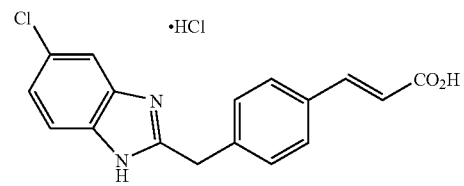

TABLE 2-continued
Compound (42)
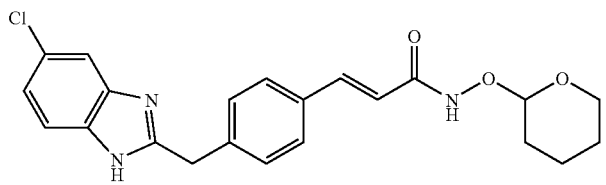
Compound (43)
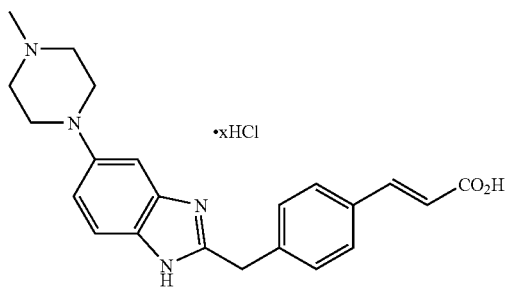
Compound (44)
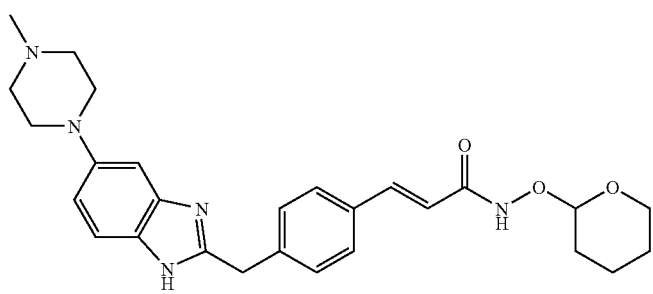
Compound (45)
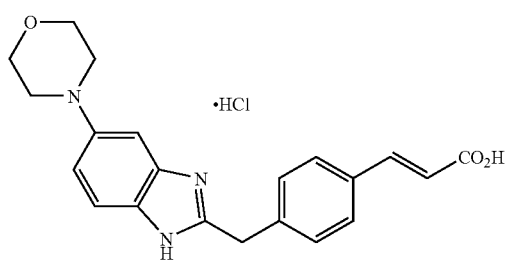
Compound (46)
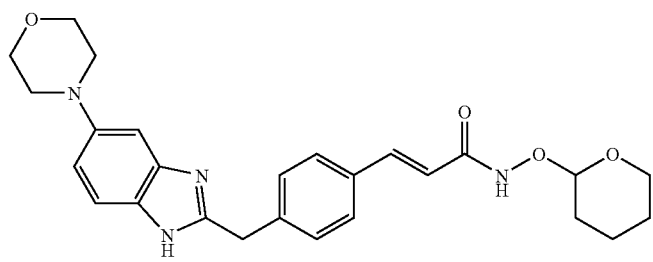

TABLE 2-continued
Compound (47)
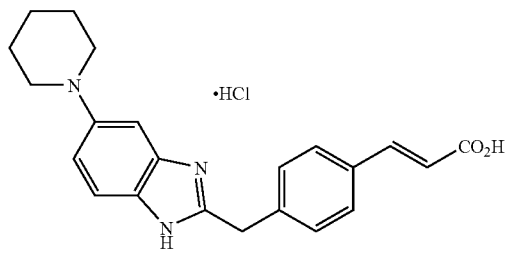
Compound (48)
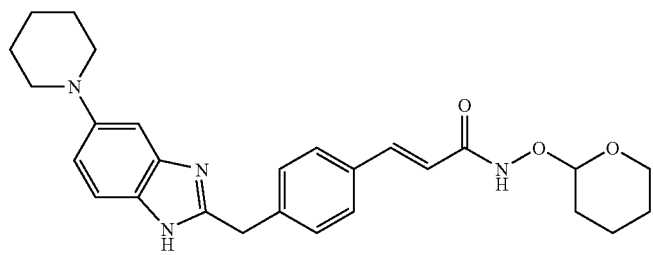
Compound (49)
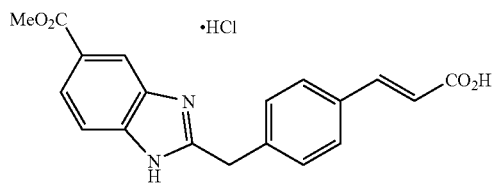
Compound (50)
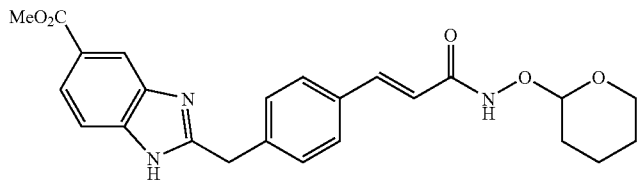
Compound (51)
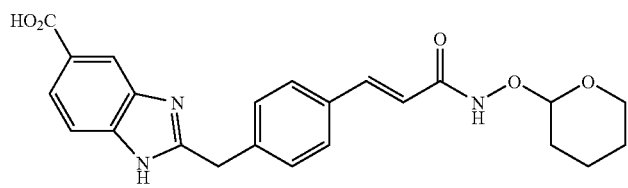

TABLE 2-continued
Compound (52)
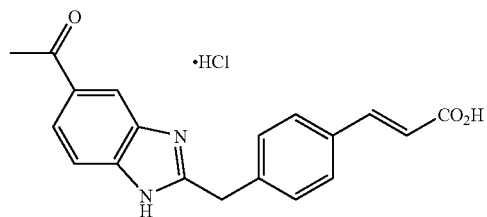
Compound (53)
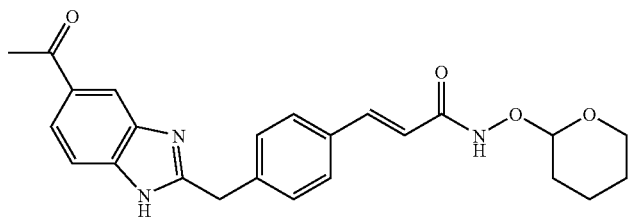
Compound (54)
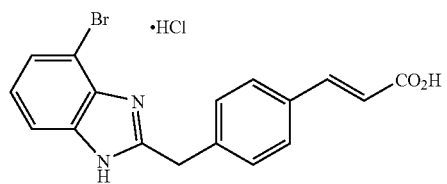
Compound (55)
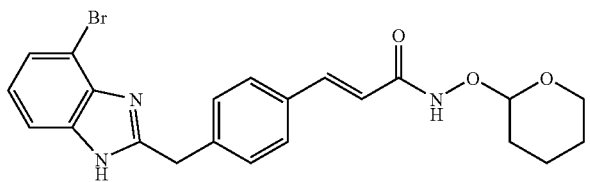
Compound (56)
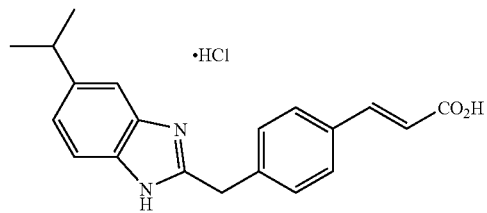
Compound (57)
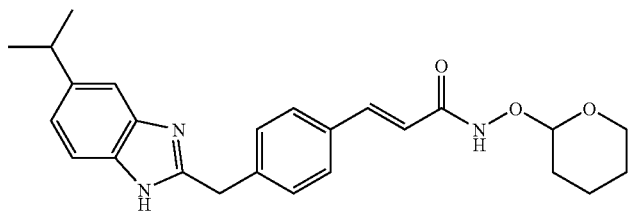

TABLE 2-continued
Compound (58)
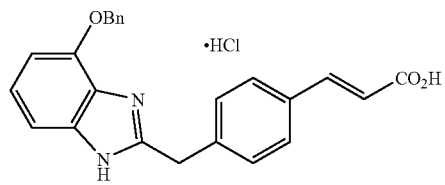
Compound (59)
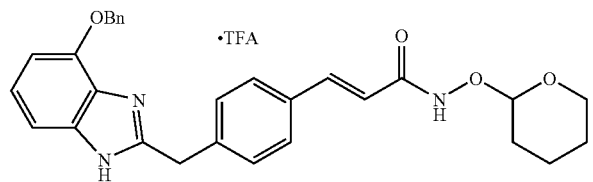
Compound (60)
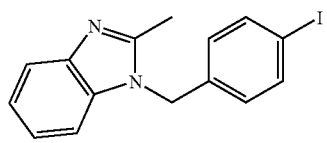
Compound (61)
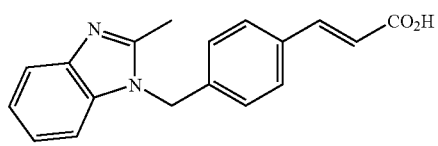
Compound (62)
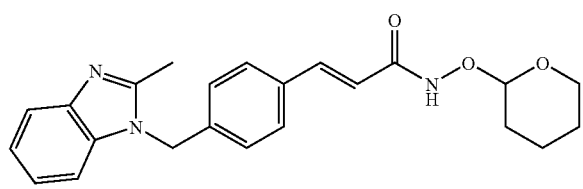
Compound (63)
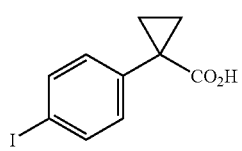
Compound (64)
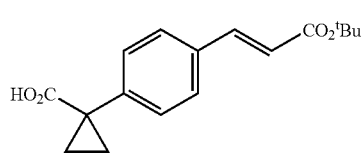

TABLE 2-continued
Compound (65)
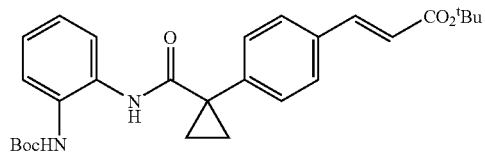
Compound (66)
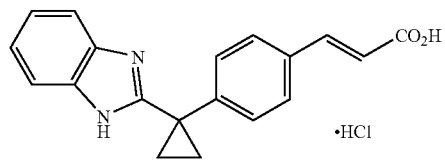
Compound (67)
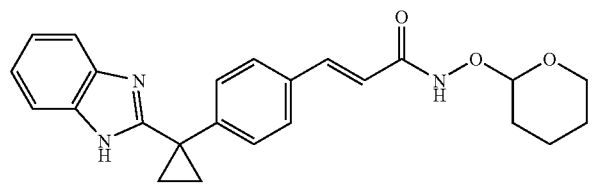
Compound (68)
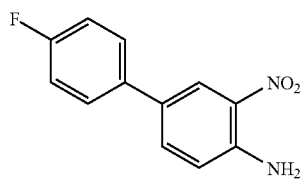
Compound (69)
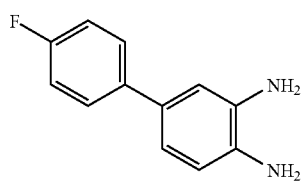
Compound (70)
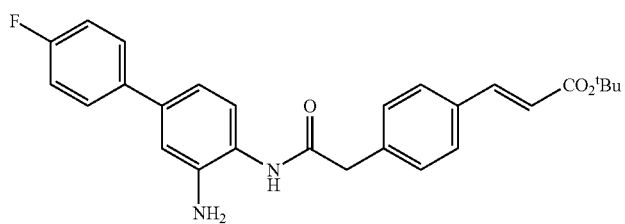

TABLE 2-continued
Compound (71)
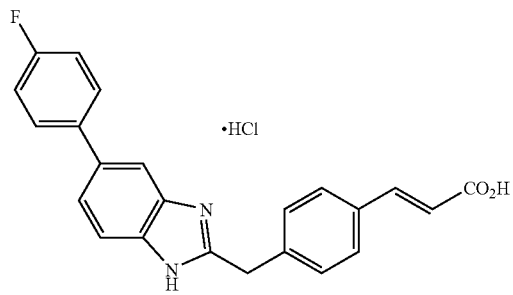
Compound (72)
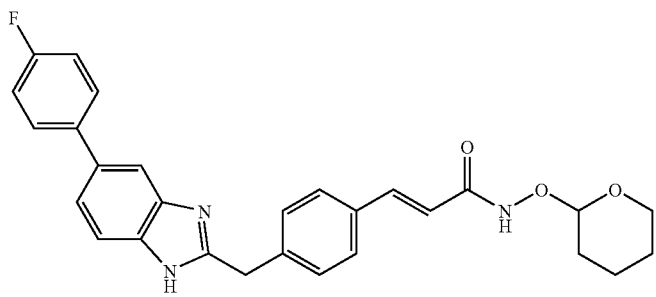
Compound (73)
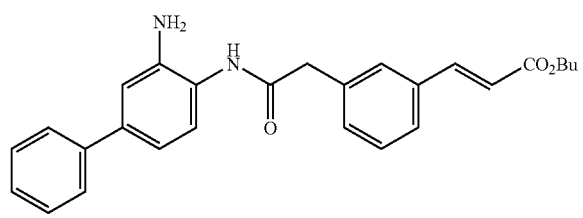
Compound (74)
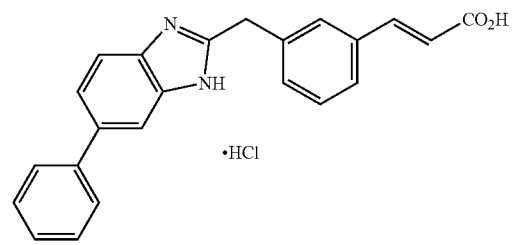
Compound (75)
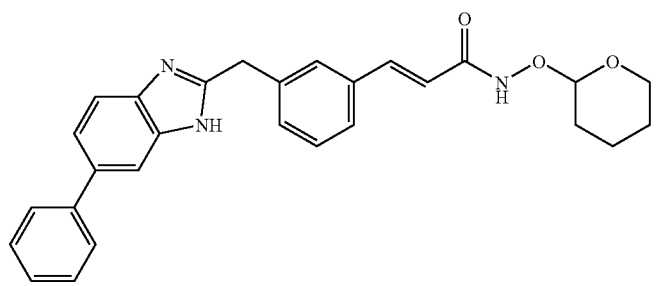

TABLE 2-continued
Compound (76)
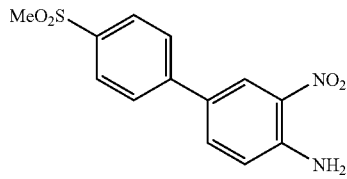
Compound (77)
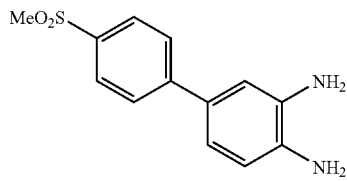
Compound (78)
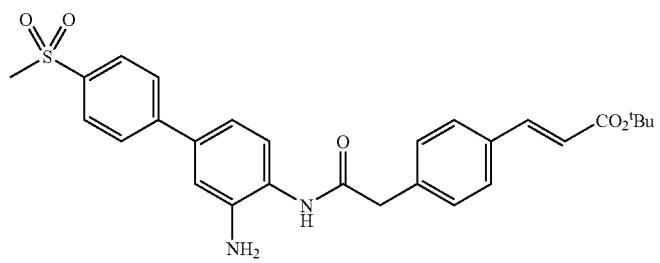
Compound (79)
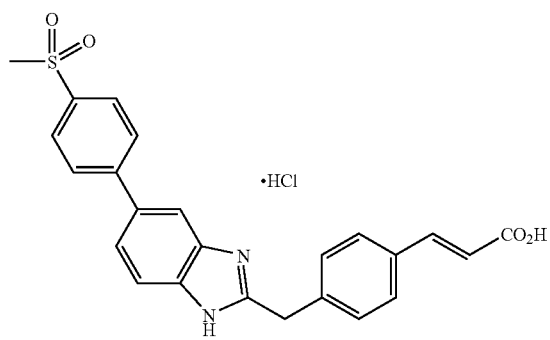
Compound (80)
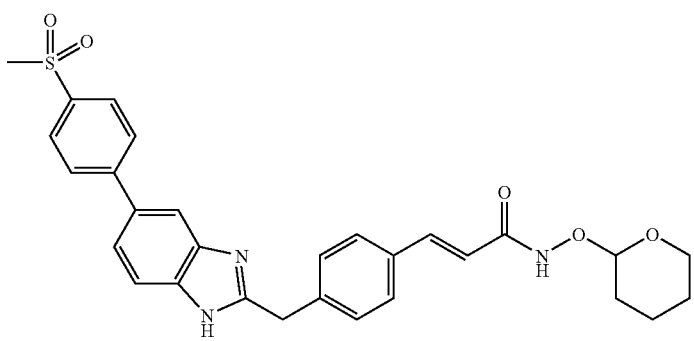

TABLE 2-continued
Compound (81)
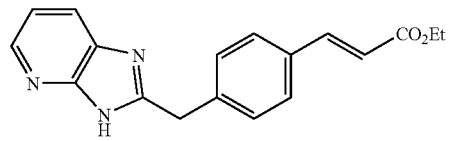
Compound (82)
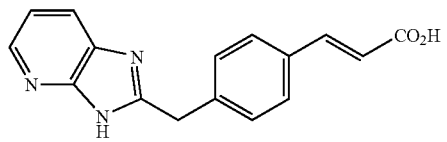
Compound (83)
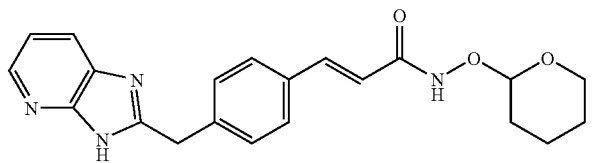
Compound (84)
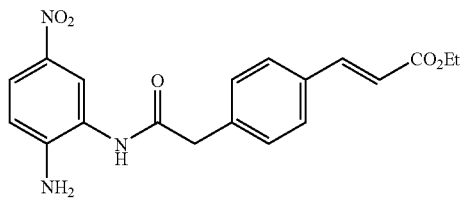
Compound (85)
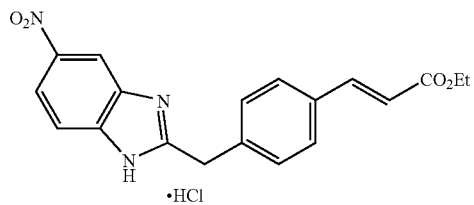
Compound (86)
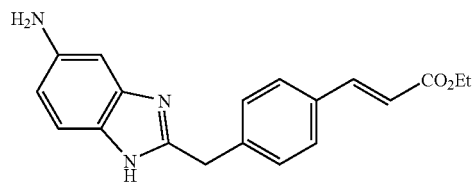

TABLE 2-continued
Compound (87)
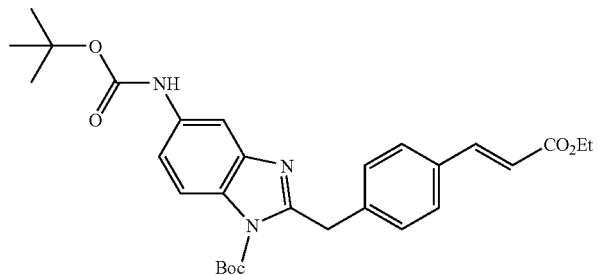
Compound (88)
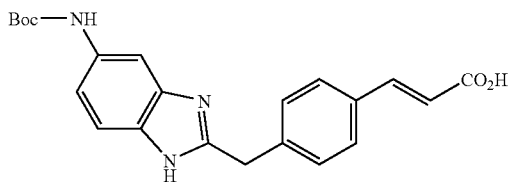
Compound (89)
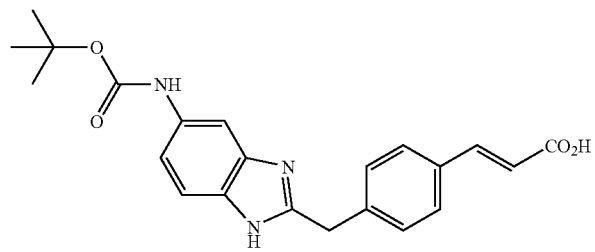
Compound (90)
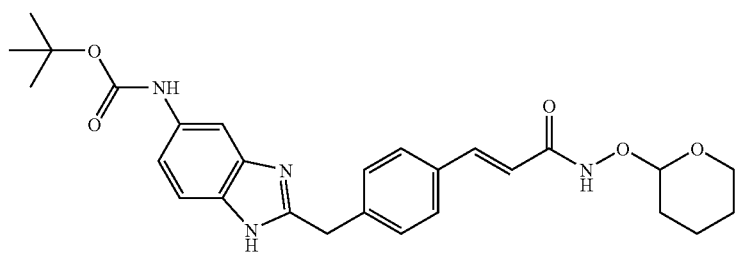
Compound (91)
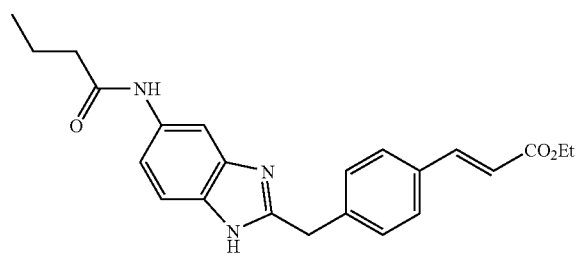

TABLE 2-continued
Compound (92)
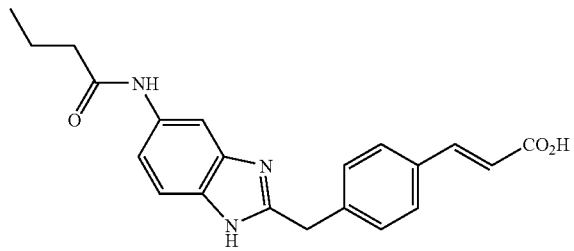
Compound (93)
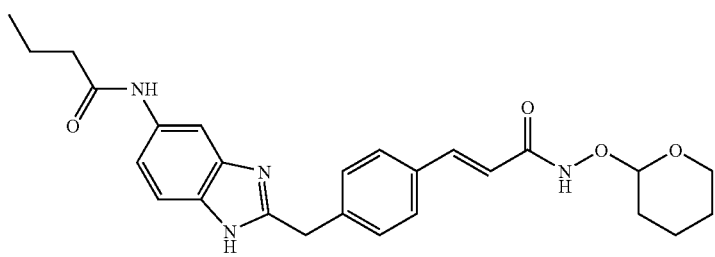
Compound (94)
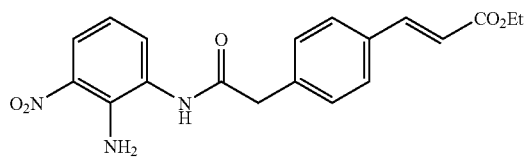
Compound (95)
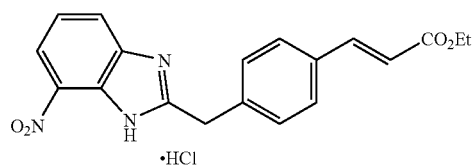
Compound (96)
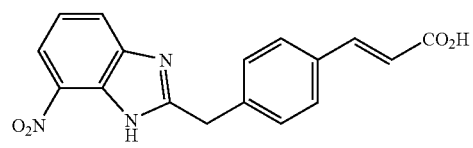
Compound (97)
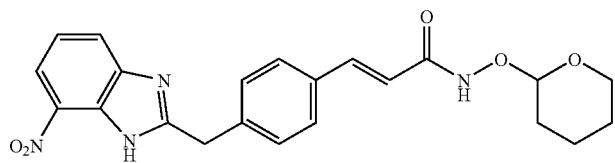

TABLE 2-continued
Compound (98)
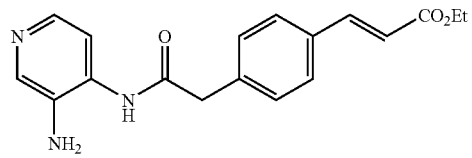
Compound (99)
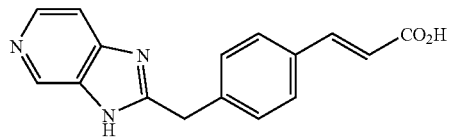
Compound (100)
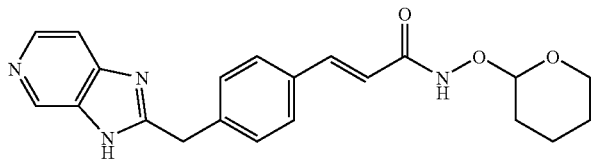
Compound (101)
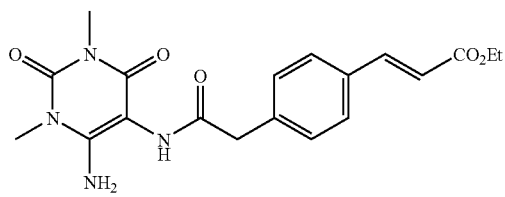
Compound (102)
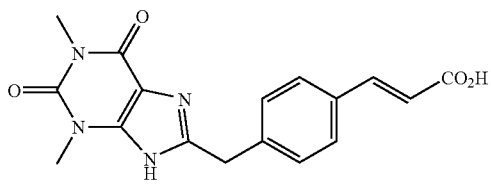
Compound (103)
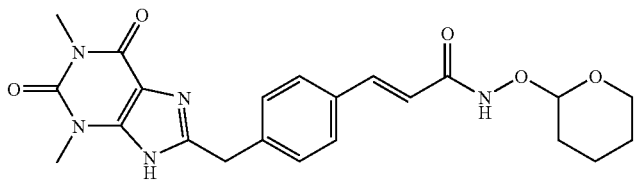
Compound (104)
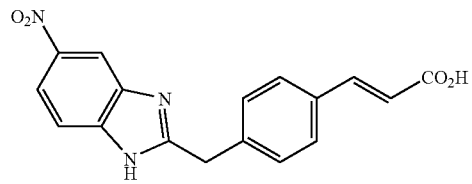

TABLE 2-continued
Compound (105)
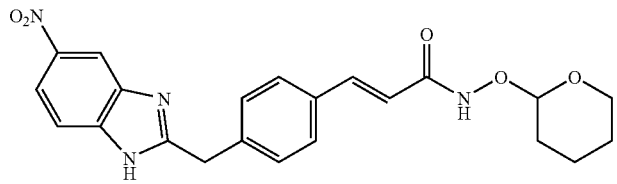
Compound (106)
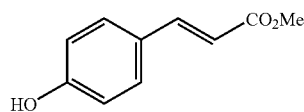
Compound (107)
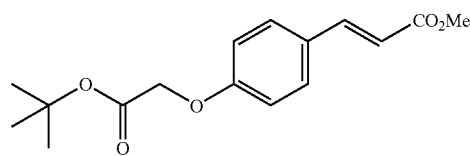
Compound (108)
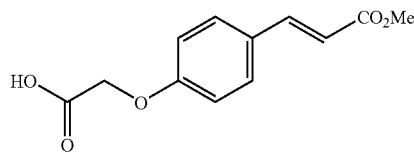
Compound (109)
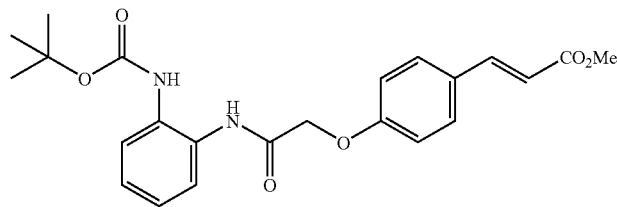
Compound (110)
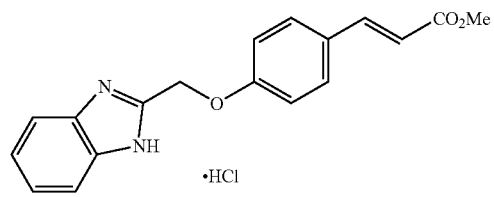
Compound (111)
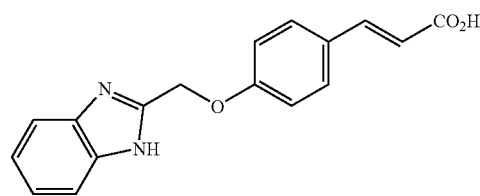

TABLE 2-continued
Compound (112)
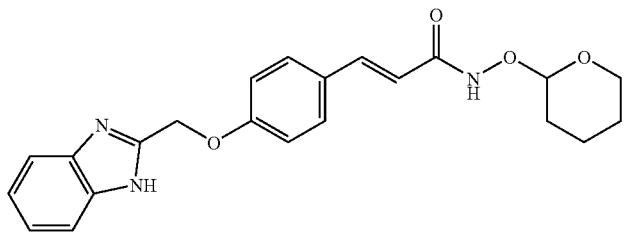
Compound (113)
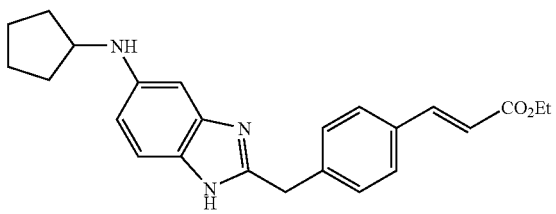
Compound (114)
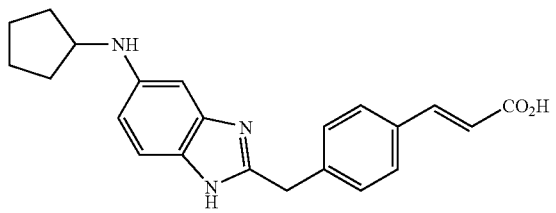
Compound (115)
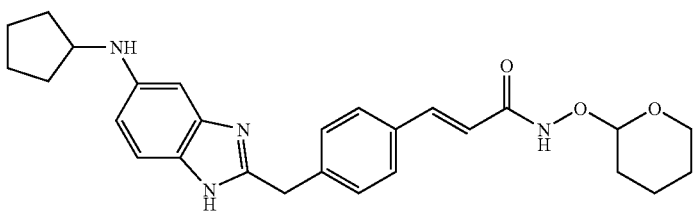
Compound (116)
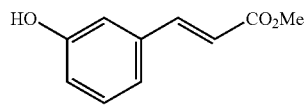
Compound (117)
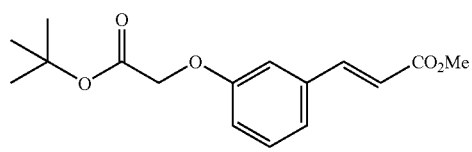

TABLE 2-continued
Compound (118)
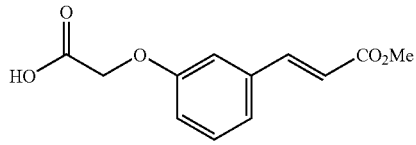
Compound (119)
Compound (120)
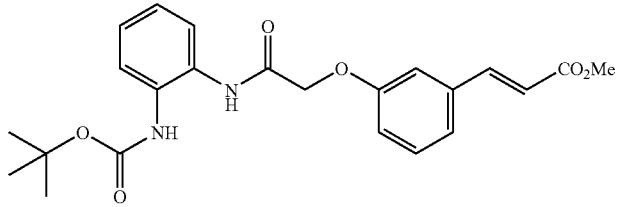
Compound (121)
Compound (122)
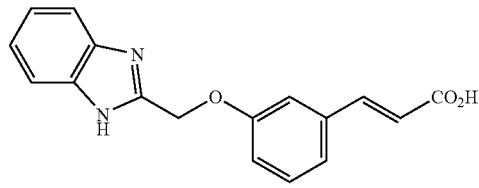
Compound (123)
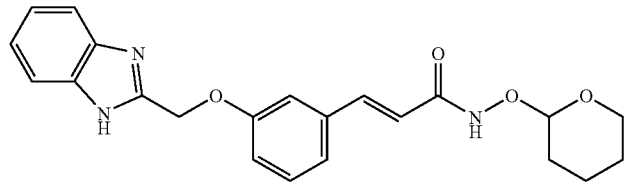
Compound (124)
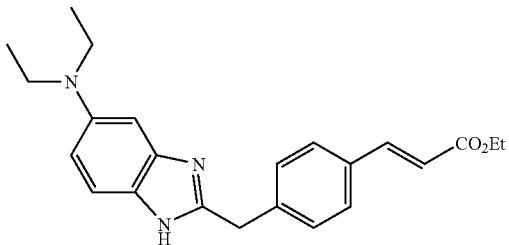
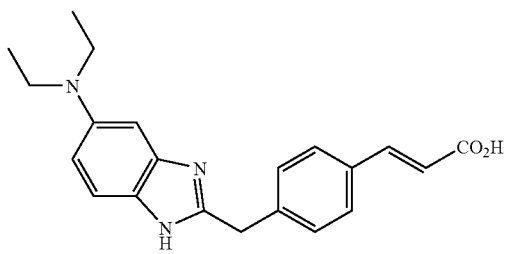

TABLE 2-continued
Compound (125)
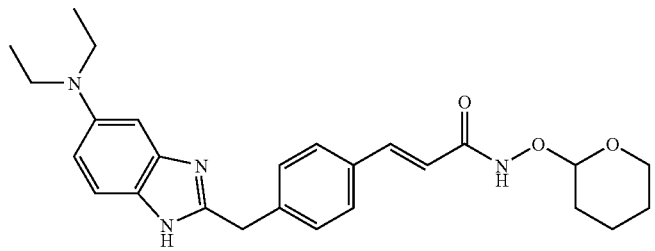
Compound (126)
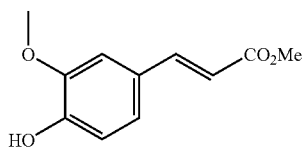
Compound (127)
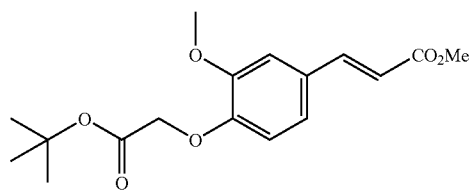
Compound (128)
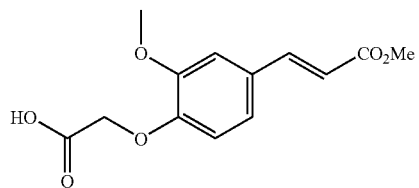
Compound (129)
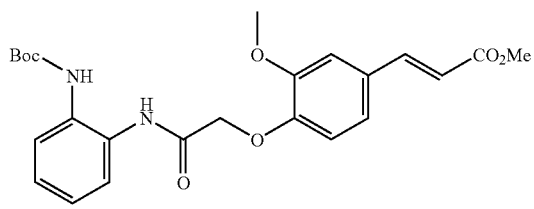
Compound (130)
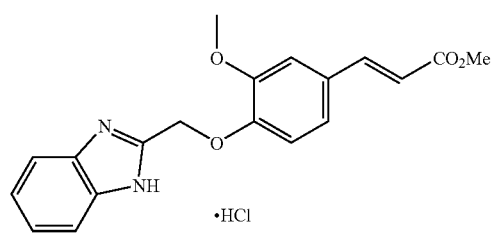

TABLE 2-continued
Compound (131)
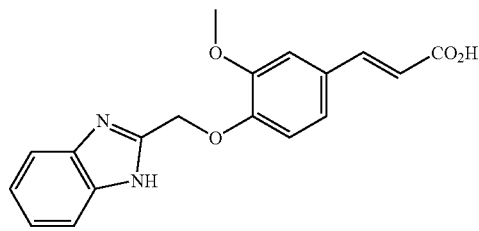
Compound (132)
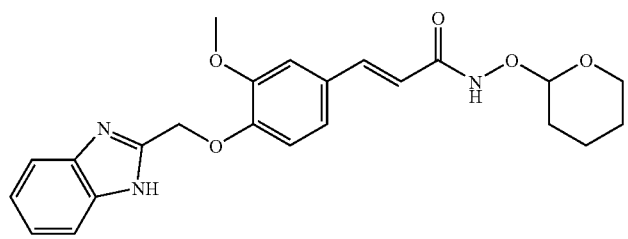
Compound (133)
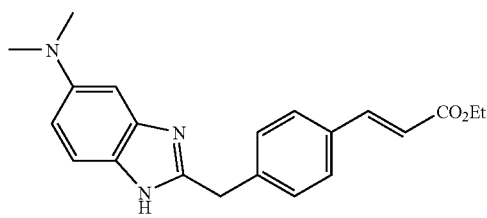
Compound (134)
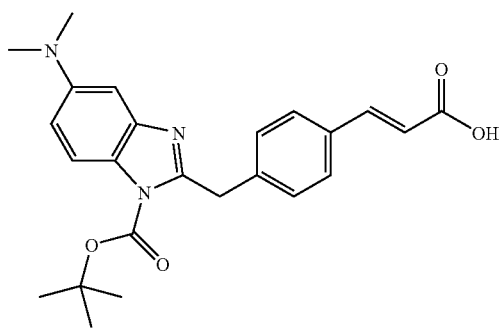
Compound (135)
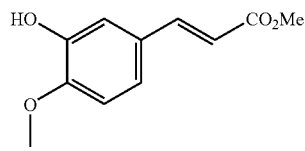

TABLE 2-continued
Compound (136)
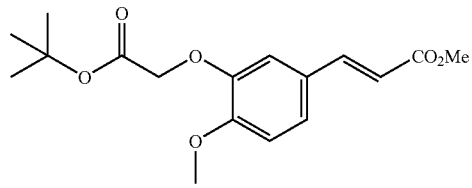
Compound (137)
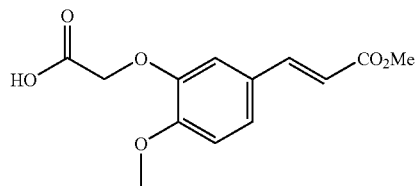
Compound (138)
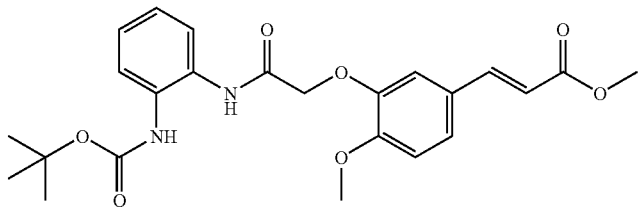
Compound (139)
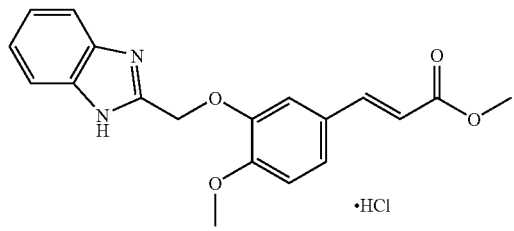
Compound (140)
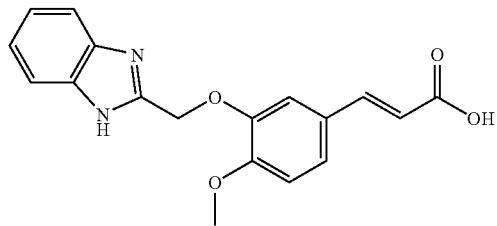
Compound (141)
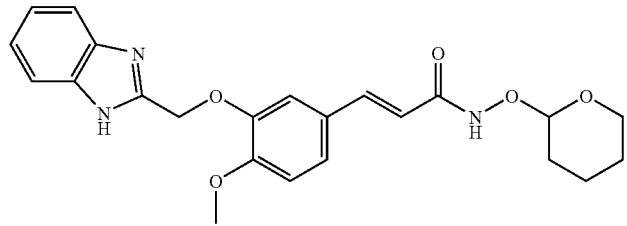

TABLE 2-continued
Compound (142)
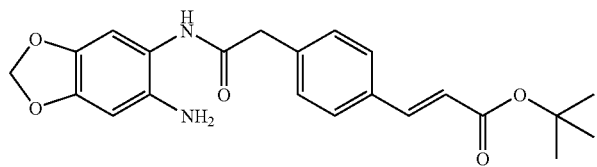
Compound (143)
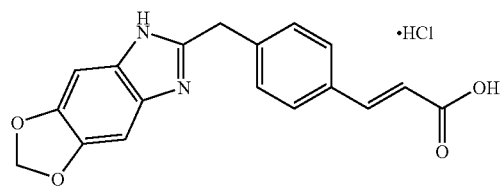
Compound (144)
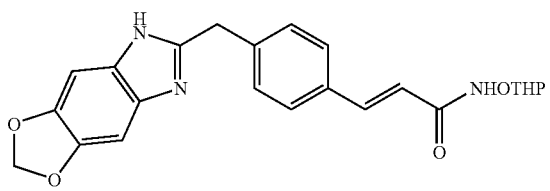
Compound (145)
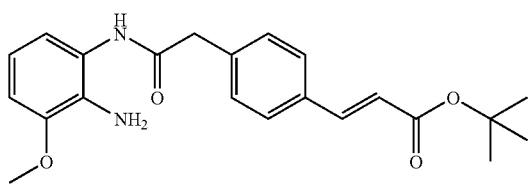
Compound (146)
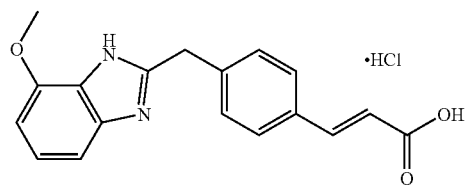
Compound (147)
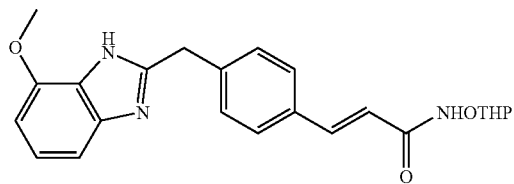

TABLE 2-continued
Compound (148)
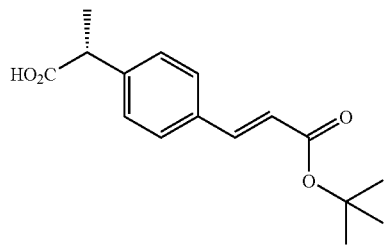
Compound (149)
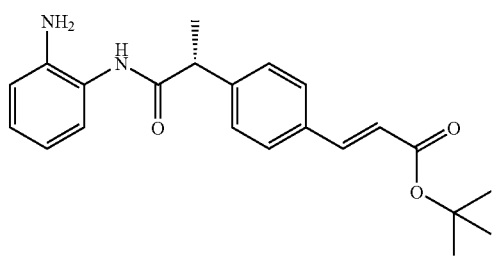
Compound (150)
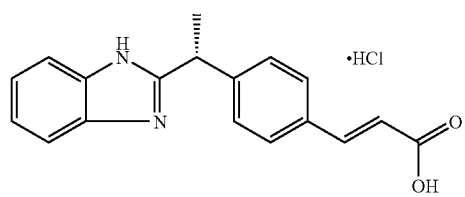
Compound (151)
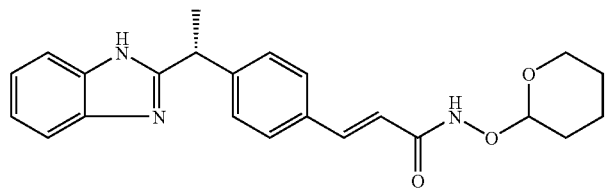
Compound (152)
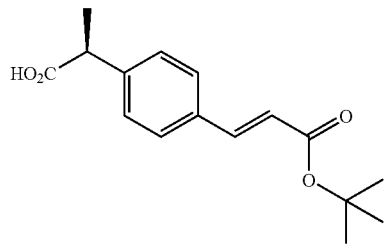

TABLE 2-continued
Compound (153)
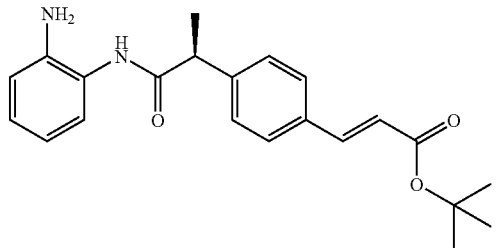
Compound (154)
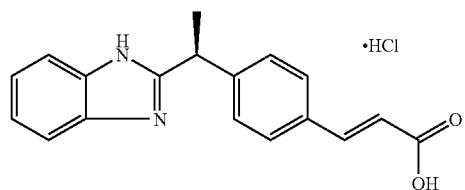
Compound (155)
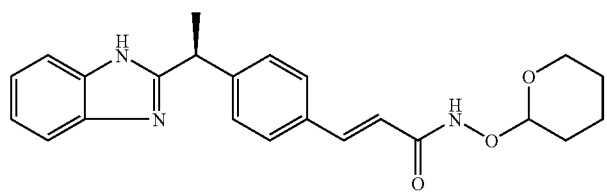
Compound (156)
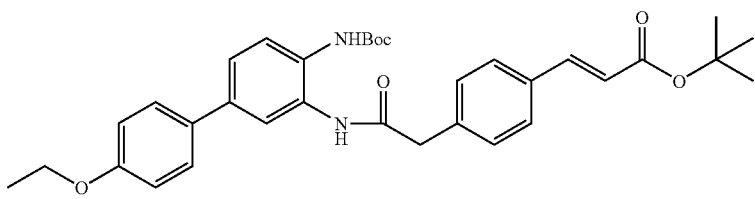
Compound (157)
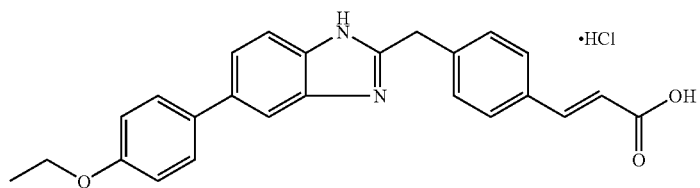
Compound (158)
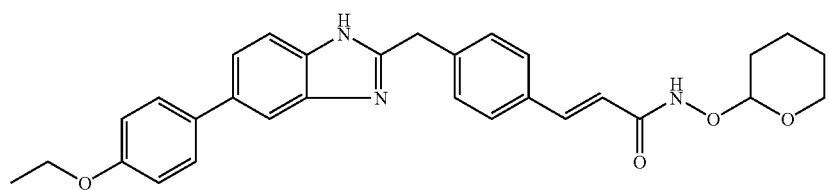

TABLE 2-continued
Compound (159)
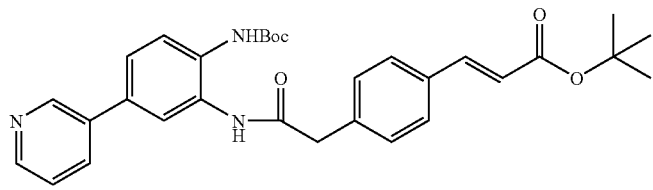
Compound (160)
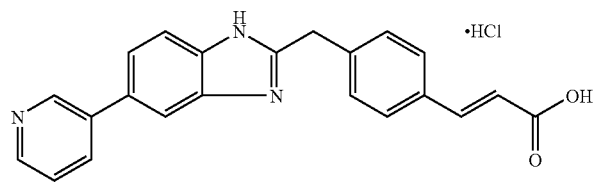
Compound (161)
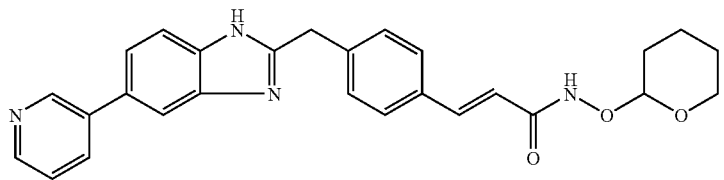
Compound (162)
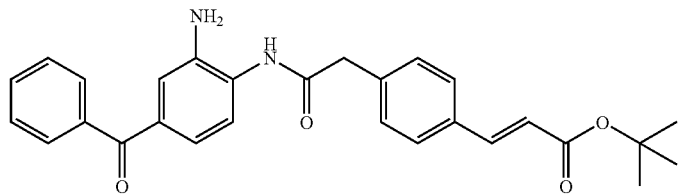
Compound (163)
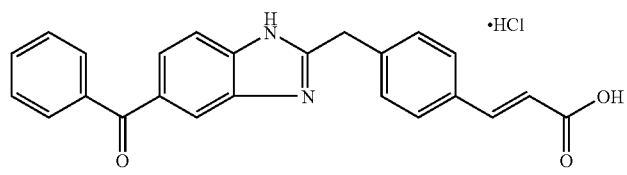
Compound (164)
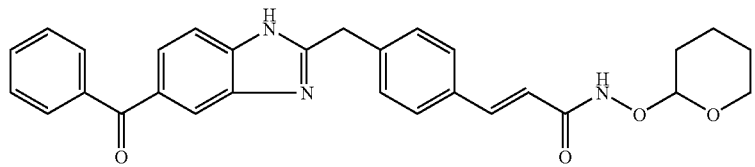

TABLE 2-continued
Compound (165)
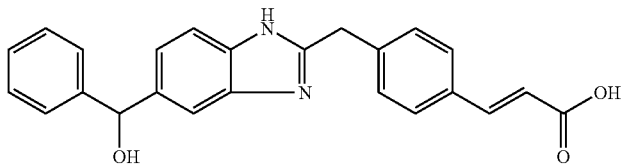
Compound (166)
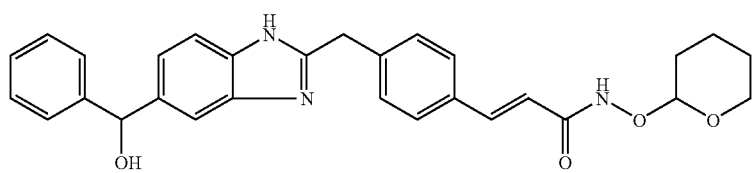
Compound (167)
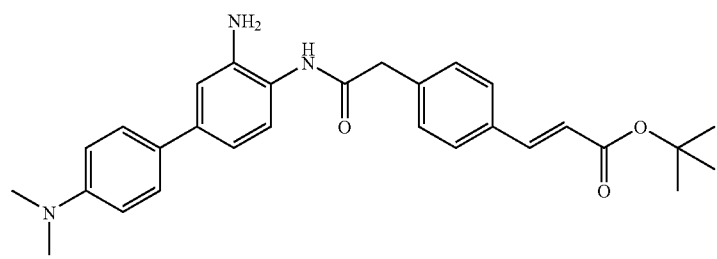
Compound (168)
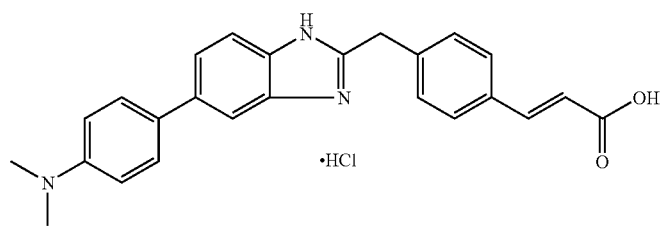
Compound (169)
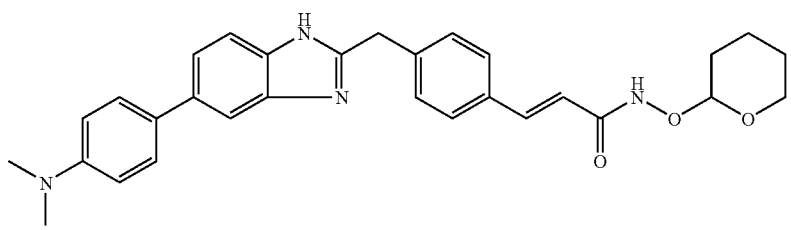
Compound (170)
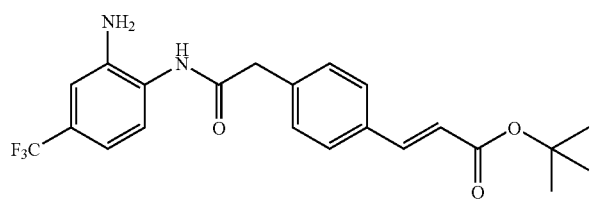

TABLE 2-continued
Compound (171)
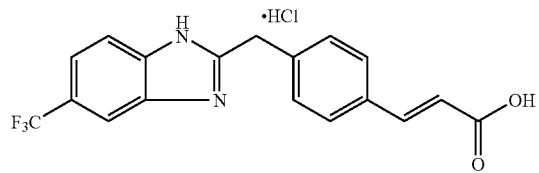
Compound (172)
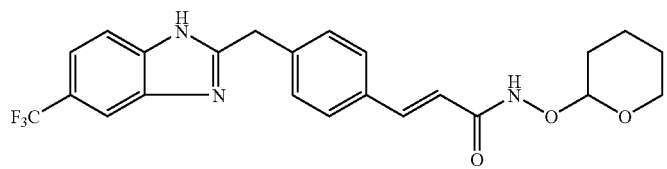
Compound (173)
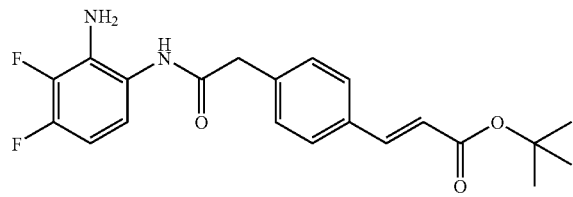
Compound (174)
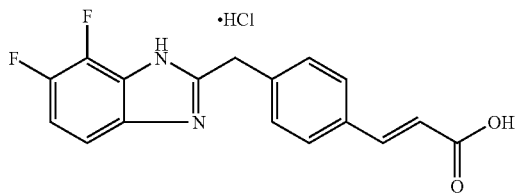
Compound (175)
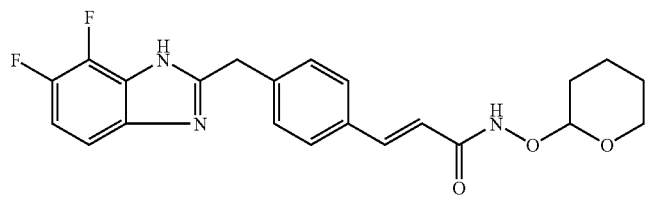
Compound (176)
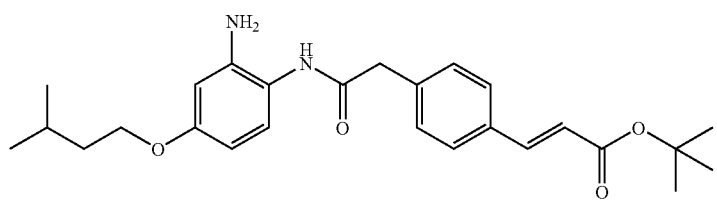

TABLE 2-continued
Compound (177)
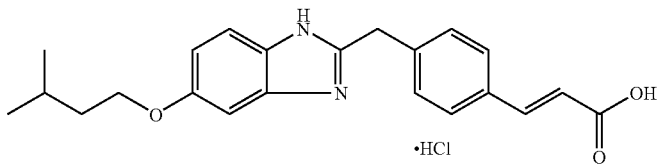
Compound (178)
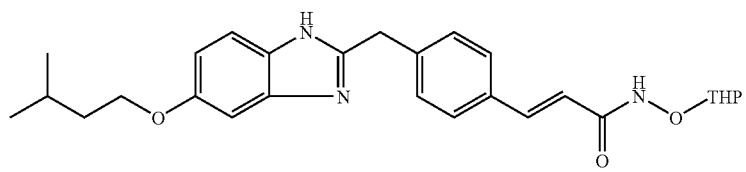
Compound (179)
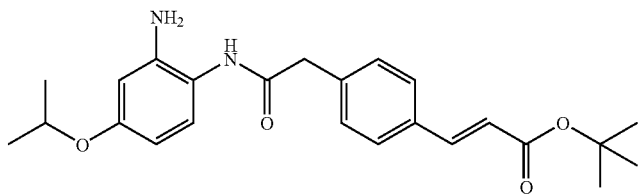
Compound (180)
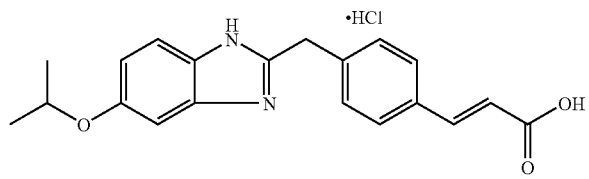
Compound (181)
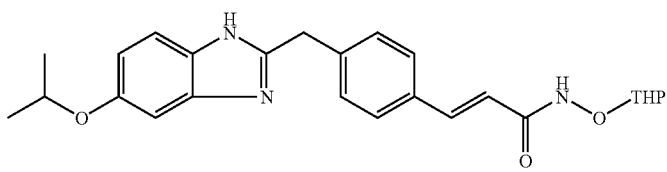
Compound (182)
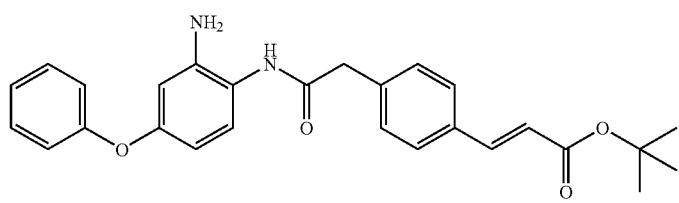
Compound (183)
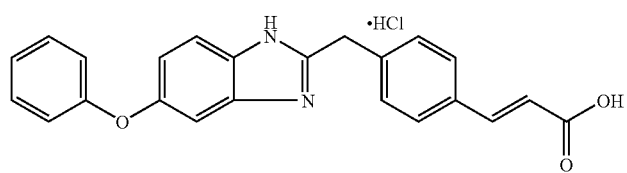

TABLE 2-continued
Compound (184)
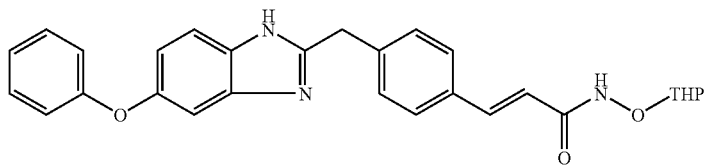
Compound (185)
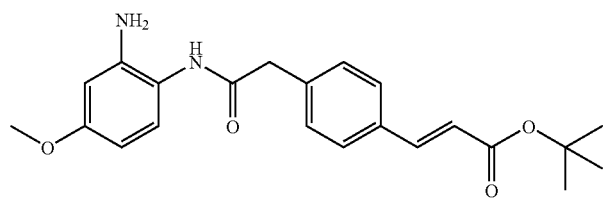
Compound (186)
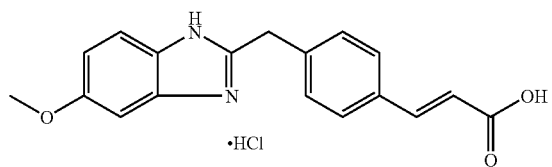
Compound (187)
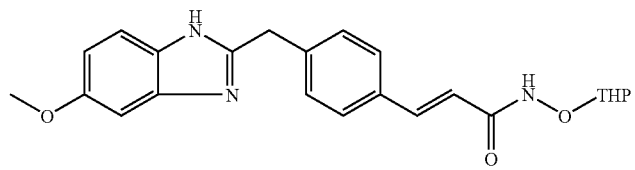
Compound (188)
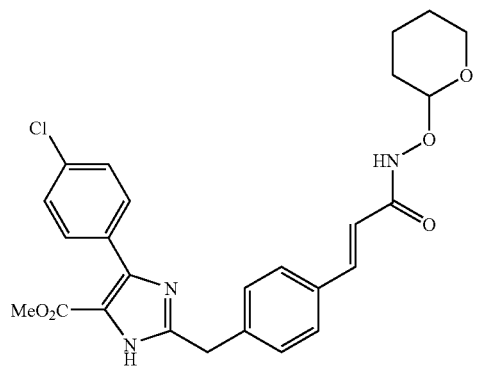

TABLE 2-continued
Compound (189)
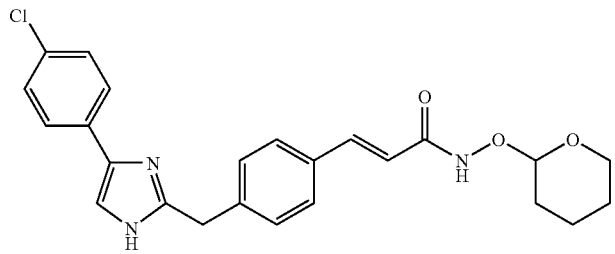
Compound (190)
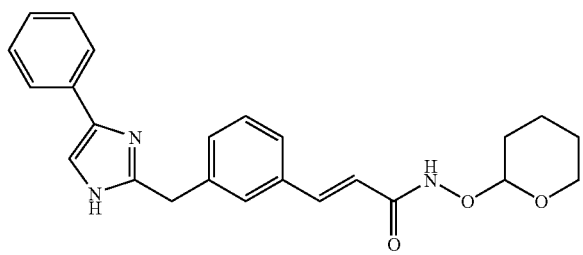
Compound (191)
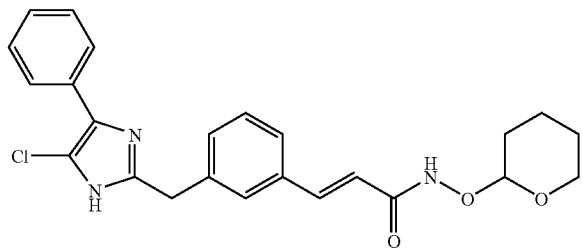
Compound (192)
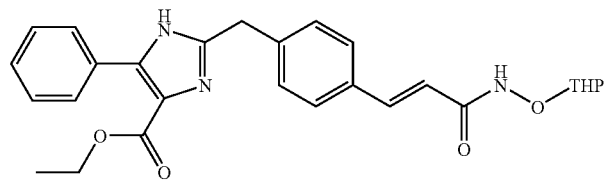
Compound (193)
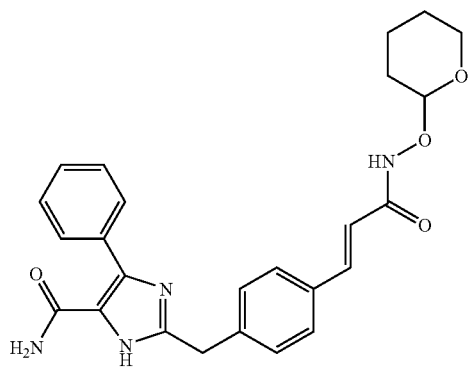

TABLE 2-continued
Compound (194)
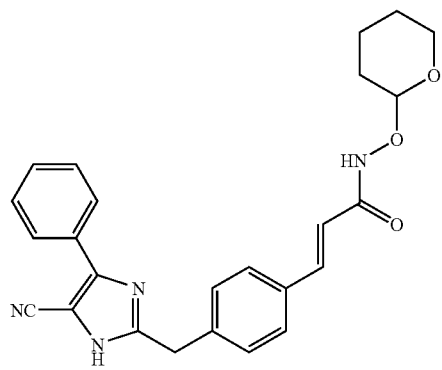
Compound (195)
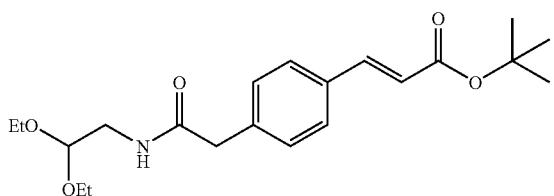
Compound (196)
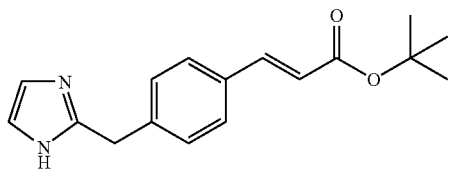
Compound (197)
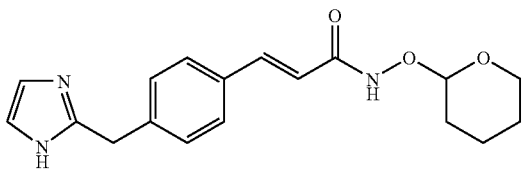
Compound (198)
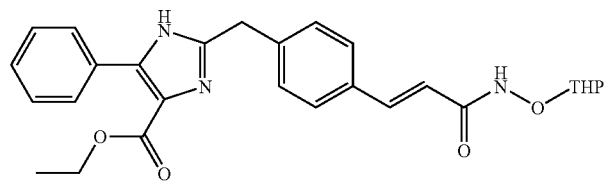

TABLE 2-continued
Compound (199)
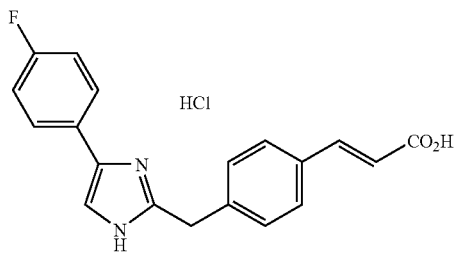
Compound (200)
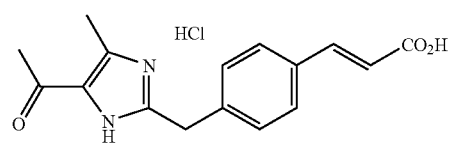
Compound (201)
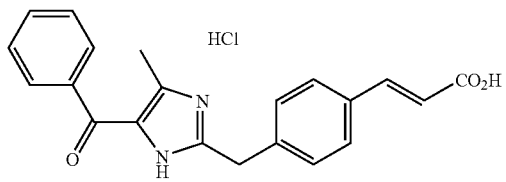
Compound (202)
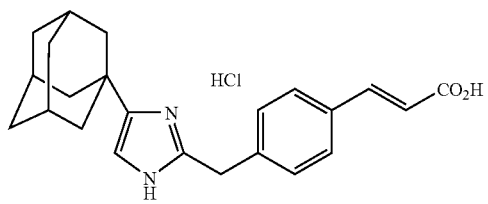
Compound (203)
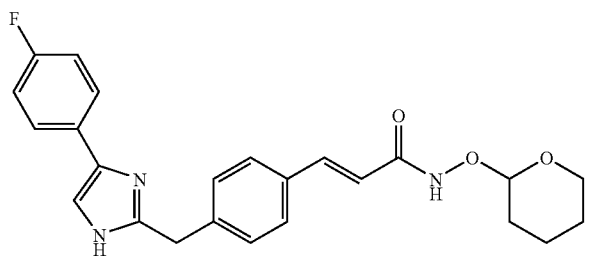
Compound (204)
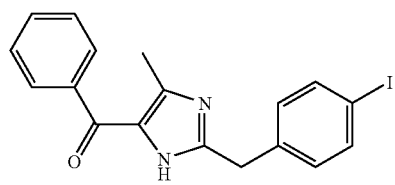

TABLE 2-continued
Compound (205)
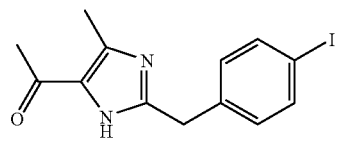
Compound (206)
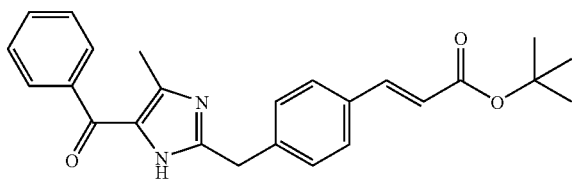
Compound (207)
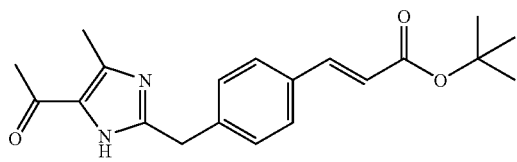
Compound (208)
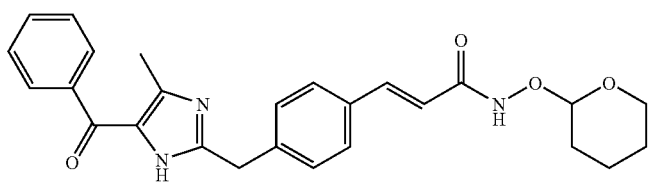
Compound (209)
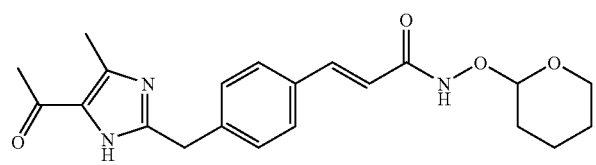
Compound (210)
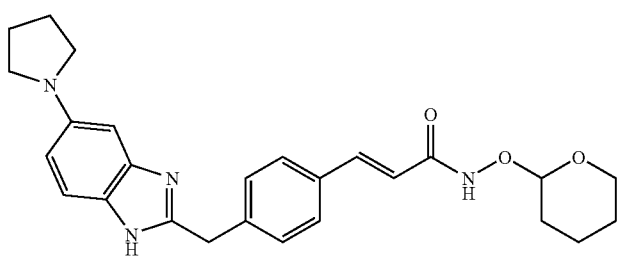
Compound (211)
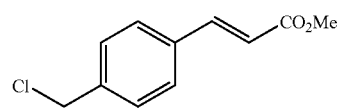

TABLE 2-continued
Compound (212)
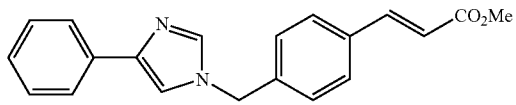
Compound (213)
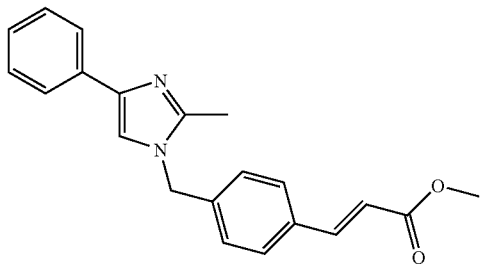
Compound (214)
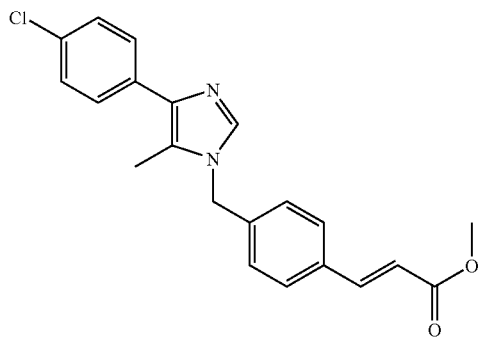
Compound (215)
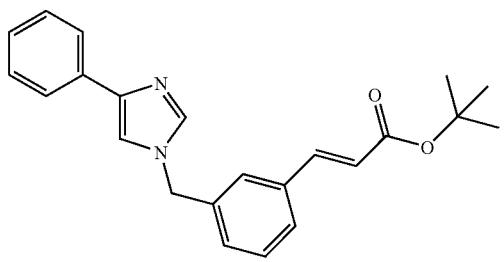
Compound (216)
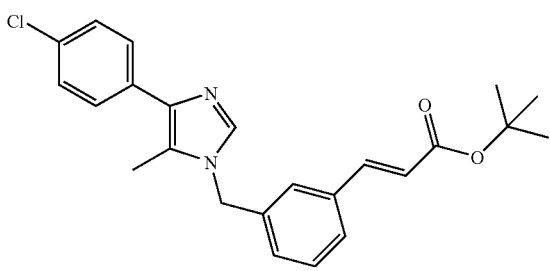

TABLE 2-continued
Compound (217)
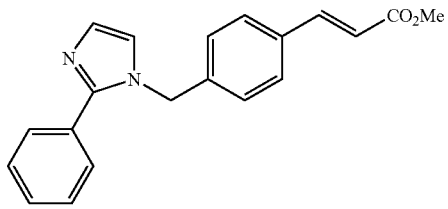
Compound (218)
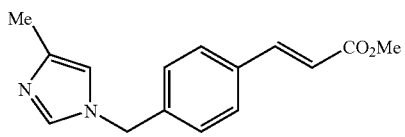
(Main product)
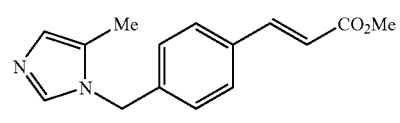
(By-product)
Compound (219)
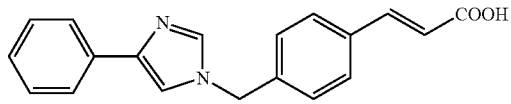
Compound (220)
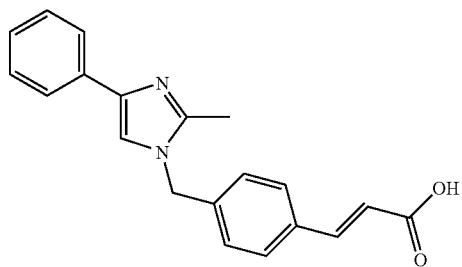
Compound (221)
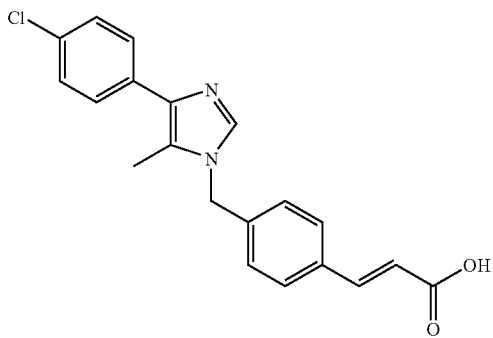

TABLE 2-continued
Compound (222)
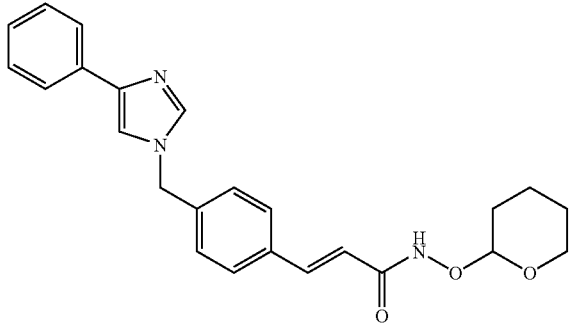
Compound (223)
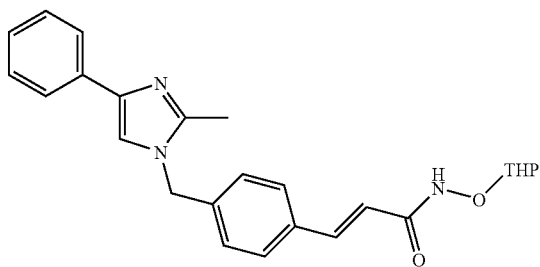
Compound (224)
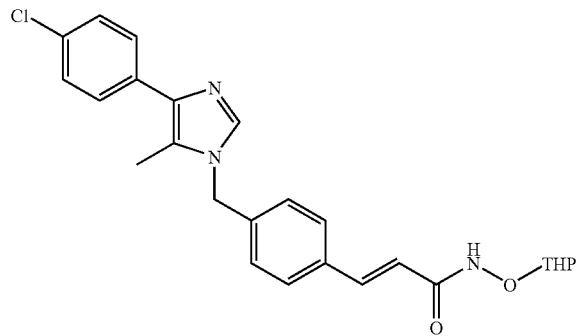
Compound (225)
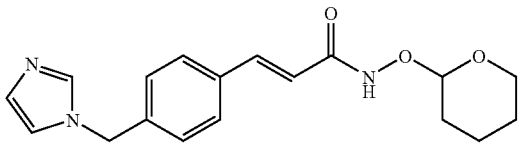
Compound (226)
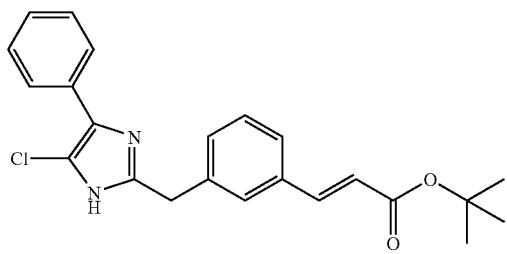

TABLE 2-continued
Compound (227)
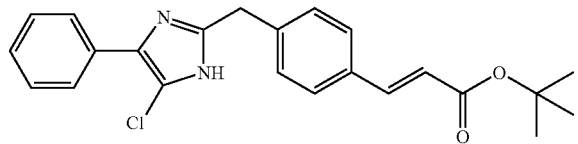
Compound (228)
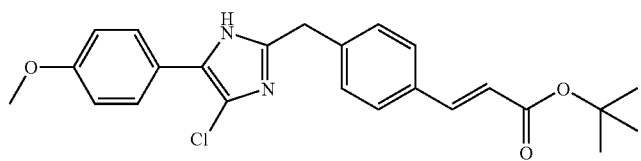
Compound (229)
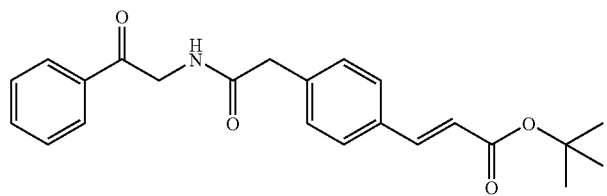
Compound (230)
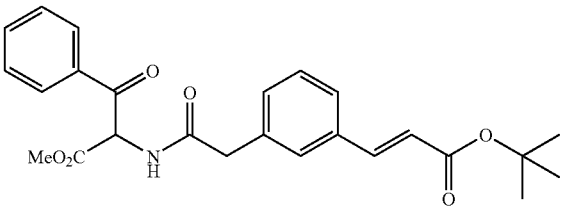
Compound (231)
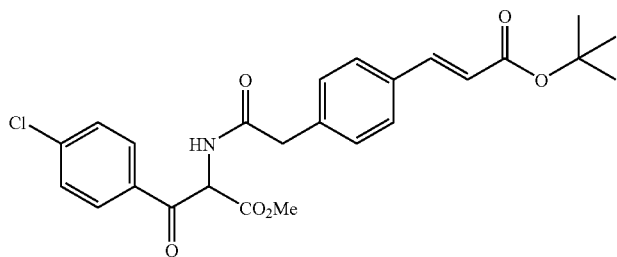
Compound (232)
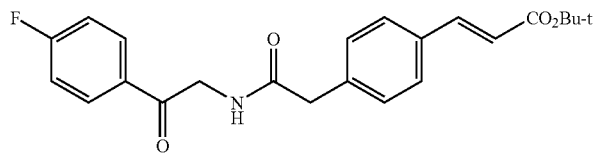

TABLE 2-continued
Compound (233)
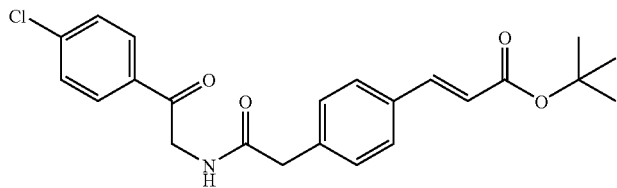
Compound (234)
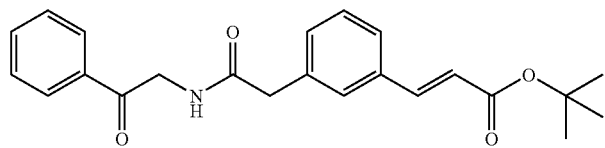
Compound (235)
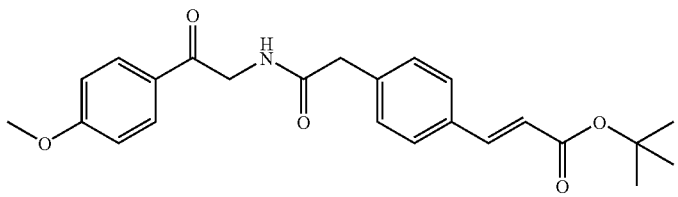
Compound (236)
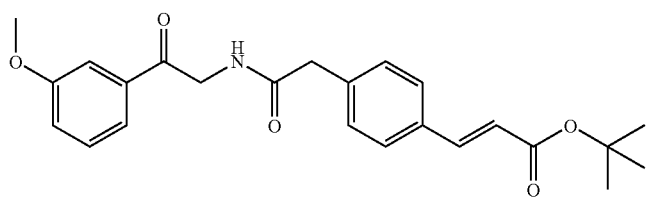
Compound (237)
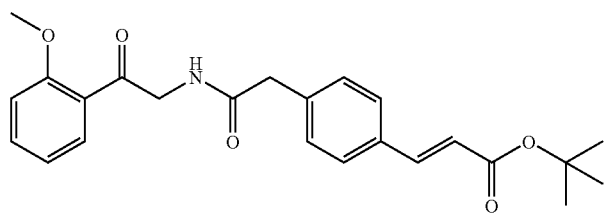
Compound (238)
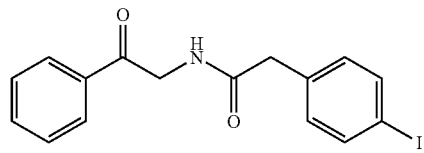

TABLE 2-continued
Compound (239)
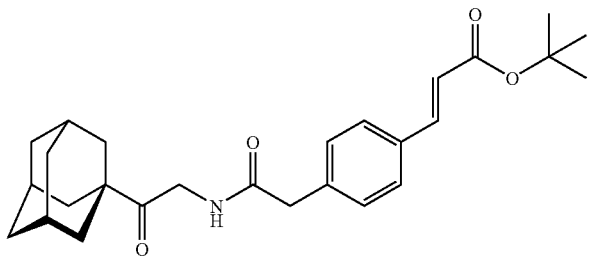
Compound (240)
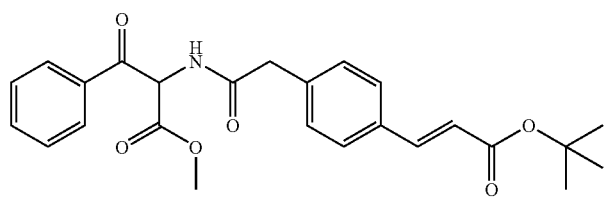
Compound (241)
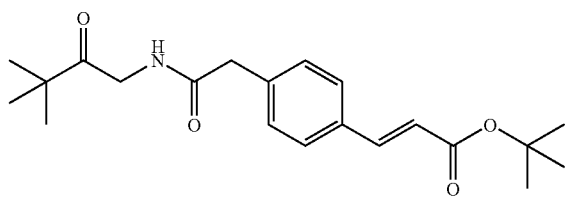
Compound (242)
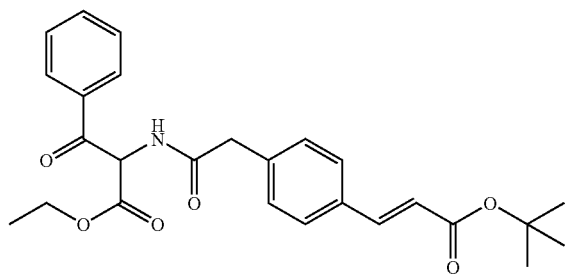
Compound (243)
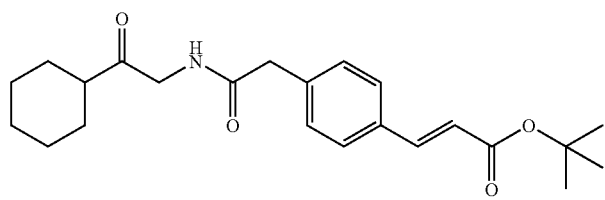
Compound (244)
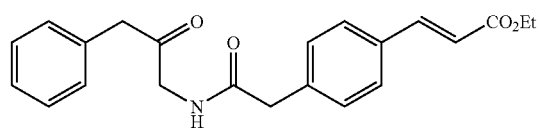

TABLE 2-continued
Compound (245)
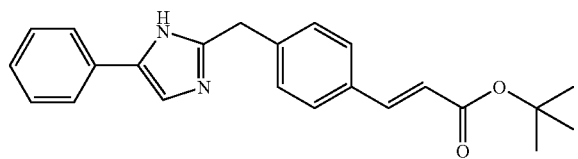
Compound (246)
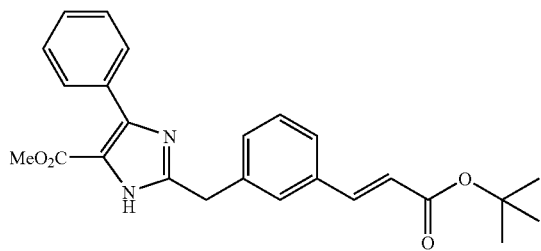
Compound (247)
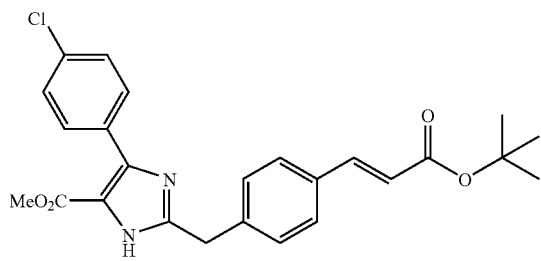
Compound (248)
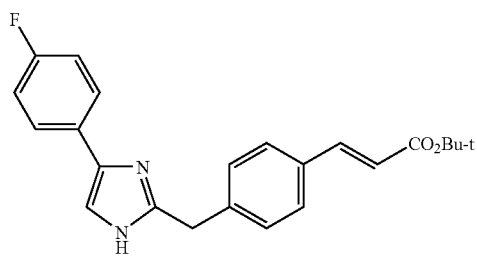
Compound (249)
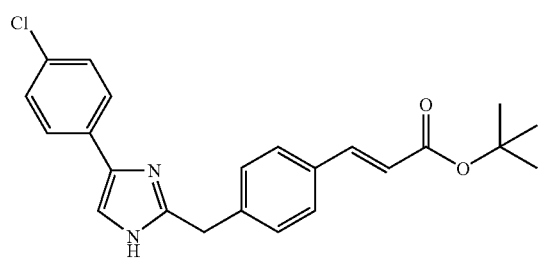

TABLE 2-continued
Compound (250)
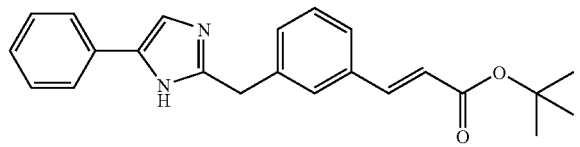
Compound (251)
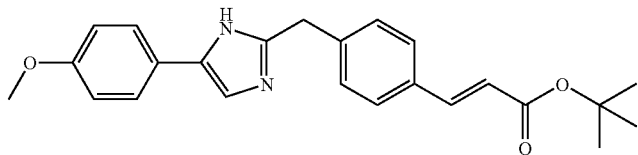
Compound (252)
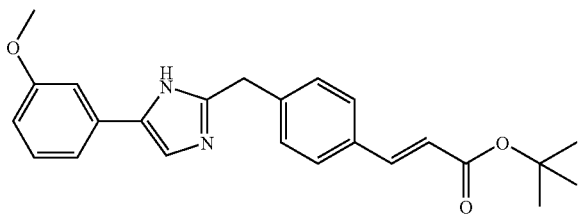
Compound (253)
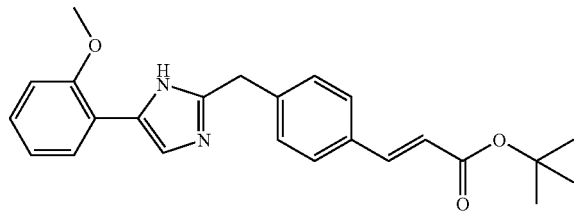
Compound (254)
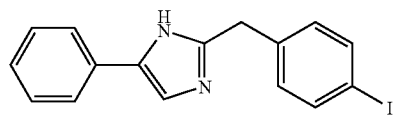
Compound (255)
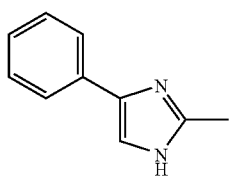
Compound (256)
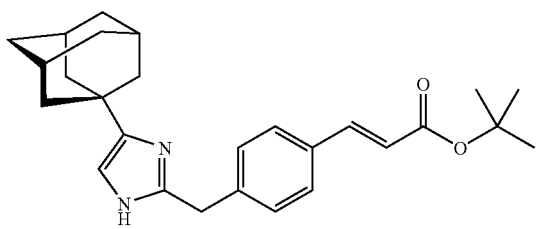

TABLE 2-continued
Compound (257)
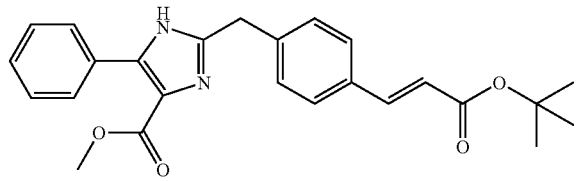
Compound (258)
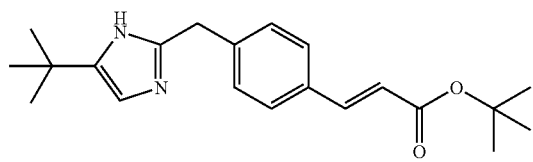
Compound (259)
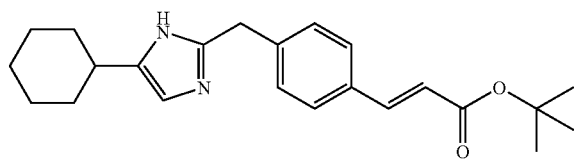
Compound (260)
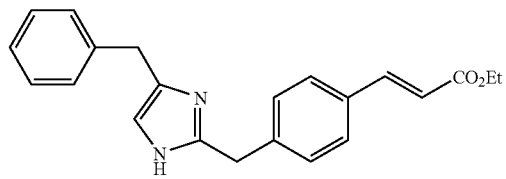
Compound (261)
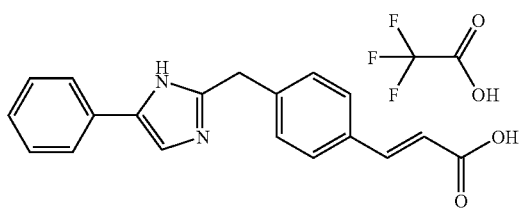
Compound (262)
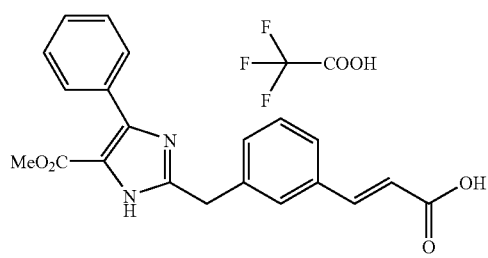

TABLE 2-continued
Compound (263)
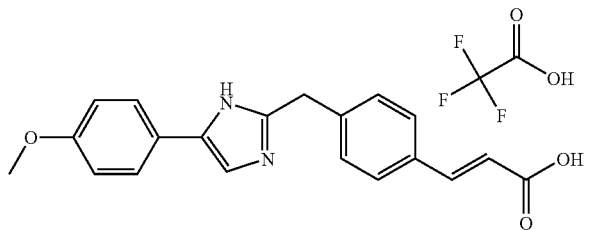
Compound (264)
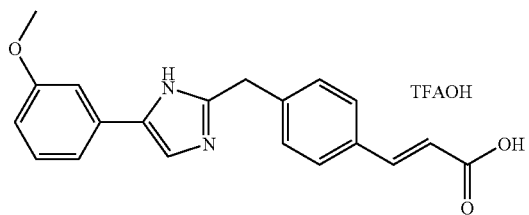
Compound (265)
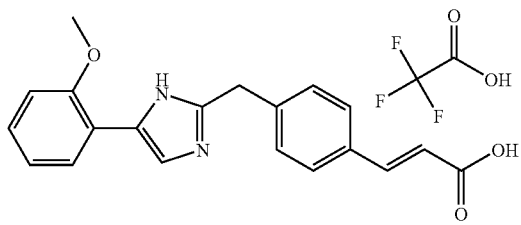
Compound (266)
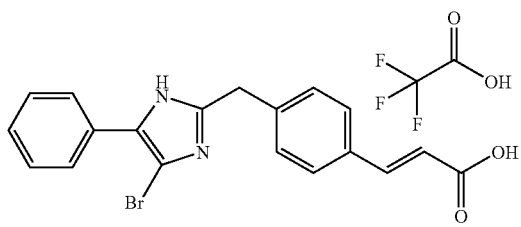
Compound (267)
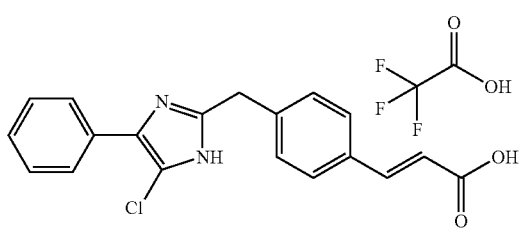

TABLE 2-continued
Compound (268)
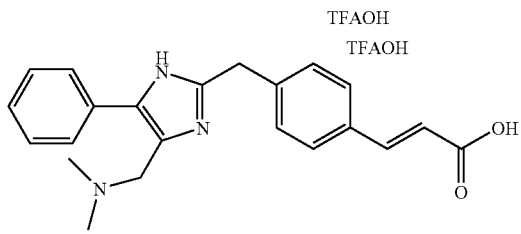
Compound (269)
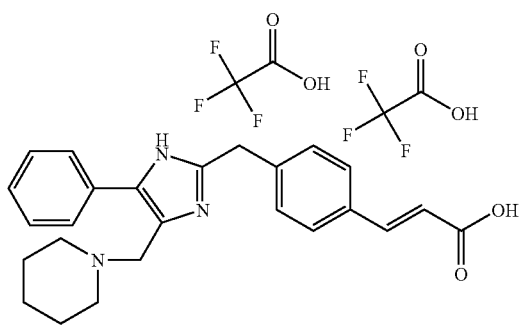
Compound (270)
Compound (271)
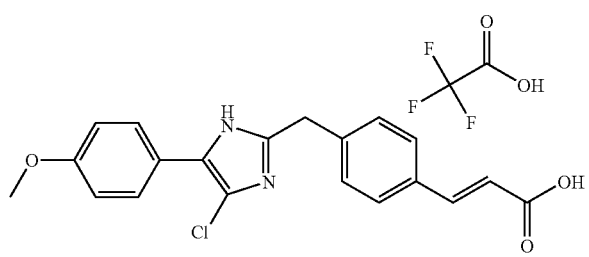
Compound (272)
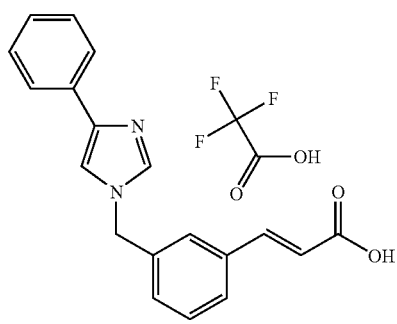

TABLE 2-continued
Compound (273)
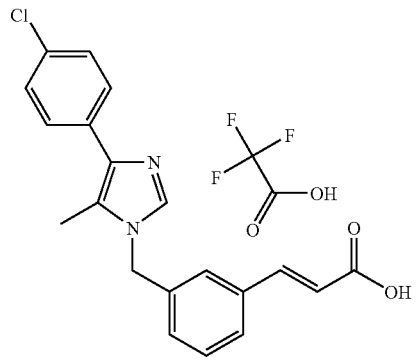
Compound (274)
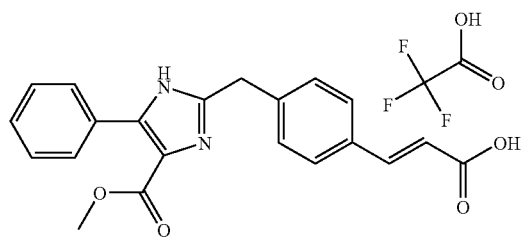
Compound (275)
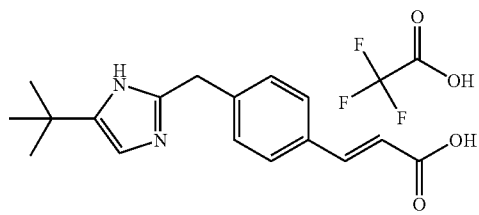
Compound (276)
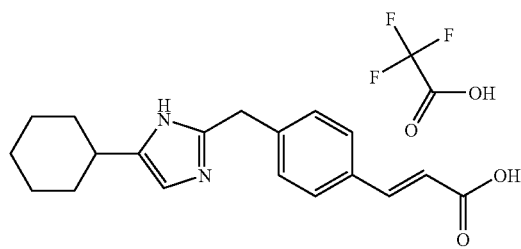
Compound (277)
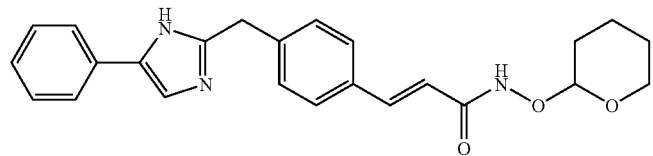

TABLE 2-continued
Compound (278)
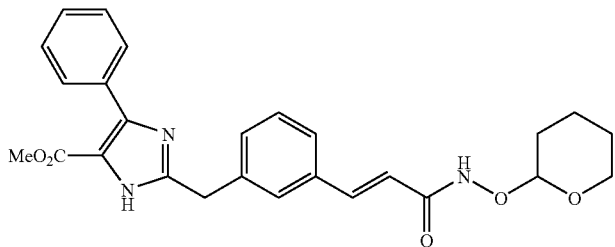
Compound (279)
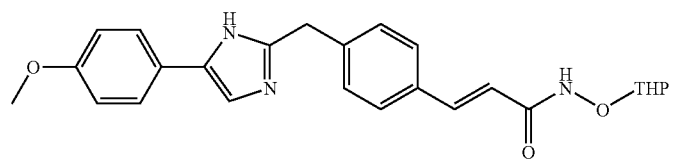
Compound (280)
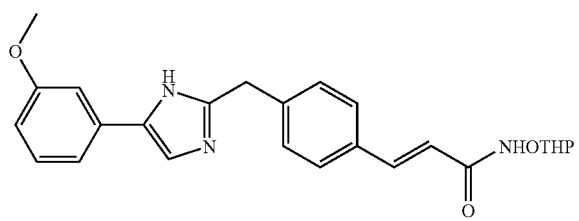
Compound (281)
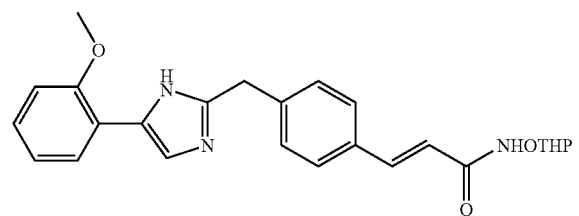
Compound (282)
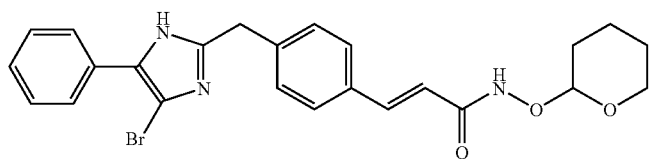
Compound (283)
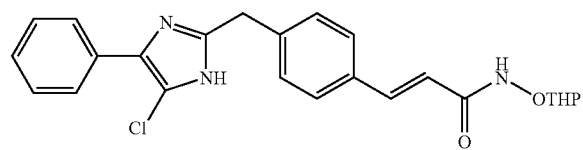

TABLE 2-continued
Compound (284)
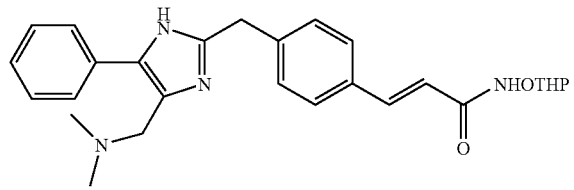
Compound (285)
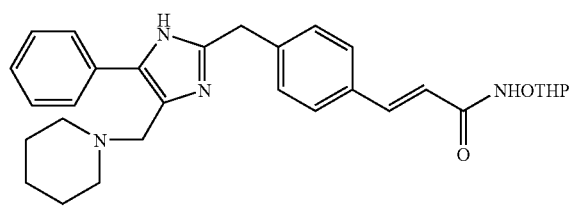
Compound (286)
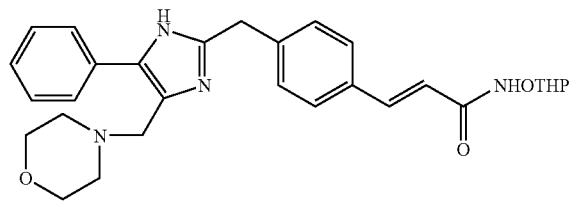
Compound (287)
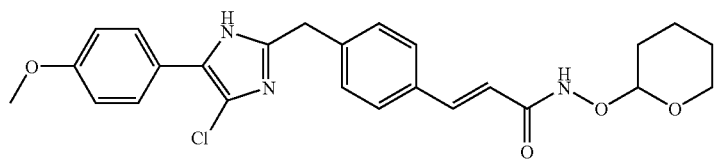
Compound (288)
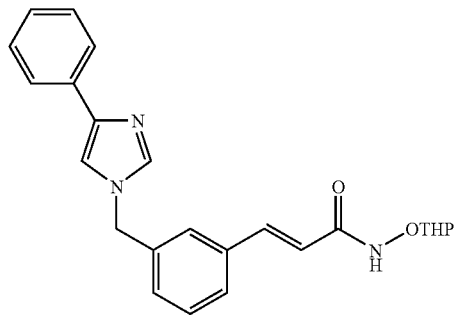

TABLE 2-continued
Compound (289)
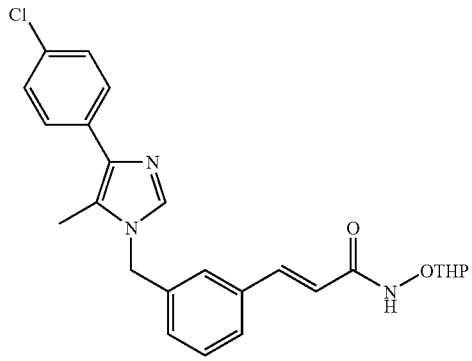
Compound (290)
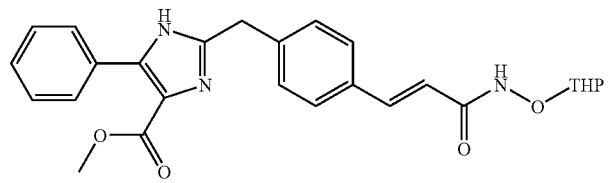
Compound (291)
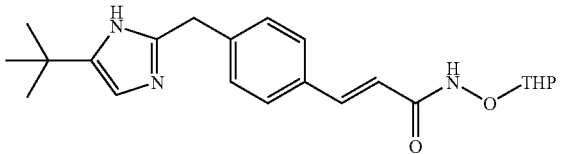
Compound (292)
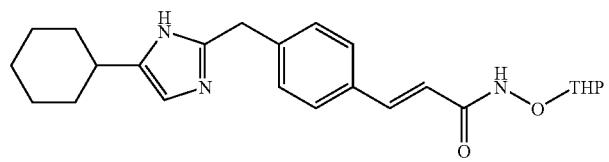
Compound (293)
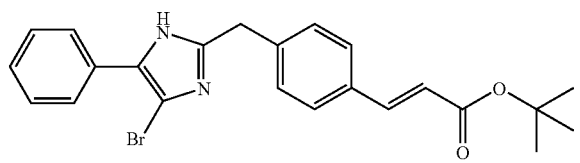
Compound (294)
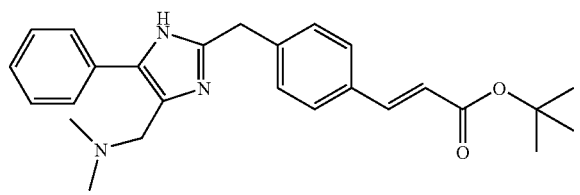

TABLE 2-continued
Compound (295)
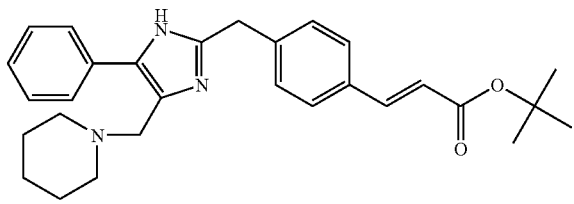
Compound (296)
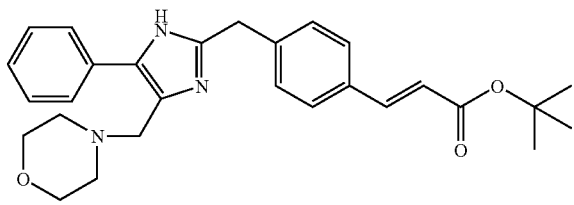
Compound (297)
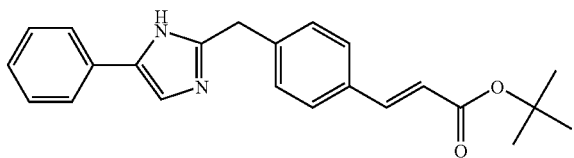
Compound (298)
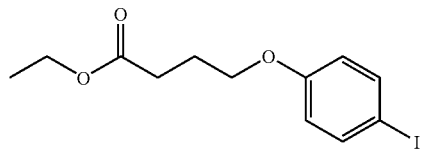
Compound (299)
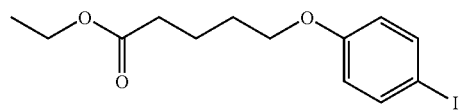
Compound (300)
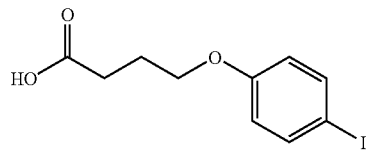
Compound (301)
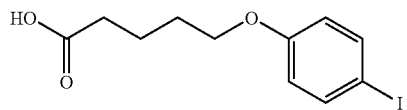

TABLE 2-continued
Compound (302)
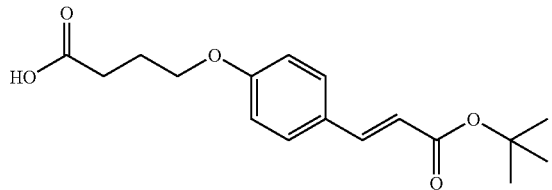
Compound (303)
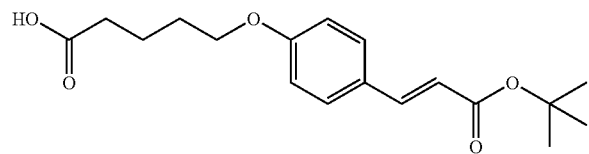
Compound (304)
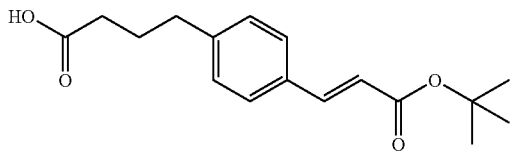
Compound (305)
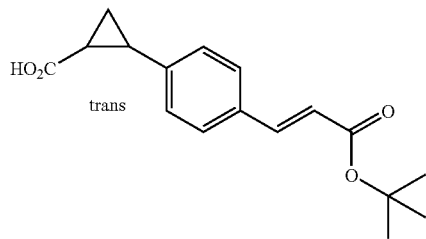
Compound (306)
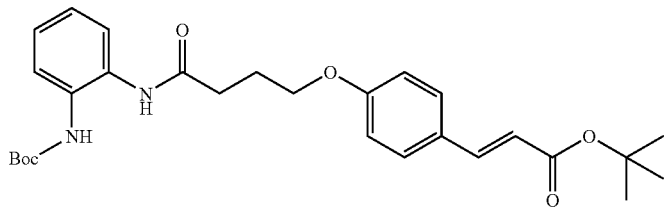
Compound (307)
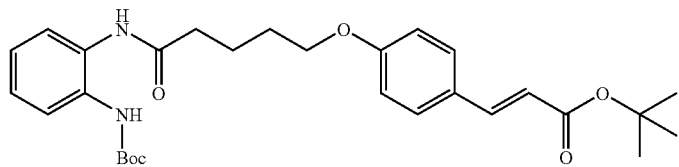

TABLE 2-continued
Compound (308)
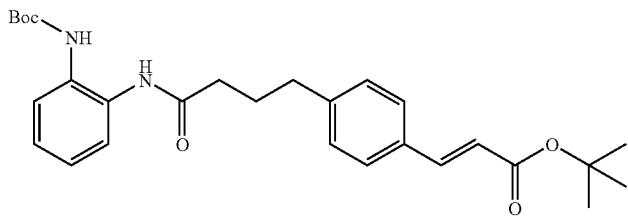
Compound (309)
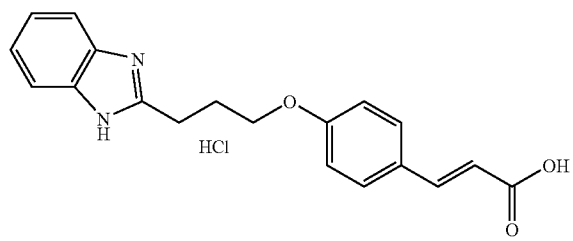
Compound (310)
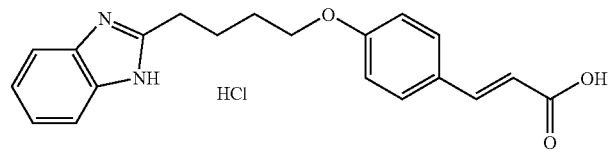
Compound (311)
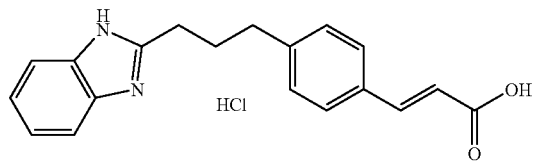
Compound (312)
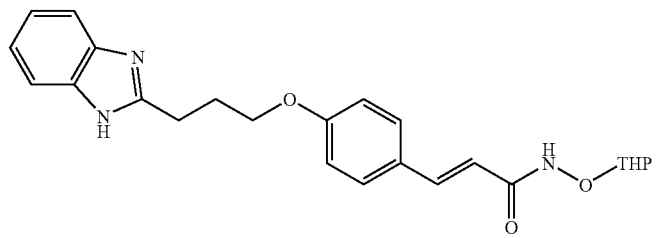
Compound (313)
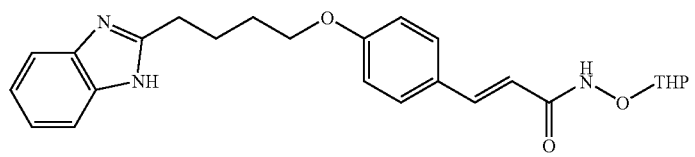

TABLE 2-continued
Compound (314)
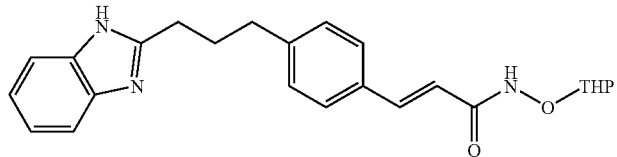
Compound (315)
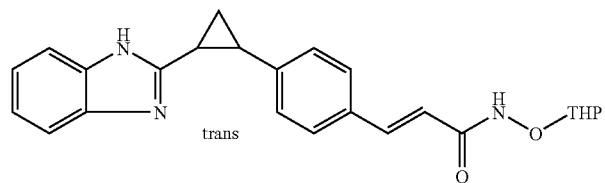
Compound (316)
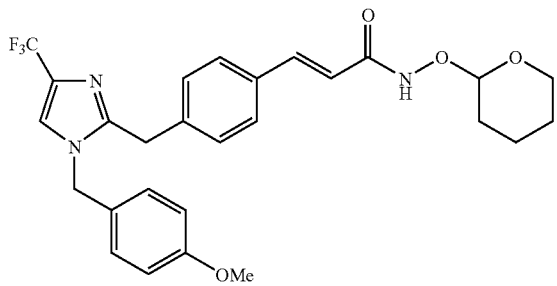
Compound (317)
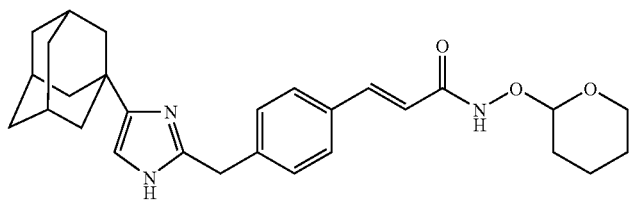
Compound (318)
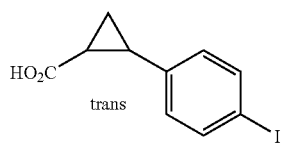
Compound (319)
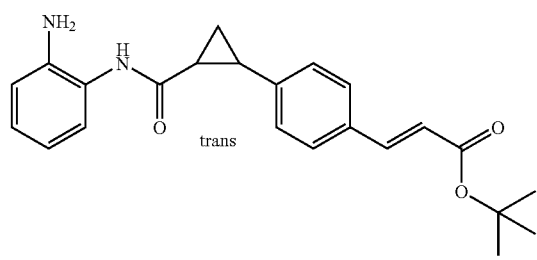

TABLE 2-continued
Compound (320)
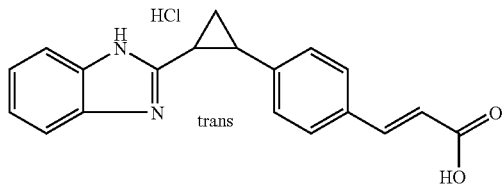
Compound (321)
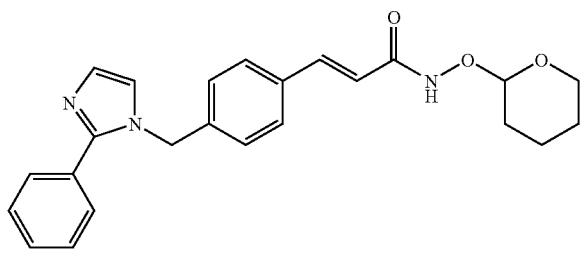
Compound (322)
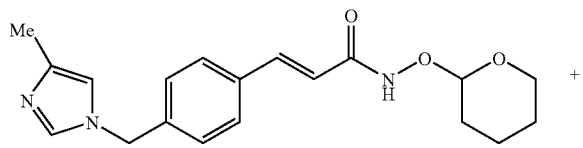
(Main product)
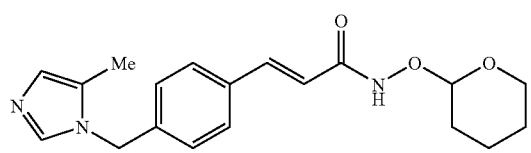
(By-product)
Compound (323)
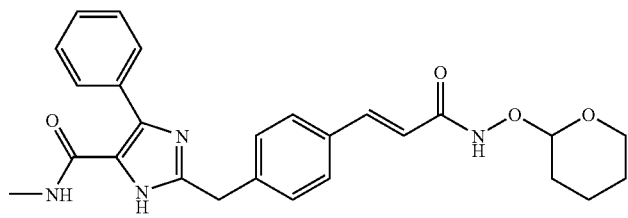
Compound (324)
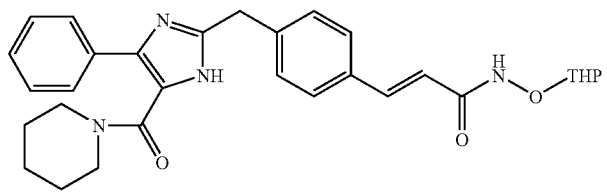

TABLE 2-continued
Compound (325)
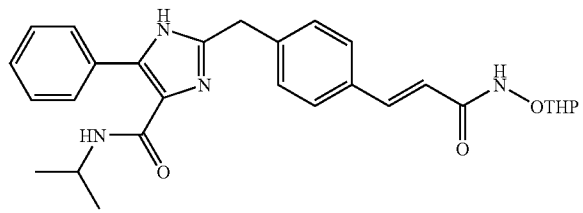
Compound (326)
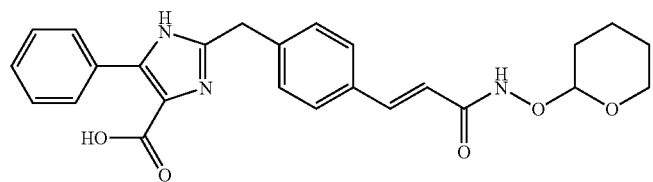
Compound (327)
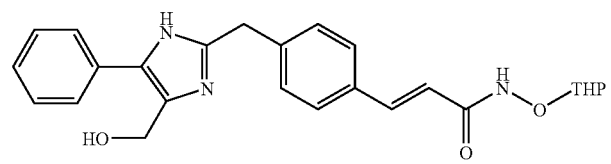
Compound (328)
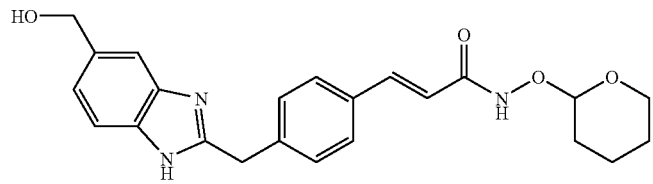
Compound (329)
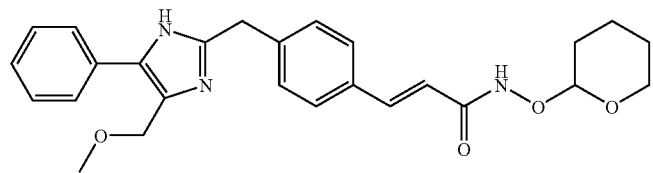
Compound (330)
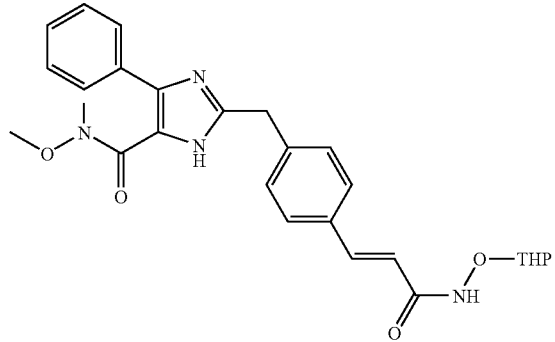

TABLE 2-continued
Compound (331)
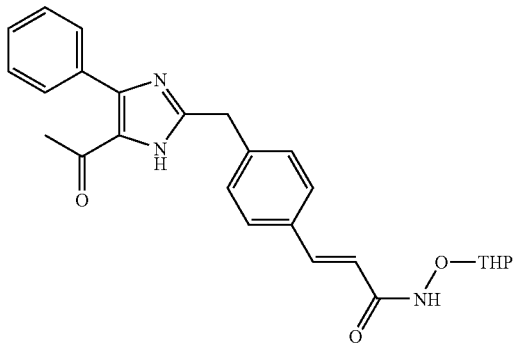
Compound (332)
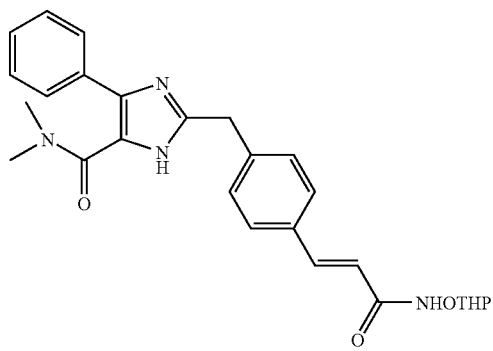
Compound (333)
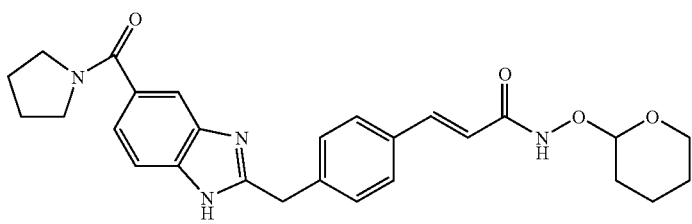
Compound (334)
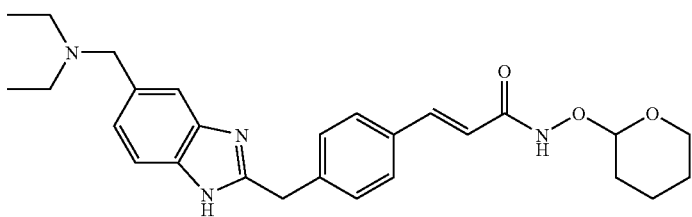
Compound (335)
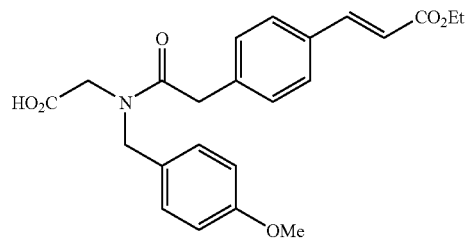

TABLE 2-continued
Compound (336)
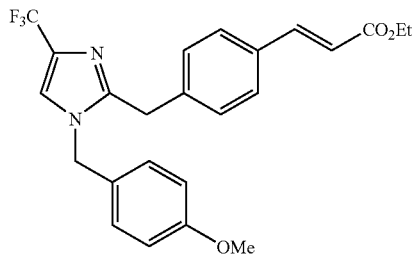
Compound (337)
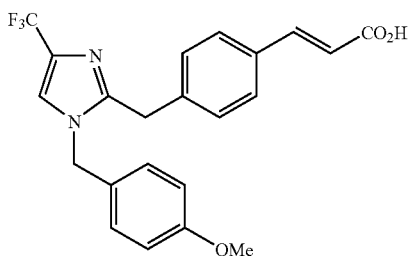
Compound (338)
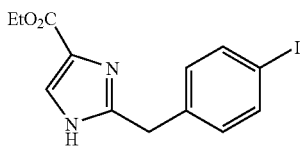
Compound (339)
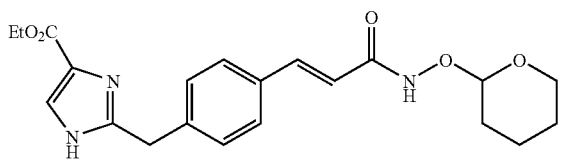
Compound (340)
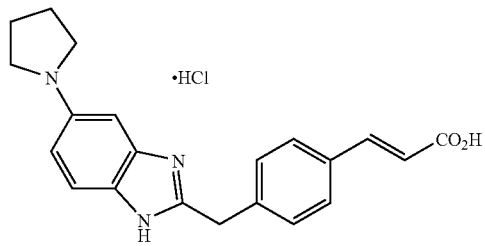

TABLE 3
Compound E1
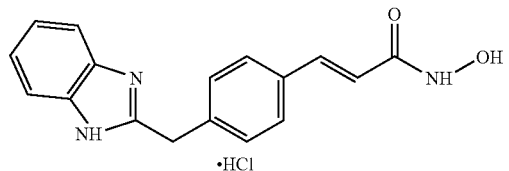
•HCl
Compound E2
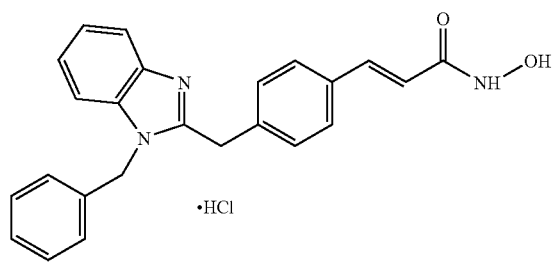
•HCl
Compound E3
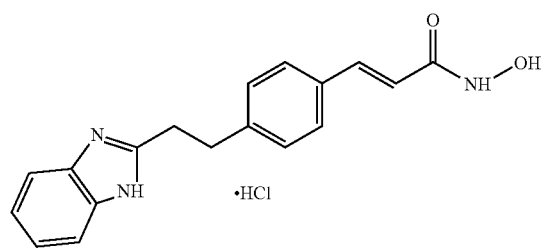
•HCl
Compound E4
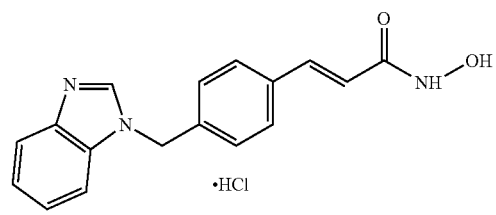
•HCl
Compound E5
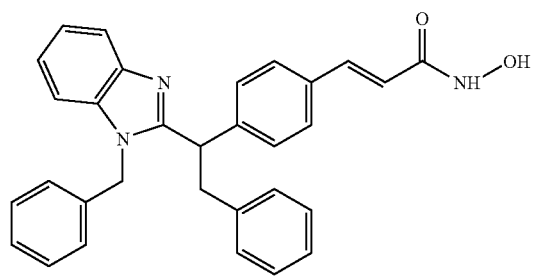

TABLE 3-continued
Compound E6
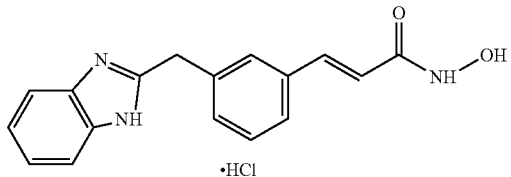
•HCl
Compound E7
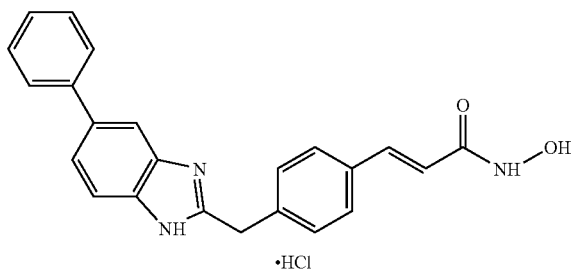
•HCl
Compound E8
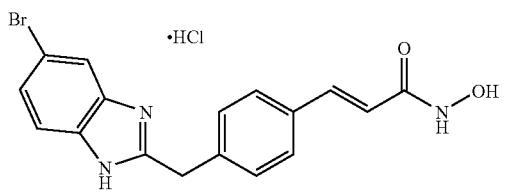
•HCl
Compound E9
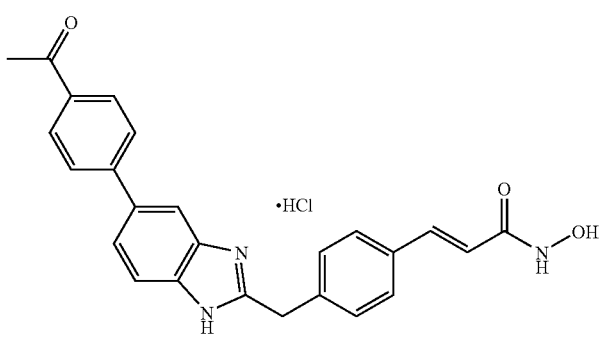
•HCl
Compound E10
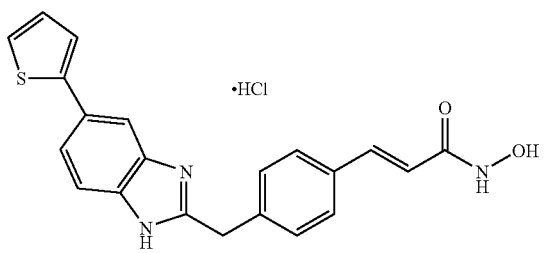
•HCl TABLE 3-continued
Compound E11
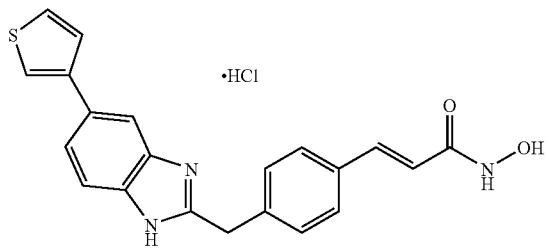
Compound E12
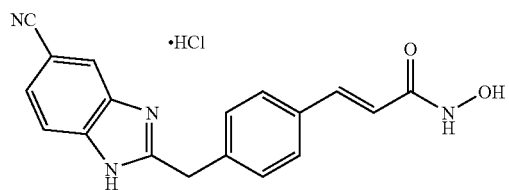
Compound E13
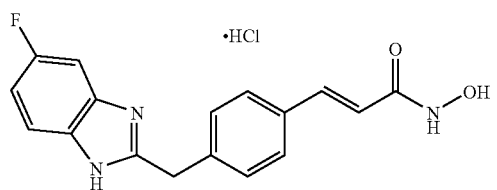
Compound E14
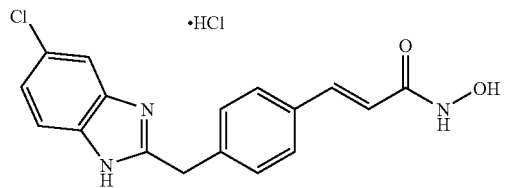
Compound E15
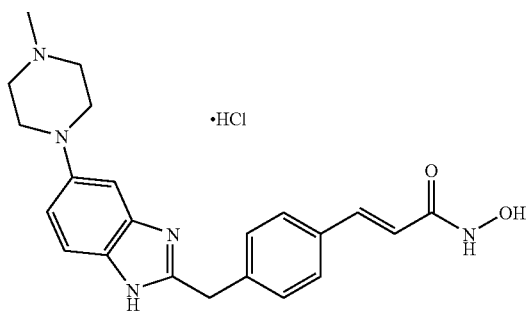

TABLE 3-continued
Compound E16
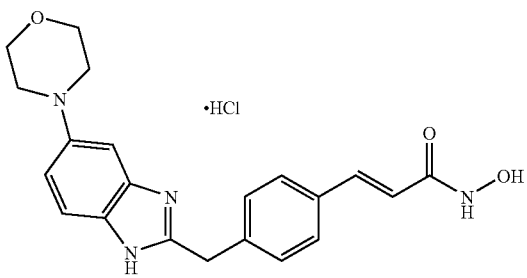
Compound E17
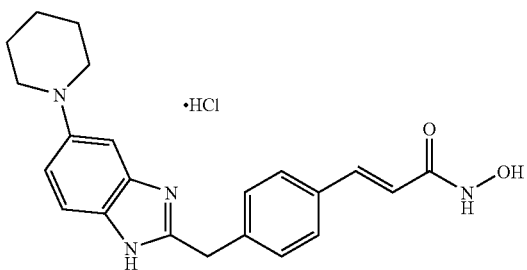
Compound E18
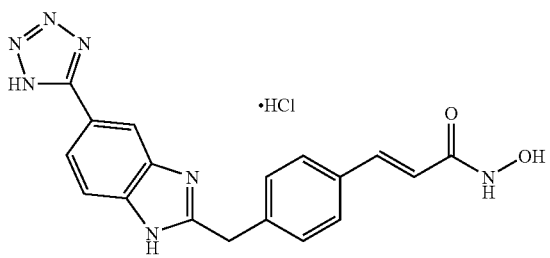
Compound E19
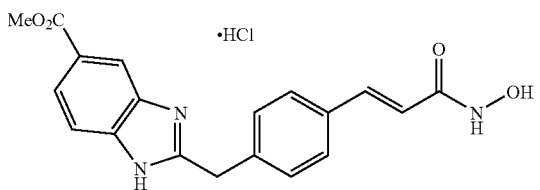
Compound E20
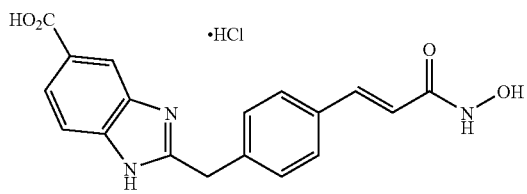

TABLE 3-continued
Compound E21
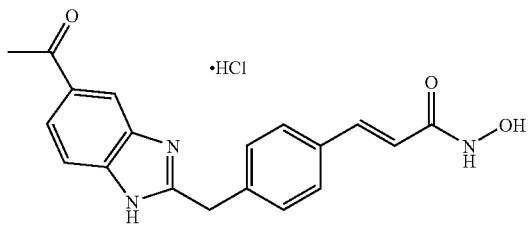
Compound E22
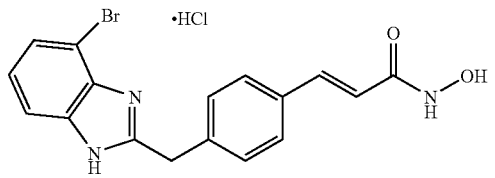
Compound E23
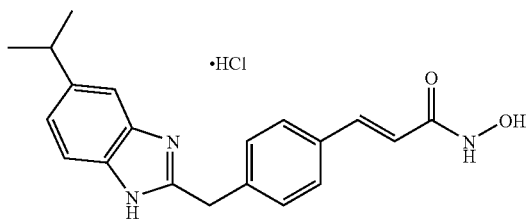
Compound E24
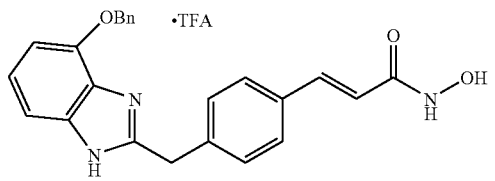
Compound E25
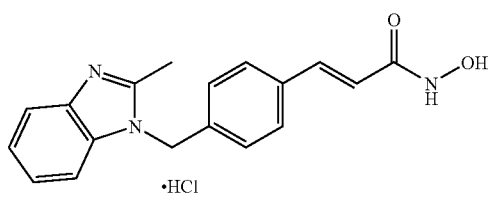
Compound E26
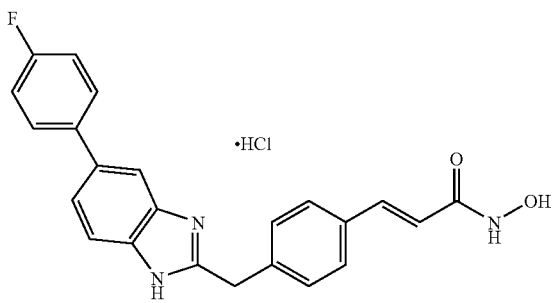

TABLE 3-continued
Compound E27
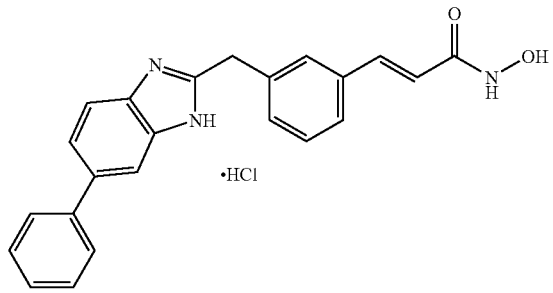
Compound E28
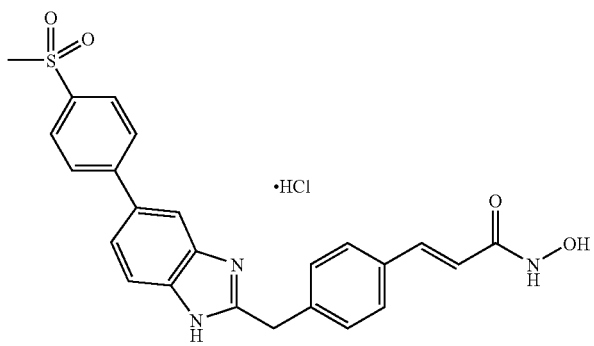
Compound E29
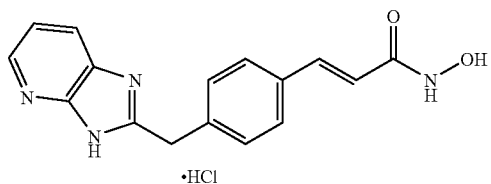
Compound E30
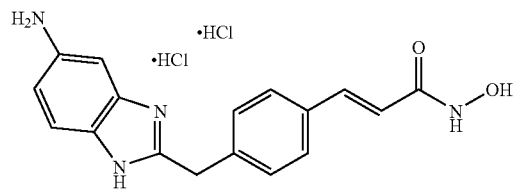
Compound E31
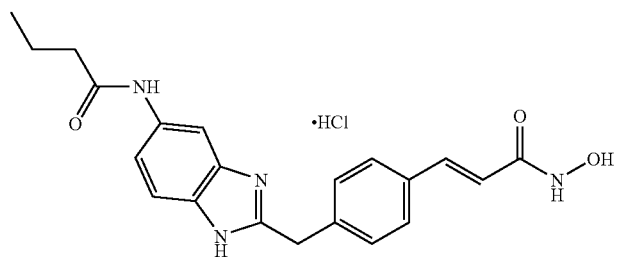

TABLE 3-continued
Compound E32
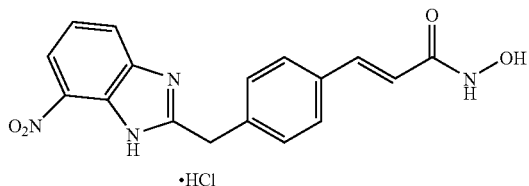
•HCl
Compound E33
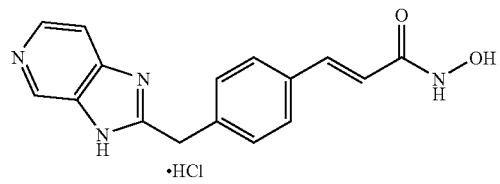
•HCl
Compound E34
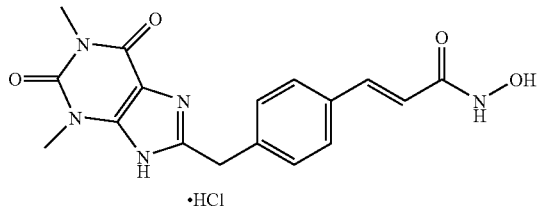
•HCl
Compound E35
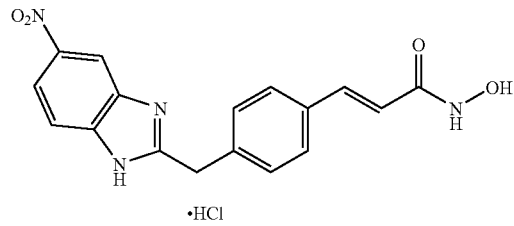
•HCl
Compound E36
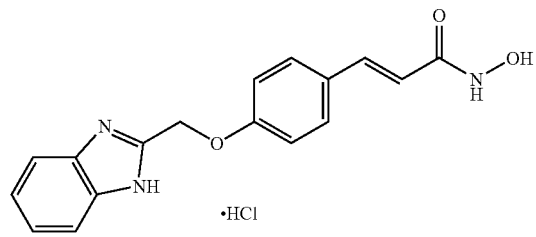
•HCl
Compound E37
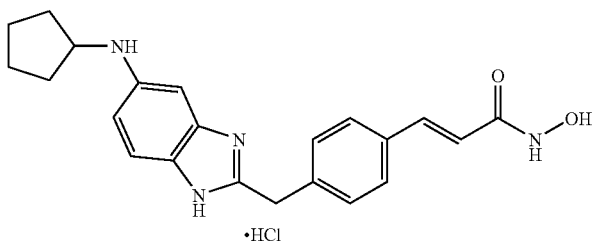
•HCl TABLE 3-continued
Compound E38
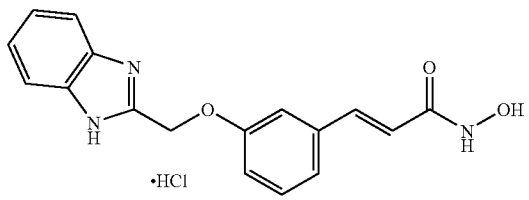
Compound E39
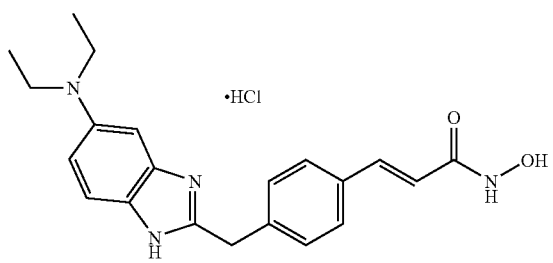
Compound E40
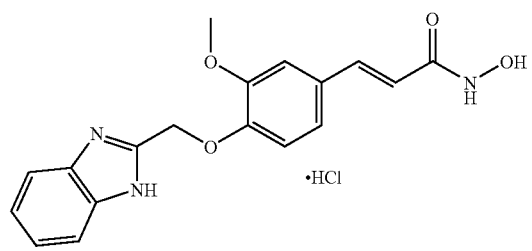
Compound E41
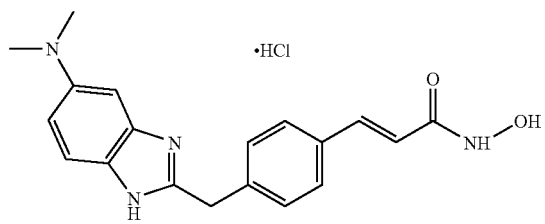
Compound E42
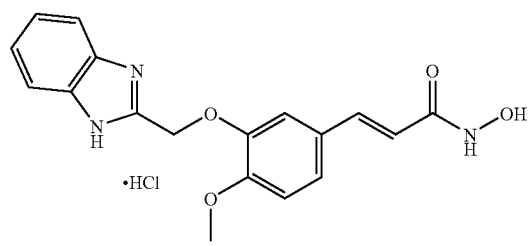

TABLE 3-continued
Compound E43
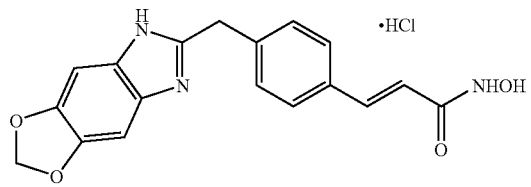
Compound E44
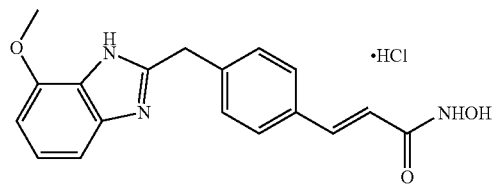
Compound E45
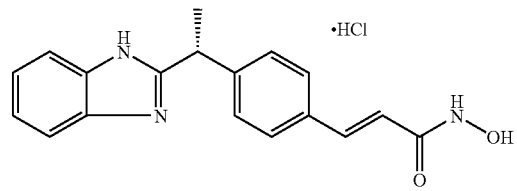
Compound E46
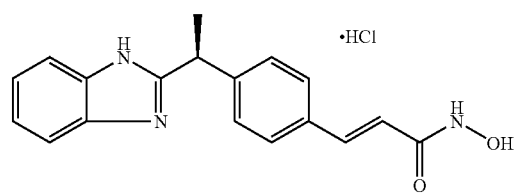
Compound E47
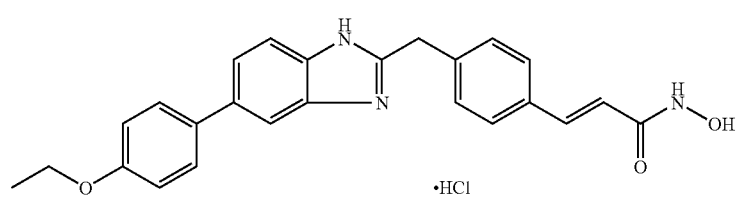
Compound E48
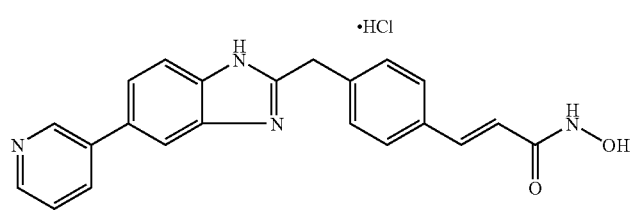

TABLE 3-continued
Compound E49
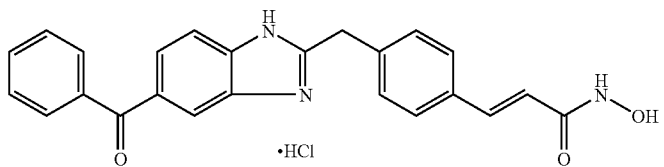
Compound E50
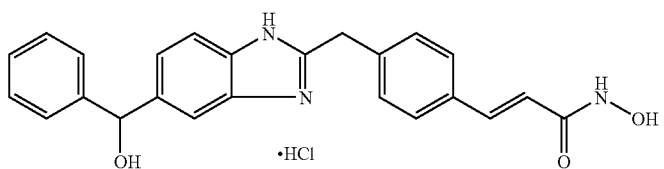
Compound E51
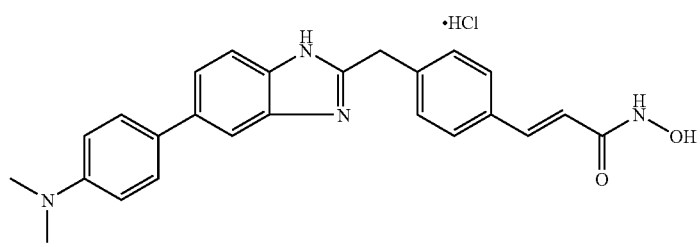
Compound E52
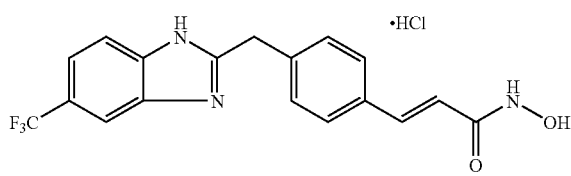
Compound E53
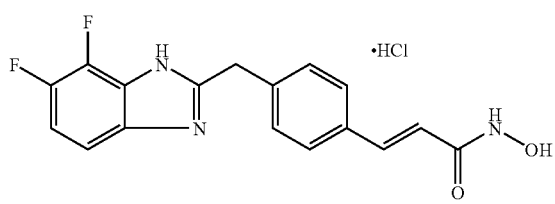
Compound E54
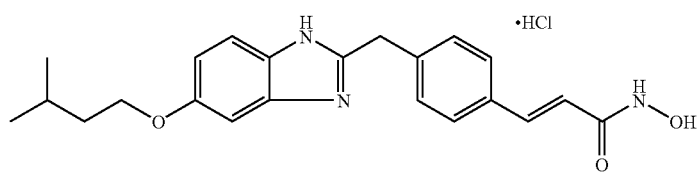

TABLE 3-continued
Compund E55
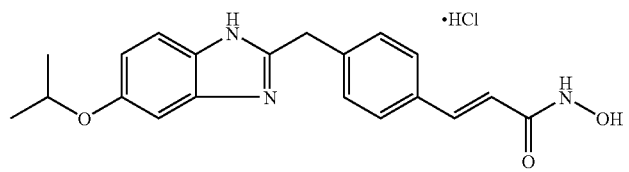
Compound E56
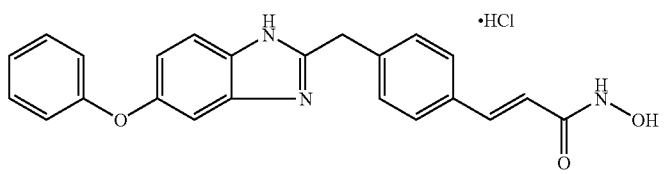
Compound E57
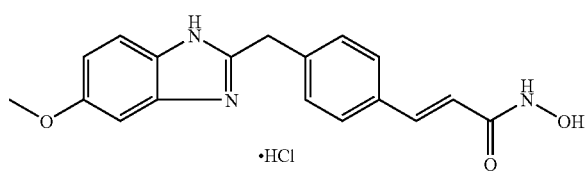
Compound E58
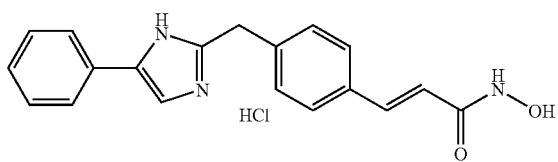
Compound E59
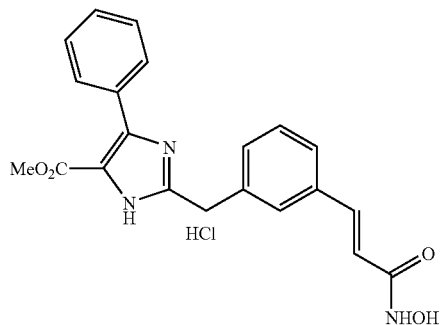
Compound E60
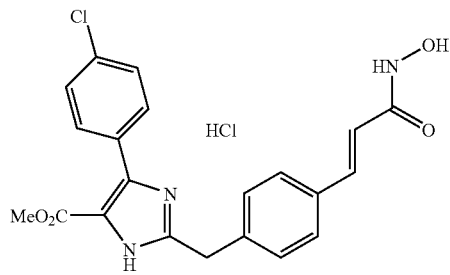

TABLE 3-continued
Compound E61
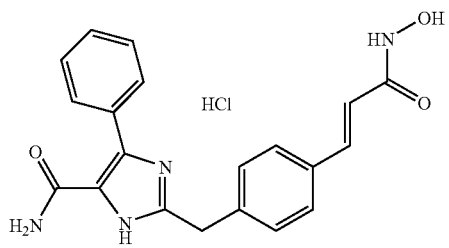
Compound E62
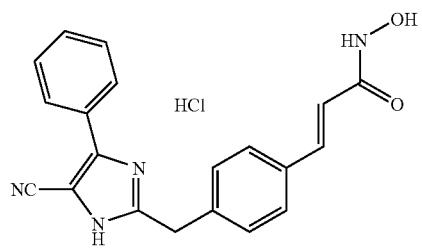
Compound E63
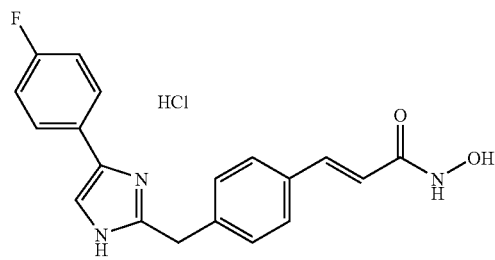
Compound E64
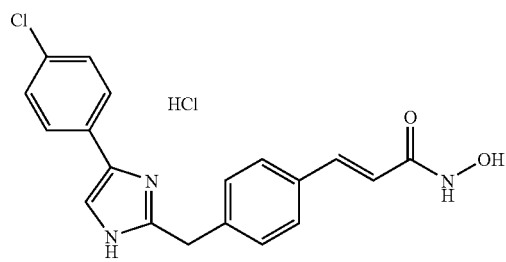
Compound E65
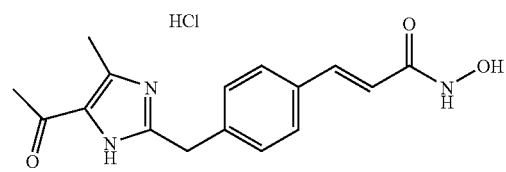

TABLE 3-continued
Compound E66
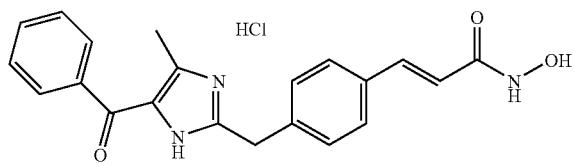
Compound E67
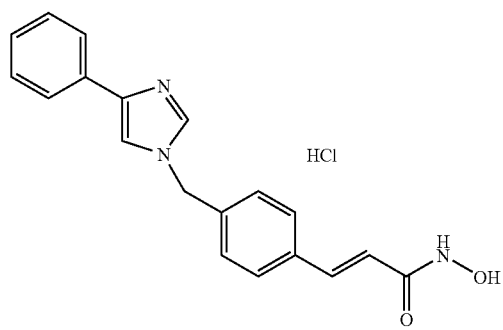
Compound E68
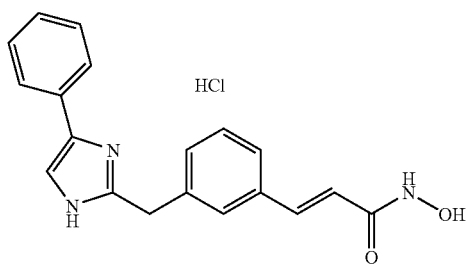
Compound E69
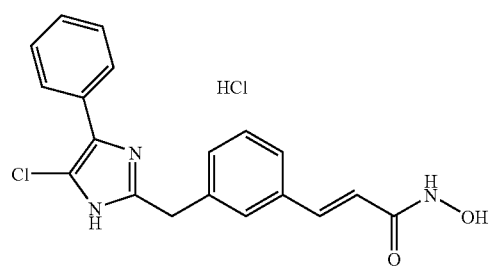
Compound E70
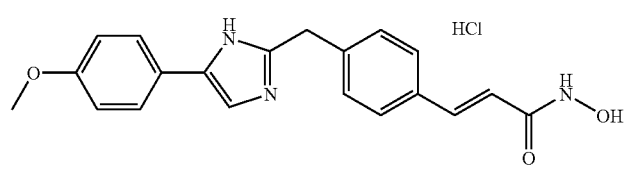

TABLE 3-continued
Compound E71
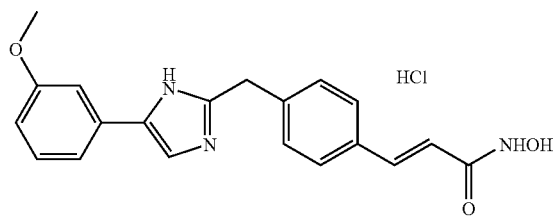
Compound E72
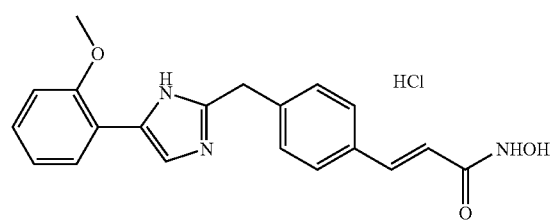
Compound E73
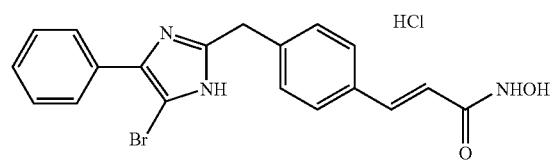
Compound E74
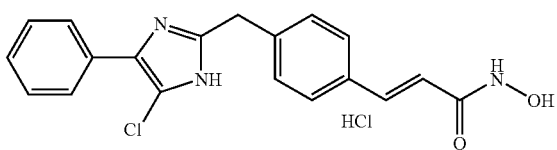
Compound E75
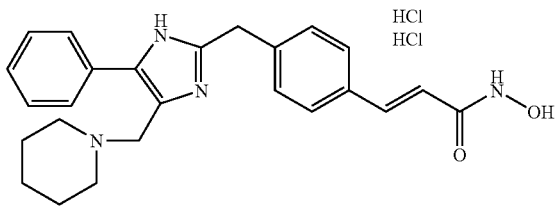
Compound E76
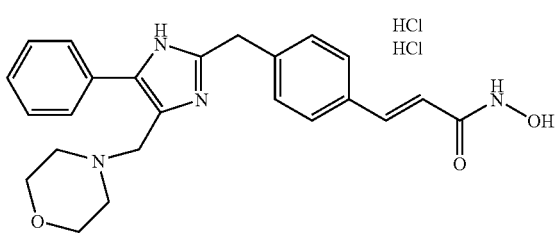

TABLE 3-continued
Compound E77
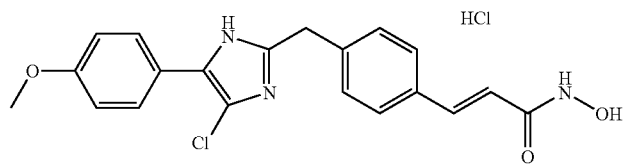
Compound E78
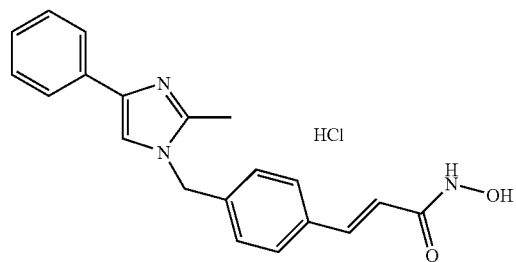
Compound E79
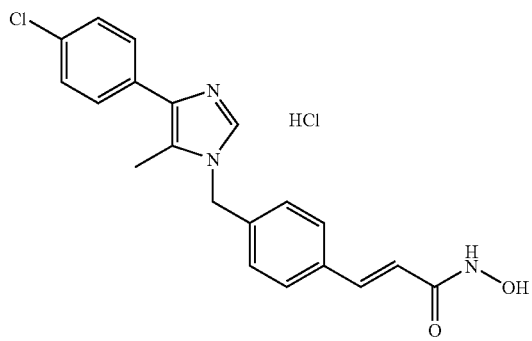
Compound E80
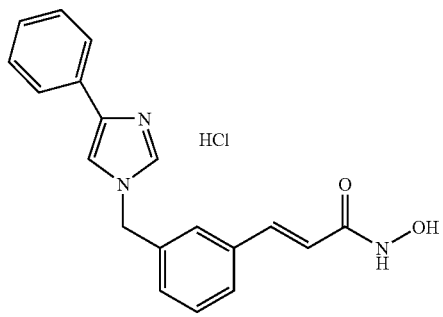

TABLE 3-continued
Compound E81
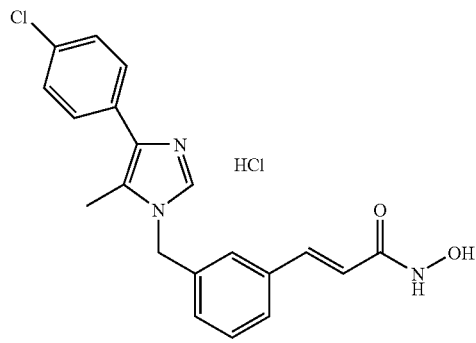
Compound E82
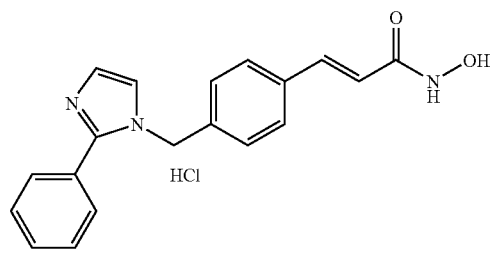
Compound E83
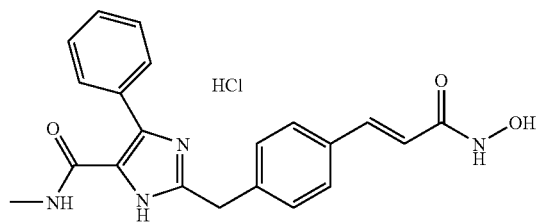
Compound E84
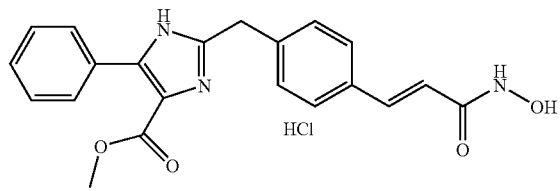
Compound E85
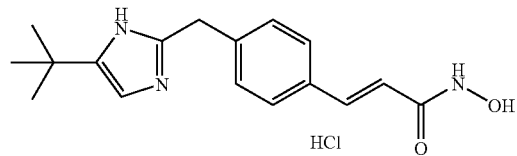

TABLE 3-continued
Compound E86
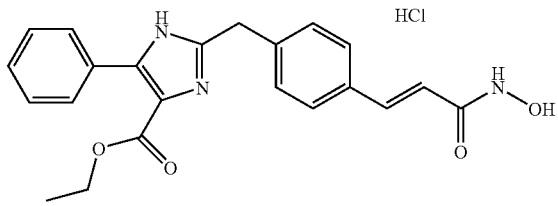
Compound E87
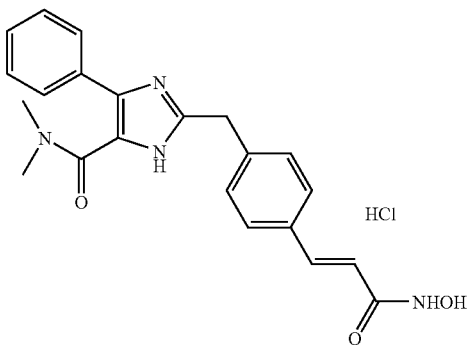
Compound E88
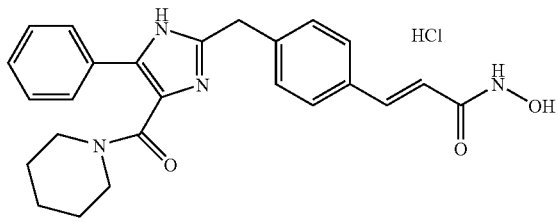
Compound E89
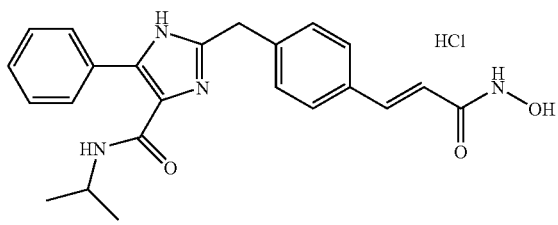
Compound E90
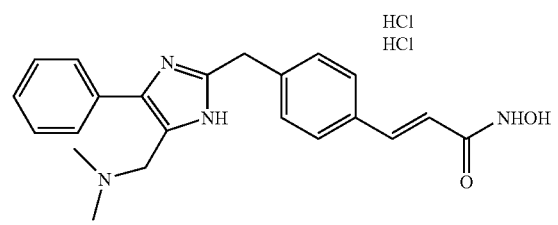

TABLE 3-continued
Compound E91
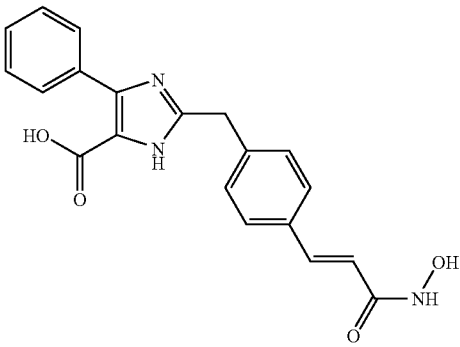
Compound E92
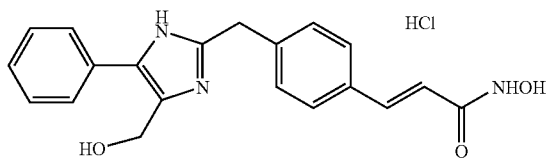
Compound E93
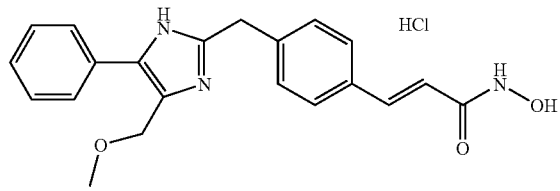
Compound E94
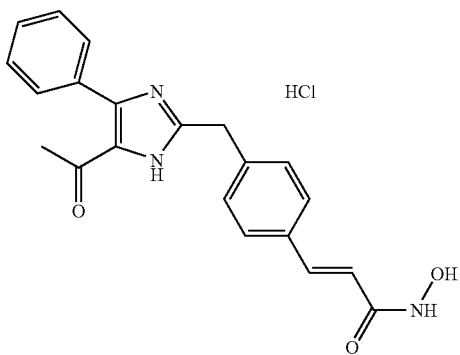
Compound E95
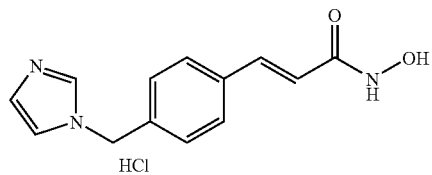

TABLE 3-continued
Compound E96
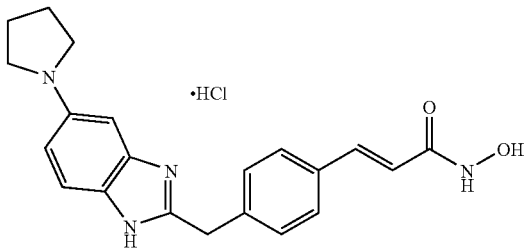
Compound E97
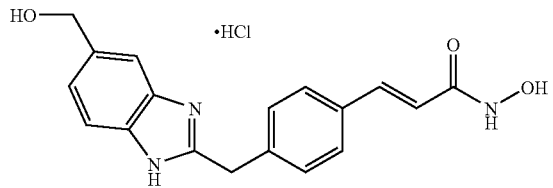
Compound E98
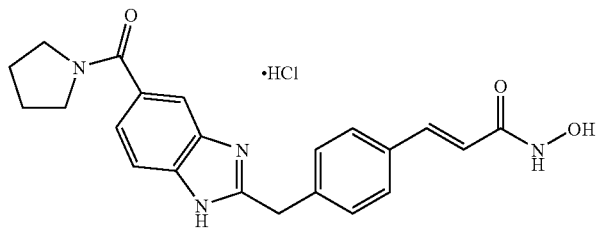
Compound E99
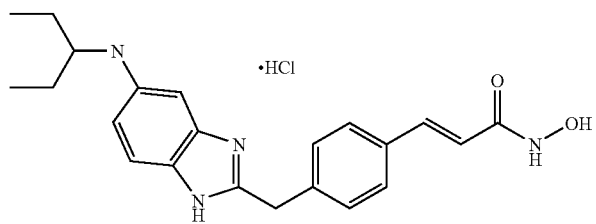
Compound E100
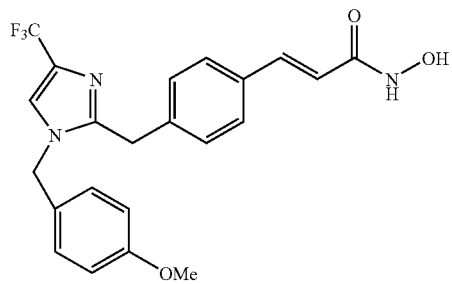

TABLE 3-continued
Compound E101
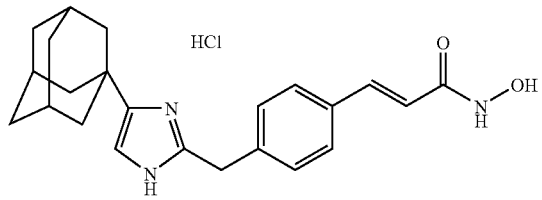
Compound E102
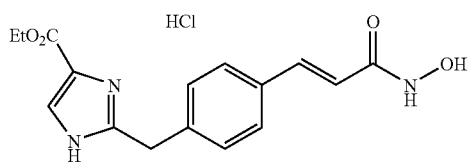
Compound E103
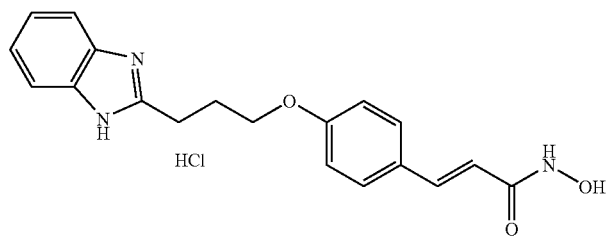
Compound E104
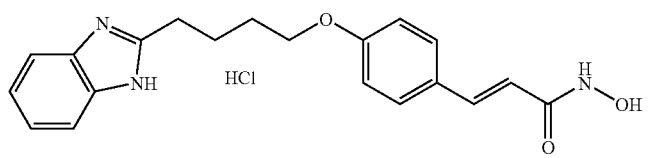
Compound E105
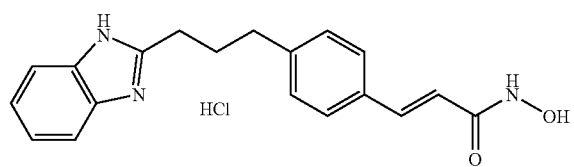
Compound E106
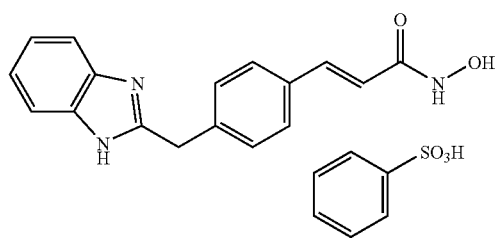

TABLE 3-continued
Compound E107
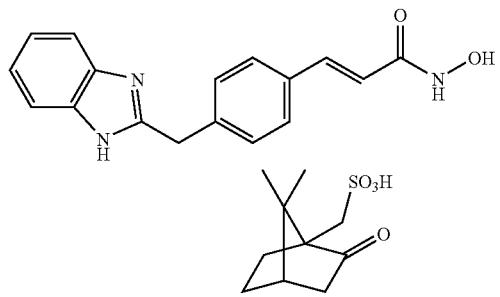
Compound E108
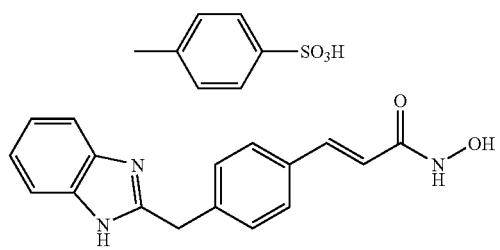
Compound E109
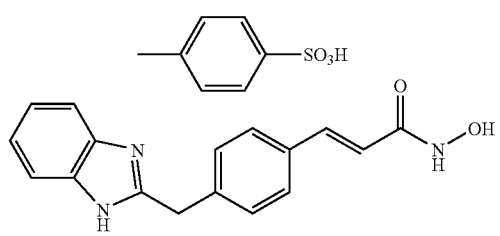
Compound E110
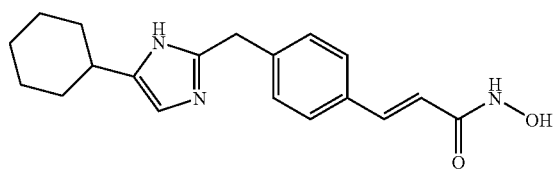
Compound E111
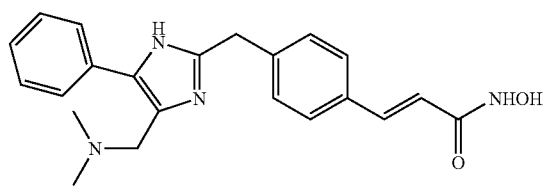
Compound E112
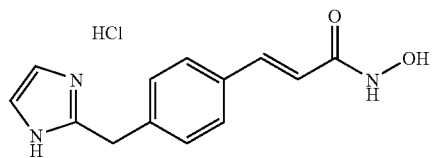

TABLE 3-continued
Compound E113
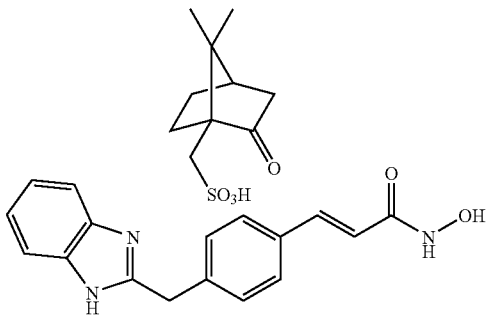
Compound E114
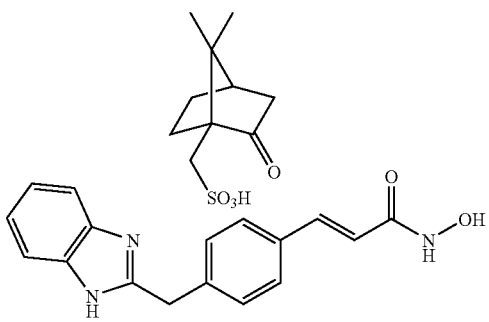
Compound E115
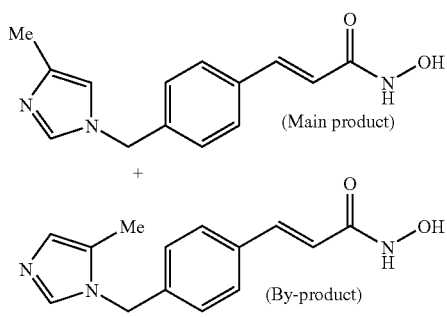
Compound E116
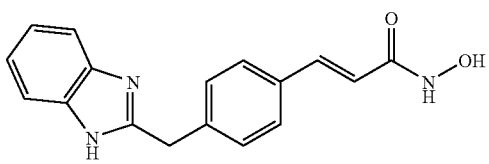
Compound E117
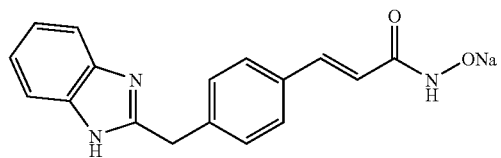

TABLE 3-continued
Compound E118
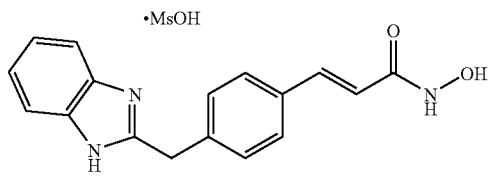
Compound E119
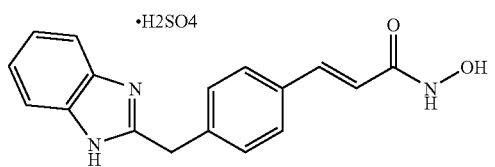
Compound E120
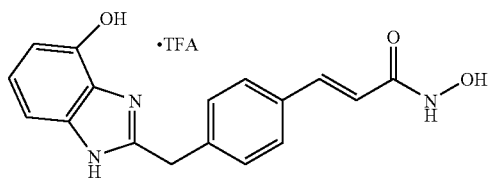
Compound E121
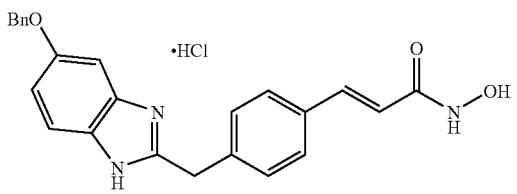
Compound E122
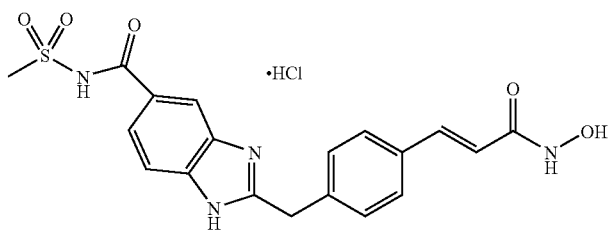
Compound E123
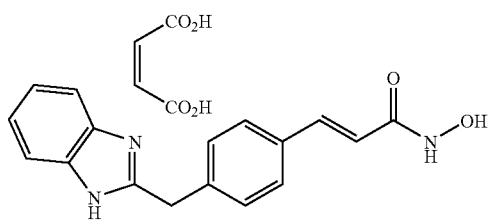

TABLE 3-continued

Compound E124

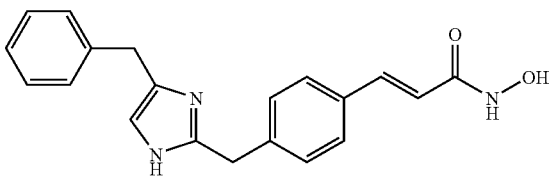

INDUSTRIAL APPLICABILITY

As mentioned above, the present invention can provide a novel compound having a potent inhibitory effect on the activity of histone deacetylase, and a pharmaceutical composition comprising the same. The compound is useful as an active ingredient of an immunosuppressant and an antitumor agent, and as an active ingredient of a therapeutic or prophylactic agent for diseases such as inflammatory disorders, diabetes, diabetic complications, homozygous thalassemia, fibrosis, cirrhosis, acute promyelocytic leukaemia (APL), organ transplant rejections, autoimmune diseases, protozoal infections, tumors, etc.

This application is based on the patent applications Nos. 2003900116 and 2003905406, both were filed in Australia, and the contents of which are incorporated hereinto by reference.

What is claimed is:

1. A compound having the following formula (I):

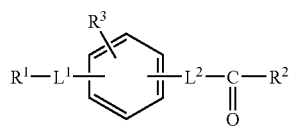

wherein $R^1$ is N-containing heterocyclic ring represented by the following formula:

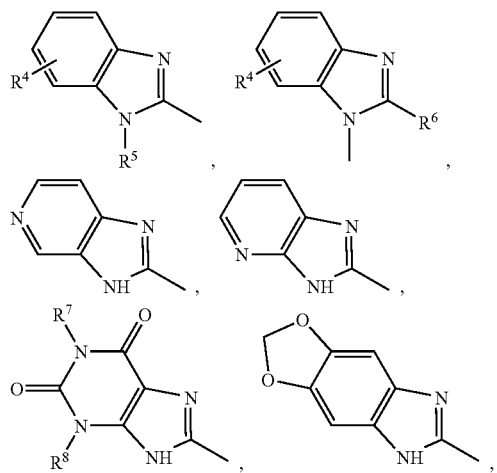

-continued

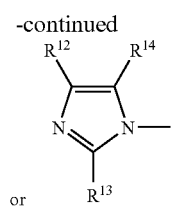

wherein $R^4$ is hydrogen or a group selected from the group consisting of:
(1) lower alkyl optionally substituted with di(lower)alkylamino or hydroxy,
(2) lower alkoxy,
(3) aryl optionally substituted with the substituent selected from the group consisting of halogen, lower alkanoyl, lower alkylsulfonyl, lower alkoxy and di(lower)alkylamino,
(4) lower alkanoyl,
(5) lower alkoxy-carbonyl,
(6) arylcarbonyl,
(7) aryl(lower)alkoxy,
(8) amino optionally mono- or di-substitited with substituent(s) selected from the group consisting of lower alkyl, lower alkanoyl and cycloalkyl,
(9) halo(lower)alkyl,
(10) aryloxy,
(11) aryl(lower)alkyl optionally substituted with hydroxy,
(12) carboxyl,
(13) nitro,
(14) cyano,
(15) halogen,
(16) heteroaryl,
(17) non-aromatic heterocycle optionally substituted with lower alkyl,
(18) hydroxy,
(19) (lower)alkylsulfonylcarbamoyl and
(20) non-aromatic heterocycle carbonyl;

$R^5$ is hydrogen or a group selected from the group consisting of lower alkyl and aryl(lower)alkyl, and $R^6$, $R^7$ and $R^8$ are each hydrogen or lower alkyl, $R^9$ is hydrogen or a group selected from the group consisting of:
(1) lower alkyl optionally substituted with di(lower)alkylamino,
(2) aryl optionally substituted with lower alkoxy,
(3) (lower)alkoxy-carbonyl,
(4) cyano, (5) carbamoyl optionally mono- or di-substituted with (lower)alkyl,
(6) halogen,
(7) (lower)alkyl-carbonyl,
(8) arylcarbonyl and
(9) cyclo(lower)alkyl, $R^{10}$ is hydrogen or a group selected from the group consisting of:
(1) (lower)alkylcarbamoyl,
(2) di(lower)alkylcarbamoyl,
(3) aryl optionally substituted with halogen,
(4) (lower)alkoxy-carbonyl,
(5) carboxy,
(6) non-aromatic heterocycle carbonyl,
(7) halogen,
(8) (lower)alkyl optionally substituted with hydroxy, (lower)alkoxy, non-aromatic heterocycle, aryl, di(lower)alkylamino or halogen, and
(9) adamantyl;

$R^{11}$ is hydrogen or aryl(lower)alkyl in which the aryl portion is substituted with lower alkoxy, $R^{12}$ is hydrogen or a group selected from the group consisting of lower alkyl and aryl optionally substituted with halogen, $R^{13}$ is hydrogen or a group selected from the group consisting of lower alkyl and aryl, $R^{14}$ is hydrogen or lower alkyl, $R^2$ is hydroxyamino, $R^3$ is hydrogen or lower alkoxy, $L^1$ is —$(CH_2)_n$— (wherein n is 1 to 5) optionally substituted with one or more substituent(s) selected from the group consisting of lower alkyl(s) and aryl(lower)alkyl, and wherein one methylene may be replaced with an oxygen atom, and $L^2$ is vinylene;
or a salt thereof.

2. The compound of claim 1, wherein
$R^1$ is an N-containing condensed heterocyclic ring represented by the following formula:

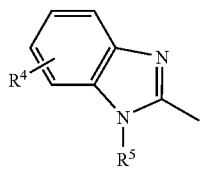

wherein $R^4$ and $R^5$ are each as defined in claim 1.

3. The compound of claim 2, wherein
$R^4$ and $R^5$ are each hydrogen,
$R^2$ is hydroxyamino,
$R^3$ is hydrogen,
$L^1$ is —$CH_2$—, and
$L^2$ is vinylene;
or a salt thereof.

4. The compound of claim 1, wherein
$R^1$ is an N-containing heterocyclic ring represented by the following formula:

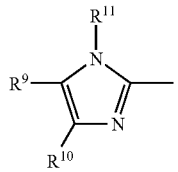

wherein $R^9$, $R^{10}$ and $R^{11}$ are each as defined in claim 1.

5. The compound of claim 4, wherein
$R^9$ is hydrogen or aryl optionally substituted with lower alkoxy,
$R^{10}$ is hydrogen or aryl optionally substituted with halogen, and
$R^{11}$ is hydrogen,
$R^2$ is hydroxyamino,
$R^3$ is hydrogen,
$L^1$ is —$CH_2$—, and
$L^2$ is vinylene;
or a salt thereof.

6. A compound of the following formula

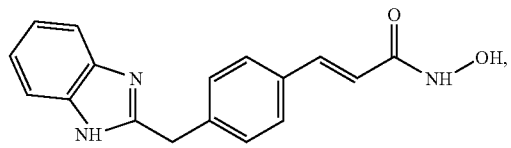

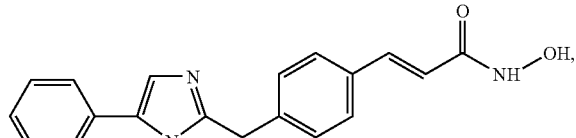

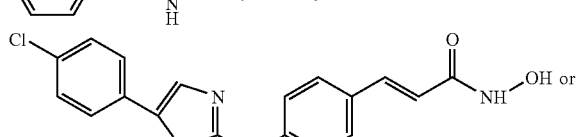

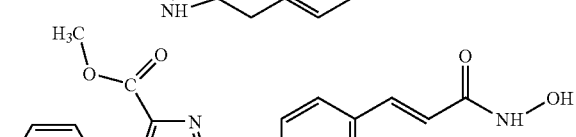

or a salt thereof.

7. A compound having the following formula (I'):

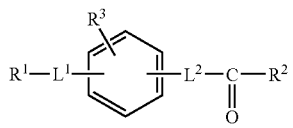

(I')

wherein
$R^1$ is N-containing condensed heterocyclic ring represented by the following formula:

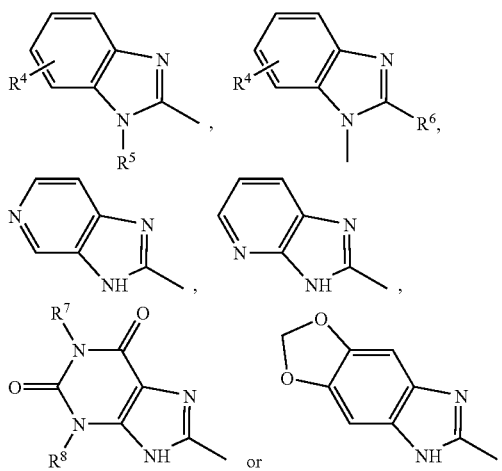

wherein
R⁴ is hydrogen or a group selected from the group consisting of
(1) lower alkyl,
(2) lower alkoxy,
(3) aryl optionally substituted with the substituent selected from the group consisting of halogen, lower alkanoyl, lower alkylsulfonyl, lower alkoxy and di(lower)alkylamino,
(4) lower alkanoyl,
(5) lower alkoxy-carbonyl,
(6) arylcarbonyl,
(7) aryl(lower)alkoxy,
(8) amino optionally mono- or di-substitited with substituent(s) selected from the group consisting of lower alkyl, lower alkanoyl and cycloalkyl,
(9) halo(lower)alkyl,
(10) aryloxy,
(11) aryl(lower)alkyl optionally substituted with hydroxy,
(12) carboxyl,
(13) nitro,
(14) cyano,
(15) halogen,
(16) heteroaryl and
(17) non-aromatic heterocycle optionally substituted with lower alkyl,
R⁵ is hydrogen or a group selected from the group consisting of lower alkyl and aryl(lower)alkyl, and
R⁶, R⁷ and R⁸ are each hydrogen or lower alkyl,
R² is hydroxyamino,
R³ is hydrogen or lower alkoxy,
L¹ is —(CH₂)ₙ— (wherein n is 1 or 2) optionally substituted with one or more substituent(s) selected from the group consisting of lower alkyl(s) and aryl(lower)alkyl, and wherein one methylene may be replaced with an oxygen atom, and
L² is vinylene;
or a salt thereof.

8. A compound having the following formula (I″):

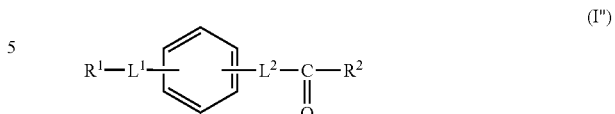

wherein
R¹ is an N-containing condensed heterocyclic ring represented by the following formula:

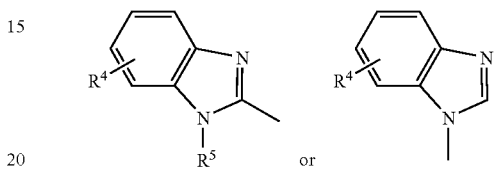

wherein
R⁴ is hydrogen or a group selected from the group consisting of lower alkyl and aryl, and
R⁵ is hydrogen or a group selected from the group consisting of lower alkyl and aryl(lower)alkyl,
R² is hydroxyamino,
L¹ is —(CH₂)ₙ— (wherein n is 1 or 2) optionally substituted with aryl(lower)alkyl, and
L² is vinylene;
or a salt thereof.

9. A composition comprising: the compound of claim 1 in an amount sufficient to inhibit histone deacetylase, and a pharmaceutically acceptable carrier or excipient.

10. A pharmaceutical composition comprising the compound of claim 1 which composition is in a solid form.

11. A pharmaceutical composition comprising: the compound of claim 1 which composition is in a liquid form.

12. The composition of claim 11 in a form suitable for intravenous or intramuscular administration.

13. A method for treating a disease or disorder caused by abnormal gene expression benefited by inhibiting histone deacetylase, comprising administering an amount of the compound of claim 1 effective to inhibit histone deacetylase to a mammal in need thereof.

14. A method for treating a disease or disorder associated with histone deacetylase selected from the group consisting of an inflammation, diabetes, diabetic complications, homozygous thalassemia, fibrosis, cirrhosis, acute promyelocytic leukaemia (APL), organ transplant rejection, and a protozoal infection, which comprises administering an effective amount of the compound of claim 1 to a mammal in need thereof.

15. A commercial package comprising: the pharmaceutical composition of claim 10 and a written matter associated therewith.

16. A composition comprising: the compound of claim 6 in an amount sufficient to inhibit histone deacetylase and a pharmaceutically acceptable carrier or excipient.

17. A pharmaceutical composition comprising an amount of the compound of claim 6 which composition is in a solid form.

18. A pharmaceutical composition comprising: the compound of claim 6 which composition is in a liquid form.

19. The composition of claim 17 in a form suitable for intravenous or intramuscular administration.

20. A method for treating a disease or disorder caused by abnormal gene expression benefited by inhibiting histone deacetylase, comprising administering an amount of the compound of claim 6 effective to inhibit histone deacetylase to a mammal in need thereof.

21. A method for treating a disease or disorder associated with histone deacetylase selected from the group consisting of an inflammation, diabetes, diabetic complications, homozygous thalassemia, fibrosis, cirrhosis, acute promyelocytic leukaemia (APL), organ transplant rejection, and a protozoal infection, which comprises administering an effective amount of the compound of claim 6 to a mammal in need thereof.

22. A commercial package comprising:
the pharmaceutical composition of claim 17, and a written matter associated therewith.

23. A composition comprising the compound of claim 7 in an amount sufficient to inhibit histone deacetylase, and a pharmaceutically acceptable carrier or excipient.

24. A pharmaceutical composition comprising the compound of claim 7 which composition is in a solid form.

25. A pharmaceutical composition comprising: the compound of claim 7 which composition is in a liquid form.

26. The composition of claim 24 in a form suitable for intravenous or intramuscular administration.

27. A method for treating a disease or disorder caused by abnormal gene expression benefited by inhibiting histone deacetylase, comprising administering an amount of the compound of claim 7 effective to inhibit histone deacetylase to a mammal in need thereof.

28. A method for treating an inflammation, diabetes, diabetic complications, homozygous thalassemia, fibrosis, cirrhosis, acute promyelocytic leukaemia (APL), organ transplant rejection, and a protozoal infection, which comprises administering an effective amount of the compound of claim 7 to a mammal in need thereof.

29. A commercial package comprising: the pharmaceutical composition of claim 24 and a written matter associated therewith.

30. A composition comprising the compound of claim 8 in an amount sufficient to inhibit histone deacetylase, and a pharmaceutically acceptable carrier or excipient.

31. A pharmaceutical composition comprising the compound of claim 8 which composition is in a solid form.

32. A pharmaceutical composition comprising: the compound of claim 8 which composition is in a liquid form.

33. The composition of claim 30 in a form suitable for intravenous or intramuscular administration.

34. A method for treating a disease or disorder associated with histone deacetylase, comprising administering an amount of the compound of claim 8 effective to inhibit histone deacetylase to a mammal in need thereof.

35. A method for treating a disease or a disorder associated with histone deacetylase selected from the group consisting of an inflammation, diabetes, diabetic complications, homozygous thalassemia, fibrosis, cirrhosis, acute promyelocytic leukaemia (APL), organ transplant rejection, and a protozoal infection, which comprises administering an effective amount of the compound of claim 8 to a mammal.

36. A commercial package comprising: the pharmaceutical composition of claim 31, and a written matter associated therewith.

* * * * *